United States Patent
Oehlenschlaeger et al.

(10) Patent No.: US 12,297,470 B2
(45) Date of Patent: *May 13, 2025

(54) POLYPEPTIDES HAVING PEPTIDOGLYCAN DEGRADING ACTIVITY AND POLYNUCLEOTIDES ENCODING SAME

(71) Applicant: Novozymes A/S, Bagsvaerd (DK)

(72) Inventors: Christian Berg Oehlenschlaeger, Valby (DK); Dorotea Raventos Segura, Runsted (DK); Jesper Salomon, Holte (DK); Fabian Barrientos Garcia, Birkerod (DK); Lillian Eva Tang Baltsen, Bagsvaerd (DK); Christian Bech Rosen, Copenhagen (DK)

(73) Assignee: Novozymes A/S, Bagsvaerd (DE)

( * ) Notice: Subject to any disclaimer, the term of this patent is extended or adjusted under 35 U.S.C. 154(b) by 0 days.

This patent is subject to a terminal disclaimer.

(21) Appl. No.: 18/586,709

(22) Filed: Feb. 26, 2024

(65) Prior Publication Data

US 2024/0209340 A1    Jun. 27, 2024

Related U.S. Application Data

(62) Division of application No. 17/298,836, filed as application No. PCT/EP2019/086399 on Dec. 19, 2019, now Pat. No. 11,959,111.

(30) Foreign Application Priority Data

Dec. 21, 2018    (EP) .................................... 18215408

(51) Int. Cl.
  *C12N 9/80*  (2006.01)
  *C11D 3/386*  (2006.01)

(52) U.S. Cl.
  CPC ............ *C12N 9/80* (2013.01); *C11D 3/38636* (2013.01); *C12Y 305/01028* (2013.01)

(58) Field of Classification Search
  None
  See application file for complete search history.

(56) References Cited

U.S. PATENT DOCUMENTS

| 10,081,782 | B2 | 9/2018 | Brooker et al. |
| 2012/0171188 | A1 | 7/2012 | Loessner et al. |
| 2012/0266329 | A1 | 10/2012 | Marthur et al. |
| 2016/0017307 | A1 | 1/2016 | Mayer et al. |
| 2017/0106058 | A1 | 4/2017 | Miller et al. |

FOREIGN PATENT DOCUMENTS

| CN | 101437532 A | 5/2009 |
| CN | 102186878 A | 9/2011 |
| CN | 103957929 A | 7/2014 |
| EP | 2782593 A2 | 5/2013 |
| WO | 2007/130655 A2 | 11/2007 |
| WO | 2010/020657 A1 | 2/2010 |
| WO | 2013/076253 A1 | 5/2013 |
| WO | 2013/076259 A2 | 5/2013 |

OTHER PUBLICATIONS

UniProt Accession No. A0A0S2FKP1, Retrieved from the Internet <https://rest.uniprot.org/unisave/A0AOS2FKP1?format=txt&versions=1>, [Retrieved on Dec. 30, 2024] (Year: 2016).*
Anonymous, 2015, UniProt Accession No. UPI0003F952BF.
Anonymous, 2016, NCBI Reference Sequence No. WP051366340.1.
Anonymous, 2016, UniProt Accession No. UPI0009084F52.

* cited by examiner

*Primary Examiner* — Suzanne M Noakes
*Assistant Examiner* — Jae W Lee
(74) *Attorney, Agent, or Firm* — Elias Lambiris

(57) ABSTRACT

The present invention relates to cleaning compositions comprising polypeptides having peptidoglycan degradation activity, as well as use of the cleaning compositions for cleaning of an item such as a textile or a surface.

13 Claims, No Drawings

Specification includes a Sequence Listing.

SEQUENCE LISTING

```
Sequence total quantity: 111
SEQ ID NO: 1            moltype = DNA  length = 1380
FEATURE                 Location/Qualifiers
sig_peptide             1..87
mat_peptide             88..1380
source                  1..1380
                        mol_type = genomic DNA
                        organism = Hamadaea tsunoensis
CDS                     1..1380
SEQUENCE: 1
atgacagtac cacctacacg tcgtgctact ttcatgttag gagcgttgat cttagccgct  60
ggtgtagctg caccgccagc aagcgctgct gctgctccag tagcgcctga cgcattaaca  120
gtagcgtcaa ctccagcatc aactggtagc cttactgctg cttttgatgc tgcagcaaca  180
```

```
cgttatggag ttccacgtga cttattgatc gctattggtt acgctgaaac acacccttgat  240
ggacacgcag gcactccatc tgcagctggt ggatatggtg ttatgaatct tactggcaat  300
ccggctgttc acactcttgc tgaagcttct cgcttaactg gccttaaagc tagcacgtta  360
gagaataacc aagctgctaa catccttggt gcggctgcag ttttacgctc ttacgctgct  420
gatttgaaaa ctgctcaacg tgactctgta gacaattgat acgcagctgt agctcgttat  480
ggtggcgcaa ctgatccgtc tgttgctcgc ctttatgctg atacagttta cgatcttctt  540
gcgacaggtt tcggagttcc agctaaaggc gttagcgtta cagctcgtgc tgtagcacct  600
caacgtggta ctcttgctac tgcgcgtgca tcattggact ctgcagacta cggtcctgct  660
gcttgggctc cagcatctac atctaactac acagttgcaa accgcgaaac agactataac  720
atcaattaca ttgttatcca cgtaactcaa ggatcttacg ctggctctat ttcttggttc  780
caaaatcctg cggctcaggt ttctgctcat tacgttgtac gttcatctga tggtgccatc  840
acgcagtctg ttcgtgaaaa agatatcgct tggcacgcag gcaactggac atacaacacg  900
caagctatcg gcatcgaaca tgaaggctat atcgacgacc cttcatggtt cactgacgca  960
atgtatcgtt cttcagcagc tcttacacgt tcacttacaa cgaaatacgc tattcctcgt 1020
gaccgcagcc acatcatcgg tcatatcgaa gttcctctg caacgcacac ggatcctggt 1080
cagtattgga actggactta ctacatgcaa ttggtaaacg gagtaacggg tatcggaaca 1140
ggaacggtaa acgtatctgg ctcattgaac attcgctcag gtcctggtac aggctacgct 1200
gttgctggat ctcttgcgaa cggagcggga gtttctgttt actgccaagc tacgggcacg 1260
acagtaacgg gtacttacgg cactagcaac atctgggacc gtatcggtac gaataagtat 1320
gttgcagatg cgtatgtatt gactggttct gacggcttta tccctggtgt accacgttgc 1380

SEQ ID NO: 2              moltype = AA   length = 460
FEATURE                   Location/Qualifiers
source                    1..460
                          mol_type = protein
                          organism = Hamadaea tsunoensis
SEQUENCE: 2
MTVPPTRRAT FMLGALILAA GVAAPPASAA AAPVAPDALT VASTPASTGS LTAAFDAAAT   60
RYGVPRDLLI AIGYAETHLD GHAGTPSAAG GYGVMNLTGN PAVHTLAEAS RLTGLKASTL  120
ENNQAANILG AAAVLRSYAA DLKTAQRDSV DNWYAAVARY GGATDPSVAR LYADTVYDLL  180
ATGFGVPAKG VSVTARAVAP QRGTLATARA SLDSADYGPA AWAPASTSNY TVANRETDYN  240
INYIVIHVTQ GSYAGSISWF QNPAAQVSAH YVVRSSDGAI TQSVREKDIA WHAGNWTYNT  300
QAIGIEHEGY IDDPSWFTDA MYRSSAALTR SLTTKYAIPR DRSHIIGHIE VPSATHTDPG  360
QYWNWTYYMQ LVNGVTGIGT GTVNVSGSLN IRSGPGTGYA VAGSLANGAG VSVYCQATGT  420
TVTGTYGTSN IWDRIGTNKY VADAYVLTGS DGFIPGVPRC                        460

SEQ ID NO: 3              moltype = AA   length = 431
FEATURE                   Location/Qualifiers
source                    1..431
                          mol_type = protein
                          organism = Hamadaea tsunoensis
SEQUENCE: 3
AAAPVAPDAL TVASTPASTG SLTAAFDAAA TRYGVPRDLL IAIGYAETHL DGHAGTPSAA   60
GGYGVMNLTG NPAVHTLAEA SRLTGLKAST LENNQAANIL GAAAVLRSYA ADLKTAQRDS  120
VDNWYAAVAR YGGATDPSVA RLYADTVYDL LATGFGVPAK GVSVTARAVA PQRGTLATAR  180
ASLDSADYGP AAWAPASTSN YTVANRETDY NINYIVIHVT QGSYAGSISW FQNPAAQVSA  240
HYVVRSSDGA ITQSVREKDI AWHAGNWTYN TQAIGIEHEG YIDDPSWFTD AMYRSSAALT  300
RSLTTKYAIP RDRSHIIGHI EVPSATHTDP GQYWNWTYYM QLVNGVTGIG TGTVNVSGSL  360
NIRSGPGTGY AVAGSLANGA GVSVYCQATG TTVTGTYGTS NIWDRIGTNK YVADAYVLTG  420
SDGFIPGVPR C                                                      431

SEQ ID NO: 4              moltype = DNA   length = 1548
FEATURE                   Location/Qualifiers
sig_peptide               1..90
mat_peptide               91..1545
source                    1..1548
                          mol_type = genomic DNA
                          organism = Micromonospora maritima
CDS                       1..1545
SEQUENCE: 4
gtgacgattc ggagaccctc gcgtcgggtg agtctgctcg gcggcgccat gatcctcatg   60
atcggcctga ccgccagcc ggcccaggcc gcgcctgcac accgcgcgca gcctctcgcc  120
gcggccttcg cgcaggccgc ggccgattcc gacgtgccgc gcgacctgct cgccgcgctc  180
gggtacgccg agacccgcct ggacggccac ggccggccgc ccaggcctc cggcgggtac  240
ggcgtgatgc acctgaccag caacccgaag gtgcggacgc tcgacgaggc cgcgcgccgg  300
acccggctgg accgcgccga gctgctgtac cgggacgcgg cgaacgtggc cggcgcggcg  360
gcggtgctgc gttcctacgc cgacgaggcc gggctcagcg cggcgcagcg cgacgacgtc  420
aaccagtggt acgcccgat cgcccgctac ggcgcgcgca ccgacggggc cacgcgccgg  480
ctgtacgccg actccgtgta cgacctgctc gcccgggggct tcatcgcgac cacggcgga  540
ggcgaggtca gcgtggacgg ccgtccggtc gcaccgcagc ggggccggta cgccgacgtg  600
gcgccgctgg gcaccggtga cttcggcacc ctgagcaccg actacggccc ggcggcctgg  660
gtgccggcca actcgtccaa ctacacggtc tccagccgcg agtcggcgta cccgatcaac  720
tacatcgtca tccacaccat gcagggcagc tacgccggct cgatcagctg gttccagaac  780
gccgccgcgc aggccaccgc gcactacctg ctccgctcct ccgacggtgc ggtgaccgag  840
atggtgcggn acaaggacat cgcctggcac gccggcaact ggacctacaa cacccagtcg  900
atcggcatcg agcacgaggg gtacgtcgac aacgcctcct ggtacaccga cgcgatgtac  960
cggtcgtcgg cggcgctgac ccggtacctg tgcgacaagt acggcatccc gaagacccgc 1020
accaacatca tcgggcacaa ccaggtgccg ggcgccacgc acaccgaccc gggtccgaac 1080
tggaactgga cctactacat gcagctcgtc accggcggca ccacgccccc gccgaccgac 1140
```

```
tggtcgacga tcgtggacaa caccaccgcc ggccggttca ccgcgagcgc caactgggc      1200
acctcgacgt actcggcgca gcgctacggc gccgactacc ggtacgccaa ccccgtcgcg      1260
gccagcgaca ccgccggta caaggtgaac atcccggcga ccgccaccta ccgggtggag      1320
gtctggtatc cggccgtggc cggctacaac acctccacgc cgtacatcgt ggcgacgacc      1380
agcggcaacc agacggtctc ggtgaaccag acggcgaacg gcggcgggtg gcggtcgctg      1440
ggcaccttca ccctggccgc cggggacgcc aacaaggtgg gtgtcagcag gtggtccggc      1500
agcaccgggt acgtgatcgc cgacgccatc cgcgtcaccc gcgtctag               1548

SEQ ID NO: 5              moltype = AA   length = 515
FEATURE                   Location/Qualifiers
source                    1..515
                          mol_type = protein
                          organism = Micromonospora maritima
SEQUENCE: 5
VTIRRPSRRV SLLGGAMILM IGLTGQPAQA APAHRAQPLA AFAQAAADS DVPRDLLAAL        60
GYAETRLDGH GGAPSASGGY GVMHLTSNPK VRTLDEAARR TRLDRAELRT RDAANVAGAA       120
AVLRSYADEA GLSAAQRDDV NQWYGPIARY GGATDGATAR LYADSVYDLL ARGFIATTAG       180
GEVSVDGRPV APQRGRYADV APLGTGDFGT LSTDYGPAAW VPANSSNYTV SSRESAYPIN       240
YIVIHTMQGS YAGSISWFQN AAAGTSAHYL LRSSDGAVTQ MVRDKDIAWH AGNWTYNTQS       300
IGIEHEGYVD NASWYTDAMY RSSAALTRYL CDKYGIPKTR TNIIGHNQVP GATHTDPGPN       360
WNWTYYMQLV TGGTTPPPTD WSTIVDNTTA GRFTASANWG TSTYSAQRYG ADYRYANPVA       420
ASDTAWYKVN IPATATYRVE VWYPAVAGYN TSTPYIVATT SGNQTVSVNQ TANGGGWRSL       480
GTFTLAAGDA NKVGVSRWSG STGYVIADAI RVTRV                                  515

SEQ ID NO: 6              moltype = AA   length = 485
FEATURE                   Location/Qualifiers
source                    1..485
                          mol_type = protein
                          organism = Micromonospora maritima
SEQUENCE: 6
APAHRAQPLA AFAQAAADS DVPRDLLAAL GYAETRLDGH GGAPSASGGY GVMHLTSNPK         60
VRTLDEAARR TRLDRAELRT RDAANVAGAA AVLRSYADEA GLSAAQRDDV NQWYGPIARY       120
GGATDGATAR LYADSVYDLL ARGFIATTAG GEVSVDGRPV APQRGRYADV APLGTGDFGT       180
LSTDYGPAAW VPANSSNYTV SSRESAYPIN YIVIHTMQGS YAGSISWFQN AAAGTSAHYL       240
LRSSDGAVTQ MVRDKDIAWH AGNWTYNTQS IGIEHEGYVD NASWYTDAMY RSSAALTRYL       300
CDKYGIPKTR TNIIGHNQVP GATHTDPGPN WNWTYYMQLV TGGTTPPPTD WSTIVDNTTA       360
GRFTASANWG TSTYSAQRYG ADYRYANPVA ASDTAWYKVN IPATATYRVE VWYPAVAGYN       420
TSTPYIVATT SGNQTVSVNQ TANGGGWRSL GTFTLAAGDA NKVGVSRWSG STGYVIADAI       480
RVTRV                                                                   485

SEQ ID NO: 7              moltype = DNA   length = 1527
FEATURE                   Location/Qualifiers
sig_peptide               1..78
mat_peptide               79..1527
source                    1..1527
                          mol_type = genomic DNA
                          organism = Paenibacillus sp.
CDS                       1..1527
SEQUENCE: 7
atgggaattc gtcgcgtttc tcgccttctt agcatctctc tttctgccat gcttcttctt        60
ccatttacag ttccagctgc atcatttgca gcagacgacg ctgcggtatc agcgaactct       120
gcatctgcag gaaaaggttc tcttcaaaaa gctttcgaag ccgctagcca agagtttggc       180
gttccagtag agatccttct tggccttagc tacgctgaga ctcgctggaa cgaccacgag       240
ggaaagcctt ctcaacttaa cggatatggc cttatgcacc ttgctgagaa cccgaaaaac       300
tcttcactta gcacagctgc tgagcaactt aaagtagaca aacaacttct taagacagac       360
aaagcagtta acattcgcgg atctgcggct gtacttgcag gccttgcaaa ggcgaaaaac       420
aacgaaaaac ttccggcttc tcttgctgac tggtatacga cagtagcagc gtattctgga       480
atcgacgacc ttccgcttgc tcgcgtttac gctgacgagg ttttcaaagt tatcaacgag       540
ggaaaacaag cgcttagcgg cacagagatc cttcaccta accctacgcg agttactccg       600
aatcgcgctg agtacacgca agctactctt gctgcgactg ctatgcacta ccctggttcg       660
atctggaacg ctgcttactc tggcaactac tctgtaggct ctcgtggccc aggagacatc       720
tctaacatcg taatccatac tacacaaggt tcatatgctg gcacaatcaa ctggttcaaa       780
gaccctgctg ctgtagtttc agcgcattat gttgttcgca gctctgacgg ccagatcaca       840
caaatggtac gcgacaaaga catcgcatac catgctcgct ctgcaaacag cacatcactt       900
ggcatcgagc atgagggcta tgtaactgac cctgcatggt atactgactc aatgtatcgc       960
tcatctgcag ctcttactcg ctggctttgc gaccagtatg gcatcccaaa aacacgcaca      1020
gctatcaaag gccattctga gatgcctggt aacgaccaca cagaccctgg cagcaactgg      1080
gactggactt actacatgtc acttgttaac cctccagtaa ctggtggcat catcgtagac      1140
aacgcaacag ctggcgcttt cacggcgagc gcaaactggg gatacagctac ttggaacact      1200
gagaagtatg gctctgacta tcgctacaca acacctcaag ctgtttcaga cccagcatgg      1260
ttccaagcga caatccctac agctggctct tatgacgttt atgcttggtg gccttcaaac      1320
gctgcgtata cgacaaaaac gccgtttatc atcagcacat ctactggtaa ccaaacagtt      1380
aacgttaacc agcaagctaa cggtggtaaa tggatgcttc ttggtaagta cactcttaac      1440
agcggcacgt ataacctagt tggcatctct cgctggacat caggaactgg caacatcttc      1500
gccgacgcta tccgccttgt aatcaaa                                           1527

SEQ ID NO: 8              moltype = AA   length = 509
FEATURE                   Location/Qualifiers
source                    1..509
```

```
                        mol_type = protein
                        organism = Paenibacillus sp.
SEQUENCE: 8
MGIRRVSRLL  SISLSAMLLL  PFTVPAASFA  ADDAAVSANS  ASAGKGSLQK  AFEAASQEFG   60
VPVEILLGLS  YAETRWNDHE  GKPSQLNGYG  LMHLAENPKN  SSLSTAAEQL  KVDKQLLKTD  120
KAVNIRGSAA  VLAGLAKAKN  NGKLPASLAD  WYTTVAAYSG  IDDLPLARVY  ADEVFKVINE  180
GKQALSGTEI  LHLNPTPVTP  NRAEYTQATL  AATAMDYPGA  IWNAAYSGNY  SVGSRGPGDI  240
SNIVIHTTQG  SYAGTINWFK  DPAAVVSAHY  VVRSSDGQIT  QMVRDKDIAY  HARSANSTSL  300
GIEHEGYVTD  PAWYTDSMYR  SSAALTRWLC  DQYGIPKTRT  AIKGHSEMPG  NDHTDPGSNW  360
DWTYYMSLVN  PPVTGGIIVD  NATAGAFTAS  ANWGTATWNT  EKYGSDYRYT  TPQAVSDPAW  420
FQATIPTAGS  YDVYAWWPSN  AAYNDKTPFI  ISTSTGNQTV  NVNQQANGGK  WMLLGKYTLN  480
SGTYNVVGIS  RWTSGTGNIF  ADAIRLVIK                                      509

SEQ ID NO: 9            moltype = AA    length = 483
FEATURE                 Location/Qualifiers
source                  1..483
                        mol_type = protein
                        organism = Paenibacillus sp.
SEQUENCE: 9
ASFAADDAAV  SANSASAGKG  SLQKAFEAAS  QEFGVPVEIL  LGLSYAETRW  NDHEGKPSQL   60
NGYGLMHLAE  NPKNSSLSTA  AEQLKVDKQL  LKTDKAVNIR  GSAAVLAGLA  KAKNNGKLPA  120
SLADWYTTVA  AYSGIDDLPL  ARVYADEVFK  VINEGKQALS  GTEILHLNPT  PVTPNRAEYT  180
QATLAATAMD  YPGAIWNAAY  SGNYSVGSRG  PGDISNIVIH  TTQGSYAGTI  NWFKDPAAVV  240
SAHYVVRSSD  GQITQMVRDK  DIAYHARSAN  STSLGIEHEG  YVTDPAWYTD  SMYRSSAALT  300
RWLCDQYGIP  KTRTAIKGHS  EMPGNDHTDP  GSNWDWTYYM  SLVNPPVTGG  IIVDNATAGA  360
FTASANWGTA  TWNTEKYGSD  YRYTTPQAVS  DPAWFQATIP  TAGSYDVYAW  WPSNAAYNDK  420
TPFIISTSTG  NQTVNVNQQA  NGGKWMLLGK  YTLNSGTYNV  VGISRWTSGT  GNIFADAIRL  480
VIK                                                                    483

SEQ ID NO: 10           moltype = DNA   length = 1479
FEATURE                 Location/Qualifiers
sig_peptide             1..66
mat_peptide             67..1479
source                  1..1479
                        mol_type = genomic DNA
                        organism = Nonomuraea sp.
CDS                     1..1479
SEQUENCE: 10
atgagccgtc  ttgcagcaat  cgttttttgct  gtacttcttg  cttttcggttt  ttctcctgcg   60
tacgcagcgg  cagacccact  tacagaagct  ttcgaccgtg  ctgcggctgc  tcacgacgta  120
cctcgtgacc  ttcttgttgc  tttggcttac  gctgaaacac  acttaaacgg  ccacaacggc  180
gaaccatctg  catcaggtgg  ctatggaatg  atgcaccttg  tttctaatcc  aacaacaaaa  240
gctcttgcta  aagctgccga  acttacagga  ttacctgcag  ctgagttacg  tgctgacgat  300
gcagcgaaca  tctlaggtgg  tgcagcagta  cttcgtagcc  atgctgatgc  tcttggtttg  360
gacgaagcag  cacgtaaaga  tgctggccgt  tggtaccaag  cagttgcgga  atacggtaac  420
gcatctacac  cagagactgc  acgtctttat  gcggatcag  tatacgaatt  ccttggcaaa  480
ggcttcgagg  ctgcaggtgt  taaagtagct  ccacaagaag  taactgccga  ccgtggtgcg  540
tacgctaaga  cacgcgagtt  aacagctgcg  gctagcccag  actaccctga  cggcacatgg  600
gttgctgctt  cttcttctaa  ctacactgca  tcttctcgcc  catcaagcta  cgcgatcgat  660
cgtgttgtaa  tccacgtaac  tcagggatca  tatgctggca  gcatcagctg  gtttcaaaac  720
ccttctgctg  gcgtttctgc  cacactacgtt  attcgttctt  ctgatggtgc  tgttactcaa  780
atggttcgta  caaaagatgt  tgccttggcat  gcaggcaact  ggggctataa  cacacgttct  840
atcggcattg  aacatgaagg  atgggtatca  gatgcttctt  ggttcactga  agctatgtat  900
cgtagctctg  gtgcattgac  tcgttacatt  tgtgacaaat  acggcatccc  taaagatcgt  960
tcacacatca  ttggtcacaa  ccaagtacca  ggagcgactc  atacagaccc  aggtagccat 1020
tgggattgga  cgaagtatat  gtcttatgtt  aatggtggag  gaggaacacc  atcttggtct 1080
gttactgtag  acaatactac  agcaggcaaa  ttcacagctt  cagcaaactg  gggtacttct 1140
gcctattctg  gccaacgcca  tggtgctgac  taccgtttcg  caactcctct  tgcagcatct 1200
gatcctgctt  ggtttcaaag  caacatccct  tctgcaggtt  cttatcgtgt  tgaagtttgg 1260
tatccgtctg  accctggcta  taactcttca  gctccttaca  tcgtagctgc  ttctggcgtt 1320
aaccaaacag  ttttcgttga  tcaacgttca  ggaggcggtg  gatggcgcac  tcttggaacg 1380
ttctctttga  cggctggcga  aacgacgtt  gtaggagtta  ccgctggac  atctggcacg 1440
ggctatgtag  tagcagatgc  tgtacgcatt  tcacattta                         1479

SEQ ID NO: 11           moltype = AA    length = 493
FEATURE                 Location/Qualifiers
source                  1..493
                        mol_type = protein
                        organism = Nonomuraea sp.
SEQUENCE: 11
MSRLAAIVFA  VLLAFGFSPA  YAAADPLTEA  FDRAAAAHDV  PRDLLVALAY  AETHLNGHNG   60
EPSASGGYGM  MHLVSNPTTK  ALAKAEELTG  LPAAELRADD  AANILGGAAV  LRSHADALGL  120
DEAARKDAGR  WYQAVAEYGN  ASTPETARLY  ADAVYEFLGK  GFEAAGVKVA  PQEVTADRGA  180
YAKTRELTAA  ASPDYPDGTW  VAASSSNYTA  SSRPSSYAID  RVVIHVTQGS  YAGSISWFQN  240
PSAGVSAHYV  IRSSDGAVTQ  MVRNKDVAWH  AGNWGYNTRS  IGIEHEGWVS  DASWFTEAMY  300
RSSGALTRYI  CDKYGIPKDR  SHIIGHNQVP  GATHTDPGSH  WDWTKYMSYV  NGGGGTPSWS  360
VTVDNTTAGK  FTASANWGTS  AYSGQRHGAD  YRFATPLAAS  DPAWFKANIP  SAGSYRVEVW  420
YPSDPGYNSS  APYIVAASGG  NQTVFVDQRS  GGGGWRTLGT  FSLTAGEHDV  VGVSRWTSGT  480
GYVVADAVRI  SHL                                                        493
```

```
SEQ ID NO: 12              moltype = AA  length = 471
FEATURE                    Location/Qualifiers
source                     1..471
                           mol_type = protein
                           organism = Nonomuraea sp.
SEQUENCE: 12
AADPLTEAFD RAAAAHDVPR DLLVALAYAE THLNGHNGEP SASGGYGMMH LVSNPTTKAL    60
AKAAELTGLP AAELRADDAA NILGGAAVLR SHADALGGLDE AARKDAGRWY QAVAEYGNAS   120
TPETARLYAD AVYEFLGKGF EAAGVKVAPQ EVTADRGAYA KTRELTAAAS PDYPDGTWVA   180
ASSSNYTASS RPSSYAIDRV VIHVTQGSYA GSISWFQNPS AGVSAHYVIR SSDGAVTQMV   240
RNKDVAWHAG NWGYNTRSIG IEHEGWVSDA SWFTEAMYRS SGALTRYICD KYGIPKDRSH   300
IIGHNQVPGA THTDPGSHWD WTKYMSYVNG GGGTPSWSVT VDNTTAGKFT ASANWGTSAY   360
SGQRHGADYR FATPLAASDP AWFKANIPSA GSYRVEVWYP SDPGYNSSAP YIVAASGGNQ   420
TVFVDQRSGG GGWRTLGTFS LTAGEHDVVG VSRWTSGTGY VVADAVRISH L           471

SEQ ID NO: 13              moltype = DNA  length = 1920
FEATURE                    Location/Qualifiers
sig_peptide                1..117
mat_peptide                118..1917
source                     1..1920
                           mol_type = genomic DNA
                           organism = Lysobacter antibioticus
CDS                        1..1917
SEQUENCE: 13
atgaacgaat attccattgc gcgccatggg gccggtaccg gcgtgcgttc gctgtcgtgg    60
tcgctgaccc tcgccctgct ggcgctcgcc gcgccgtggg ccgcgcaggc ccaggccgca   120
cccgaagacc gcgcccctggc ccagcgcctg cagatcgagg aatcgctgca acgcgtcgac   180
cgcgcgctgt acgcggacta cttccgccag gcctatgcgc gttacccgtc gatcccggcc   240
ggcaccctgg aatcgatcgc ctacgtgatg agccgctggc agcaactgca gccccgcccg   300
gccgcgggct atggcgaaca gcaccagcac atgccgcgct cgtacggcgt catgggcctg   360
taccacggcg aggggttcgc cgatcaagtc agcgaaggcg cgcgcctgat cggcgtgccc   420
gcggcgcgcg tgcagcgcga tccgctcagc aacatcctcg cctcggcggc cttgctcgat   480
cgcgagctgc gcgccgacgg ggtcggtgcc aagtcggcga tcgaagccac cgtccggcg   540
ctggagcgct acgccggttt cgccggcaat gcgggcaaga gcgcgatcca ggatcacgcc   600
cgttccagtt tcgccttcga cgtgctgctg gcgcaggaca agggcgtcaa cgaccgcggc   660
atcgtcgtgc ccacgcgcgc ggtcgcctgg aacgcgcct tcgatgcgcg caagctggtg   720
cagctgcgcg cgccgttcgt gcgtctggac gtgagccgcg atcgggtcga ggccggcgcg   780
ttgagggacg acggcgcgtt cgccgatcgat ccgctcgcag aaaccctgcg cgcgccatcg   840
ctgaccgcgg ccgacgaaaa gagcaccgat tacggcccgg cgctgtgggt cgcttcgcct   900
taccactcca cccgcacgtc gtacgactcg gtgaccatcc acacgatgca gggctattac   960
gccggcagca tctcgtggtt ccagaacaac cccaacagcg tcagcgcgca ttacctgatc   1020
cgcagctccg acggccagat cacccagatg gtgcgcgaaa accgcgcggc ccatcacgtc   1080
ggcgtgcata acaagaccac gctcggcatc gagcacgaag gcttcatcaa caacgcgagt   1140
tggtacaccg cggcgatgta caacgcctcg gcggcgttga cccggcactt ctgcgcgacc   1200
tacagcgcga tcagctgcgc gagcgcgttc aagggcccgg ccggcagcgg catcaacgtg   1260
ttgccggcca gcgtcaaggt caagggccac cagcactaca gcgccagac cacaccgat   1320
ccgggcatca actgggattg ggcgcgctac tacaacctgc tcaatccggg caatccgccc   1380
ggcggcggca gcgtgatcga cagtttcgaa agcacggtcg gcatttcga caccggcccg   1440
gcgtattcgg gcagcaccac cggcatcgcc gcgacctcgc tgagcgaacg caactgcacc   1500
acgcgcaaga acggcgagtg ctcgctgcgg ctgctgctga aagacgatgc cgccagcgcc   1560
gatgcctggg cggtgcggct gttgtcgggc agcggcaatc cgggcagcaa cgcggccctg   1620
acgcgcgcca acggcaaggt cggtttctgg gtcttcaccg gcgcgaccgg gatgagcgcg   1680
gcgatcggca tcgacgacag cgacggcacc gagcgctcgg tgagccgcgc gattgcggcc   1740
aacacctgga cctatctgga gtggagcctg accgacgacg cgcagtggga tgcgtgggtc   1800
ggcggcgcca acggcgcgat caccgccgcg tcggtgaagc tcgatgcggt gtggttctac   1860
cgcgatcaga cctcgttcga cgtgaacgtg tacgtcgacg atgtgcaggt gaagaactga   1920

SEQ ID NO: 14              moltype = AA  length = 639
FEATURE                    Location/Qualifiers
source                     1..639
                           mol_type = protein
                           organism = Lysobacter antibioticus
SEQUENCE: 14
MNEYSIARHG AGTGVRSLSW SLTLALLALA APWAAQAQAA PEDRALAQRL QIEESLQRVD    60
RALYADYFRQ AYARYPSIPA GTLESIAYVM SRWQQLQPGP AAGYGEQHQH MPRSYGVMGL   120
YHGEGFADQV SEGARLIGVP AARVQRDPLS NILASAALLD RELRADVGA KSAIEATRPA   180
LERYAGPAGN AGKSAIQDHA RSSFAFDVLL AQDKGVNDRG IVVPTRAVAW ERAFDARKLV   240
QLRAPFVRLD VSRDRVEAGA LRDDGAFAID PLSETLRAPS LTAADEKSTD YGPALWVASP   300
YHSTRTSYDS VTIHTMQGYY AGSISWFQNN PNSVSAHYLI RSSDGQITQM VRENRAAHHV   360
GVHNKTTLGI EHEGFINNAS WYTAAMYNAS AALTRHFCAT YSAISCASAF KGPAGSGINV   420
LPASVKVKGH QHYSSQTHTD PGINWDWARY YNLLNPGNPP GGGSVIDSFE STVGHFDTGP   480
AYSGSTTGIA ATSLSERNCT TRKNGECSLR LLLKDDAASA DAWAVRLLSG SGNPGSNAAL   540
TRANGKVGFW VFTGATGMSA AIGIDDSDGT ERSVSRAIAA NTWTYLEWSL TDDAQWDAWV   600
GGANGAITAA SVKLDAVWFY RDQTSFDVNV YVDDVQVKN                           639

SEQ ID NO: 15              moltype = AA  length = 600
FEATURE                    Location/Qualifiers
source                     1..600
```

```
                        mol_type = protein
                        organism = Lysobacter antibioticus
SEQUENCE: 15
APEDRALAQR LQIEESLQRV DRALYADYFR QAYARYPSIP AGTLESIAYV MSRWQQLQPG    60
PAAGYGEQHQ HMPRSYGVMG LYHGEGFADQ VSEGARLIGV PAARVQRDPL SNILASAALL   120
DRELRADGVG AKSAIEATRP ALERYAGFAG NAGKSAIQDH ARSSFAFDVL LAQDKGVNDR   180
GIVVPTRAVA WERAFDARKL VQLRAPFVRL DVSRDRVEAG ALRDDGAFAI DPLSETLRAP   240
SLTAADEKST DYGPALWVAS PYHSTRTSYD SVTIHTMQGY YAGSISWFQN NPNSVSAHYL   300
IRSSDGQITQ MVRENRAAHH VGVHNKTTLG IEHEGFINNA SWYTAAMYNA SAALTRHFCA   360
TYSAISCASA FKGPAGSGIN VLPASVKVKG HQHYSSQTHT DPGINWDWAR YYNLLNPGNP   420
PGGGSVIDSF ESTVGHFDTG PAYSGSTTGI AATSLSERNC TTRKNGECSL RLLLKDDAAS   480
ADAWAVRLLS GSGNPGSNAA LTRANGKVGF WVFTGATGMS AAIGIDDSDG TERSVSRAIA   540
ANTWTYLEWS LTDDAQWDAW VGGANGAITA ASVKLDAVWF YRDQTSFDVN VYVDDVQVKN   600

SEQ ID NO: 16           moltype = DNA  length = 1548
FEATURE                 Location/Qualifiers
sig_peptide             1..93
mat_peptide             94..1545
source                  1..1548
                        mol_type = genomic DNA
                        organism = Micromonospora sp.
CDS                     1..1545
SEQUENCE: 16
gtgactgttc ggagaccctc gcgtcgggtg agccaactgc tcggcggcgc agcgattttg    60
atgatcggc tgaccagcca gccggcccag gccgcgccgc agcagggcgc ggagacgctc   120
gccgccgcct tcgaccaggc ggccgccgcc tccgacgtgc ccgcgacct gctcgccgcg   180
ctcgggtacg cggagacccg gctgacggt cacaacggcg agcccagcgc ctccggcggg   240
tacggcgtga tgcacctgac cagcaacccg aaggtgcgga ccctgacga ggcccgcgcc   300
cgtgcccgac tggaccgcac cgaactcgcg acccgtgacg cggcgaacgt cgccggcgcg   360
gcggcgggtgc tccgctcgta cgccgatcag gccgggctca ccgcgaagca gcgcgacgac   420
gtcaaccagt ggtacggctt gatcgccgc tacgccggt cgtcggacaa ggccaccgcc   480
cggctgtacg ccgacgccgt gtacgacctg ctcggcagcg gcttcagggc gaccacggcc   540
accggcgagg tcaccgtgga cggccgtccg gtcgcgcccc agcgggggcga ctacgccgcg   600
gtggcgccgc tgggcgccgc cgacatgggc acccagagca ccgactacgg cccggcggcc   660
tgggtggcgg cgaactcgtc caactacacg gcctccagcc gcgagtcgtc gtacccgatc   720
aactacatca tcatccacac catgcagggc agctacgccg gctcgatcag ctggttccag   780
aacgcagcgg ccggcaccag cgcgcactac ctgctccgtt cctcggacgg cgcggtgacc   840
cagatggtgc gggacaagga cgtcgcctgg cacgccggca actggaccta caacacccag   900
tcgatcggta tcgagcacga gggctacgtc gacaacgcct cctggtacac cgacgcgatg   960
taccggtcgt cggccgcgct gacgcggcac ctggccgaca agtacggcat cccgaagacc  1020
cgcagcaaca tcatcggtca caaccaggtg ccgggcgcca cgcacaccga cccggggtccg  1080
aactggaact ggacctacta catgcagctc gtcaccggca ccacgacgcc gccgccgacc  1140
tggtcgacca tcgtggacaa caccaccgcc tcgcggttca ccgcgagcgc caactggagc  1200
acctcgtcgt actcgtcgca gcgctacggg gccgactacc gctacgccaa ccctgtcgcg  1260
gccagcgacg ccgcctggta caaggtgaac atcccggcca ccgccaccta ccgggtggag  1320
gtctggtacc cggccgtcgc cggttacaac gccaccacgc cgtacatcgt ggcgaccagc  1380
agcggcaacc agacggtcaa cgtgaaccag tcggccaacg gtggtggttg gcgctcgctg  1440
ggcaacttca ccctgccgc cggggacgcc aacaaggtgg gcatcagccg ttggtccggt  1500
agcaccggct acgtgatcgc cgacgcgatc cgcatcaccc gcgtctaa              1548

SEQ ID NO: 17           moltype = AA  length = 515
FEATURE                 Location/Qualifiers
source                  1..515
                        mol_type = protein
                        organism = Micromonospora sp.
SEQUENCE: 17
VTVRRPSRRV SQLLGGAAIL MIGLTSQPAQ AAPQQGAETL AAAFDQAAAR SDVPRDLLAA    60
LGYAETRLDG HNGEPSASGG YGVMHLTSNP KVRTLDEAAR RARLDRTELR TRDAANVAGA   120
AAVLRSYADQ AGLTAKQRDD VNQWYGLIAR YGGSSDKATA RLYADAVYDL LGSGFRATTA   180
TGEVTVDGRP VAPQRGDYAA VAPLGAADMG TQSTDYGPAA WVAANSSNYT ASSRESSYPI   240
NYIIIHTMQG SYAGSISWFQ NAAAGTSAHY LLRSSDGAVT QMVRDKDVAW HAGNWTYNTQ   300
SIGIEHEGYV DNASWYTDAM YRSSAALTRH LADKYGIPKT RSNIIGHNQV PGATHTDPGP   360
NWNWTYYMQL VTGTTTPPPT WSTIVDNTTA GRFTASANWS TSSYSSQRYG ADYRYANPVA   420
ASDAAWYKVN IPATATYRVE VWYPAVAGYN ATTPYIVATS SGNQTVNVNQ SANGGGWRSL   480
GNFTLAAGDA NKVGISRWSG STGYVIADAI RITRV                             515

SEQ ID NO: 18           moltype = AA  length = 484
FEATURE                 Location/Qualifiers
source                  1..484
                        mol_type = protein
                        organism = Micromonospora sp.
SEQUENCE: 18
APQQGAETLA AAFDQAAARS DVPRDLLAAL GYAETRLDGH NGEPSASGGY GVMHLTSNPK    60
VRTLDEAARR ARLDRTELRT RDAANVAGAA AVLRSYADQA GLTAKQRDDV NQWYGLIARY   120
GGSSDKATAR LYADAVYDLL GSGFRATTAT GEVTVDGRPV APQRGDYAAV APLGAADMGT   180
QSTDYGPAAW VAANSSNYTA SSRESSYPIN YIIIHTMQGS YAGSISWFQN AAAGTSAHYL   240
LRSSDGAVTQ MVRDKDVAWH AGNWTYNTQS IGIEHEGYVD NASWYTDAMY RSSAALTRHL   300
ADKYGIPKTR SNIIGHNQVP GATHTDPGPN WNWTYYMQLV TGTTTPPPTW STIVDNTTAG   360
RFTASANWST SSYSSQRYGA DYRYANPVAA SDAAWYKVNI PATATYRVEV WYPAVAGYNA   420
```

```
TTPYIVATSS GNQTVNVNQS ANGGGWRSLG NFTLAAGDAN KVGISRWSGS TGYVIADAIR    480
ITRV                                                                484

SEQ ID NO: 19              moltype = DNA  length = 1533
FEATURE                    Location/Qualifiers
sig_peptide                1..90
mat_peptide                91..1530
source                     1..1533
                           mol_type = genomic DNA
                           organism = Nonomuraea coxensis
CDS                        1..1530
SEQUENCE: 19
atggaactcg cccgcacgcg attaacagcc ctcgccacct ccttcctcgc cgtcctcgtc    60
ctcgtcgcca cgggccgccc cgccctggcc gcgcccacgg ccgcggacgg caccctcacc   120
gccgccttcg ccaaggcggc ggccgcgtac gacgtgcccc gcgacctgct ggtcgccctc   180
ggctacgccg agacccacct cgacggtcac gacggcaagc ccagcgccag cggcggctac   240
ggcgtcatgc acctggtcag caaccccacc aaccactccc tggagaaggc cgccgagctc   300
accggccgct ccaccggcga actgcgcgcc gacgacgccg ccaacgtgct cggcggcgcc   360
gccgtactcc gctcccacgc cgacgccctc ggcctcgacg aaacggccag gaaggacgcc   420
ggacgctggt accaggccgt cgccaagtac ggcaacgcca cctcgcccga gctcgcccgc   480
ctctacgccg acgccgtcta cgagagcctc ggcctcggca tcgacatccg cggcgtccag   540
gtcaagccgc aggaggtcac cgccgaccgc ggcgagtacg ccaaggcccg cgacctcaac   600
gccaaggccg acgccggcgt cctcagcacc gactacgcc ccgccgcctg ggtcgccgcc    660
agctccagca actacaccgc ctccagccgc ccgtcgagct acgccatcga ccgcgtgatc    720
atccacgtga cgcagggctc gtacgccggc accatctcct ggttccagaa ccctccgcc    780
caggtctcgg cccactacgt ggtcaagtcc tccaacggcg ccatcaccca gatggtgcgc   840
gagaaggacg tcgcctggca cgccggcaac tggacctaca caccccgtc gatcggcatc     900
gagcacgagg gctacgtcaa cgacgcctcg tggttcaccg acgcgatgta ccgggcgtcc    960
gcggccctca ccaagaacat ctgcgagaag tacggcatcc ccaaggaccg cagccacatc  1020
atcggccaca accaggtgcc cggcgccacc cacactgacc cgggctccaa ctggaactgg  1080
accacgtaca tgaactacgt gaccggtggc ggcggcaccc cctcgtggac caccacgatc  1140
gacaacgcca cctccggcca gttcaccgcc agcgccaact ggggcaccc cacctactcc   1200
agccagcgct acggctccga ctaccgcttc gccgacccgg tctccgccag cgacgcggcg  1260
tggtactcgg ccgccatccc cagcgcgggc acctaccgcg tcgaggtctg gtatccggcc  1320
gacgcgggct acaacagctc ggcgccgtac atcgtggcga cgtcaggcgg caaccagacc  1380
gtctacgtcg accaacgcag cggcggcggc tcctggaaga gcatcggcac gttctctg    1440
aacgcgggga cgtacaacgt ggtcggaatc agcggtgga ccgccggcac cggctacgtc   1500
atcgccgacg ccgtccgcat cagccgcgtc tga                               1533

SEQ ID NO: 20              moltype = AA  length = 510
FEATURE                    Location/Qualifiers
source                     1..510
                           mol_type = protein
                           organism = Nonomuraea coxensis
SEQUENCE: 20
MELARTRLTA LATSFLAVLV LVATGRPALA APTAADGTLT AAFAKAAAAY DVPRDLLVAL    60
GYAETHLDGH DGKPSASGGY GVMHLVSNPT NHSLEKAAEL TGRSTGELRA DDAANVLGGA   120
AVLRSHADAL GLDETARKDA GRWYQAVAKY GNATSPELAR LYADAVYESL GLGIDIRGVQ   180
VKPQEVTADR GEYAKARDLN AKADAGVLST DYGPAAWVAA SSSNYTASSR PSSYAIDRVI   240
IHVTQGSYAG TISWFQNPSA QVSAHYVVKS SNGAITQMVR EKDVAWHAGN WTYNTRSIGI   300
EHEGYVNDAS WFTDAMYRAS AALTKNICEK YGIPKDRSHI IGHNQVPGAT HTDPGSNWNW   360
TTYMNYVTGG GGTPSWTTTI DNATSGQFTA SANWGTSTYS SQRYGSDYRF ADPVSASDAA   420
WYSAAIPSAG TYRVEVWYPA DAGYNSSAPY IVATSGGNQT VYVDQRSGGG SWKSIGTFSL   480
NAGTYNVVGI SRWTAGTGYV IADAVRISRV                                   510

SEQ ID NO: 21              moltype = AA  length = 480
FEATURE                    Location/Qualifiers
source                     1..480
                           mol_type = protein
                           organism = Nonomuraea coxensis
SEQUENCE: 21
APTAADGTLT AAFAKAAAAY DVPRDLLVAL GYAETHLDGH DGKPSASGGY GVMHLVSNPT    60
NHSLEKAAEL TGRSTGELRA DDAANVLGGA AVLRSHADAL GLDETARKDA GRWYQAVAKY   120
GNATSPELAR LYADAVYESL GLGIDIRGVQ VKPQEVTADR GEYAKARDLN AKADAGVLST   180
DYGPAAWVAA SSSNYTASSR PSSYAIDRVI IHVTQGSYAG TISWFQNPSA QVSAHYVVKS   240
SNGAITQMVR EKDVAWHAGN WTYNTRSIGI EHEGYVNDAS WFTDAMYRAS AALTKNICEK   300
YGIPKDRSHI IGHNQVPGAT HTDPGSNWNW TTYMNYVTGG GGTPSWTTTI DNATSGQFTA   360
SANWGTSTYS SQRYGSDYRF ADPVSASDAA WYSAAIPSAG TYRVEVWYPA DAGYNSSAPY   420
IVATSGGNQT VYVDQRSGGG SWKSIGTFSL NAGTYNVVGI SRWTAGTGYV IADAVRISRV   480

SEQ ID NO: 22              moltype = DNA  length = 1548
FEATURE                    Location/Qualifiers
sig_peptide                1..93
mat_peptide                94..1548
source                     1..1548
                           mol_type = genomic DNA
                           organism = Micromonospora fulvopurpurea
CDS                        1..1548
SEQUENCE: 22
```

-continued

```
atgacgatcc gtcgtccacc acgtcgcgtt tcacaccttt taggaggagc aatgattctt    60
atgattggat taactggtca acctgcacag gctgcgccag ctcatggagc tcaacctttg   120
gctgccgcat tcgaccgtgc agctgcgtca tcagatgttc ctcgtgacgt tcttgcggct   180
cttggatacg cggaaactcg cttggatggt catggtggtg agccgtctgt atcaggtgga   240
tacggtgtaa tgcatcttac atcaaaccca aaagttcgta cttagatga agctgcgcgt   300
cgcacacgtt tagaccgtgc agaccttcgt actcgtgacg ctgcgaacgt agctggagct   360
gctgcagtac ttcgctctta cgcggatgaa gcgggtctta cggctgctca gcgcgacgac   420
gtaaaccagt ggtatggccc aattgctcgt tatggcggaa gcactgatgc tgcaactgct   480
cgtctttacg cagattctgt atatgacttg cttgcgcgtg gattcatcgc gactactgca   540
ggtggcgaag tttctgtaga tggccgtccg gttgcgcctc aacgtggtcg ttatgctgct   600
gtagctccac ttggcactgg tgatttcggt actctttcta ctgattacgg tccagctgct   660
tgggttccag cgaacagctc taactacaca gtttcatctc gtgaatcagc ataccggatc   720
aattacattg ttatccatac tatgcaaggt tcatacgcag gctcaatttc ttggtttcag   780
aacgctgcag ctggcacatc tgctcactac cttcttcgtt cttcagatgg tgcggttact   840
caaatggtac gtgacaaaga tattgcatgg cacgctggca attggactta caacactcag   900
tctatcggaa tcgagcatga aggatatgta gacaatgcgt cttggtacac agacgcaatg   960
tatcgttctt ctgctgcgct tacacgctac ttatgcgaca agtatggaat cccgaaaaca  1020
cgcactaaca ttatcggtca taatcaagtt cctggagcaa ctcatactga tccaggccgt  1080
aactggaact ggacgtatta catgcaactt gttactggtg gcacgacgcc accgcctaca  1140
acatggtcta cagttgttga taacacaact gctggtcgct tcactgcatc tgctaactgg  1200
tctacatcta catacagcgc tcaacgctat ggaactgatt atcgttacgc gaatcctgta  1260
gctgctagcg atacacggt gtataaggtt aacattcctg ccacggccac gtatcgtgtt  1320
gaagtatggt atccagcagt agctggctat aacacttcta caccatacat cgtagctaca  1380
acaagcggaa accaaacggt atcgttaac caaacagcta atggcggtac ttggcgttca  1440
ttaggtactt tcacacttgc cgctggtgat gcgaacaagg taggtgtatc tcgttggtca  1500
ggatctacgg gatacgtaat cgccgatgct attcgtgtta ctcgcgta              1548
```

```
SEQ ID NO: 23           moltype = AA  length = 516
FEATURE                 Location/Qualifiers
source                  1..516
                        mol_type = protein
                        organism = Micromonospora fulvopurpurea
SEQUENCE: 23
MTIRRPPRRV SHLLGGAMIL MIGLTGQPAQ AAPAHGAQPL AAAFDRAAAS SDVPRDVLAA    60
LGYAETRLDG HGGEPSVSGG YGVMHLTSNP KVRTLDEAAR RTRLDRADLR TRDAANVAGA   120
AAVLRSYADE AGLTAAQRDD VNQWYGPIAR YGGSTDAATA RLYADSVYDL LARGFIATTA   180
GGEVSVDGRP VAPQRGRYAA VAPLGTGDFG TLSTDYGPAA WVPANSSNYT VSSRESAYPI   240
NYIVIHTMQG SYAGSISWFQ NAAAGTSAHY LLRSSDGAVT QMVRDKDIAW HAGNWTYNTQ   300
SIGIEHEGYV DNASWYTDAM YRSSAALTRY LCDKYGIPKT RTNIIGHNQV PGATHTDPGP   360
NWNWTYYMQL VTGGTTPPPT TWSTVVDNTT AGRFTASANW STSTYSAQRY GTDYRYANPV   420
AASDTAWYKV NIPATATYRV EVWYPAVAGY NTSTPYIVAT TSGNQTVSVN QTANGGTWRS   480
LGTFTLAAGD ANKVGVSRWS GSTGYVIADA IRVTRV                             516

SEQ ID NO: 24           moltype = AA  length = 485
FEATURE                 Location/Qualifiers
source                  1..485
                        mol_type = protein
                        organism = Micromonospora fulvopurpurea
SEQUENCE: 24
APAHGAQPLA AAFDRAAASS DVPRDVLAAL GYAETRLDGH GGEPSVSGGY GVMHLTSNPK    60
VRTLDEAARR TRLDRADLRT RDAANVAGAA AVLRSYADEA GLTAAQRDDV NQWYGPIARY   120
GGSTDAATAR LYADSVYDLL ARGFIATTAG GEVSVDGRPV APQRGRYAAV APLGTGDFGT   180
LSTDYGPAAW VPANSSNYTV SSRESAYPIN YIVIHTMQGS YAGSISWFQN AAAGTSAHYL   240
LRSSDGAVTQ MVRDKDIAWH AGNWTYNTQS IGIEHEGYVD NASWYTDAMY RSSAALTRYL   300
CDKYGIPKTR TNIIGHNQVP GATHTDPGPN WNWTYYMQLV TGGTTPPPTT WSTVVDNTTA   360
GRFTASANWS TSTYSAQRYG TDYRYANPVA ASDTAWYKVN IPATATYRVE VWYPAVAGYN   420
TSTPYIVATT SGNQTVSVNQ TANGGTWRSL GTFTLAAGDA NKVGVSRWSG STGYVIADAI   480
RVTRV                                                               485

SEQ ID NO: 25           moltype = DNA  length = 1560
FEATURE                 Location/Qualifiers
sig_peptide             1..84
mat_peptide             85..1557
source                  1..1560
                        mol_type = genomic DNA
                        organism = Alicyclobacillus sp.
CDS                     1..1557
SEQUENCE: 25
atgaagaaaa cttgggttac ggtcctggct accaccgcat tgaccttctc cgtcggcgca    60
agctacgcaa ctccctcgtt tgcagcgaaa tcggacgcgc agtcgcaaac gaccgcaccg   120
gcgttggaca atgcgttcac cgcagcgcg aaggaattca agtcccgaa agatctgctg    180
atggcgatct cctacgcgga atcccgttgg caagtgccgg ctgagacggt cgccgatgac   240
gaccatgcgc acgcaaagg cttgatgcac ttgacggaca actcgttcaa aaagaacctg   300
agcgacacgg cgaaaggtct tgggatcacg gcgaagcaac tggagacaca cagggggtgg   360
aacatccgcg cgcggcgta cctgctcgcc aaagcgcaac atgagctcgg caaaccctc    420
tccgacaacg tcaacgactg gtacgaagcg gtcgcttcct ttgaaggcgc ttctgacaag   480
agcgacaaag tgctgttcgc cgatgaagtc tatcgcatcc tgaaggacgg gacctcgctt   540
gccatcgacg gcggcaccct ctcgatcttc ccgaacaaaa ccgtcgctcc ggtcaaagga   600
caactgtcgg acgtcaccta cggcgtgacg accaaccgt cggcgacccc ggactactcc   660
```

```
ggcgcgatct ggaatgcggc gagcacatcg aactaccaag tggcgagccg tccgacttcc   720
aacccgatca cctacgtggt catccacgat accgagggtt cctactccgg cacgatcaac   780
tggttcaaag acccgagcgc gcaagtttcg gcacactatg tcgtccgttc ttccgacggc   840
cagatcacgc agatggtgca ggacaaggac atcgcttggc atgcgcgtac cttcaacacg   900
aacggcacga gcatccaaca tgaaggatat gaagcgcaaa ccggttggta caccgacgcg   960
atgtacaccc aatcggcggc gttgacccgt gcgatctgcc aaaaatacgg cattccgatg  1020
gaccgcgacc acatcctcgg ccactccgaa ctgtggggca tgaccacac  cgatccgggc  1080
gtgaactggg attggaacaa atacatgacc aaagtcaccg cgtctccaa  gaactggacc  1140
gtcgtcgacg tcgatgacaa agacacggca tccggcgcct tcaccatga  cggcgcttcg  1200
caatactggc acccggtctc cggctatggc gtgcacaacg aaatcaacta caccaacggc  1260
aacggcgcga cgatctacaa ctacgcgatc tggaagccga cgatcccggt cgccggcaac  1320
tacgaagtca aagtgttcgt cccgtccaac tacgcgggca cgaccagcgc gaagtatgaa  1380
atccactaca acggcggcgt cgtaaccaag accgtctcgc aaagcgccta ctccaaccaa  1440
tgggtatcgc ttggcaccta caacttcgca accggcaccg gcggctacgt caagttgggc  1500
gacaacaccg gcgacaccaa cacgatcgca ttcgataacg tccgcttcat gggtcaataa  1560

SEQ ID NO: 26             moltype = AA   length = 519
FEATURE                   Location/Qualifiers
source                    1..519
                          mol_type = protein
                          organism = Alicyclobacillus sp.
SEQUENCE: 26
MKKTWVTVLA TTALTFSVGA SYATPSFAAK SDAQSQTTAP ALDNAFTAAA KEFKVPKDLL    60
MAISYAESRW QVPAETVADD DHAHGKGLMH LTDNSFKKNL SDTAKGLGIT AKQLEDNAGL   120
NIRGGAYLLA KAQHELGKPL SDNVNDWYEA VASFEGASDK SDKVLFADEV YRILKDGTSL   180
AIDGGTLSIF PNKTVAPVKG QLSDVTYGVT TNPSATPDYS GAIWNAASTS NYQVASRPTS   240
NPITYVVIHD TEGSYSGTIN WFKDPSAQVS AHYVVRSSDG QITQMVQDKD IAWHARTFNT   300
NGIGIEHEGY EAQTGWYTDA MYTQSAALTR AICQKYGIPM DRDHILGHSE LWGNDHTDPG   360
VNWDWNKYMT KVTGVSKNWT VVDVDDKDTA SGAFTMYGAS QYWHPVSGYG VHNEINYTNG   420
NGATIYNYAI WKPTIPVAGN YEVKVFVPSN YAGTTSAKYE IHYNGGVVTK TVSQSAYSNQ   480
WVSLGTYNFA TGTGGYVKLG DNTGDTNTIA FDTIRFMGQ                          519

SEQ ID NO: 27             moltype = AA   length = 491
FEATURE                   Location/Qualifiers
source                    1..491
                          mol_type = protein
                          organism = Alicyclobacillus sp.
SEQUENCE: 27
AKSDAQSQTT APALDNAFTA AAKEFKVPKD LLMAISYAES RWQVPAETVA DDDHAHGKGL    60
MHLTDNSFKK NLSDTAKGLG ITAKQLEDNA GLNIRGGAYL LAKAQHELGK PLSDNVNDWY   120
EAVASFEGAS DKSDKVLFAD EVYRILKDGT SLAIDGGTLS IFPNKTVAPV KGQLSDVTYG   180
VTTNPSATPD YSGAIWNAAS TSNYQVASRP TSNPITYVVI HDTEGSYSGT INWFKDPSAQ   240
VSAHYVVRSS DGQITQMVQD KDIAWHARTF NTNGIGIEHE GYEAQTGWYT DAMYTQSAAL   300
TRAICQKYGI PMDRDHILGH SELWGNDHTD PGVNWDWNKY MTKVTGVSKN WTVVDVDDKD   360
TASGAFTMYG ASQYWHPVSG YGVHNEINYT NGNGATIYNY AIWKPTIPVA GNYEVKVFVP   420
SNYAGTTSAK YEIHYNGGVV TKTVSQSAYS NQWVSLGTYN FATGTGGYVK LGDNTGDTNT   480
IAFDTIRFMG Q                                                       491

SEQ ID NO: 28             moltype = DNA   length = 927
FEATURE                   Location/Qualifiers
sig_peptide               1..57
mat_peptide               58..924
source                    1..927
                          mol_type = genomic DNA
                          organism = Halomonas sp.
CDS                       1..924
SEQUENCE: 28
gtgctgcgcc attggaccgc cgtgatgggc atcgccatgg caagtgcatg gctggccggc    60
tgcgcctccc cggaacacct ggagcgacgc gacggctacg tggtggatca cttcacctt   120
tcgccgtccg acaccagccg ggtgcgccac ttggtgatgc actacaccga cgtcgacgag   180
gccgagtcgc tggccgtgct caccggtcct cacgtcagcg cccactacgt actgccgttg   240
ccgcccggg  agcgtcgagg cctgccgctg gtctatcagc tcgtcgacga ggagcgccgc   300
gcctggcacg ccggcgccag cgcgtggaaa ggccgccccc atatcaacga cacttcgatc   360
ggcatcgaa  tcgtcaatac cgggcccgac cgacccctca tcgaggtgga cggtgttgctg   420
gaagggcatc ccgaggacgc cgtggaagtg aactgggcac cttatccaga cgcgcagatc   480
gaggcgctga ttgcgctgtc gcgcgacatc atcgagcgcc acgacatcca ccccaccgac   540
gttgtcgccc actccgacat cgcgccgacg cgcaagatcg accccggccc acgcttcccc   600
tggcgcaaac tctaccaggc aggcatcggc gtctggccgg aggaggaagc ggtatcgcac   660
tggcagggct gcttcgaggc agagcaggcta ccgctccagca ctctgcagca ggcgcttcg   720
gcctggggct atccgctgga ggcgacgggc gagctggacc gccagacccg cgcggtgcta   780
cgcgccttcc agatgcgctt ccggcctgcc gactaccgcg gcaagccgga cgcagagagc   840
gccgccattc tctgggcgct gctggaagcg tatcgccccc tcgagctgga acggctcgaa   900
ggagcgatga cgcagccgga aagctag                                      927

SEQ ID NO: 29             moltype = AA   length = 308
FEATURE                   Location/Qualifiers
source                    1..308
                          mol_type = protein
                          organism = Halomonas sp.
```

-continued

```
SEQUENCE: 29
VLRHWTAVMG IAMASAWLAG CASPEHLERR DGYVVDHTHL SPSHTSRVRH LVMHYTDVDE      60
AESLAVLTGP HVSAHYVLPL PPRERRGLPL VYQLVDEERR AWHAGASAWK GRPHINDTSI     120
GIEIVNTGPD RPYIEVERLL EGHPEDAVEV NWAPYPDAQI EALIALSRDI IERHDIHPTD     180
VVAHSDIAPT RKIDPGPRFP WRKLYQAGIG VWPEEEAVSH WQARFEAEQL PLATLQQALR     240
AWGYPLEATG ELDRQTRAVL RAFQMRFRPA DYRGKPDAES AAILWALLEA YRPLELERLE     300
GAMTQPES                                                             308

SEQ ID NO: 30           moltype = AA   length = 289
FEATURE                 Location/Qualifiers
source                  1..289
                        mol_type = protein
                        organism = Halomonas sp.
SEQUENCE: 30
GCASPEHLER RDGYVVDHTH LSPSHTSRVR HLVMHYTDVD EAESLAVLTG PHVSAHYVLP      60
LPPRERRGLP LVYQLVDEER RAWHAGASAW KGRPHINDTS IGIEIVNTGP DRPYIEVERL     120
LEGHPEDAVE VNWAPYPDAQ IEALIALSRD IIERHDIHPT DVVAHSDIAP TRKIDPGPRF     180
PWRKLYQAGI GVWPEEEAVS HWQARFEAEQ LPLATLQQAL RAWGYPLEAT GELDRQTRAV     240
LRAFQMRFRP ADYRGKPDAE SAAILWALLE AYRPLELERL EGAMTQPES                289

SEQ ID NO: 31           moltype = DNA   length = 783
FEATURE                 Location/Qualifiers
sig_peptide             1..45
mat_peptide             46..780
source                  1..783
                        mol_type = genomic DNA
                        organism = Pseudomonas peli
CDS                     1..780
SEQUENCE: 31
atgagaattc ttgctcttgc cctgctgatc accctgttga ctgcctgcac cagcggcctg      60
cccatcgaca cccgctatga ggcgctaggc cagaacagcc gggtgcagta catcatcctg     120
cactacacct cgaccaacct gcagcactcc ctggagctgc tgacccaggg cgaggtgagc     180
agccattacc tgatcggcga gaacccgccg accatctacc gcctggtgga tgagaatcgg     240
cgcgcctggc atgccggggt cagtcagtgg cagggacgca cctggctcaa tggcaccagc     300
atcggtatcg aactggtcaa ccagggtttc tatgatgggc ccaatgggcg ctactggcag     360
ccctatgcgc cggcgcagat tgatgcgctg atcctcctgc tcaaggacat catgcagcgt     420
catgagctgc ccctgggcag catcattggt catagcgata tcgcccccca gcgcaaggtc     480
gatccgggcc cgttattccc ctggcagcgt ctggccgagg ccggattgat accctggccg     540
gaagccggtg cagtggcgcg ccagcaggcc gtgtacgagc agcaactgcc tgatgtggcc     600
tggtttcagc agcaactggc cagccacggc tacgaggtgc cagccatggg cgagctggat     660
caggccacgg gcaatgtgat cgccgccttc cagatgaaat accgccaggc caactatgac     720
ggcgagccgg acagcgaaac tggcgccctg ctctgggtgc taaacaatag cgccagccgc     780
tga                                                                  783

SEQ ID NO: 32           moltype = AA   length = 260
FEATURE                 Location/Qualifiers
source                  1..260
                        mol_type = protein
                        organism = Pseudomonas peli
SEQUENCE: 32
MRILALALLI TLLTACTSGL PIDTRYEALG QNSRVQYIIL HYTSTNLQHS LELLTQGEVS      60
SHYLIGENPP TIYRLVDENR RAWHAGVSQW QGRTWLNGTS IGIELVNQGF YDGPNGRYWQ     120
PYAPAQIDAL ILLLKDIMQR HELPLGSIIG HSDIAPQRKV DPGPLFPWQR LAEAGLIPWP     180
EAGAVARQQA VYEQQLPDVA WFQQQLASHG YEVPSHGELD QATRNVIAAF QMKYRQANYD     240
GEPDSETGAL LWVLNNSASR                                                260

SEQ ID NO: 33           moltype = AA   length = 245
FEATURE                 Location/Qualifiers
source                  1..245
                        mol_type = protein
                        organism = Pseudomonas peli
SEQUENCE: 33
CTSGLPIDTR YEALGQNSRV QYIILHYTST NLQHSLELLT QGEVSSHYLI GENPPTIYRL      60
VDENRRAWHA GVSQWQGRTW LNGTSIGIEL VNQGFYDGPN GRYWQPYAPA QIDALILLLK     120
DIMQRHELPL GSIIGHSDIA PQRKVDPGPL FPWQRLAEAG LIPWPEAGAV ARQQAVYEQQ     180
LPDVAWFQQQ LASHGYEVPS HGELDQATRN VIAAFQMKYR QANYDGEPDS ETGALLWVLN     240
NSASR                                                                245

SEQ ID NO: 34           moltype = DNA   length = 900
FEATURE                 Location/Qualifiers
sig_peptide             1..57
mat_peptide             58..897
source                  1..900
                        mol_type = genomic DNA
                        organism = Halomonas sp.
CDS                     1..897
SEQUENCE: 34
atgtggcgaa agcgtgttgt cgttgcatcc ctgaccctgc tgctcactgc ctgtgcgggg      60
cccggccacc gggaacaacg caatggttat gtggtggacc acacccatgt ggcaccttcc     120
```

```
cacaacagcc gagtacggca cctggtgatg cactacacgg atgtggatga agcggagtcg  180
ctcgccgtgc tcaccggccc ccaggtcagc agccactacg tgctgccgct accggcacgg  240
gagcatcgcg gccagccgct ggtctaccag ctcgtcgacg aggagcgccg cgcctggcac  300
gccggggcca gcgcctggaa gcgccgcacc aatatcaacg atacgtccat cggcatcgag  360
atcgtcaata ccggcccgga tcgcccctac gccgaggtgc tggggctgct ggagcagcac  420
cccgaggcga cggtggagat cggttgggca ccctaccccg aggcacagat ccaggcgctg  480
atcgccctgt cgcgggatat catcgagcgc cacaatatcc atcccaccga cgtggtggcc  540
cactcggata tctcgccgac gcgcaagatc gacccgggcc cggcgtttcc ctggcatgcc  600
ctttacgaag cgggtatcgg cgtatggccc gaagaggcca ccgtggcgcg ctatcgcgac  660
cgcttcgacc aggcgctgcc cgagctctcc acgctgcagg cggcacttca tgcctgggc   720
tatccgctgg tggtaagcga cgaactggat tcagactc gcgcggtact tcgcgccttc  780
cagatgcgct ttcgccccac cgactatcgc ggcctgccg atgccgagac cgccgcaatc  840
ctctgggcac ttctggcacg ctatcgaccc gatgaactca ccgcgctgga gccccgatag  900

SEQ ID NO: 35        moltype = AA  length = 299
FEATURE              Location/Qualifiers
source               1..299
                     mol_type = protein
                     organism = Halomonas sp.
SEQUENCE: 35
MWRKRVVVAS LTLLLTACAG PGHREQRNGY VVDHTHVAPS HNSRVRHLVM HYTDVDEAES   60
LAVLTGPQVS SHYVLPLPAR EHRGQPLVYQ LVDEERRAWH AGASAWKRRT NINDTSIGIE  120
IVNTGPDRPY AEVERLLEQH PEATVEIGWA PYPEAQIQAL IALSRDIIER HNIHPTDVVA  180
HSDISPTRKI DPGPAFPWHA LYEAGIGVWP EEATVARYRD RFDQALPELS TLQAALHAWG  240
YPLVVSDELD SQTRAVLRAF QMRFRPTDYR GLPDAETAAI LWALLARYRP DELTALEPR   299

SEQ ID NO: 36        moltype = AA  length = 280
FEATURE              Location/Qualifiers
source               1..280
                     mol_type = protein
                     organism = Halomonas sp.
SEQUENCE: 36
GPGHREQRNG YVVDHTHVAP SHNSRVRHLV MHYTDVDEAE SLAVLTGPQV SSHYVLPLPA   60
REHRGQPLVY QLVDEERRAW HAGASAWKRR TNINDTSIGI EIVNTGPDRP YAEVERLLEQ  120
HPEATVEIGW APYPEAQIQA LIALSRDIIE RHNIHPTDVV AHSDISPTRK IDPGPAFPWH  180
ALYEAGIGVW PEEATVARYR DRFDQALPEL STLQAALHAW GYPLVVSDEL DSQTRAVLRA  240
FQMRFRPTDY RGLPDAETAA ILWALLARYR PDELTALEPR                       280

SEQ ID NO: 37        moltype = DNA  length = 783
FEATURE              Location/Qualifiers
sig_peptide          1..66
mat_peptide          67..780
source               1..783
                     mol_type = genomic DNA
                     organism = Pseudomonas pseudoalcaligenes
CDS                  1..780
SEQUENCE: 37
atgaagtctc tttgccttgc cctcgccctt gttctgcttg ccggttgcac cggtggtcta   60
cgtatcgatg acagccacac ggcgaccggc cagaacagtc gtgtgcaata cgtcgtgctg  120
cactacacct ccgctgacct gcagcgctcg ctcgacctgc tgacgcagac cgaggtgagc  180
agccactacc tgatcgggga tgcaccaccg accgtctacc gcctggtgga tgagaaccgt  240
cgcgcctggc acgtgggtgt cagcgagtgg aaggggcgca cctggctcaa cagcaccacg  300
atcggcatcg agctggtcaa ccagggctac taccagacgc cggccggccg ctactggcag  360
cctttcgcgc cgcagcagat cgataccctg atcgtgctgc tcaaggacat cgtcaagcgt  420
caccagctac cgctgggctc gatcatcgcg cacagcgatg tggccgcca gcgcaaggtc  480
gatccgggcc cttttgttcc cctggaagcgt ctggccgacg agggcctggt gccctgccg  540
aacgaggacg ccgtggcgcg ccagcaggcg ctgttcagca ccagcctgcc cagcgtgcag  600
tggttccagg agcagttggc gcaaaacggc tacacggtgc cgcagcatgg cgagctggat  660
gaggcaacgc gcaatgtcat tgccgctttc cagatgaaat atcgtccggc caactacgac  720
ggccagccgg acgccgaaac tgcagcgcgg ttgctggtgc tcaatctgca ggcggcagga  780
tag                                                                783

SEQ ID NO: 38        moltype = AA  length = 260
FEATURE              Location/Qualifiers
source               1..260
                     mol_type = protein
                     organism = Pseudomonas pseudoalcaligenes
SEQUENCE: 38
MKSLCLALAL VLLAGCTGGL RIDDSHTATG QNSRVQYVVL HYTSADLQRS LDLLTQTEVS   60
SHYLIGDAPP TVYRLVDENR RAWHVGVSEW KGRTWLNSTT IGIELVNQGY YQTPAGRYWQ  120
PFAPQQIDTL IVLLKDIVKR HQLPLGSIIA HSDVAPQRKV DPGPLFPWKR LADEGLVPWP  180
NEDAVARQQA LFSTSLPSVQ WFQEQLAQNG YTVPQHGELD EATRNVIAAF QMKYRPANYD  240
GQPDAETAAR LLVLNLQAAG                                             260

SEQ ID NO: 39        moltype = AA  length = 238
FEATURE              Location/Qualifiers
source               1..238
                     mol_type = protein
                     organism = Pseudomonas pseudoalcaligenes
```

-continued

```
SEQUENCE: 39
DDSHTATGQN SRVQYVVLHY TSADLQRSLD LLTQTEVSSH YLIGDAPPTV YRLVDENRRA    60
WHVGVSEWKG RTWLNSTTIG IELVNQGYYQ TPAGRYWQPF APQQIDTLIV LLKDIVKRHQ   120
LPLGSIIAHS DVAPQRKVDP GPLFPWKRLA DEGLVPWPNE DAVARQQALF STSLPSVQWF   180
QEQLAQNGYT VPQHGELDEA TRNVIAAFQM KYRPANYDGQ PDAETAARLL VLNLQAAG     238

SEQ ID NO: 40          moltype = DNA   length = 1566
FEATURE                Location/Qualifiers
sig_peptide            1..69
mat_peptide            70..1563
source                 1..1566
                       mol_type = genomic DNA
                       organism = Tumebacillus sp.
CDS                    1..1563
SEQUENCE: 40
atgaacaaaa cgtgggtatc ggtcctcgcg accaccgcac tgaccctgtc ggtcagcagc     60
gtgtatgcgc aaccaacgca tgcagccaaa ctcgacaacc aaacggtcgc gacagcaccg    120
gttttggaaa gcaccttcag ctctgctgcg aaggaatttg gcgttccgaa ggaactgctg    180
atggcgatct cctacagcga atcgcgctgg cagatcgcgc cagaggaaac acatctcacc    240
gctgagccgg acaaaaacaa cggcaaaggc ctgatgcacc tcaacgacaa ctccttcaaa    300
aaaggcctga gcgatgctgc aaaagcgctc ggcgtctcca agaaacagat ggaagacgat    360
gtgcaactga acatccgcgg cggtgcttac ctgctcgcga aggcacaaaa agacctcggc    420
aaggcgctta catccaacgt caacgattgg tatgaagcgg ttgcttcctt tgaaggtgcc    480
aaggacaagg acgttgccgc cttgtttgca gatgaagtct accgtgtgct acaagaagga    540
accgcactgg cgatcgaagg cggcacgctg accctcgacc cgaactccaa agtcgatccg    600
agcaaaggcg tctacgcagg cttgaacaac ggcggcacaa actatggact gactccgaac    660
tactccggcg cgatctggaa cccggcgagc acgtccaact atgccgtcgc ctctcgcccg    720
acttcgaacc cgatcaactc ggtcatcatc catgacaccg agggttccta ctccggttcg    780
atcaactggt tcaagaccc ggcggcacaa gtttccgcac actacatcgt ccgttcctcc    840
gatggccaaa tcacccagtt ggtacaggac aaagacatcg catggcatgc acgcagcttc    900
aacaccaacg gaatcggcat cgaacacgaa ggctatgcgg cacaaaccgg ctggtacacc    960
gacgcgatgt acaccgcatc ggcggcgctc accgtgctgt gctgcctcaa atacaacatc   1020
ccgatggacc gcgaccacat cctcgctcac tccgaactgt ggggcaatga ccacaccgat   1080
ccgggcgtga actgggattg gaacaaatac atgagcaaag tgaccggtgt gacgaaaaac   1140
tacgcggcgg tactggtcga caaccgac gcatcctccg gcttcacgct gggtggcccg   1200
tcccaatact ggcaccccgac cgcagggtac ggcatccaca accagatgac gtacacgatg   1260
ggcaacggca caacccgat ctccaactac gcgacgtgga agccgacgat cccgactgct   1320
ggcaactacc aagtcaaagt cttcatcccg tccaacttcg cagcgaccac caacgcgaag   1380
tatgaaatcc actacaacgg tggcgtcatc accaaaacga tctcccaagc agcctactcc   1440
aaccaatggg tgagccttgg cacgtacagc ttcgcagcag gcaccgcagg ctacgtgaaa   1500
ctcggtgaca caccggcga cacggcgtac gtcggcatcg acggcatgcg tttcctcgct   1560
caataa                                                             1566

SEQ ID NO: 41          moltype = AA   length = 521
FEATURE                Location/Qualifiers
source                 1..521
                       mol_type = protein
                       organism = Tumebacillus sp.
SEQUENCE: 41
MNKTWVSVLA TTALTLSVSS VYAQPTHAAK LDNQTVATAP VLESTFSSAA KEFGVPKELL    60
MAISYSESRW QIAPEETHLT AEPDKNNGKG LMHLNDNSFK KGLSDAAKAL GVSKKQMEDD   120
VQLNIRGGAY LLAKAQKDLG KALTSNVNDW YEAVASFEGA KDKDVAALFA DEVYRVLQEG   180
TALAIEGGTL TLDPNSKVDP SKGVYAGLTN GGTNYGLTPD YSGAIWNPAS TSNYAVASRP   240
TSNPINSVII HDTEGSYSGS INWFKDPAAQ VSAHYIVRSS DGQITQLVQD KDIAWHARSF   300
NTNGIGIEHE GYAAQTGWYT DAMYTASAAL TRAVCLKYNI PMDRDHILAH SELWGNDHTD   360
PGVNWDWNKY MSKVTGVTKN YAAVLVDNTD ASSGFTLGGP SQYWHPTAGY GIHNQMTYTM   420
GNGTNPISNY ATWKPTIPTA GNYQVKVFIP SNFAATTNAK YEIHYNGGVI TKTISQAAYS   480
NQWVSLGTYS FAAGTAGYVK LGDNTGDTAY VGIDGMRFLA Q                      521

SEQ ID NO: 42          moltype = AA   length = 498
FEATURE                Location/Qualifiers
source                 1..498
                       mol_type = protein
                       organism = Tumebacillus sp.
SEQUENCE: 42
QPTHAAKLDN QTVATAPVLE STFSSAAKEF GVPKELLMAI SYSESRWQIA PEETHLTAEP    60
DKNNGKGLMH LNDNSFKKGL SDAAKALGVS KKQMEDDVQL NIRGGAYLLA KAQKDLGKAL   120
TSNVNDWYEA VASFEGAKDK DVAALFADEV YRVLQEGTAL AIEGGTLTLD PNSKVDPSKG   180
VYAGLTNGGT NYGLTPDYSG AIWNPASTSN YAVASRPTSN PINSVIIHDT EGSYSGSINW   240
FKDPAAQVSA HYIVRSSDGQ ITQLVQDKDI AWHARSFNTN GIGIEHEGYA AQTGWYTDAM   300
YTASAALTRA VCLKYNIPMD RDHILAHSEL WGNDHTDPGV NWDWNKYMSK VTGVTKNYAA   360
VLVDNTDASS GFTLGGPSQY WHPTAGYGIH NQMTYTMGNG TNPISNYATW KPTIPTAGNY   420
QVKVFIPSNF AATTNAKYEI HYNGGVITKT ISQAAYSNQW VSLGTYSFAA GTAGYVKLGD   480
NTGDTAYVGI DGMRFLAQ                                                498

SEQ ID NO: 43          moltype = DNA   length = 1506
FEATURE                Location/Qualifiers
sig_peptide            1..75
mat_peptide            76..1503
```

|  |  |  |
|---|---|---|
| source | 1..1506 | |
| | mol_type = genomic DNA | |
| | organism = Pseudomonas pseudoalcaligenes | |
| CDS | 1..1503 | |

SEQUENCE: 43

```
atgactcgat tagccgctct tgtcgcctca gccctctccg ccctcctcat cctcgccggt    60
cagcccgccg ccgccgaccg ggcgaccccg ctcggcgccg ccttcgacaa ggccgccgcc   120
gcccaggacg tccccgtga  cctgctcgcc gcgatcgcct acgccgagac ccacctcgac   180
ggtcacaacg gcgagccgag cgccagcggc ggctacggtg tgatgcacct ggtcagcaac   240
cccaccacgc acaccctgga gaaggccgcc gagctcacgg gcctgcccgc ggagaagctg   300
cgcgccgaca ccgaggccaa catcctcggc ggcgcggccg tcctgcgctc catcgccgac   360
gggctcggcc tcgacgaggc cgccaggaag gaggagggcc gctggtacga ggccgtcgcc   420
acgtacggca acgcctcctc gccggagctg gcccgcctct acgccgacgc cgtctacgag   480
ctgctgggc  tcggcttcaa ggccaagggc ctgcgtgtgg cccccgcga ggtcaccgcc    540
gacaggggag tgtacgcagg ggccaggac  ctgaacgcca aggactccaa cgccctggcc   600
gccgccggcc ctgactaccc gaacgccagc tgggtgcccg ccagttcgag caactacacc   660
gtgtcgagcc gtccttcgag ctacgccatc gaccgggtgg tcatccacgt gacccagggc   720
tcctacgccg ggtccatctc ctggttccag aacccgagcg ccaggtctc  cgcgcactac   780
gtgatccgtt cctcggacgg cgccatcacc cagatgtcc  gtgagaagga cgtcgcatgg   840
cacgcgggca actggagcta caacacccgc tccgtcggca tcgagcacga gggcttcgtc   900
aacgacgcct cctggttcac cgacgcgatg taccgcgcgt ccgccgccct gacccgcaac   960
atctgcgaca agtacggcat cccgaaggac cgcagccaca tcatcggcca cgtggaggtc  1020
cccggctcca cgcacaccga ccccggcccg cactggaact ggaacaccta catgtcgtac  1080
gtgaccggtg gcggcggcgg ctcgtggtcc accacggtcg acaacaccgg cgcgttcacc  1140
gcgagcggca actgggcac  ttccagctac tccgcccagc gctacggcgc cgactaccgc  1200
ttcgccaacc cggtggccgc cagcgaccct gcctggtacc gcgaacct   gcccagcacg  1260
ggcagctacc gggtcgaggt ctggtacccc tccgaccccg gctacaacag ctcggccccc  1320
tacatcgtcg ccgcctcggg cggcaaccag acggtgtacg tcgaccagcg atccggcggc  1380
ggtggctggc gcaccatcgg caccttcacc ctcaacgccg gtgaccgaga cgtcgtgggt  1440
gtcagccgct ggacctcggg caccggctac gtcgtcgccg acgccgtccg catcacccgc  1500
ctgtaa                                                              1506
```

|  |  |  |
|---|---|---|
| SEQ ID NO: 44 | moltype = AA   length = 501 | |
| FEATURE | Location/Qualifiers | |
| source | 1..501 | |
| | mol_type = protein | |
| | organism = Nonomuraea dietziae | |

SEQUENCE: 44

```
MTRLAALVAS ALSALLILAG QPAAADRATP LGAAFDKAAA AQDVPRDLLA AIAYAETHLD    60
GHNGEPSASG GYGVMHLVSN PTTHTLEKAA ELTGLPAEKL RADTEANILG GAAVLRSIAD   120
GLGLDEAARK EEGRWYEAVA TYGNASSPEL ARLYADAVYE LLGLGFKAKG LRVAPREVTA   180
DRGVYAGARD LNAKDSNALA AAGPDYPNAS WVPASSSNYT VSSRPSSYAI DRVVIHVTQG   240
SYAGSISWFQ NPSAQVSAHY VIRSSDGAIT QMVREKDVAW HAGNWSYNTR SVGIEHEGFV   300
NDASWFTDAM YRASAALTRN ICDKYGIPKD RSHIIGHVEV PGSTHTDPGP HWNWNTYMSY   360
VTGGGGGSWS TTVDNTGAFT ASGNWGTSSY SAQRYGADYR FANPVAASDP AWYRANLPST   420
GSYRVEVWYP SDPGYNSSAP YIVAASGGNQ TVYVDQRSGG GGWRTIGTFT LNAGDRDVVG   480
VSRWTSGTGY VVADAVRITR L                                             501
```

|  |  |  |
|---|---|---|
| SEQ ID NO: 45 | moltype = AA   length = 476 | |
| FEATURE | Location/Qualifiers | |
| source | 1..476 | |
| | mol_type = protein | |
| | organism = Nonomuraea dietziae | |

SEQUENCE: 45

```
DRATPLGAAF DKAAAAQDVP RDLLAAIAYA ETHLDGHNGE PSASGGYGVM HLVSNPTTHT    60
LEKAAELTGL PAEKLRADTE ANILGGAAVL RSIADGLGLD EAARKEEGRW YEAVATYGNA   120
SSPELARLYA DAVYELLGLG FKAKGLRVAP REVTADRGVY AGARDLNAKD SNALAAAGPD   180
YPNASWVPAS SSNYTVSSRP SSYAIDRVVI HVTQGSYAGS ISWFQNPSAQ VSAHYVIRSS   240
DGAITQMVRE KDVAWHAGNW SYNTRSVGIE HEGFVNDASW FTDAMYRASA ALTRNICDKY   300
GIPKDRSHII GHVEVPGSTH TDPGPHWNWN TYMSYVTGGG GGSWSTTVDN TGAFTASGNW   360
GTSSYSAQRY GADYRFANPV AASDPAWYRA NLPSTGSYRV EVWYPSDPGY NSSAPYIVAA   420
SGGNQTVYVD QRSGGGGWRT IGTFTLNAGD RDVVGVSRWT SGTGYVVADA VRITRL       476
```

|  |  |  |
|---|---|---|
| SEQ ID NO: 46 | moltype = DNA   length = 1509 | |
| FEATURE | Location/Qualifiers | |
| sig_peptide | 1..84 | |
| mat_peptide | 85..1506 | |
| source | 1..1509 | |
| | mol_type = genomic DNA | |
| | organism = Laceyella sacchari | |
| CDS | 1..1506 | |

SEQUENCE: 46

```
ttgagaaagc gtttgctctc ttggttagct atttgctgtc tgctcactct gcctttcctt    60
tcagctccac cgcccgcttgc agccgaggaa cagccgtctt tgtcccatgt cttcgagatg   120
gccgccgcag agtttgaggt gcccgttgaa gtgttgttgg ctattggcta tgccgagacg   180
aggtggatgg accatcaggg ccaacccagc cagctcaacg gatacggcat tatgcatttg   240
gccgaaaacc ccaccaatga ctcattggta caagccagcc gattgctggg catagataaa   300
caagtgctga cccgggacat ccaggctaac atccgtggcg cggcagccgt gttgcagcaa   360
atctccaaag aacaaaacca ggggcaggtg ccgaaaaagc tggccgattg gtacactgtt   420
```

```
gtagcggaat acagcggact atccagccaa caaaccaaag catggtatgc cgatgatgta    480
tatgctctga tcaaccgcgg cgtctctcgt gttatcaacg gccaagaggt gcgattagaa    540
cccacaccgg tcacacccaa ccgcggggaa tacggtgaac ctcgcgatcc gtccggccaa    600
gccacacccg attatcccga agcgcgctgg gtggcggcat ccagtgccaa ctatactgcc    660
gccaacaggg aatccgacgg caatgccatc aactacgtaa tcatccacac cacgcaaggc    720
tcttataatg ggacgatcag ttggtttcaa aatccctctg cccagtgagc gcacattat    780
gtcattcgct ccagtgatgg gcaagtgacc caaatggtgc agaacaaaga catcgcttgg    840
catgcgggca actgggatta caatgtccac tccgtgggga tcgagcatga agggtatgtc    900
aatgatccag cctggtacac tgatgccatg taccgcgcct ctgccaagct gaccgcgtcg    960
ttgtgcaaca ggtacgggat tcccaaagac cgcagtcaca ttatcggcca taaccaagtt    1020
ccaggcgcca cccacaccga ccccggcccc aattgggatt ggaactatta catgagcttg    1080
gtcaatcagt cgggcggcgg tgccgatttg gtcactgata cgccacttc gaaccgcttc    1140
actgccagcg ccaattgggc gataggcacg accaatgccc aaaaatacgg agcggattac    1200
cgctatgcca agcctgaaac gatcagtgac gcagctggt acaaagtaaa cctccccacc    1260
tctggaagtt atgatgtata tgcttggtgg ccgtcaggct ccatctacaa tgatcggaca    1320
ccttatgtga tcaacaccac cagcggtagc cagaccgtcc acgtttccca acaatccagc    1380
ggaggtgtct ggaaccatct gggaaccttt aactttgcgg cgggcgatgc caaccggatt    1440
gccgtgtcgc gatggacgac aggcaccggt tatgtcatcg ctgatgctgt caaattcgtg    1500
aaaagatga                                                            1509

SEQ ID NO: 47           moltype = AA  length = 502
FEATURE                 Location/Qualifiers
source                  1..502
                        mol_type = protein
                        organism = Laceyella sacchari
SEQUENCE: 47
LRKRLLSWLA ICCLLTLPFL SAPPPVAAEE QPSLSHVFEM AAAEFEVPVE VLLAIGYAET     60
RWMDHQGQPS QLNGYGIMHL AENPTNDSLV QASRLLGIDK QVLTRDIQAN IRGAAAVLQQ    120
ISKEQNGQV PKKLADWYTV VAEYSGLSSQ QTKAWYADDV YALINRGVSR VINGQEVRLE    180
PTPVTPNRGE YGEPRDPSGQ ATPDYPEARW VAASSANYTA ANRESDGNAI NYVIIHTTQG    240
SYNGTISWFQ NPSAQVSAHY VIRSSDGQVT QMVQNKDIAW HAGNWDYNVH SVGIEHEGYV    300
NDPAWYTDAM YRASAKLTRW LCNRYGIPKD RSHIIGHNQV PGATHTDPGP NWDWNYYMSL    360
VNQSGGGADL VTDNATSNRF TASANWAIGT TNAQKYGADY RYAKPETISD AAWYKVNLPT    420
SGSYDVYAWW PSGSIYNDRT PYVINTTSGS QTVHVSQQSS GGVWNHLGTF NFAAGDANRI    480
AVSRWTTGTG YVIADAVKFV KR                                             502

SEQ ID NO: 48           moltype = AA  length = 474
FEATURE                 Location/Qualifiers
source                  1..474
                        mol_type = protein
                        organism = Laceyella sacchari
SEQUENCE: 48
EEQPSLSHVF EMAAAEFEVP VEVLLAIGYA ETRWMDHQGQ PSQLNGYGIM HLAENPTNDS     60
LVQASRLLGI DKQVLTRDIQ ANIRGAAAVL QQISKEQNQG QVPKKLADWY TVVAEYSGLS    120
SQQTKAWYAD DVYALINRGV SRVINGQEVR LEPTPVTPNR GEYGEPRDPS GQATPDYPEA    180
RWVAASSANY TAANRESDGN AINYVIIHTT QGSYNGTISW FQNPSAQVSA HYVIRSSDGQ    240
VTQMVQNKDI AWHAGNWDYN VHSVGIEHEG YVNDPAWYTD AMYRASAKLT RWLCNRYGIP    300
KDRSHIIGHN QVPGATHTDP GPNWDWNYYM SLVNQSGGGA DLVTDNATSN RFTASANWAI    360
GTTNAQKYGA DYRYAKPETI SDAAWYKVNL PTSGSYDVYA WWPSGSIYND RTPYVINTTS    420
GSQTVHVSQQ SSGGVWNHLG TFNFAAGDAN RIAVSRWTTG TGYVIADAVK FVKR          474

SEQ ID NO: 49           moltype = DNA  length = 1506
FEATURE                 Location/Qualifiers
sig_peptide             1..87
mat_peptide             88..1506
source                  1..1506
                        mol_type = genomic DNA
                        organism = Thermostaphylospora chromogena
CDS                     1..1506
SEQUENCE: 49
atgcgctctc gcttaatggc ggtattggcg tgcgctttca cagttttgtt tcttactgct     60
gcgccacaag caggccacgc acgtgctaat cctcttgctg acgcatttgc agaagcggct    120
gcagcgcatg acgttccacg cgaccttta gtagcgcttg cttacgctga aactcgttta    180
gatgatcacg atggtgaacc tagcgctagc ggaggatagt gtgttatgca tttagtttta    240
aaccctacaa atcactcttt agaacgtgca gcagagctta ctggcttgcc tgttgaaaaa    300
cttcgtggcg atacagcagc taacatcatg ggtggtgctg ctgttttacg tgcgcatgct    360
gatgaattag tcttgatgaa ggctgcacgt aaagacccag tcgttggta cactgctgtt    420
gcgcgttatg gtggcgcttc agatcctcgt gtagcgcctg tttacgcgga tgccgtattc    480
gaattgcttg gattgggcat tgcacgcagca gcgctaactg tagcaccaca agaagtaacg    540
gttgaccgtg tgaatacgc tgatgttgaa gacttaaacg ctccaaaagc tcgcgttttg    600
tctgcagatt atccgcctgc tgcatgggta gctgcacaca gcagcaatta cacggctagc    660
tctcgtcctt cttcttatgc tatcgaccgt gttatcatcc acgttactca aggttcttac    720
gctggtacta tctcttggtt ccaaaaccct tcagcgaacg tatctgctca ctatgttatt    780
cgttcttctg acggagcagt aactcaaatg tacgtgaaa actggattgc ttgcatgct    840
ggaaattgga attacaacac acgctctatc ggtattgagc atgaaggttg gttgataac    900
ccatcttggt tcactgacgc tatgtaccgt gcgtctgcag cgcttacacg tcacatttgc    960
gacaagtacg gtatcccaaa agaccgtact catatcattg gtcataacca agttccaggt   1020
gcgactcaca ctgatccggg acctaattgg gattggaacc gcttcatgga atacgtaact   1080
ggtaatggcg gaactccgac ttggcaggtt actgtagata cgctacagc tggcaagttt   1140
```

```
acagcttctg aaaactgggg cacttctaca tggtcttctc aacgttacgg agctgattac  1200
cgttttgcga cgccagtact tgcatcagat cctgcatggt tccgtgcaac aatcccttct  1260
gcgggtgaat accgtatcga agtttactac ccttcagatc ctggctacaa ttcatctact  1320
ccgtatatca tcgcgacgtc ttcaggtaac cgcactgtat atgttgacca gcttctggt   1380
ggtggcacgt ggcgcagcct tggtactttt agccttaatg caggcgatca gaatgttgtt  1440
gctgtatcac gttggacatc tggaacaggc tacgttatcg cggacgctgt tcgcatcaca  1500
cgttac                                                             1506

SEQ ID NO: 50         moltype = AA  length = 502
FEATURE               Location/Qualifiers
source                1..502
                      mol_type = protein
                      organism = Thermostaphylospora chromogena
SEQUENCE: 50
MRSRLMAVLA CAFTVLFLTA APQAGHARAN PLADAFAEAA AAHDVPRDLL VALAYAETRL   60
DDDHDGEPSAS GGYGVMHLVS NPTNHSLERA AELTGLPVEK LRGDTAANIM GGAAVLRAHA 120
DELGLDEAAR KDPGRWYTAV ARYGGASDPR VARLYADAVF ELLGLGIDAA GVTVAPQEVT  180
VDRGEYADVE DLNAPKARVL SADYPPAAWV AAHSSNYTAS SRPSSYAIDR VIIHVTQGSY  240
AGTISWFQNP SANVSAHYVI RSSDGAVTQM VREKDVAWHA GNWNYNTRSI GIEHEGWVDN  300
PSWFTDAMYR ASAALTRHIC DKYGIPKDRT HIIGHNQVPG ATHTDPGPNW DWNRFMEYVT  360
GNGGTPTWQV TVDNATAGKF TASENWGTST WSSQRYGADY RFATPVLASD PAWFRATIPS  420
AGEYRIEVYY PSDPGYNSST PYIIATSSGN RTVYVDQRSG GGTWRSLGTF SLNAGDQNVV  480
AVSRWTSGTG YVIADAVRIT RY                                           502

SEQ ID NO: 51         moltype = AA  length = 473
FEATURE               Location/Qualifiers
source                1..473
                      mol_type = protein
                      organism = Thermostaphylospora chromogena
SEQUENCE: 51
NPLADAFAEA AAAHDVPRDL LVALAYAETR LDDHDGEPSA SGGYGVMHLV SNPTNHSLER   60
AAELTGLPVE KLRGDTAANI MGGAAVLRAH ADELGLDEAA RKDPGRWYTA VARYGGASDP  120
RVARLYADAV FELLGLGIDA AGVTVAPQEV TVDRGEYADV EDLNAPKARV LSADYPPAAW  180
VAAHSSNYTA SSRPSSYAID RVIIHVTQGS YAGTISWFQN PSANVSAHYV IRSSDGAVTQ  240
MVREKDVAWH AGNWNYNTRS IGIEHEGWVD NPSWFTDAMY RASAALTRHI CDKYGIPKDR  300
THIIGHNQVP GATHTDPGPN WDWNRFMEYV TGNGGTPTWQ VTVDNATAGK FTASENWGTS  360
TWSSQRYGAD YRFATPVLAS DPAWFRATIP SAGEYRIEVY YPSDPGYNSS TPYIIATSSG  420
NRTVYVDQRS GGGTWRSLGT FSLNAGDQNV VAVSRWTSGT GYVIADAVRI TRY         473

SEQ ID NO: 52         moltype = DNA  length = 1320
FEATURE               Location/Qualifiers
sig_peptide           1..75
mat_peptide           76..1317
source                1..1320
                      mol_type = genomic DNA
                      organism = Kribbella aluminosa
CDS                   1..1317
SEQUENCE: 52
atgtcccgat tagcaaagct gtgcgcagcc ctggccgtcg gcgcgctcgc gctgaccgcc   60
ctcccgagca acgcggcatc gccacccgcc ggctctcacc tcgccgaggc cttcacgacc  120
gccgccgcga agtacgacgt accgcgggaa gtgctggtcg gtgtcggctt cgccgaaacc  180
catctcgacg gtcacgacgg cacgccgagc caggccaacg ggtacggcgt gatgcacctg  240
gcgagcaaca acgtgaacaa gacgatgtcc gaggcaagca aactgaccgg cgtgccggtc  300
gcgaagctgt ccaaggacga cgcgtcgaac gtcctcggcg ccgccgcggt cctcgactcc  360
tacgcggagc aggccaagct caaagaccgg gcagacctcg gcaagtggta cggcgtgatc  420
gcgaagtact cgcactccgc cgacgcgtcg accgcacggc tctacaccga cgaggtctac  480
cgaatcattg cccgggtgt ccgccgccgc ggctgtcga ccgacccgaa gccggtcagc    540
ccggaccgcg gcgcgtacgc cgaaggccgc tccgtcggga ccgccgccgt cgactacccg  600
agcgcgatct ggaacccggc gagcaccagc aactaccgcg tcggccggac cgccgccgtc  660
accacgatcg tcatccacgt caccacgggc tcgtacgccg gcaccatcag ctggttcaag  720
aacccgtccg cgcaggtcag cgcgcactac gtgtccgct cgagcgacgg cgaggtcacc   780
cagatggtgg ccgagaagga caccgcgtgg cacgtccgga ccgagaaccc gtacacgatc  840
ggcatcgagc acgaagggta cgtcgaccag ccgtcgtggt tcaccgatgc gatgtaccgg  900
tcgtcggccg cgctgaccg caacatcgcc gaccggcggg gcatcccgaa ggaccgcacc  960
cacatcaagg gccacaacga gatgccgaac aacgaccaca ccgacccggg accgaactgg  1020
aactgggact actacacgca gctggtgaac ggcggcgacc gaacccgcc ggagtacaac  1080
ttcaccacct ggggtgaggg cgtgaacgtc cgctcggcgc cgaagctgtc cgcgtcggtc  1140
gtcaccacgc ttcccggccc gacccgcgta ttcgtcgagt gccaggtgca gggcgacacc  1200
gtgacgggcg gcggctacac caacaactgg tgggccaagc tgcgcgacca gcacgggtac  1260
atgaccaaca tctacatcga cgacccgaac cagaagctgc aggcgtacc ggactgctag   1320

SEQ ID NO: 53         moltype = AA  length = 439
FEATURE               Location/Qualifiers
source                1..439
                      mol_type = protein
                      organism = Kribbella aluminosa
SEQUENCE: 53
MSRLAKLCAA LAVGALALTA LPSNAASPPA GSHLAEAFTT AAAKYDVPRE VLVGVGFAET   60
HLDGHDGTPS QANGYGVMHL ASNNVNKTMS EASKLTGPV AKLSKDDASN VLGAAAVLDS   120
```

```
YAEQAKLKDR ADLGKWYGVI AKYSHSADAS TARLYTDEVY RIIARGVRAA GVSTDPKPVS    180
PDRGAYAKAA PLGTAAVDYP SAIWNPASTS NYRVGRTAAI TTIVIHVTQG SYAGTISWFK    240
NPSAQVSAHY VVRSSDGEVT QMVAEKDTAW HVRTENPYTI GIEHEGYVDQ PSWFTDAMYR    300
SSAALTRNIA DRRGIPKDRA HIKGHNEMPN NDHTDPGPNW NWDYYTQLVN GGDPNPPEYN    360
FTTWGEGVNV RSAPKLSASV VTTLPGPTRV FVECQVQGDT VTAGGYTNNW WAKLRDQHGY    420
MTNIYIDDPN QKLPGVPDC                                                439

SEQ ID NO: 54           moltype = AA  length = 414
FEATURE                 Location/Qualifiers
source                  1..414
                        mol_type = protein
                        organism = Kribbella aluminosa
SEQUENCE: 54
ASPPAGSHLA EAFTTAAAKY DVPREVLVGV GFAETHLDGH DGTPSQANGY GVMHLASNNV     60
NKTMSEASKL TGVPVAKLSK DDASNVLGAA AVLDSYAEQA KLKDRADLGK WYGVIAKYSH    120
SADASTARLY TDEVYRIIAR GVRAAGVSTD PKPVSPDRGA YAKAAPLGTA AVDYPSAIWN    180
PASTSNYRVG RTAAITTIVI HVTQGSYAGT ISWFKNPSAQ VSAHYVVRSS DGEVTQMVAE    240
KDTAWHVRTE NPYTIGIEHE GYVDQPSWFT DAMYRSSAAL TRNIADRRGI PKDRAHIKGH    300
NEMPNNDHTD PGPNWNWDYY TQLVNGGDPN PPEYNFTTWG EGVNVRSAPK LSASVVTTLP    360
GPTRVFVECQ VQGDTVTAGG YTNNWWAKLR DQHGYMTNIY IDDPNQKLPG VPDC          414

SEQ ID NO: 55           moltype = DNA  length = 1332
FEATURE                 Location/Qualifiers
sig_peptide             1..93
mat_peptide             94..1329
source                  1..1332
                        mol_type = genomic DNA
                        organism = Streptomyces griseus
CDS                     1..1329
SEQUENCE: 55
atgacgtcga agcagaggat gagactcgcg ctcgcactga ccgcggccgg ggcgctgagc     60
gtggcgctcc tctccccggc cgcagccggc gcggacaccg tacgaccgga atgcccgcgg    120
tccctggcct gcgactgggt ccccgcggcc taccagcaga ccggagatcc ggaggacaag    180
gacacctacg gcaactacga cacgaaccgt ccggacagca acgccgt caagttcatc       240
gtcctgcacg acaccgaggt cgactacgac accaccctga agatcttcca gaacccggcc    300
aaccagacgt ccgcccacta cgtggtcgcg tcgcggacg gccacgtcac acagatggtg     360
aagaacaagg acgtcgcctg caggcgggc aactggtacc tcaacaccca ctccatcggc     420
atcgagcagg agggcgtcgc agcggagggt gccacgtggt acacctccga gatgtaccgg    480
tcgaccgcgc gcctggtgcg gtacctggcc gcgaagtacg acatcccgct cgaccggcaa    540
cacatcctcg ggcacgacgg tgtgccgccc accagcgccg ccggaacgaa gaacatgcac    600
tgggacccgg gcccctactg ggactggaac cgcttcatgg cgctactcgg cgcgcccacc    660
gcgcccagcc ccccgaagcg cagcgaactg gtcaccgtca gcgcggactt cgcgaggaac    720
cagcaggagt tccgcgactg cgagaagaac gtcgaccttc cccggcaggg gagcagcgg    780
gtccctctgc acacggagcc gtcggcggac gcgcctctct tctccgaccc ggggctgcat    840
ccggacggct cgccggggac gaactgcgcc gctgactggg gcagcaagat cagtgcgacc    900
cagcaggccg tcgtcgccga ccgggtaccc ggctggacgg cgatctggtg gtacggggag    960
aaggcttggt tcagcactcc gccccggtacc agggtcacca ccccgaccgg acggcagtgtg   1020
gtgcggccga agccgggcac gtccgaagtg ctggtgtacg gcgtcgccta ccccgagaag    1080
gccgagtacc ccacggactt cgtcaagccg accgtgggca cgccgctcgt ctacaccatc    1140
aaggcgggtc aggccttccc cggcggcggc gaggcgccca ccggctacta ctacgcaccg    1200
acgatcgaca cctcgaagcc gtacgaccac acgtacttcg gtggtgcgca agtacgtg      1260
acggtccaga tcggccaccg catcggcttc gtcaaggcgt ccgacgtgga cgtggtccga   1320
gccggctcat ga                                                        1332

SEQ ID NO: 56           moltype = AA  length = 443
FEATURE                 Location/Qualifiers
source                  1..443
                        mol_type = protein
                        organism = Streptomyces griseus
SEQUENCE: 56
MTSKQRMRLA LALTAAGALS VALLSPAAAG ADTVRPECPR SLACDWVPAA YQQTGDPEDK     60
DTYGNYDTAN RPDSNAVKFI VLHDTEVDYD TTLKIFQNPA NQTSAHYVVR SADGHVTQMV    120
KNKDVAWQAG NWYLNTHSIG IEQEGVAAEG ATWYTSEMYR STARLVRYLA AKYDIPLDRQ    180
HILGHDGVPP TSAAGTKNMH WDPGPYWDWN RFMALLGAPT APSAPKRSEL VTVSADFARN    240
QQEFRDCEKN VDLPRQGSSA VPLHTEPSAD APLFSDPGLH PDGSPGTNCA ADWGSKISAT    300
QQAVVADRVP GWTAIWWYGE KAWFSTPPGT RVTTPTRGSV VRPKPGTSEV LVYGVAYPEK    360
AEYPTDFVKP TVGTPLVYTI KAGQAFPGGG EAPTGYYYAP TIDTSKPYDH TYFGGAQKYV    420
TVQIGHRIGF VKASDVDVVR AGS                                            443

SEQ ID NO: 57           moltype = AA  length = 412
FEATURE                 Location/Qualifiers
source                  1..412
                        mol_type = protein
                        organism = Streptomyces griseus
SEQUENCE: 57
DTVRPECPRS LACDWVPAAY QQTGDPEDKD TYGNYDTANR PDSNAVKFIV LHDTEVDYDT     60
TLKIFQNPAN QTSAHYVVRS ADGHVTQMVK NKDVAWQAGN WYLNTHSIGI EQEGVAAEGA    120
TWYTSEMYRS TARLVRYLAA KYDIPLDRQH ILGHDGVPPT SAAGTKNMHW DPGPYWDWNR    180
FMALLGAPTA PSAPKRSELV TVSADFARNQ QEFRDCEKNV DLPRQGSSAV PLHTEPSADA    240
```

```
PLFSDPGLHP DGSPGTNCAA DWGSKISATQ QAVVADRVPG WTAIWWYGEK AWFSTPPGTR       300
VTTPTRGSVV RPKPGTSEVL VYGVAYPEKA EYPTDFVKPT VGTPLVYTIK AGQAFPGGGE       360
APTGYYYAPT IDTSKPYDHT YFGGAQKYVT VQIGHRIGFV KASDVDVVRA GS               412

SEQ ID NO: 58           moltype = DNA   length = 2019
FEATURE                 Location/Qualifiers
sig_peptide             1..105
mat_peptide             106..2016
source                  1..2019
                        mol_type = genomic DNA
                        organism = Micromonospora peucetia
CDS                     1..2016
SEQUENCE: 58
atgcacctgt cagcgacaac gaggagcaga cgcgtcctgc tggccaccgc cgtggccgcc        60
gtcatggtgg cgacgccgct caccgccgcc ggatccgccg ccgccgcacc ggcgaccgac       120
cggcagcagc agtacgccgc cgcggcagcc gagtacggcg tgccgagag cgtcctgctc       180
ggcgtctcct atctacagtc ccgctgggac accaacgccg gcacgccgag caccagcgcc       240
ggctacggac cgatgcacct caccgacgcc gagcacgtcg ccgccctgcc cgggggcacc       300
caccacgacg agggcaccga ggacccgcgc ggcgacgact cccgcccgtc cctggccgag       360
gcgcgcgagc cggccgagcc ggctcccgcc gaggcggcgc tccggacgct cgacgccgcc       420
gccggactca ccgcgccag cgaggaggcg ctgcggacgg acgtcacggc gaacatccgg        480
ggcggcgcgg cgctgctggc cgcgtaccag aaggagatcg gtgcccggt cggtgccgag        540
accgaccccg cggcctggta cggcgcggtg gcccgctact ccggcgccga caccaccgac       600
gccgcggcgg ccttcgccaa cgaggtgtac gccaccatcg ccacgggcga cacccgactg       660
accgacgacg ggcagcgggt caccctcgcc gcccgcgagg tccagccgga gcgttcctgg       720
ctggaccggc tgggcctgcg caagctcgcc cgccccgacg ggctggagtg ccgagcgac       780
atctcgtgcg agtggatccc ggcgcctac cagaactacg gcaccaccct cggcgcgtac        840
ggcaaccacg acctggctga ccggcccgca cagcagaaga tcgagtacat cgtcatccac       900
gacaccgagg gctacttcgg gcccagcgtg aacctggtca aggacccgaa gcgggtgggt       960
tggcactaca ccctgcgctc ggtggacggc cacatcgccc agcacatcaa gaccaagaac      1020
gtcggctggc acgccggcaa ctggtacgtg aactccaagt ccatcggcct tgagcacgag      1080
ggcttcgcgg gacacggcac ctggtacacc gaggcgatgt accgcacctc cgccaagctg      1140
gtccgccacc tggcgcggca gtacaacatc ccgctggacc gcaaccacat catcgggcac      1200
gacaacgtcc ccggcacggt cgccgcgaac gtcgtggca tgcactggga cgcgggcccg       1260
tactgggact ggtcgcacta cttcgacctg gtcaaggcgc cgttctggtc gaccggcacg      1320
caccggaccg gactggtcac catcgacccg gacttcgcca ccaaccagcc gcagttcacc      1380
ggctgcaacc ggcagccgcc gggcgtgccg aacccgcccc cgccgacggc tccctgcccg      1440
ctgcgcggct cgtcggcgct gccccctgcac aacgcgccga gccaggacgc gccgctggtc      1500
aacgacatcg cgctgcggcc cgacggcacc ccgaacaccc tgtacgtctc cgaccacggc      1560
gcccgggtct cggcaggaca gacgtacgcc ctggccgagg tgcgggtga ctggacggcg       1620
atctggtacc tcgccagaa ggcgtggttc cacaacccgg cctcggcgcg gaccgccaag       1680
tggtccgtcg gcctggtcgc caccccgaag gcaggcaaga ccaccatccc ggtgtacggc      1740
cgggcgtacc cggaggagc ggcctacccg gccggcgtac cgtaccagac gatctcgccg       1800
ctccagtaca cgctctcggc cggtgagcgg tacgccgtcg gcaacctgct ccccggcgag      1860
tactaccggg ccaccacgtt cgacggctcc gccccgggtg accggaccgt catccgcggc      1920
gagaacaagt acgtgcagat ccagttcggc caccgcatca tgtacgtcaa cctggccgac      1980
gtgaacctgc tgccctcgcc gctgggcgcg ccccgctga                             2019

SEQ ID NO: 59           moltype = AA   length = 672
FEATURE                 Location/Qualifiers
source                  1..672
                        mol_type = protein
                        organism = Micromonospora peucetia
SEQUENCE: 59
MHLSATTRSR RVLLATAVAA VMVATPLTAA GSAAAAPATD RQQQYAAAAA EYGVPESVLL        60
GVSYLQSRWD TNAGTPSTSA GYGPMHLTDA EHVAALPGGT HHDEGTEDPR GDDSRPSLAE       120
AREPAEPAPA EAALRTLDAA AGLTGASEEA LRTDVTANIR GGAALLAAYQ KEIGAPVGAE       180
TDPAAWYGAV ARYSGADTTD AAAAFANEVY ATIATGDTRL TDDGQRVTLA AREVQPERSW       240
LDRLGLRKLA RPDGLECPSD ISCEWIPAPY QNYGTTLGAY GNHDLADRPA QQKIEYIVIH       300
DTEGYFGPSV NLVKDPKRVG WHYTLRSVDG HIAQHIKTKN VGWHAGNWYV NSKSIGLEHE       360
GFAGHGTWYT EAMYRTSAKL VRHLARQYNI PLDRNHIIGH DNVPGTVAAN VRGMHWDAGP       420
YWDWSHYFDL LKAPFWSTGT HRTGLVTIDP DFATNQPQFT GCNRQPPGVP NPPPPTAPCP       480
LRGSSALPLH NAPSQDAPLV NDIALRPDGT PNTMYVSDHG ARVSAGQTYA LAEVRGDWTA       540
IWYLGQKAWF HNPASARTAK WSVGLVATPK AGKTTIPVYG RAYPEEAAYP AGVPYQTISP       600
LQYTLSAGER YAVGNLLPGE YYRATTFDGS APGDRTVIRG ENKYVQIQFG HRIMYVNLAD       660
VNLLPSPLGA PR                                                          672

SEQ ID NO: 60           moltype = AA   length = 637
FEATURE                 Location/Qualifiers
source                  1..637
                        mol_type = protein
                        organism = Micromonospora peucetia
SEQUENCE: 60
APATDRQQQY AAAAAEYGVP ESVLLGVSYL QSRWDTNAGT PSTSAGYGPM HLTDAEHVAA        60
LPGGTHHDEG TEDPRGDDSR PSLAEAREPA EPAPAEAALR TLDAAAGLTG ASEEALRTDV       120
TANIRGGAAL LAAYQKEIGA PVGAETDPAA WYGAVARYSG ADTTDAAAAF ANEVYATIAT       180
GDTRLTDDGQ RVTLAAREVQ PERSWLDRLG LRKLARPDGL ECPSDISCEW IPAPYQNYGT       240
TLGAYGNHDL ADRPAQQKIE YIVIHDTEGY FGPSVNLVKD PKRVGWHYTL RSVDGHIAQH       300
IKTKNVGWHA GNWYVSNKSI GLEHEGFAGH GTWYTEAMYR TSAKLVRHLA RQYNIPLDRN       360
```

```
HIIGHDNVPG  TVAANVRGMH  WDAGPYWDWS  HYFDLLKAPF  WSTGTHRTGL  VTIDPDFATN   420
QPQFTGCNRQ  PPGVPNPPPP  TAPCPLRGSS  ALPLHNAPSQ  DAPLVNDIAL  RPDGTPNTMY   480
VSDHGARVSA  GQTYALAEVR  GDWTAIWYLG  QKAWFHNPAS  ARTAKWSVGL  VATPKAGKTT   540
IPVYGRAYPE  EAAYPAGVPY  QTISPLQYTL  SAGERYAVGN  LLPGEYYRAT  TFDGSAPGDR   600
TVIRGENKYV  QIQFGHRIMY  VNLADVNLLP  SPLGAPR                             637

SEQ ID NO: 61           moltype = DNA   length = 1899
FEATURE                 Location/Qualifiers
sig_peptide             1..99
mat_peptide             100..1896
source                  1..1899
                        mol_type = genomic DNA
                        organism = Bacillus sp.
CDS                     1..1896
SEQUENCE: 61
ttgggattta aaaagctatc atcagccatt ttaacgttct ccttaaccgc aagcctcttg    60
gctatcccg ctgactttac accaagcgca acttctgcag cctcaacaga aaacagcaat   120
gaagcgcacc acctgcaaaa ggcttttgaa acagcggcga aggaatttgg agtacctgaa   180
tctgtccttc tcgccgtcgc ttataaccag tcacgctggg agcaccatga aggccatagt   240
gaggtcggag gctatggcat tatgaatctt gcagacttgc cagccgacat gagcgccagg   300
ggcaagcatg acgacggaat cattgcggct ttggataatg aaaatagcat gcttaaaaca   360
gccgcaaatc ttctaaatga agatccggaa gccttaaaag agaccctgaa acaaaaatatc   420
cggggcgggg cagctctttt agcagagttt gcacgccaaa cgacaggga acttccttcc   480
gatgaagcag actggtacgg tgccgtcgtt aaatacagcg gaacagatca ggaagtcatc   540
gctaaggact ttgcagatca agtctttgag accattcagc aaggtgctgc cagaaaaaac   600
cttgatggac aaaagagtcgt attaaacgcc aaggaaatta caccaaataa gactacagct   660
ggcactatcc ctcttcgcaa caccaaatac acaaataccg actgtccaaa tggccttgat   720
tgcactttca ttcctgctgc ttataagcaa ttttcgagca gcacaagtaa ttacggcaac   780
tacgatatcg ccaatcggcc aaaggacgat ttagatattc gctatattat tattcatgat   840
attgagggca cggctgaatc cgccatcagc cacttccaga atccgtccta cgttagtgca   900
cactatgtca tagattcaga gaccggaaaa atcacccaga tggtacgtcc tgaagatgtg   960
ccatggcatg caggaaactg gtattttaat atgcattcga tcggattgga gcatgaagga  1020
tatgctgcag aagcgctga ctggtacagt gagcaaatgt atcgctctac cgcaaaactt  1080
gtaagatacc tttcagaccg atttaacatt cctttggaca gacagcacat tatcggccat  1140
gatgagatac ctggcttaac aacagcaaaa cataggagca tgcactggga tccgggcgct  1200
tattgggatt ggggacactt tttcgacctt cttggagctt ccattaatcc aagcagcgga  1260
gacaaagaca gtaatatcgt cacaatccgc ccaaatttca atacaaatca gccagacttt  1320
acgtatagag gaattaaaca ggaacctgag tcttcaagcc tgattcattt atacagcgaa  1380
cccagctttg aggcaccatt ggtcagtgat cccctgcttc atcctggcgg caccagcaca  1440
agaaatatta atgactgggg caataaagct gcgatgggac agagtttcta taagcgggga  1500
caggaaggcg attggacagc tatttactac gccggccaaa aagcctggtt ctataatccg  1560
aacaataaaa atagcgtccc aggcagcggg accctcatca cgccaaaaga agggcttgat  1620
tccatacctg tatatggtgc cgcctatcct gacgacggca cttacgaaga ggccggaatt  1680
gcggaatggg caagaggaaa agcacaggtt ctataccaga tgccggctgg ccaaatctat  1740
acagcaacag caccaattca gtccgattac tatcatgcga agtattataa tgacccggct  1800
acaaataagg ttgtaaaggg gaatgatgaa tactatcaga tttttttacaa tcatcgtctg  1860
ggattcgtga agaaaagcga tgtagaagtt gtaaattaa                           1899

SEQ ID NO: 62           moltype = AA   length = 632
FEATURE                 Location/Qualifiers
source                  1..632
                        mol_type = protein
                        organism = Bacillus sp.
SEQUENCE: 62
LGFKKLSSAI  LTFSLTASLL  AIPADFTPSA  TSAASTENSN  EAHHLQKAFE  TAAKEFGVPE    60
SVLLAVAYNQ  SRWEHHEGHS  EVGGYGIMNL  ADLPADMSAR  GKHDDGIIAA  LDNENSMLKT   120
AANLLNEDPE  ALKKDPEQNI  RGGAALLAEF  ARQTTGELPS  DEADWYGAVV  KYSGTDQEVI   180
AKDFADQVFE  TIQQGAARKN  LDGQRVVLNA  KEITPNKTTA  GTIPLRNTKY  TNTDCPNGLD   240
CTFIPAAYKQ  FSSSTSNYGN  YDIANRPKDD  LDIRYIIIHD  IEGTAESAIS  HFQNPSYVSA   300
HYVIDSETGK  ITQMVRPEDV  PWHAGNWYFN  MHSIGLEHEG  YAAEGADWYS  EQMYRSTAKL   360
VRYLSDRFNI  PLDRQHIIGH  DEIPGLTTAK  HRSMHWDPGA  YWDWGHFFDL  LGASINPSSG   420
DKDSNIVTIR  PNFNTNQPDF  TYRGIKQEPE  SSSLIHLYSE  PSFEAPLVSD  PLLHPGGTST   480
RNINDWGNKA  AMGQSFYKAG  QEGDWTAIYY  AGQKAWFYNP  NNKNSVPGSG  TLITPKEGLD   540
SIPVYGAAYP  DDAAYEEAGI  AEWARGKAQV  LYQMPAGQIY  TATAPIQSDY  YHAKYYNDPA   600
TNKVVKGNDE  YYQIFYNHRL  GFVKKSDVEV  VN                                  632

SEQ ID NO: 63           moltype = AA   length = 599
FEATURE                 Location/Qualifiers
source                  1..599
                        mol_type = protein
                        organism = Bacillus sp.
SEQUENCE: 63
ASTENSNEAH  HLQKAFETAA  KEFGVPESVL  LAVAYNQSRW  EHHEGHSEVG  GYGIMNLADL    60
PADMSARGKH  DDGIIAALDN  ENSMLKTAAN  LLNEDPEALK  KDPEQNIRGG  AALLAEFARQ   120
TTGELPSDEA  DWYGAVVKYS  GTDQEVIAKD  FADQVFETIQ  QGAARKNLDG  QRVVLNAKEI   180
TPNKTTAGTI  PLRNTKYTNT  DCPNGLDCTF  IPAAYKQFSS  STSNYGNYDI  ANRPKDDLDI   240
RYIIIHDIEG  TAESAISHFQ  NPSYVSAHYV  IDSETGKITQ  MVRPEDVPWH  AGNWYFNMHS   300
IGLEHEGYAA  EGADWYSEQM  YRSTAKLVRY  LSDRFNIPLD  RQHIIGHDEI  PGLTTAKHRS   360
MHWDPGAYWD  WGHFFDLLGA  SINPSSGDKD  SNIVTIRPNF  NTNQPDFTYR  GIKQEPESSS   420
```

```
LIHLYSEPSF EAPLVSDPLL HPGGTSTRNI NDWGNKAAMG QSFYKAGQEG DWTAIYYAGQ    480
KAWFYNPNNK NSVPGSGTLI TPKEGLDSIP VYGAAYPDDA AYEEAGIAEW ARGKAQVLYQ    540
MPAGQIYTAT APIQSDYYHA KYYNDPATNK VVKGNDEYYQ IFYNHRLGFV KKSDVEVVN     599

SEQ ID NO: 64          moltype = DNA   length = 1911
FEATURE                Location/Qualifiers
sig_peptide            1..93
mat_peptide            94..1908
source                 1..1911
                       mol_type = genomic DNA
                       organism = Bacillus sporothermodurans
CDS                    1..1908
SEQUENCE: 64
atgttattac gacgtcttaa aaatcgtaca ttattgttca cattcatcct tatttttagc     60
ttacttgtta tgccattcgg agtatcagaa gcaagtaaac attatacgat tgatacaaat    120
catcattctc ctttgcagca agcatttact aaggctgcaa aagagtttca tgtcccagaa    180
agcttattaa tgtccgttgc ctacaatgag tcacgttggc tagatcatca tggtcagcca    240
agcacatcag gtggctatgg aatcatgcat ttaactgaag ccaagccttc acaaagtttg    300
agtgctaaag gaaacggaat agcacattca tctgctatta atgtgcaaca aatgtatacg    360
ttgaaaacgg cagctaaact tctaggagta aaggacaatg tgataaaagt taaccccgaa    420
cagaacattc gcggtggtgc tgcattactt ttggaatatg ctcgtgatac ggttggccat    480
ataccgagaa gtctcgctga ttggtatgga gcagttgcta agtatagcgg ctcaaacaat    540
caagttgtcg ctaatgattt tgcagaccaa gtgtatgcta cgattcaaga aggtgcagaa    600
gaggtgttgg ccgatgggca acatcttgtc ctcaaaccaa ataaggtgat tccaaataaa    660
aagacaagtg acaaactgaa gtttcaaaaa acgaaagaaa tggatgtaga ttgtcctaaa    720
ggagtagatt gcagatatat tccagcagca tataaacaat tttctagtct tacagattac    780
ggaaattatg atcttgctac caggccaaag gatggaaatg atattcgtta tattattatc    840
cacgatactg aaggcagcta tgattcggcc atcaactggt tcaagatca gtcatatgct    900
agtgctcact atgttattcg ttcttccgat ggtcaaatta cagaaatggt aaaaccggag    960
gatgttgctt ggcaagcagg caactggtac tttaatgcat attccatcgg aattgagcat   1020
gagggttatg cagtccaagg ggctacttgg tatagtgaac aaatgtatca tgcatctgca   1080
aaactagtaa aatatttagc tgaaaaatat catgttccgt tagatcgagc acatattctc   1140
ggccacgaca acgtccctgg tttaacgcca gccgcccaaa cccgtatgca ttgggatcct   1200
gcagccttat ggaactggga gcatttttc aaaaaactgg gagtaccgat tcatccaacg   1260
aaaggaaaga aaaacagtcg gatcgttacg attgcccta aatatttaaa gaacatgccg   1320
ccattaactt atcaaaatga acaattagag aagcaaccgg caaatttcgt ctatttgcac   1380
acggaaccaa gtttctctgc cccgtacatt ggtgatccgg cacttcatgc ggatggatca   1440
cctggtacga cagcaatcaa tgactgggga gataaagcat cgactggaca aagtttctat   1500
gtagctgatc ataagggtga ctggatggca atctattatg gagggaaaaa agcttggttt   1560
ttcaacccga aaaggaaaaa tacggtatct ggaaaaggaa ttcttgtaac accaaagaaa   1620
ggtctcgatg ccatccctgt atatggtacc gcctatccag aaaacagcgc ttatgaagga   1680
acaggcattc ctactgggtc agaagggaaa attacaccgc tacaatatac cattgcagcc   1740
ggccaagtat atgtcgcaac aaatcctgta aaagctatgc caagttattt   1800
aatcggcttt cagaaaataa agtcgtaaaa ggcaatgacg aatactatca aattttcttt   1860
aaccaccgtg tcgcatttgt aaagaagagt gatgtagagg tgaaaaagta a            1911

SEQ ID NO: 65          moltype = AA   length = 636
FEATURE                Location/Qualifiers
source                 1..636
                       mol_type = protein
                       organism = Bacillus sporothermodurans
SEQUENCE: 65
MLLRRLKNRT LLFTFILIFS LLVMPFGVSE ASKHYTIDTN HHSPLQQAFT KAAKEFHVPE     60
SLLMSVAYNE SRWLDHHGQP STSGGYGIMH LTEAKPSQSL SAKGNGIAHS SAINVQQMYT    120
LKTAAKLLGV KDNVIKVNPE QNIRGGAALL LEYARDTVGH IPRSLADWYG AVAKYSGSNN    180
QVVANDFADQ VYATIQEGAE EVLADGQHLV LKPNKVIPNK KTSDKLKFQK TKEMDVDCPK    240
GVDCRYIPAA YKQFSSLTDY GNYDLATRPK DGNDIRYIII HDTEGSYDSA INWFQDQSYA    300
SAHYVIRSSD GQITEMVKPE DVAWQAGNWY FNAHSIGIEH EGYAVQGATW YSEQMYHASA    360
KLVKYLAEKY HVPLDRAHIL GHDNVPGLTP AAQTRMHWDP AAYWNWEHFF KKLGVPIHPT    420
KGKKNSRIVT IAPKYLKNMP PLTYQNEQLE KQPANFVYLH TEPSFSAPYI GDPALHADGS    480
PGTTAINDWG DKASTGQSFY VADHKGDWMA IYYGGKKAWF FNPKRKNTVS GKGILVTPKK    540
GLDAIPVYGT AYPENSAYEG TGIPTGSEGK ITPLQYTIAA GQVYVATNPV KADYYYAKLF    600
NRLSENKVVK GNDEYYQIFF NHRVAFVKKS DVEVKK                              636

SEQ ID NO: 66          moltype = AA   length = 605
FEATURE                Location/Qualifiers
source                 1..605
                       mol_type = protein
                       organism = Bacillus sporothermodurans
SEQUENCE: 66
SKHYTIDTNH HSPLQQAFTK AAKEFHVPES LLMSVAYNES RWLDHHGQPS TSGGYGIMHL     60
TEAKPSQSLS AKGNGIAHSS AINVQQMYTL KTAAKLLGVK DNVIKVNPEQ NIRGGAALLL    120
EYARDTVGHI PRSLADWYGA VAKYSGSNNQ VVANDFADQV YATIQEGAEE VLADGQHLVL    180
KPNKVIPNKK TSDKLKFQKT KEMDVDCPKG VDCRYIPAAY KQFSSLTDYG NYDLATRPKD    240
GNDIRYIIIH DTEGSYDSAI NWFQDQSYAS AHYVIRSSDG QITEMVKPED VAWQAGNWYF    300
NAHSIGIEHE GYAVQGATWY SEQMYHASAK LVKYLAEKYH VPLDRAHILG HDNVPGLTPA    360
AQTRMHWDPA AYWNWEHFFK KLGVPIHPTK GKKNSRIVTI APKYLKNMPP LTYQNEQLEK    420
QPANFVYLHT EPSFSAPYIG DPALHADGSP GTTAINDWGD KASTGQSFYV ADHKGDWMAI    480
YYGGKKAWFF NPKRKNTVSG KGILVTPKKG LDAIPVYGTA YPENSAYEGT GIPTGSEGKI    540
```

| | | |
|---|---|---|
| TPLQYTIAAG QVYVATNPVK ADYYYAKLFN RLSENKVVKG NDEYYQIFFN HRVAFVKKSD | 600 |
| VEVKK | 605 |

| SEQ ID NO: 67 | moltype = DNA length = 1941 |
|---|---|
| FEATURE | Location/Qualifiers |
| sig_peptide | 1..108 |
| mat_peptide | 109..1938 |
| source | 1..1941 |
| | mol_type = genomic DNA |
| | organism = Paenibacillus pini |
| CDS | 1..1938 |

SEQUENCE: 67

```
ttgaaactac tgcgaacaat ccaatggaaa aagctgtcgc tcgcactcac agtcgcctca   60
ctggcggttt ccggattcac acccggactt cctgatccat tcaaggccgt accttctgta  120
tatgcggagc aagacaagac gaattcgttg caacaagcct tcgaatcagc ggctaaggag  180
tcggagtgc ctgtgagcat tttgatgtcc gtttcctaca accttacaag gtgggagcat  240
catcatggcc aacccagtac ttctggtgga tacggtatca tgcatttgac cgacttgccg  300
gtacaggata aagaagacca taacggaacc gacgacgagg aaacccatc gacttcggac  360
gatccgagcg ttcataccct atctgcggcg cacaactat tgaatcttga tccggactta  420
ctgaagcagg atcctgtgtg caacattcga ggcggagccg cattgctggc gaagtacgct  480
caggaaaccc tcggtaaact gacggcatcg gaatccgatt ggtatggtgg cgttgccaaa  540
tacgcggtt ctcaagattc gggggcctct ctggagtttg ccaataatgt atttgatacg  600
attcagcagg gaatatcgcg gcaaacttcg gaaggacaga tgctacgtct tccatccaag  660
gaggtgaagc taacctgga taccgttcaa acgcttcatc tgcgtccatc gaaacccgat  720
aacgtcgagt gccctcgcaa tctccactgc agatctgttc ctgcagccta tcagcagaac  780
ggggatgacc cgtcggatta ttccaattat gatcttgcg accgtcccaa atttggtcct  840
gatattcgct atattgtcat tcatgatacc gaagaaacct atcaggatac gctcaatata  900
tttaccaatc cgaattcgaa tgtcagcgcc cactatgttc tccgttcgtc cgacgggcag  960
atcacgcaaa tggtcaagac aaaggatgta ccgtggcatg caggcaactg gtatttcaat 1020
atgcactcga ttggcgtaga gcatgagggc tttgctatgg aaggagcaac ctggttcacc 1080
gagaggcttt accgttcatc tgcagcattg gtacattatc tggcggagaa atatgatatt 1140
ccgctcgatc gggcccatat tatcggccat gatgaaatac cggtctcac tccagcccgt 1200
caaggtgtta tgcatcagga tcccggccct tttgggattg ggagcacta catggagcta 1260
gttggagcac cgatccactc caaacatggt actaaagaca ttgtgacaat caagcctggc 1320
tttaaaacca atcaaccaga tatcaatgat gcgcctgctc agccatctaa cttccttac 1380
ttatataaag agcccgactt taacgctgag ctgattgatg atcccgccct tgtctctcaa 1440
aacaagaaag acgggttcag cataggagcc aaggctacca tagggcaaac cttctcactt 1500
gccggcaagc aggggattg gaccgcaatc tggttcggag gacagaaagc ctggttctat 1560
aatccgaaag gaaaaaatac ggtttcaggt aaggggatgc tagtcactcc gaaagccggc 1620
gcagcttcca ttccggtcta tggtgcagct tatccggaag ccgcagcata tccagccgat 1680
atcacgccta atgtgctggt tccgctgcag tacactattt cgcatggaca gtcgtatgtt 1740
gccgtagaaa aaaacaaaag cgatgattac tatgctccgg tatacacgaa tgaccccttat 1800
gcgacgaata agctgatcaa gagcaaagaa gagttctacc gaatatactt caatcaccgt 1860
ttcgcctttg tgaaagcctc tgatgtcgag aaggtacgga agcagtcggt gaatgaaaca 1920
acacgtcagg atatcccata a                                          1941
```

| SEQ ID NO: 68 | moltype = AA length = 646 |
|---|---|
| FEATURE | Location/Qualifiers |
| source | 1..646 |
| | mol_type = protein |
| | organism = Paenibacillus pini |

SEQUENCE: 68

```
LKLLRTIQWK KLSLALTVAS LAVSGFTPGL PDPFKAVPSV YAEQDKTNSL QQAFESAAKE  60
FGVPVSILMS VSYNLTRWEH HHGQPSTSGG YGIMHLTDLP VQDKEDHNGT DDEENPSTSD 120
DPSVHTLSAA AQLLNLDPDL LKQDPVCNIR GGAALLAKYA QETLGKLTAS ESDWYGGVAK 180
YSGSQDSGAS LEFANNVFDT IQQGISRQTS EGQMLRLPSK EVKPNLDTVQ TLHLRPSKPD 240
NVECPRNLHC RSVPAAYQQN GDDPSDYSNY DLADRPKFGP DIRYIVIHDT EETYQDTLNI 300
FTNPNSNVSA HYVLRSSDGQ ITQMVKTKDV PWHAGNWYFN MHSIGVEHEG FAMEGATWFT 360
ERLYRSSAAL VHYLAEKYDI PLDRAHIIGH DEIPGLTPAR QGVMHQDPGP FWDWEHYMEL 420
VGAPIHSKHG TKDIVTIKPG FKTNQPDIND APAQPSNFLY LYKEPDFNAE LIDDPALVSQ 480
NKKDGFSIGA KATIGQTFSL AGKQGDWTAI WFGGQKAWFY NPKGKNTVSG KGMLVTPKAG 540
AASIPVYGAA YPEAAAYPAD ITPNVLVPLQ YTISHGQSYV AVEKNKSDDY YAPVYTNDPY 600
ATNKLIKSKE EFYRIYFNHR FAFVKASDVE KVRKQSVNET TRQDIP              646
```

| SEQ ID NO: 69 | moltype = AA length = 610 |
|---|---|
| FEATURE | Location/Qualifiers |
| source | 1..610 |
| | mol_type = protein |
| | organism = Paenibacillus pini |

SEQUENCE: 69

```
VPSVYAEQDK TNSLQQAFES AAKEFGVPVS ILMSVSYNLT RWEHHHGQPS TSGGYGIMHL  60
TDLPVQDKED HNGTDDEENP STSDDPSVHT LSAAAQLLNL DPDLLKQDPV CNIRGGAALL 120
AKYAQETLGK LTASESDWYG GVAKYSGSQD SGASLEFANN VFDTIQQGIS RQTSEGQMLR 180
LPSKEVKPNL DTVQTLHLRP SKPDNVECPR NLHCRSVPAA YQQNGDDPSD YSNYDLADRP 240
KFGPDIRYIV IHDTEETYQD TLNIFTNPNS NVSAHYVLRS SDGQITQMVK TKDVPWHAGN 300
WYFNMHSIGV EHEGFAMEGA TWFTERLYRS SAALVHYLAE KYDIPLDRAH IIGHDEIPGL 360
TPARQGVMHQ DPGPFWDWEH YMELVGAPIH SKHGTKDIVT IKPGFKTNQP DINDAPAQPS 420
NFLYLYKEPD FNAELIDDPA LVSQNKKDGF SIGAKATIGQ TFSLAGKQGD WTAIWFGGQK 480
AWFYNPKGKN TVSGKGMLVT PKAGAASIPV YGAAYPEAAA YPADITPNVL VPLQYTISHG 540
```

| QSYVAVEKNK SDDYYAPVYT NDPYATNKLI KSKEEFYRIY FNHRFAFVKA SDVEKVRKQS | 600 |
| VNETTRQDIP | 610 |

```
SEQ ID NO: 70            moltype = DNA   length = 711
FEATURE                  Location/Qualifiers
sig_peptide              1..60
mat_peptide              61..708
source                   1..711
                         mol_type = genomic DNA
                         organism = Bacillus cohnii
CDS                      1..708
SEQUENCE: 70
atgaaaatag tagcaacttt tttatgtgta tttattttg tctgtggttg ttcaaaggct   60
gaagtcacaa atgtcgagag tgatgagaca atatcattag ttaaaaaga agatgaatta   120
acttataaaa agccagatac aaatccgagt gaatctttat atgtaacttc gtactattta   180
cctaacgata attcgcgacg gagaacagca gaagttacac atataatgat tcattacacc   240
agtaacgcag caaggaatcc acagaacccg tatgtaaatg aagatattta cgcactgttt   300
gaagaatatg gcgtttcagc acattatatt attgatcgcg aaggtaatat ttttcaatta   360
gtggatgaga gtagagtggc gtttcatgca ggaaaaggaa acgatttaaa cttttttggac  420
taccgaaata acatgaatga atattcaatt ggtatcgaac ttatggcaat tggaacgaaa   480
gaagaaatga gcctaaattt acaggaaggt caatacgaac taataccacc atcacatata   540
ggttatacag atgagcaata tcactcatta gcaaaactgt tagaagactt gtatgagcgt   600
tatccaaagg tattaaaaaa cagagagaac gtagtagggc atgatgaata cgcacctgtt   660
cgaaaatcag atcctggaag tttattcgat tggaataaaa ttggtttctg a            711

SEQ ID NO: 71            moltype = AA   length = 236
FEATURE                  Location/Qualifiers
source                   1..236
                         mol_type = protein
                         organism = Bacillus cohnii
SEQUENCE: 71
MKIVATFLCV FIFVCGCSKA EVTNVESDET ISLVKKEDEL TYKKPDTNPS ESLYVTSYYL   60
PNDNSRRRTA EVTHIMIHYT SNAARNPQNP YVIEDIYALF EEYGVSAHYI IDREGNIFQL   120
VDESRVAFHA GKGNDLNFLD YRNNMNEYSI GIELMAIGTK EEMSLNLQEG QYELIPPSHI   180
GYTDEQYHSL AKLLEDLYER YPKVLKNREN VVGHDEYAPV RKSDPGSLFD WNKIGF       236

SEQ ID NO: 72            moltype = AA   length = 216
FEATURE                  Location/Qualifiers
source                   1..216
                         mol_type = protein
                         organism = Bacillus cohnii
SEQUENCE: 72
EVTNVESDET ISLVKKEDEL TYKKPDTNPS ESLYVTSYYL PNDNSRRRTA EVTHIMIHYT   60
SNAARNPQNP YVIEDIYALF EEYGVSAHYI IDREGNIFQL VDESRVAFHA GKGNDLNFLD   120
YRNNMNEYSI GIELMAIGTK EEMSLNLQEG QYELIPPSHI GYTDEQYHSL AKLLEDLYER   180
YPKVLKNREN VVGHDEYAPV RKSDPGSLFD WNKIGF                             216

SEQ ID NO: 73            moltype = DNA   length = 1356
FEATURE                  Location/Qualifiers
sig_peptide              1..78
mat_peptide              79..1353
source                   1..1356
                         mol_type = genomic DNA
                         organism = Kribbella sp.
CDS                      1..1353
SEQUENCE: 73
atgagtcaca aagttcccag actggtcgcg gtgctcgccg ccggcgcact ggccttcagc   60
gcgctcccca gcaacgcatc cacgccggtc gagaccggca gcacctcgac gctgtccgag   120
gccttcaaga ccgccgcgac ccagtacgac gtaccgcgtg agctcctggt cggcatcggg   180
tacgccgagt cgcaccctga cggccacgac ggtcagccca gccaggccaa cgggtacgac   240
gtcatgcacc tggccagcaa cccgagcaac ccgaccatgt ccgaggcggc gaagctcacc   300
ggcctccgg  tcgagaagct ggccaaggac gagagcgcga acgtgctcgg cgcggccgcc    360
gtactcgacg cgtacgccga caaggccggc ctgcaagggc aaacgcgtga cgacatcggc   420
aagtggtacg aggtcgtcgc ccagtactcg cactccgcga acggccgac acgggccgctc   480
tacaccgacg aggtctaccg gatcgtcggc ctcggagtcg gcgccgaagg cgtctccacc   540
cagccggtca aggtgacgcc ggaccgcggc aagtacgcga acgtcgcccc gctcggcacc   600
cggacgccgg cctcgatcca ggccgtcgac tacccgggcg cgatctggaa cgcggccagc   660
accagcaact accgcgtcgg acgcaccctcc gcgatcagca cgtcgtcat ccacgtgacc   720
caaggctcgt acgccggcac gatcagctgg ttcaagaacg cgtcggcgca ggtcagcgcg   780
cactacgtgg tgcgttccag cgacgggcag atcaccagga tggtggccga gaaggacacc   840
gcctggcacg cccgcagcgc gaacccgtac tcggtcggca tcgagcacga gggctgggtc   900
gaccagccgt cgtggttcac cgacgcgatg taccgcgcgt ccgcggcgct gacccgcaac   960
atcgccgacc ggcgcggcat cccgaagacc cggacgtaca tcaagggcca cagcgagatg   1020
cccgacaacg accacaccga cccgggtccg aactggaacg acgggccttat catgcagctg   1080
gtgaacggca gcaaccccga acccgccgacg tacaacttca ccacgtacgg cagtggcgtc   1140
cgggtccgct cggacgcgaa gctgaccgcg tccatcgtca ccaccctgcc cggcccgacg   1200
caggtcttcg tcacctgcca gaagcagggc gacctggtca ccgccgaggg caccagcaac   1260
aactggtggt ccaagctgcg cgaccagggc ggctacatga ccaacatcta catcgaccac   1320
cccgacgcca agctcccggg cgtccccgtc tgctga                             1356
```

```
SEQ ID NO: 74            moltype = AA   length = 451
FEATURE                  Location/Qualifiers
source                   1..451
                         mol_type = protein
                         organism = Kribbella sp.
SEQUENCE: 74
MSHKVPRLVA VLAAGALAFS ALPSNASTPV ETGSTSTLSE AFKTAATQYD VPRELLVGIG   60
YAESHLDGHD GQPSQANGYG VMHLASNPSN PTMSEAAKLT GLPVEKLAKD ESANVLGAAA  120
VLDAYADKAG LQGQTRDDIG KWYEVVAQYS HSADGPTARL YTDEVYRIVG LGVGAEGVST  180
QPVKVTPDRG KYANVAPLGT RTPASIQAVD YPGAIWNAAS TSNYRVGRTS AISTIVIHVT  240
QGSYAGTISW FKNASAQVSA HYVVRSSDGQ ITQMVAEKDT AWHARSANPY SVGIEHEGWV  300
DQPSWFTDAM YRASAALTRN IADRRGIPKT RTYIKGHSEM PDNDHTDPGP NWNWTYYMQL  360
VNGSNPNPPT YNFTTYGSGV RVRSDAKLTA SIVTTLPGPT QVFVTCQKQG DLVTAEGTSN  420
NWWSKLRDQG GYMTNIYIDH PDAKLPGVPV C                                451

SEQ ID NO: 75            moltype = AA   length = 425
FEATURE                  Location/Qualifiers
source                   1..425
                         mol_type = protein
                         organism = Kribbella sp.
SEQUENCE: 75
STPVETGSTS TLSEAFKTAA TQYDVPRELL VGIGYAESHL DGHDGQPSQA NGYGVMHLAS   60
NPSNPTMSEA AKLTGLPVEK LAKDESANVL GAAAVLDAYA DKAGLQGQTR DDIGKWYEVV  120
AQYSHSADGP TARLYTDEVY RIVGLGVGAE GVSTQPVKVT PDRGKYANVA PLGTRTPASI  180
QAVDYPGAIW NAASTSNYRV GRTSAISTIV IHVTQGSYAG TISWFKNASA QVSAHYVVRS  240
SDGQITQMVA EKDTAWHARS ANPYSVGIEH EGWVDQPSWF TDAMYRASAA LTRNIADRRG  300
IPKTRTYIKG HSEMPDNDHT DPGPNWNWTY YMQLVNGSNP NPPTYNFTTY GSGVRVRSDA  360
KLTASIVTTL PGPTQVFVTC QKQGDLVTAE GTSNNWWSKL RDQGGYMTNI YIDHPDAKLP  420
GVPVC                                                             425

SEQ ID NO: 76            moltype = DNA   length = 990
FEATURE                  Location/Qualifiers
sig_peptide              1..75
mat_peptide              76..987
source                   1..990
                         mol_type = genomic DNA
                         organism = Bacillus sp.
CDS                      1..987
SEQUENCE: 76
atgaaaaggc tcgttcttgt atttagtatc attgccgtac tttttatgag catttctcct   60
gttcatacag ttgcagaaaa cccatagcaat ctgtatgatg tgagatccgg agatacatta  120
tggaagatcg ccaataaata cggtacatct tccaaaatc taaaagaaac aaatggattg  180
caatctgatt tattgttagt tggtcagaga ttgtttgttc caatgaggta tgaagtcgtt  240
gctggagata cactttggaa gctttcaaga gcatataact cttccgttca agcgataaaa  300
gcaacaaatg gacttacatc ggatgtattg tacataggc aaaagttgaa aattcctcct  360
aagaaattac ctatgatgg tcagtatgtt ctcatgacgg aggaatt taaagactgg  420
ttatttaacc atgaattcac gaggaacata agcctcattc aacagcacca cacgtggtca  480
ccggcttatg gacattttaa tggcaaaaat cacttttcgt tgcttaaggg gatgagtat  540
tatcatacga agaagtgggg ctgggaaaac attgcccaga acattacaac attcccagac  600
ggaaaaatag ccgtatctag accatttaac agtgctcctg acggctcgat tggtccaaaa  660
gcaaattctg ttgggttaaa catcgaacat gttgggaatt ttgacttagg caatgatcaa  720
atgactgccg aacataggga aacgattatc tatcttacgg cattgctttg tatgaagttt  780
gggttaactc cttctgttga cagcatcaca tatcatcgtt ggtgggatat gaacacaaag  840
gagagagtgt tggatcgaag tgaaggagtt tctgtaaaaa catgcccagg aacgggattt  900
tccggaggga atacaacaga aagtgcaaag aataattttt atcctttagt gtcacgtaaa  960
atgcaagaga ttagggcatc catgaattaa                                   990

SEQ ID NO: 77            moltype = AA   length = 329
FEATURE                  Location/Qualifiers
source                   1..329
                         mol_type = protein
                         organism = Bacillus sp.
SEQUENCE: 77
MKRLVLVFSI IAVLFMSISP VHTVAENHSN LYDVRSGDTL WKIANKYGTS VQNLKETNGL   60
QSDLLLVGQR LFVPMRYEVV AGDTLWKLSR AYNSSVQAIK ATNGLTSDVL YIGQKLKIPP  120
KKLPMDGQYV LMTREEFKDW LFNHEFTRNI SLIQQHHTWS PAYGHFNGKN HFSLLKGMEY  180
YHTKEVGWEN IAQNITTFPD GKIAVSRPFN SAPDGSIGPK ANSVGLNIEH VGNFDLGNDQ  240
MTAEHRETII YLTALLCMKF GLTPSVDSIT YHRWWDMNTK ERVLDRSEGV SVKTCPGTGF  300
FGGNTTESAK NNFYPLVSRK MQEIRASMN                                   329

SEQ ID NO: 78            moltype = AA   length = 304
FEATURE                  Location/Qualifiers
source                   1..304
                         mol_type = protein
                         organism = Bacillus sp.
SEQUENCE: 78
ENHSNLYDVR SGDTLWKIAN KYGTSVQNLK ETNGLQSDLL LVGQRLFVPM RYEVVAGDTL   60
WKLSRAYNSS VQAIKATNGL TSDVLYIGQK LKIPPKKLPM DGQYVLMTRE EFKDWLFNHE  120
```

```
FTRNISLIQQ HHTWSPAYGH FNGKNHFSLL KGMEYYHTKE VGWENIAQNI TTFPDGKIAV    180
SRPFNSAPDG SIGPKANSVG LNIEHVGNFD LGNDQMTAEH RETIIYLTAL LCMKFGLTPS    240
VDSITYHRWW DMNTKERVLD RSEGVSVKTC PGTGFFGGNT TESAKNNFYP LVSRKMQEIR    300
ASMN                                                                 304

SEQ ID NO: 79           moltype = DNA   length = 993
FEATURE                 Location/Qualifiers
sig_peptide             1..72
mat_peptide             73..990
source                  1..993
                        mol_type = genomic DNA
                        organism = Bacillus sp.
CDS                     1..990
SEQUENCE: 79
atgaagaaaa accttgtcct catttgtagt ttaatcctaa tcatattcat gaatatcctt    60
cctgttcacg cgatttcaaa taaccatagc aacctttatg tagtaaaagc tggagataca   120
ttacctgaaa ttgcagataa attcgatact accatagagg agttgaagct aacaaatggt   180
ttgcaatccg attctctatt tgttgaacaa aaattgtggg ttcctattat gcatgaagtt   240
gttacaggag aaacactgca ggacattgca tcaacttacc attcttcaat agaaaccata   300
aaaaaagcaa atggactcgt ttctgatgag ctatatgcag gcaaatatt aaaagttact   360
cctaaaaaaa tgatcatgca aggtcaacat atccttatga caaggaaga atttaaagat   420
tggttgttta caaccaatt taatcgtgat attcgtatca tccaacaaca tcacacatgg   480
ttaccttctt ataagcaatt taaggtaca aaccattttc aaatgttaca agtatggag   540
aattttcata gaaggaaat gggctggcat aatattgcgc aaaacataac gaccttccct   600
gatgaaaag tagcagtatc tagaccattt aacattgccc cagaaggttc aattggatca   660
aaggcgaatt cagtagggct aaccatcgaa aatattgata ctttgatct aggtcacgat   720
gtaatgacca aggaacagca ggatacaatt gtttacataa ctgccttgct ttgtatcaag   780
ttcggcttaa ccccttcaat tgacagtatt acttatcatc attggtggaa tttacaaaca   840
aaggaaagag tattagataa cggaccggat tataatgtga agacttgtcc cggtactaat   900
ttttcggag gcaatgccac taacgatgca aagaaacact tttaccctct tgtatccgca   960
aagatagaag aaattgtagc aacaatggat tga                                 993

SEQ ID NO: 80           moltype = AA    length = 330
FEATURE                 Location/Qualifiers
source                  1..330
                        mol_type = protein
                        organism = Bacillus sp.
SEQUENCE: 80
MKKNLVLICS LIIIFMNIL PVHAISNNHS NLYVVKAGDT LPEIADKFDT TIEELKLTNG     60
LQSDSLFVEQ KLWVPIMHEV VTGETLQDIA STYHSSIETI KKANGLVSDE LYAGQILKVT   120
PKKMIMQGQH ILMTKEEFKD WLFNNQFNRD IRIIQQHHTW LPSYKQFKGT NHFQMLQSME   180
NFHKKEMGWH NIAQNITTFP DGKVAVSRPF NIAPEGSIGS KANSVGLTIE NIGNFDLGHD   240
VMTKEQQDTI VYITALLCIK FGLTPSIDSI TYHHWWNLQT KERVLDNGPD YNVKTCPGTN   300
FFGGNATNDA KKHFYPLVSA KIEEIVATMD                                    330

SEQ ID NO: 81           moltype = AA    length = 306
FEATURE                 Location/Qualifiers
source                  1..306
                        mol_type = protein
                        organism = Bacillus sp.
SEQUENCE: 81
ISNNHSNLYV VKAGDTLPEI ADKFDTTIEE LKLTNGLQSD SLFVEQKLWV PIMHEVVTGE    60
TLQDIASTYH SSIETIKKAN GLVSDELYAG QILKVTPKKM IMQGQHILMT KEEFKDWLFN   120
NQFNRDIRII QQHHTWLPSY KQFKGTNHFQ MLQSMENFHK KEMGWHNIAQ NITTFPDGKV   180
AVSRPFNIAP EGSIGSKANS VGLTIENIGN FDLGHDVMTK EQQDTIVYIT ALLCIKFGLT   240
PSIDSITYHH WWNLQTKERV LDNGPDYNVK TCPGTNFFGG NATNDAKKHF YPLVSAKIEE   300
IVATMD                                                              306

SEQ ID NO: 82           moltype = DNA   length = 990
FEATURE                 Location/Qualifiers
sig_peptide             1..69
mat_peptide             70..987
source                  1..990
                        mol_type = genomic DNA
                        organism = Bacillus sp.
CDS                     1..987
SEQUENCE: 82
atgaaaaggc tcgttcttgt agttagttta attgccatac ttttttgtgag catttctcct    60
gtttctgcag ctgccgaaaa ccatagcaat ctgtatgatg tgagatctgg agatacatta   120
tggaagatcg ccaataaata tggtacatct gtccaaaatt taaagaaac aaatggactg   180
caatctgatt tgctgttagt tggtcaaaga ttgtttgttc aatgagcta cgaagtcgtt   240
tctggagata cactttggaa gctttcaaga gcatataatt cttcagtcca agcaataaaa   300
gaaacaaatg gacttacatc ggatgtattg tacatagggc aaaagttaaa aatccctcct   360
aagaaattac ctatgatgg tcagtatgtt ctcatgacgc gagaggaatt taaagattgg   420
ttatttaacc atgaatttac gagaaacata agccttattc aacagcacca cacgtggtcg   480
ccggcctatg gcatttaa tggaaacaat cacttttcgt tacttaaggg aatggagtat   540
tatcatacga aagaagtggg ttgggaaaat atagctcaga accttacaac attccccgat   600
gggagaatag cagtctctag gccatttaac agtgctccgg atggtagtat tggaccaaaa   660
gctaactcga taggattaaa catcgaacat atcgggaatt tgatttagg taatgatcaa    720
```

```
atgacagctg aacatagaga aacgattatc tatcttacgg cgttgctatg tatgaagttc    780
ggattaactc cttctattga cagcatcaca tatcatcgtt ggtgggatat gaacacaaag    840
gagcgtgtgt tggatcgaag tgaaggagtt tctgtgaaaa cttgtccagg tactggattt    900
ttcggcggga atacgacaga aagtgctaag agtaattttt atcctttagt gtcacgtaaa    960
atagaagaga ttagagcaac tttgaattaa                                     990

SEQ ID NO: 83          moltype = AA   length = 329
FEATURE                Location/Qualifiers
source                 1..329
                       mol_type = protein
                       organism = Bacillus sp.
SEQUENCE: 83
MKRLVLVVSL IAILFVSISP VSAAAENHSN LYDVRSGDTL WKIANKYGTS VQNLKETNGL     60
QSDLLLVGQR LFVPMSYEVV SGDTLWKLSR AYNSSVQAIK ETNGLTSDVL YIGQKLKIPP    120
KKLPMDGQYV LMTREEFKDW LFNHEFTRNI SLIQQHHTWS PAYGHFNGNN HFSLLKGMEY    180
YHTKEVGWEN IAQNLTTFPD GRIAVSRPFN SAPDGSIGPK ANSIGLNIEH IGNFDLGNDQ    240
MTAEHRETII YLTALLCMKF GLTPSIDSIT YHRWWDMNTK ERVLDRSEGV SVKTCPGTGF    300
FGGNTTESAK SNFYPLVSRK IEEIRATLN                                     329

SEQ ID NO: 84          moltype = AA   length = 306
FEATURE                Location/Qualifiers
source                 1..306
                       mol_type = protein
                       organism = Bacillus sp.
SEQUENCE: 84
AAENHSNLYD VRSGDTLWKI ANKYGTSVQN LKETNGLQSD LLLVGQRLFV PMSYEVVSGD     60
TLWKLSRAYN SSVQAIKETN GLTSDVLYIG QKLKIPPKKL PMDGQYVLMT REEFKDWLFN    120
HEFTRNISLI QQHHTWSPAY GHFNGNNHFS LLKGMEYYHT KEVGWENIAQ NLTTFPDGRI    180
AVSRPFNSAP DGSIGPKANS IGLNIEHIGN FDLGNDQMTA EHRETIIYLT ALLCMKFGLT    240
PSIDSITYHR WWDMNTKERV LDRSEGVSVK TCPGTGFFGG NTTESAKSNF YPLVSRKIEE    300
IRATLN                                                              306

SEQ ID NO: 85          moltype = DNA   length = 2004
FEATURE                Location/Qualifiers
sig_peptide            1..105
mat_peptide            106..2001
source                 1..2004
                       mol_type = genomic DNA
                       organism = Streptomyces sp.
CDS                    1..2001
SEQUENCE: 85
atgaagaaac cgttggggaa aattgtcgca agcaccgcac tactcatttc tgttgctttt     60
agttcatcga tagcatcagc acatcatcat caccatcatc ctagggacga cgacaccggc    120
gtgctccagg cggcgttcgc cgacgcggcc gagcgctacc aggtgccgga ggaagtgctg    180
ctcggcgtct cctatctcca gtcccgctgg gacggccacc gtggcgcggc gagcgtgacc    240
ggcggctacg gcccgatgca tctgacggac gcgcacaccg cgctcagccg ggaggcgggc    300
gcggtggaca accaccatct gcacggggag gaggaccgc gcggcacga cgacgggtc      360
cttgagatgc cggaggagga gatcccgccg gttccggagc gctccgaggt gcccgaacgg    420
ctccagacgt tggaccgggc ggcggagctg accgggctcg acccggagga cctgcggtcc    480
agcaacgcgg cgaacgtaca gggcggcgcc gcgctgctgg ccgcggcgca gcgcgacctc    540
ggcctgcagc cgagcgacga cccggcggac tggtacgacg ccgtcgcctc ctacgccggg    600
tccgcctcgc gggaggcggc gcggttcttc gccgacgagg tgtactcggt gatcaacgag    660
ggcgcccggc acaccaccgg cgagggccag gtggtggagc tgcccgccac cgaggtgacc    720
ccgcgcaccg gcaggcgtc cgcgctggcc ctgccggagc agcggcgcga tcccggggtg    780
gagtgcccgc ccacggtctc ctgcgagtgg atcccggcgg cctacgagga gtacgagcgc    840
gccgacggct cggtgacgta cggcaaccac gacaagggcg accggccgga cgggcagcgg    900
gtgcgctaca tcgtcatcca cgacatggag ggctacttct ggccgtccat cggactggtg    960
cagaacccga cctgggcgtc ctggcagtac agcctccagg cgtcggacgg gcacatcgcg   1020
cagcacatcc tggccaagga cgtcggctgg caggccggca actggtacgt caacgccacg   1080
tccatcggcc tggagcacga gggtttcctg cgggccccgg acgcctggta caccgaggtg   1140
atgtaccgct cctcggcgcg gctggtgcgc tacctggccc ggcagcacga catcccgctg   1200
gaccggcacc acatcatcgg ccactacaac gtgcccgggca tcggcaccgc caacatcccc   1260
gggatgcaca ccgaccccgg tccgtactgg gactgggcgc actacttccg gctgatgggc   1320
gcgccgatca cgcccagcgc ccggccgcac agcgcgctg tgacgatccg tcccgactac   1380
gacaaccacc gcccggtgtt caccggctgc gaccccggcg gacgccgccgc gccgtgcgcg   1440
ccgcacggct ccagcgcggt gcggctgcac gtggcgccga tcatgacgc ggcgctggtg   1500
ccggacatcg gcacccatcc gggcagcggc ggccggtccg gcatctcgat ctacgacatc   1560
ggcgcccgcg cctcgaccgg ccagcagtac gcggtggcgg agcgcgccgg cgagtggacg   1620
gcgatctggt tcaacgacga gaaggcgtgg ttccacgagc ccggccggca gcggacctcg   1680
gtcccgagcc ggggctggat cgccaccccg aaggagggcg tggaccgggt gccggtctac   1740
ggcgtggcgt acccggagcc ggaggactac ccgcggggcg tgccggtgcg cgcgttcgcg   1800
ccgctgccgt accagttcac ggccggtcag tcgtacgcgg tggggcgcgg cggcgaggcg   1860
ttcgacgggg agttctactc ggcgacccgc ttcgacacgt gggcagcca ggtgatccgg   1920
gggcacggt actaccagat ccagctcggc caccggcacg cgtatgtgaa ggcggaggac   1980
gtggacgtgg tgcccgtgcg ctga                                          2004

SEQ ID NO: 86          moltype = AA   length = 667
FEATURE                Location/Qualifiers
source                 1..667
```

```
                        mol_type = protein
                        organism = Streptomyces sp.
SEQUENCE: 86
MKKPLGKIVA STALLISVAF SSSIASAHHH HHHPRDDDTG VLQAAFADAA ERYQVPEEVL   60
LGVSYLQSRW DGHRGAASVT GGYGPMHLTD AHTALSREAG AVDNHHLHGE EDPRGDDGRV  120
LEMPEEEIPP VPERSEVPER LQTVDRAAEL TGLDPEDLRS SNAANVQGGA ALLAAAQRDL  180
GLEPSDDPAD WYAAVASYAG SASREAARFF ADEVYSVINE GARHTTGEGQ VVELPATEVT  240
PRTGQASALA LPEQRRDPRV ECPPTVSCEW IPAAYEEYER ADGSVTYGNH DKGDRPDGQR  300
VRYIVIHDME GYFWPSIGLV QNPTWASWQY SLQASDGHIA QHILAKDVGW QAGNWYVNAT  360
SIGLEHEGFL RAPDAWYTEV MYRSSARLVR YLARQHDIPL DRHHIIGHYN VPGIGTANIP  420
GMHTDPGPYW DWAHYFRLMG APITPSARPH SALVTIRPDY DNHRPVFTGC DPADAAAPCA  480
PHGSSAVRLH VAPSHDAALV PDIGTHPGSG GRSGISIYDI GARASTGQQY AVAERAGEWT  540
AIWFNGEKAW FHDPARQRTS VPSRGWIATP KEGVDRVPVY GVAYPEPEDY PPGVPVRAFA  600
PLPYQFTAGQ SYAVGRGGEA FDGEFYSATR FDTVGSQVIR GQRYYQIQLG HRHAYVKAED  660
VDVVPVR                                                            667

SEQ ID NO: 87           moltype = AA  length = 632
FEATURE                 Location/Qualifiers
source                  1..632
                        mol_type = protein
                        organism = Streptomyces sp.
SEQUENCE: 87
DDDTGVLQAA FADAAERYQV PEEVLLGVSY LQSRWDGHRG AASVTGGYGP MHLTDAHTAL   60
SREAGAVDNH HLHGEEDPRG DDGRVLEMPE EEIPPVPERS EVPERLQTVD RAAELTGLDP  120
EDLRSSNAAN VQGGAALLAA AQRDLGLEPS DDPADWYAAV ASYAGSASRE AARFFADEVY  180
SVINEGARHT TGEGQVVELP ATEVTPRTGQ ASALALPEQR RDPRVECPPT VSCEWIPAAY  240
EEYERADGSV TYGNHDKGDR PDGQRVRYIV IHDMEGYFWP SIGLVQNPTW ASWQYSLQAS  300
DGHIAQHILA KDVGWQAGNW YVNATSIGLE HEGFLRAPDA WYTEVMYRSS ARLVRYLARQ  360
HDIPLDRHHI IGHYNVPGIG TANIPGMHTD PGPYWDWAHY FRLMGAPITP SARPHSALVT  420
IRPDYDNHRP VFTGCDPADA AAPCAPHGSS AVRLHVAPSH PDIGT HPGSGGRSGI       480
SIYDIGARAS TGQQYAVAER AGEWTAIWFN GEKAWFHDPA RQRTSVPSRG WIATPKEGVD  540
RVPVYGVAYP EPEDYPPGVP VRAFAPLPYQ FTAGQSYAVG RGGEAFDGEF YSATRFDTVG  600
SQVIRGQRYY QIQLGHRHAY VKAEDVDVVP VR                                632

SEQ ID NO: 88           moltype = DNA  length = 723
FEATURE                 Location/Qualifiers
sig_peptide             1..72
mat_peptide             73..720
source                  1..723
                        mol_type = genomic DNA
                        organism = Bacillus sp.
CDS                     1..720
SEQUENCE: 88
atggtaagaa acttaggaat aaatatactc attgtaacct tatttttaat aggatgcaca   60
acagctgaaa attcccaaac gatcggaaaa gacacattac aagcaatgga agattcgaag  120
atagagaaga aggacttgat gcttcagtcg gcggagacaa gaaacgataa taatcccgta  180
gattcttcttc taccactgga aaactcaaaa ccgcggaacg aggcaatcac catgtcatg  240
gttcatttta taagcaatgc tgcgagaaat ccagaagatc cttataatac tattgatatc  300
tattccattt ttgtggaata tggtgtgtca gcacattata tgattggaag agatgggaca  360
gtgttcggc ttgtatcaga agatcgtgtc gcttatcatg ctgggcagg agagcttgaa   420
gattatcctg actatacgga cagcttaaat gaattttcga taggtattga actccttagt  480
atcggcacta gggaagagat gtttcctgct ataccagtac gtgtctacaa tgtaatagat  540
ccaagattag taggctatac agatgaacaa tacgaatcgc ttaacgtttt attggatgat  600
attttccaga gaaacccatc aataaataga gatagaaatc atgtgattgg gcatgatgaa  660
tacgcacctg gaagaaaagc tgatccaggc tcattatttg attggtctaa actcgggtta  720
tag                                                                723

SEQ ID NO: 89           moltype = AA  length = 240
FEATURE                 Location/Qualifiers
source                  1..240
                        mol_type = protein
                        organism = Bacillus sp.
SEQUENCE: 89
MVRNLGINIL IVTLFLIGCT TAENSQTIGK DTLQAMEDSK IEKKDLMLQS AETRNDNNPV   60
DYLLPLENSK PRTEAITHVM VHFISNAARN PEDPYNTIDI YSIFVEYGVS AHYMIGRDGT  120
VFRLVSEDRV AYHAGAGELE DYPDYTDSLN EFSIGIELLA IGTREEMFPA IPVRVYNVID  180
PRLVGYTDEQ YESLNVLLDD IFQRNPSINR DRNHVIGHDE YAPGRKADPG SLFDWSKLGL  240

SEQ ID NO: 90           moltype = AA  length = 216
FEATURE                 Location/Qualifiers
source                  1..216
                        mol_type = protein
                        organism = Bacillus sp.
SEQUENCE: 90
SQTIGKDTLQ AMEDSKIEKK DLMLQSAETR NDNNPVDYLL PLENSKPRTE AITHVMVHFI   60
SNAARNPEDP YNTIDIYSIF VEYGVSAHYM IGRDGTVFRL VSEDRVAYHA GAGELEDYPD  120
YTDSLNEFSI GIELLAIGTR EEMFPAIPVR VYNVIDPRLV GYTDEQYESL NVLLDDIFQR  180
NPSINRDRNH VIGHDEYAPG RKADPGSLFD WSKLGL                            216
```

```
SEQ ID NO: 91            moltype = DNA  length = 1002
FEATURE                  Location/Qualifiers
sig_peptide              1..81
mat_peptide              82..999
source                   1..1002
                         mol_type = genomic DNA
                         organism = Bacillus sp.
CDS                      1..999
SEQUENCE: 91
atggttagag ggatatgtat agcggttttt atttgttttc ttagtatgac aggtttttg    60
aatttaccac aagcccaagc aatagcgcac aatcatagca acatttatga catcaaatca   120
ggtgatacat tgtggaaaat agctcaaagc tatgggacaa ctgtgaaaga tttaaagcaa   180
acgaacggat taacctccga tttactttta ataggtcaaa ggttgttcgt acctatgaga   240
tatgaagtcg tctctggaga tacgctatgg aaattgtcac agcaatacaa ctccacagta   300
ccgtcaatca aattggcaaa cggtttacca tcagacatga tttacatagg acaaaagtta   360
aaaatcccac aacgaaagtt acgaatggat ggccaacatg ttttaatgac aaaagaggag   420
tttaggggct ggctatttaa tcaaaaaatc aaccgtaata tttctatcat ccaagaacac   480
cacacttggt taccagatta tagtcgcttt aatgaaacaa accatttcca actacttaaa   540
ggaatggaat actttcatgt gcatgaaatg ggatggagta acattgccca gaatatcacg   600
accttcccag atggaacagt ggcggtttct cgtccactaa acgtgcctcc agacggttct   660
attgggaatt acgcgaactc tatcggaatc aacattgaaa gcgtaggaaa tttcgacata   720
ggaaacgata aaatgtcaca ggcgcaaaaa gaaacaattc tctatgttac tgctcttcta   780
tcaattaaac taggccttac gccatctatt gacaccatca catatcacca ctggtgggat   840
atgcgtacag gtaaaagagt gttagacaat aacgaaggat attccgtcaa acatgcccca   900
gggacagcat tctttggcgg caatagcaca aaaagtgcca aaacaaactt ttatccactt   960
gtatctaaga aaatagagga aatcaagaaa acaatggatt ag                     1002

SEQ ID NO: 92            moltype = AA  length = 333
FEATURE                  Location/Qualifiers
source                   1..333
                         mol_type = protein
                         organism = Bacillus sp.
SEQUENCE: 92
MVRGICIAVF ICFLSMTGFL NLPQAQAIAH NHSNIYDIKS GDTLWKIAQS YGTTVKDLKQ   60
TNGLTSDLLL IGQRLFVPMR YEVVSGDTLW KLSQQYNSTV PSIKLANGLP SDMIYIGQKL  120
KIPQRKLRMD GQHVLMTKEE FRGWLFNQKI NRNISIIQEH HTWLPDYSRF NETNHFQLLK  180
GMEYFHVHEM GWSNIAQNIT TFPDGTVAVS RPLNVPPDGS IGNYANSIGI NIESVGNFDI  240
GNDQMSQAQK ETILYVTALL SIKLGLTPSI DTITYHHWWD MRTGKRVLDN NEGYSVKTCP  300
GTAFFGGNST KSAKTNFYPL VSKKIEEIKK TMD                               333

SEQ ID NO: 93            moltype = AA  length = 306
FEATURE                  Location/Qualifiers
source                   1..306
                         mol_type = protein
                         organism = Bacillus sp.
SEQUENCE: 93
IAHNHSNIYD IKSGDTLWKI AQSYGTTVKD LKQTNGLTSD LLLIGQRLFV PMRYEVVSGD   60
TLWKLSQQYN STVPSIKLAN GLPSDMIYIG QKLKIPQRKL RMDGQHVLMT KEEFRGWLFN  120
QKINRNISII QEHHTWLPDY SRFNETNHFQ LLKGMEYFHV HEMGWSNIAQ NITTFPDGTV  180
AVSRPLNVPP DGSIGNYANS IGINIESVGN FDIGNDQMSQ AQKETILYVT ALLSIKLGLT  240
PSIDTITYHH WWDMRTGKRV LDNNEGYSVK TCPGTAFFGG NSTKSAKTNF YPLVSKKIEE  300
IKKTMD                                                             306

SEQ ID NO: 94            moltype = DNA  length = 1449
FEATURE                  Location/Qualifiers
sig_peptide              1..87
mat_peptide              88..1446
source                   1..1449
                         mol_type = genomic DNA
                         organism = Nonomuraea guangzhouensis
CDS                      1..1446
SEQUENCE: 94
ttgaaggccc gactccgcca ttcggccgcg ctgctggccg gcgcgctcat ccccctctcg    60
ctgctcgcag ggcagccggc cggagccgca tccgctgatc ccatgagcga cgcgttcgcc   120
cgtgcggcca ccacgtacga ggtgccccgc gacctgctgg tctcgctcgc ctacgccgaa   180
acccacctgg acggacaccg cggcgaaccc agccgcgagc gcggctacgg ggtgatgcac   240
ctggtcagca cccccgtcag gcacacgctc gagcgcgcgg ccacgctgac gaagcagccc   300
gtctcggcct tgaaggcgga cgacgcggcc aacatcacgg gcggcgccgc cgtgctgcgc   360
gcctacgccg acgagctcgg actgacgccg cgggcccgca ggaacgcggg caagtggtat   420
caggcggtgg ccaagtacgg cggcgcctcc tcgcccgacg tcgcccggtt gtacgccgac   480
accgtctacg accagctgtc caagggatc aaggtcacca cgccggccgg tgagaccctc   540
acggcgacgc cgcggaccgt ccagcccgac gcggctcct acgccaaggc acaggagctg   600
ggcaagacca atacgctcgc ggcggcagtg gactaccgt cggcggcgtg ggcggcggcg   660
cacagcatcg ctccaaccgc ccgacggtg acgcatcga cccgcatcatc                720
atccacgtgg cccagggcac gtacgccggg acgatcgact ggttccagac cgggcccagg   780
ccgaaccccac cctcgtcgca ctacgtcgtc cgttcgtcgg acggcgccgt cacccagatg   840
gtcagggaga aggaccgggc cttccacgcg ggcgactcca caggcgctc ggtcggcatc    900
gagcacgagg gctgggtcga gcaggcctcc tggttcaccg acacgatgta ccgttcctcg   960
gccgcgctga cccgcaacat cgccgacagg tacggcatcc caaggaccg cacccacatc  1020
```

```
atcggccaca gcgaggctcc cggcgccagc cacaccgacc ccgtccgaa ctggaactgg  1080
accaagtaca tgcagtacgt caccaacggc agcggtggcg gcaccaaccc gcacaccgcc  1140
gagtcggtgt gcggcaccgg cttcacggtg atcgactcgg cgcccctggg acgcgcgggc  1200
aacgtctacc tgacgtacaa ctcgggcacc ggcgccaact gcgtggccac gatcaagctg  1260
accaacctcg gcacggccac ggccacgagc gcctacctgg aggtggaggg ccagacacgc  1320
gtcaccgaca gcggtaactt cggctactac gcgggtccgg tgcggcccag cgcggccgac  1380
aagtgcgtct actggggcgg caaggccggt acggccacct acaacagccc cctcgaacac  1440
tgcgggtaa                                                         1449

SEQ ID NO: 95         moltype = AA  length = 482
FEATURE               Location/Qualifiers
source                1..482
                      mol_type = protein
                      organism = Nonomuraea guangzhouensis
SEQUENCE: 95
LKARLRHSAA LLAGALIPLS LLAGQPAGAA SADPMSDAFA RAATTYEVPR DLLVSLAYAE   60
THLDGHRGEP SASGGYGVMH LVSNPVRHTL ERAATLTKQP VSALKADDAA NITGGAAVLR  120
AYADELGLDA AARKDAGKWY QAVAKYGGAS SADVARLYAD TVYDQLSQGI KVTTPAGETL  180
TATPRTVQPD RGSYAKAQEL GKTNTLAAAV DYPSAAWAAA HSTNYAVSNR PTSDAIDRII  240
IHVAQGTYAG TIDWFQTGPR PNPTSSHYVV RSSDGAVTQM VREKDRAFHA GDSNRRSVGI  300
EHEGWVEQAS WFTDTMYRSS AALTRNIADR YGIPKDRTHI IGHSEAPGAS HTDPGPNWNW  360
TKYMQYVTNG SGGGTNPHTA ESVCGTGFTV IDSAPLGTAG NVYLTYNSGT GANCVATIKL  420
TNLGTATATS AYLEVEGQTR VTDSGNFGYY AGPVRASAAD KCVYWGGKAG TATYNSPLEH  480
CG                                                                482

SEQ ID NO: 96         moltype = AA  length = 453
FEATURE               Location/Qualifiers
source                1..453
                      mol_type = protein
                      organism = Nonomuraea guangzhouensis
SEQUENCE: 96
ASADPMSDAF ARAATTYEVP RDLLVSLAYA ETHLDGHRGE PSASGGYGVM HLVSNPVRHT   60
LERAATLTKQ PVSALKADDA ANITGGAAVL RAYADELGLD AAARKDAGKW YQAVAKYGGA  120
SSADVARLYA DTVYDQLSQG IKVTTPAGET LTATPRTVQP DRGSYAKAQE LGKTNTLAAA  180
VDYPSAAWAA AHSTNYAVSN RPTSDAIDRI IIHVAQGTYA GTIDWFQTGP RPNPTSSHYV  240
VRSSDGAVTQ MVREKDRAFH AGDSNRRSVG IEHEGWVEQA SWFTDTMYRS SAALTRNIAD  300
RYGIPKDRTH IIGHSEAPGA SHTDPGPNWN WTKYMQYVTN GSGGGTNPHT AESVCGTGFT  360
VIDSAPLGTA GNVYLTYNSG TGANCVATIK LTNLGTATAT SAYLEVEGQT RVTDSGNFGY  420
YAGPVRASAA DKCVYWGGKA GTATYNSPLE HCG                              453

SEQ ID NO: 97         moltype = DNA  length = 1509
FEATURE               Location/Qualifiers
sig_peptide           1..87
mat_peptide           88..1506
source                1..1509
                      mol_type = genomic DNA
                      organism = Nonomuraea guangzhouensis
CDS                   1..1506
SEQUENCE: 97
atgtcactct cccccaagcg attaacagct ctcgtctctt ccgtcctcgc cgccctcctg   60
gtcttcgccg gccagcccgc catcgcggcc aaggacaacc cgctatccga cgcgttcgcc  120
cgcgccgccg cggcccagga catccccgc gacctgctcg tcgcgctcgc ctacgccgag  180
acccacctgg acgccacaa cggcgagccc agccagcg gcggctacgg tgtgatgcac  240
ctggtcagca ccccaccac gaaagcgctg gagaaggcgt cggggctcac cgggctgccg  300
gtcaagaagt tgcgcgccga caccgaggcc aacatcctgg ggcgcgcac actgctgcgc  360
gccaacgccg acgagctcgg cctgacgag gccgccagga aggacccgg ccgctggtac  420
gagtccgtgg ccaagtacgg caacgccgcc tcgcccagc tcgcccgcgt ctacgccgac  480
gccgtctacg agctgctcgg cctcggcatc caggccaagg acgtgcgcgt ggcaccgcaa  540
gaggtgaccg ccgaccgcgg caagtacgcc gacacaccct cgctcaaggc cgaggtggcc  600
agccccgact acccggacgc cgcctgggtg cccgcgaact ccggcaacta caccgcctcc  660
agccgcccgt cgagctacgc catcgaccgc gtgatcattc acgtggccca gggctcgtac  720
gccgggacca tctcctggtt ccagaacccg agcgccaacg tctcggccca ctacgtggtc  780
aagtcgtcga cggggccgt cacccagacg gtccgcgaca aggacgtcgc ctggcacgcc  840
ggcaactggt cctacaacac caggtccatc ggcatcgagt acgagggctt cgtcaacgag  900
gcctcgtggt tcaccgacgc gatgtaccgc tcctcggccg cgctgaccaa gtacatctgc  960
gacaagtacg gcatcccgaa ggaccgcacg cacatcatcg gccacaacca ggtgccgggc 1020
gccacccaca ccgacccggg tccgaactgg aactggacca cgtacatgaa ctacgtgacc 1080
ggtggcggcg gcacgccgtc gtggaccacc acggccaccc acgccacctc cggacagttc 1140
accgccagcg cgaactgggg cacctccacc tactccaccc agcgctacgg cgcggactac 1200
cggttcgccg accccgtgtc cgccagtgac gccgccggt atcaggcgac cctcccagc 1260
gcgggcacct accgcgtgga ggtctggtat ccgacgacg ccggctacaa cagctccgcg 1320
ccctacatcg tcgccgcctc cagcggcaac cagacggtgt acgtggacca acgctccggc 1380
ggcggcagct ggcacagctt gggcaatttc ccctcaacg cgggcaccgc caacgtcgtg 1440
ggagtcagcc ggtggacctc cggcaccggc ctcgtcatcg cggacgccgt ccgcatcagc 1500
aaggtctga                                                        1509

SEQ ID NO: 98         moltype = AA  length = 502
FEATURE               Location/Qualifiers
source                1..502
```

```
                    mol_type = protein
                    organism = Nonomuraea guangzhouensis
SEQUENCE: 98
MSLSPKRLTA LVSSVLAALL VFAGQPAIAA KDTPLSDAFA RAAAAQDIPR DLLVALAYAE    60
THLDGHNGEP SASGGYGVMH LVSNPTTKAL EKASGLTGLP VKKLRADTEA NILGGAALLR   120
ANADELGLDE AARKDPGRWY ESVAKYGNAA SPQLARVYAD AVYELLGLGI QAKDVRVAPQ   180
EVTADRGKYA DTPSLKAEVA SPDYPDAAWV PANSGNYTAS SRPSSYAIDR VIIHVAQGSY   240
AGTISWFQNP SANVSAHYVV KSSNGAVTQT VRDKDVAWHA GNWSYNTRSI GIEHEGFVNE   300
ASWFTDAMYR SSAALTKYIC DKYGIPKDRT HIIGHNQVPG ATHTDPGPNW NWTTYMNYVT   360
GGGGTPSWTT TVDNATSGQF TASANWGTST YSTQRYGADY RFADPVSASD AAWYQATLPS   420
AGTYRVEVWY PDDAGYNSSA PYIVAASSGN QTVYVDQRSG GGSWHSLGNF SLNAGTANVV   480
GVSRWTSGTG LVIADAVRIS KV                                           502

SEQ ID NO: 99           moltype = AA  length = 473
FEATURE                 Location/Qualifiers
source                  1..473
                        mol_type = protein
                        organism = Nonomuraea guangzhouensis
SEQUENCE: 99
AKDTPLSDAF ARAAAAQDIP RDLLVALAYA ETHLDGHNGE PSASGGYGVM HLVSNPTTKA    60
LEKASGLTGL PVKKLRADTE ANILGGAALL RANADELGLD EAARKDPGRW YESVAKYGNA   120
ASPQLARVYA DAVYELLGLG IQAKDVRVAP QEVTADRGKY ADTPSLKAEV ASPDYPDAAW   180
VPANSGNYTA SSRPSSYAID RVIIHVAQGS YAGTISWFQN PSANVSAHYV VKSSNGAVTQ   240
TVRDKDVAWH AGNWSYNTRS IGIEHEGFVN EASWFTDAMY RSSAALTKYI CDKYGIPKDR   300
THIIGHNQVP GATHTDPGPN WNWTTYMNYV TGGGGTPSWT TTVDNATSGQ FTASANWGTS   360
TYSTQRYGAD YRFADPVSAS DAAWYQATLP SAGTYRVEVW YPDDAGYNSS APYIVAASSG   420
NQTVYVDQRS GGGSWHSLGN FSLNAGTANV VGVSRWTSGT GLVIADAVRI SKV          473

SEQ ID NO: 100          moltype = DNA  length = 711
FEATURE                 Location/Qualifiers
sig_peptide             1..81
mat_peptide             82..708
source                  1..711
                        mol_type = genomic DNA
                        organism = Bacillus cohnii
CDS                     1..708
SEQUENCE: 100
atgaaaaaaa tagcaactat cttatgtgtc gttatgttag tcaacggttg ttcaaacgtt    60
ggaatcacaa atgttgagag aaatgagaca gtttcattag ttaaaaataa agatgaatta   120
acttataaaa agccaaatac aaatccgagt gaatctttac atgtaactcc ctactattta   180
cctgacgaaa attcgcgacg aagaactgca gaagttacac atgtaatgat tcattacaca   240
agtaatgcag caagaaatcc agagaatccg tatgttattag aagacattta ctcgctgttt   300
gaagaaatatg gcgtttctgc acattatatt attgatcgga aaggtactat ctttcaatta   360
gtagatgaaa gtagagtagc gtttcatgca ggaaaaggaa tggatttaaa ctacctacaa   420
taccgaaata gcatgaatga atattcaatt ggtatcgaac ttatggcaat tggaacaaag   480
gaagaaatga atttaaattt gcaggaaggt caatacgaac taatacc gcc atcctatata   540
gggtatacag atgagcaata tcactcatta gcaaaactgt tagaagactt gtatgagcgt   600
tatccaaaag tattgagaaa cagagagaac gtagtagggc atgatgaata cgcacctgtt   660
cgaaaatcag accctggaag tttatttgac tgggaaaaaa ttgggttctg a            711

SEQ ID NO: 101          moltype = AA  length = 236
FEATURE                 Location/Qualifiers
source                  1..236
                        mol_type = protein
                        organism = Bacillus cohnii
SEQUENCE: 101
MKKIATILCV VMLVNGCSNV GITNVERNET VSLVKNKDEL TYKKPNTNPS ESLHVTPYYL    60
PDENSRRRTA EVTHVMIHYT SNAARNPENP YVLEDIYSLF EEYGVSAHYI IDREGTIFQL   120
VDESRVAFHA GKGMDLNYLQ YRNSMNEYSI GIELMAIGTK EEMNLNLQEG QYELIPPSYI   180
GYTDEQYHSL AKLLEDLYER YPKVLRNREN VVGHDEYAPV RKSDPGSLFD WEKIGF       236

SEQ ID NO: 102          moltype = AA  length = 209
FEATURE                 Location/Qualifiers
source                  1..209
                        mol_type = protein
                        organism = Bacillus cohnii
SEQUENCE: 102
NETVSLVKNK DELTYKKPNT NPSESLHVTP YYLPDENSRR RTAEVTHVMI HYTSNAARNP    60
ENPYVLEDIY SLFEEYGVSA HYIIDREGTI FQLVDESRVA FHAGKGMDLN YLQYRNSMNE   120
YSIGIELMAI GTKEEMNLNL QEGQYELIPP SYIGYTDEQY HSLAKLLEDL YERYPKVLRN   180
RENVVGHDEY APVRKSDPGS LFDWEKIGF                                    209

SEQ ID NO: 103          moltype = DNA  length = 918
FEATURE                 Location/Qualifiers
sig_peptide             1..72
mat_peptide             73..915
source                  1..918
                        mol_type = genomic DNA
                        organism = Halomonas sp.
```

```
CDS                       1..915
SEQUENCE: 103
atggcgcgct ttttcgtcgt cactctcgcc atgctggtgc tgctggccgg ctgcgccacg    60
ccggagcaat acgagcggcg tgacggctat gtggtggacc acacccatgt gtcgccctcc   120
cacaacagcc gggtacgcca tctggtgatg cactacacgg atgtggacga ggccgaatcc   180
ctggcgaccc tgaccggtcc ccatgtcagc agccactacg tgctgccgct accggcacgg   240
gcacatcgcg gcgagccgct ggtctaccag ctcgtcgacg aggagcgccg cgcctggcac   300
gccggggcca gcgcctggaa gcgccgcacc aacatcaacg acacctccat cggcatcgag   360
atcgtcaata ccggccccga ccgccctac gccgaggtgg agcgggcgct ggaggagcac   420
ccggaaagcg atcccgccat ccactgggcg ccctacccg aggcacagat cgaggcgctg    480
atcgccctgt cgcgggatat catcacgcgc aacaatattc accctaccga cgtggtggcc   540
cactcggata tctcgccgac gcgcaagatc gacccgggcc cggcgtttcc ctggcatgcc   600
ctgtacgaag cgggtatcgg cgtatggccc gaagcagcca ccgtggcacg ctatcgcacc   660
cgcttcgatc aggcgctgcc cgaactcgcc accctgcagg cggcgctcca ggcctggggc   720
tatccgctgg cggtcagcga cgaactggat tcagactc gcgcggtact gcgcgccttc     780
cagatgcgct ttcgtcccgc cgactatcgt ggccggcccg acgccgagac tgcggcgatc   840
ctctgggcac tgctggaaag atatcgcccc ctcgacctgg agcggttcga gggggcgatg   900
gaagagccgg aggcatga                                                 918

SEQ ID NO: 104            moltype = AA  length = 305
FEATURE                   Location/Qualifiers
source                    1..305
                          mol_type = protein
                          organism = Halomonas sp.
SEQUENCE: 104
MARFFVVTLA MLVLLAGCAT PEQYERRDGY VVDHTHVSPS HNSRVRHLVM HYTDVDEAES    60
LATLTGPHVS SHYVLPLPAR AHRGEPLVYQ LVDEERRAWH AGASAWKRRT NINDTSIGIE   120
IVNTGPDRPY AEVERALEEH PESDPAIHWA PYPEAQIEAL IALSRDIITR NNIHPTDVVA   180
HSDISPTRKI DPGPAFPWHA LYEAGIGVWP EAATVARYRT RFDQALPELA TLQAALQAWG   240
YPLAVSDELD SQTRAVLRAF QMRFRPADYR GRPDAETAAI LWALLERYRP LDLERFEGAM   300
EEPEA                                                               305

SEQ ID NO: 105            moltype = AA  length = 281
FEATURE                   Location/Qualifiers
source                    1..281
                          mol_type = protein
                          organism = Halomonas sp.
SEQUENCE: 105
ERRDGYVVDH THVSPSHNSR VRHLVMHYTD VDEAESLATL TGPHVSSHYV LPLPARAHRG    60
EPLVYQLVDE ERRAWHAGAS AWKRRTNIND TSIGIEIVNT GPDRPYAEVE RALEEHPESD   120
PAIHWAPYPE AQIEALIALS RDIITRNNIH PTDVVAHSDI SPTRKIDPGP APFWHALYEA   180
GIGVWPEAAT VARYRTRFDQ ALPELATLQA ALQAWGYPLA VSDELDSQTR AVLRAFQMRF   240
RPADYRGRPD AETAAILWAL LERYRPLDLE RFEGAMEEPE A                       281

SEQ ID NO: 106            moltype = DNA  length = 1920
FEATURE                   Location/Qualifiers
sig_peptide               1..171
mat_peptide               172..1917
source                    1..1920
                          mol_type = genomic DNA
                          organism = Lysobacter capsici
CDS                       1..1917
SEQUENCE: 106
atgaacgaat attccactgc acgccgtggg gtggtgaccg gcgtgcgttc gttgtcgggg    60
tcgttgaccg tcgctgtgct ggcgctcgcc gcgccattgg ccgcgcaggc gcaggccgcg   120
cccgaagacc gcgccctggc acagcacctg cagatcgagg aatcgctgca acgcgtcgac   180
cgcgcgctgt acgcggacta cttccgccag gcctatgcgc gttacccgtc gattccggcc   240
ggcacgctgg aatccatcgc ctacgtgatg agccgctggc agcaactgca gcccggctcg   300
gtcgcggcct acggcgaaca gcaccagcac atgccgcgct cgtacgggcg catgggcttg   360
taccacgcgg aaggcttcgc cgatcaagtc ggcgaaggcg cgccctgat cggcgtgccg   420
gccgcgcgcg tgcagcgcga tccgctcagc aacatcctcg cctcggcggc cttgctcgat   480
cgcgagttgc gcgccgacgg gatcggcgcc aagtcggcgg tcgaagccac gcgcccggcg   540
ctggagcgtt acgccggttt cgccggcaat gcgggcaaga gtgcgatcca ggatcacgcc   600
cgttccagtt tcgccttcga cgtgttgctg gcgcaggaca aggtcgca cgatccgcgc    660
atcgtcgtgc cgatgcgcgc ggtcgcctgg aacgcgcct cgacgcgcg caagctggtg    720
cggctgcgcg cgccgttcgt gcgcctggac gtgagccgcg accgggtcga ggcgggtagc   780
ttgaaggacg acggcgcgtt cgcgatcgac ccgctcagcg aaaccctgcg cgcgccggcg   840
ctgaccgccg ccgacgaaaa gacaccgac tacgccccgg cgctgtgggt cgcctcgccg    900
tatcactccg cgcgacgtc ctacgactcg gtcaccatcc acacgatgca gggttattac    960
gccggcagca tctcctggtt ccagaacaac cccagcagcg tcagcgcgca ttacctgatc   1020
cgcagttccg acgccagat cacccagatg gtgcgcgaga accgcggc catcacgtc     1080
ggcgtgcaca acaagaccac gctcggcatc gagcacgaag gtttcatcaa caacgccagc   1140
tggtacaccg ccgcgatgta caacgcctcg gcggcgttga cccggcactt ctgcgcgacc   1200
tacgcgcgga tcagctcgcg gagcgcgttc aggggccgg tcgcagcgg catcaacgtg    1260
ctgccggcca gcgtcaaggt caagggccac cagcattaca gcagcagac ccataccgat    1320
ccgggcatca actgggattg gcgcgttac tacaacctgc tcaacccggg caatccgccc    1380
ggcggcggca cgtgatcga cagtttcgaa agcacggtcg gcatttcga taccggcccg    1440
gcgtactcgg gcagcaccac cggcatcgcc gacgcgtcgc tgagcgaacg caactgcacc   1500
acgcgcaaga acggcgagtg ctcgctgcgg ctgttgctga aagacgacgc ggccagcgcc   1560
```

```
ggcgcctggg cggtgaggct gttgtcgggc agcggcaatc cgggcagcaa cgcggccttg 1620
acccgcgcca acggcaaggt cggcttctgg gtcttcaccg gcgcgaccgg catgagcgcg 1680
gcggtcggca tcgacgacag cgacggcacc gagcgttcga tcagccgcgc gatcccggcc 1740
aacacctgga cctacctgga gtggagcctg agcgacgacg cgcagtggga tgcgtgggtc 1800
ggcggcgcca acggcgcgat caccgccgcg tcggtgaagc tcgacgcggt gtggttctac 1860
cgcgatcaga cctcgttcga tgtgaatgtg tatgtcgacg atgtgcaggt gaagaactga 1920

SEQ ID NO: 107        moltype = AA  length = 639
FEATURE               Location/Qualifiers
source                1..639
                      mol_type = protein
                      organism = Lysobacter capsici
SEQUENCE: 107
MNEYSTARRG VVTGVRSLSG SLTVAVLALA APLAAQAQAA PEDRALAQHL QIEESLQRVD    60
RALYADYFRQ AYARYPSIPA GTLESIAYVM SRWQQLQPGS VAAYGEQHQH MPRSYGVMGL   120
YHGEGFADQV GEGARLIGVP AARVQRDPLS NILASAALLD RELRADGIGA KSAVEATRPA   180
LERYAGFAGN AGKSAIQDHA RSSFAFDVLL AQDKGVNDRG IVVPMRAVAW ERAFDARKLV   240
RLRAPFVRLD VSRDRVEAGS LKDDGAFAID PLSETLRAPA LTAADEKSTD YGPALWVASP   300
YHSARTSYDS VTIHTMQGYY AGSISWFQNN PSSVSAHYLI RSSDGQITQM VRENRAAHHV   360
GVHNKTTLGI EHEGFINNAS WYTAAMYNAS AALTRHFCAT YSAISCASAF RGPAGSGINV   420
LPASVKVKGH QHYSSQTHTD PGINWDWARY YNLLNPGNPP GGGSVIDSFE STVGHFDTGP   480
AYSGSTTGIA ATSLSERNCT TRKNGECSLR LLLKDDAASA GAWAVRLLSG SGNPGSNAAL   540
TRANGKVGFW VFTGATGMSA AVGIDDSDGT ERSISRAIPA NTWTYLEWSL SDDAQWDAWV   600
GGANGAITAA SVKLDAVWFY RDQTSFDVNV YVDDVQVKN                          639

SEQ ID NO: 108        moltype = AA  length = 582
FEATURE               Location/Qualifiers
source                1..582
                      mol_type = protein
                      organism = Lysobacter capsici
SEQUENCE: 108
RVDRALYADY FRQAYARYPS IPAGTLESIA YVMSRWQQLQ PGSVAAYGEQ HQHMPRSYGV    60
MGLYHGEGFA DQVGEGARLI GVPAARVQRD PLSNILASAA LLDRELRADG IGAKSAVEAT   120
RPALERYAGF AGNAGKSAIQ DHARSSFAFD VLLAQDKGVN DRGIVVPMRA VAWERAFDAR   180
KLVRLRAPFV RLDVSRDRVE AGSLKDDGAF AIDPLSETLR APALTAADEK STDYGPALWV   240
ASPYHSARTS YDSVTIHTMQ GYYAGSISWF QNNPSSVSAH YLIRSSDGQI TQMVRENRAA   300
HHVGVHNKTT LGIEHEGFIN NASWYTAAMY NASAALTRHF CATYSAISCA SAFRGPAGSG   360
INVLPASVKV KGHQHYSSQT HTDPGINWDW ARYYNLLNPG NPPGGGSVID SFESTVGHFD   420
TGPAYSGSTT GIAATSLSER NCTTRKNGEC SLRLLLKDDA ASAGAWAVRL LSGSGNPGSN   480
AALTRANGKV GFWVFTGATG MSAAVGIDDS DGTERSISRA IPANTWTYLE WSLSDDAQWD   540
AWVGGANGAI TAASVKLDAV WFYRDQTSFD VNVYVDDVQV KN                      582

SEQ ID NO: 109        moltype = AA  length = 27
FEATURE               Location/Qualifiers
REGION                1..27
                      note = Signal peptide
source                1..27
                      mol_type = protein
                      organism = Synthetic construct
SEQUENCE: 109
MKKPLGKIVA STALLISVAF SSSIASA                                        27

SEQ ID NO: 110        moltype = AA  length = 8
FEATURE               Location/Qualifiers
REGION                1..8
                      note = His-TAG
source                1..8
                      mol_type = protein
                      organism = Synthetic construct
SEQUENCE: 110
HHHHHHPR                                                              8

SEQ ID NO: 111        moltype =    length =
SEQUENCE: 111
000
```

POLYPEPTIDES HAVING PEPTIDOGLYCAN DEGRADING ACTIVITY AND POLYNUCLEOTIDES ENCODING SAME

CROSS-REFERENCE TO RELATED APPLICATIONS

This application is a division of U.S. application Ser. No. 17/298,836 filed on Jun. 1, 2021, now U.S. Pat. No. 11,959,111, which is a 35 U.S.C. 371 national application of international application no. PCT/EP2019/086399 filed Dec. 19, 2019, which claims priority or the benefit under 35 U.S.C. 119 of EP application no. 18215408.8 filed Dec. 21, 2018. The content of each application is fully incorporated herein by reference.

REFERENCE TO A SEQUENCE LISTING

This application contains a Sequence Listing in computer readable form, which is incorporated herein by reference. The Sequence Listing was created on Feb. 26, 2024, and is named SQ.xml and is 133,811 bytes in size.

BACKGROUND OF THE INVENTION

Field of the Invention

The present invention relates to polypeptides having peptidoglycan degrading activity, polynucleotides encoding the polypeptides and catalytic domains belonging to peptidoglycan degrading enzyme families. The invention further relates to compositions comprising such polypeptides, in particular cleaning compositions, use of polypeptides having peptidoglycan degrading activity in cleaning processes and/or for removal or reduction of bacterial-derived peptidoglycan, and methods for removal or reduction of peptidoglycan. The invention further relates to nucleic acid constructs, vectors, and host cells comprising polynucleotides encoding the polypeptides as well as methods of producing and using the polypeptides and catalytic domains.

Description of the Related Art

Enzymes have been used in detergents for decades. Usually, a cocktail of various enzymes is added to detergent compositions. The enzyme cocktail often comprises various enzymes, wherein each enzyme targets a specific substrate, e.g., amylases are active towards starch stains, proteases on protein stains and so forth. Textiles and surfaces such as laundry and dishes become soiled with many different types of soiling. The soiling may be composed of proteins, grease, starch etc. Complex stains composed of different organic materials such as food stains, sebum, dead cell material, EPS (extracellular polymeric matrix) from, e.g., biofilm are difficult to remove completely with traditional ADW (automatic dishwashing) and laundry detergent compositions. Contributing to the organic matter is peptidoglycan, originating from the bacterial cell wall. Bacteria are present in high numbers in laundry items. When the bacteria lyse, the destroyed cells leave a high amount of cell wall-derived peptidoglycan in the textile or on hard surfaces such as the inner surfaces of a washing machine. This peptidoglycan substrate may be sticky or gluing, which when present on textile attracts soils and may cause redeposition or back-staining of soil, resulting in a greying of the textile. Also, malodors from, e.g., sweat, cigarette smoke and pollution are particularly difficult to remove from, e.g., textiles. Malodor is a growing problem, particularly in laundry, with the changed habits of lower temperature washing, front loading wash machines that save water but leave behind residual water between loads, thus allowing bacterial biofilms to flourish, line drying clothes to save energy rather than appliance drying, and the increased popularity of synthetic fabrics, such as athletic wear, that appear to retain odors more than natural fabrics. In conventional detergent compositions such as laundry detergents the above problems are often solved by adding perfumes. This solution is not completely effective, however, as it is short term and furthermore only serves to mask malodor rather than dealing with the underlying cause of malodor. There is thus a need in the art for new solutions for overcoming the problems of malodor and redeposition.

SUMMARY OF THE INVENTION

The invention relates to a cleaning composition comprising a peptidoglycan degradation enzyme, at least one surfactant and at least one additional cleaning component selected from builders and bleach components. The cleaning composition may, e.g., comprise a peptidoglycan degradation enzyme, at least 5 wt % anionic surfactants, and at least one additional cleaning component selected from at least one builder and at least one bleach component.

The invention further relates to the use of such a composition for cleaning of an item such as a textile or a surface. The invention further relates to a method of cleaning an item, comprising the steps of:
a) contacting the item with a solution comprising a peptidoglycan degradation enzyme having peptidoglycan lyase activity and preferably N-acetylmuramyl-L-alanine amidase activity; and a cleaning component, wherein the cleaning component is selected from 5 to 60 wt % of at least one surfactant; 5 to 50 wt % of at least one builder; and 1 to 20 wt % of at least one bleach component; and optionally
b) rinsing the item,
wherein the item is preferably a textile.
Overview of Sequences
  SEQ ID NO: 1 DNA encoding full length polypeptide from *Hamadaea tsunoensis*
  SEQ ID NO: 2 polypeptide derived from SEQ ID NO: 1
  SEQ ID NO: 3 mature polypeptide obtained from *Hamadaea tsunoensis*
  SEQ ID NO: 4 DNA encoding full length polypeptide from *Micromonospora maritima*
  SEQ ID NO: 5 polypeptide derived from SEQ ID NO: 4
  SEQ ID NO: 6 mature polypeptide obtained from *Micromonospora maritima*
  SEQ ID NO: 7 DNA encoding full length polypeptide from *Paenibacillus* sp.
  SEQ ID NO: 8 polypeptide derived from SEQ ID NO: 7
  SEQ ID NO: 9 mature polypeptide obtained from *Paenibacillus* sp.
  SEQ ID NO: 10 DNA encoding full length polypeptide from *Nonomuraea* sp.
  SEQ ID NO: 11 polypeptide derived from SEQ ID NO: 10
  SEQ ID NO: 12 mature polypeptide obtained from *Nonomuraea* sp.
  SEQ ID NO: 13 DNA encoding full length polypeptide from *Lysobacter antibioticus*
  SEQ ID NO: 14 polypeptide derived from SEQ ID NO: 13
  SEQ ID NO: 15 mature polypeptide obtained from *Lysobacter antibioticus*

SEQ ID NO: 16 DNA encoding full length polypeptide from *Micromonospora* sp.
SEQ ID NO: 17 polypeptide derived from SEQ ID NO: 16
SEQ ID NO: 18 mature polypeptide obtained from *Micromonospora* sp.
SEQ ID NO: 19 DNA encoding full length polypeptide from *Nonomuraea coxensis*
SEQ ID NO: 20 polypeptide derived from SEQ ID NO: 19
SEQ ID NO: 21 mature polypeptide obtained from *Nonomuraea coxensis*
SEQ ID NO: 22 DNA encoding full length polypeptide from *Micromonospora fulvopurpurea*
SEQ ID NO: 23 polypeptide derived from SEQ ID NO: 22
SEQ ID NO: 24 mature polypeptide obtained from *Micromonospora fulvopurpurea*
SEQ ID NO: 25 DNA encoding full length polypeptide from *Alicyclobacillus* sp.
SEQ ID NO: 26 polypeptide derived from SEQ ID NO: 25
SEQ ID NO: 27 mature polypeptide obtained from *Alicyclobacillus* sp.
SEQ ID NO: 28 DNA encoding full length polypeptide from *Halomonas* sp.
SEQ ID NO: 29 polypeptide derived from SEQ ID NO: 28
SEQ ID NO: 30 mature polypeptide obtained from *Halomonas* sp.
SEQ ID NO: 31 DNA encoding full length polypeptide from *Pseudomonas peli*
SEQ ID NO: 32 polypeptide derived from SEQ ID NO: 31
SEQ ID NO: 33 mature polypeptide obtained from *Pseudomonas peli*
SEQ ID NO: 34 DNA encoding full length polypeptide from *Halomonas* sp.
SEQ ID NO: 35 polypeptide derived from SEQ ID NO: 34
SEQ ID NO: 36 mature polypeptide obtained from *Halomonas* sp.
SEQ ID NO: 37 DNA encoding full length polypeptide from *Pseudomonas pseudoalcaligenes*
SEQ ID NO: 38 polypeptide derived from SEQ ID NO: 37
SEQ ID NO: 39 mature polypeptide obtained from *Pseudomonas pseudoalcaligenes*
SEQ ID NO: 40 DNA encoding full length polypeptide from *Tumebacillus* sp.
SEQ ID NO: 41 polypeptide derived from SEQ ID NO: 40
SEQ ID NO: 42 mature polypeptide obtained from *Tumebacillus* sp.
SEQ ID NO: 43 DNA encoding full length polypeptide from *Nonomuraea dietziae*
SEQ ID NO: 44 polypeptide derived from SEQ ID NO: 43
SEQ ID NO: 45 mature polypeptide obtained from *Nonomuraea dietziae*
SEQ ID NO: 46 DNA encoding full length polypeptide from *Laceyella sacchari*
SEQ ID NO: 47 polypeptide derived from SEQ ID NO: 46
SEQ ID NO: 48 mature polypeptide obtained from *Laceyella sacchari*
SEQ ID NO: 49 DNA encoding full length polypeptide from *Thermostaphylospora chromogena*
SEQ ID NO: 50 polypeptide derived from SEQ ID NO: 49
SEQ ID NO: 51 mature polypeptide obtained from *Thermostaphylospora chromogena*
SEQ ID NO: 52 DNA encoding full length polypeptide from *Kribbella aluminosa*
SEQ ID NO: 53 polypeptide derived from SEQ ID NO: 52
SEQ ID NO: 54 mature polypeptide obtained from *Kribbella aluminosa*
SEQ ID NO: 55 DNA encoding full length polypeptide from *Streptomyces griseus*
SEQ ID NO: 56 polypeptide derived from SEQ ID NO: 55
SEQ ID NO: 57 mature polypeptide obtained from *Streptomyces griseus*
SEQ ID NO: 58 DNA encoding full length polypeptide from *Micromonospora peucetia*
SEQ ID NO: 59 polypeptide derived from SEQ ID NO: 58
SEQ ID NO: 60 mature polypeptide obtained from *Micromonospora peucetia*
SEQ ID NO: 61 DNA encoding full length polypeptide from *Bacillus* sp.
SEQ ID NO: 62 polypeptide derived from SEQ ID NO: 61
SEQ ID NO: 63 mature polypeptide obtained from *Bacillus* sp.
SEQ ID NO: 64 DNA encoding full length polypeptide from *Bacillus sporothermodurans*
SEQ ID NO: 65 polypeptide derived from SEQ ID NO: 64
SEQ ID NO: 66 mature polypeptide obtained from *Bacillus sporothermodurans*
SEQ ID NO: 67 DNA encoding full length polypeptide from *Paenibacillus pini*
SEQ ID NO: 68 polypeptide derived from SEQ ID NO: 67
SEQ ID NO: 69 mature polypeptide obtained from *Paenibacillus pini*
SEQ ID NO: 70 DNA encoding full length polypeptide from *Bacillus cohnii*
SEQ ID NO: 71 polypeptide derived from SEQ ID NO: 70
SEQ ID NO: 72 mature polypeptide obtained from *Bacillus cohnii*
SEQ ID NO: 73 DNA encoding full length polypeptide from *Kribbella* sp.
SEQ ID NO: 74 polypeptide derived from SEQ ID NO: 73
SEQ ID NO: 75 mature polypeptide obtained from *Kribbella* sp.
SEQ ID NO: 76 DNA encoding full length polypeptide from *Bacillus* sp.
SEQ ID NO: 77 polypeptide derived from SEQ ID NO: 76
SEQ ID NO: 78 mature polypeptide obtained from *Bacillus* sp.
SEQ ID NO: 79 DNA encoding full length polypeptide from *Bacillus* sp.
SEQ ID NO: 80 polypeptide derived from SEQ ID NO: 79
SEQ ID NO: 81 mature polypeptide obtained from *Bacillus* sp.
SEQ ID NO: 82 DNA encoding full length polypeptide from *Bacillus* sp.
SEQ ID NO: 83 polypeptide derived from SEQ ID NO: 82
SEQ ID NO: 84 mature polypeptide obtained from *Bacillus* sp.
SEQ ID NO: 85 DNA encoding full length polypeptide from *Streptomyces* sp.
SEQ ID NO: 86 polypeptide derived from SEQ ID NO: 85
SEQ ID NO: 87 mature polypeptide obtained from *Streptomyces* sp.
SEQ ID NO: 88 DNA encoding full length polypeptide from *Bacillus* sp.
SEQ ID NO: 89 polypeptide derived from SEQ ID NO: 88
SEQ ID NO: 90 mature polypeptide obtained from *Bacillus* sp.
SEQ ID NO: 91 DNA encoding full length polypeptide from *Bacillus* sp.
SEQ ID NO: 92 polypeptide derived from SEQ ID NO: 91
SEQ ID NO: 93 mature polypeptide obtained from *Bacillus* sp.
SEQ ID NO: 94 DNA encoding full length polypeptide from *Nonomuraea guangzhouensis*
SEQ ID NO: 95 polypeptide derived from SEQ ID NO: 94

SEQ ID NO: 96 mature polypeptide obtained from *Nonomuraea guangzhouensis*
SEQ ID NO: 97 DNA encoding full length polypeptide from *Nonomuraea guangzhouensis*
SEQ ID NO: 98 polypeptide derived from SEQ ID NO: 97
SEQ ID NO: 99 mature polypeptide obtained from *Nonomuraea guangzhouensis*
SEQ ID NO: 100 DNA encoding full length polypeptide from *Bacillus cohnii*
SEQ ID NO: 101 polypeptide derived from SEQ ID NO: 100
SEQ ID NO: 102 mature polypeptide obtained from *Bacillus cohnii*
SEQ ID NO: 103 DNA encoding full length polypeptide from *Halomonas* sp.
SEQ ID NO: 104 polypeptide derived from SEQ ID NO: 103
SEQ ID NO: 105 mature polypeptide obtained from *Halomonas* sp.
SEQ ID NO: 106 DNA encoding full length polypeptide from *Lysobacter capsici*
SEQ ID NO: 107 polypeptide derived from SEQ ID NO: 106
SEQ ID NO: 108 mature polypeptide obtained from *Lysobacter capsica*
SEQ ID NO: 109 MKKPLGKIVASTALLISVAFSS-SIASA (signal peptide)
SEQ ID NO: 110 HHHHHHPR (His-tag)
SEQ ID NO: 111 Motif Definitions Peptidoglycan degrading enzymes: The term "peptidoglycan degrading enzyme" means an enzyme having activity towards peptidoglycan. Peptidoglycan (PGN) is a major component of the bacterial cell envelope in both Gram-positive and Gram-negative bacteria (Human et al., 2009, *J. Innate Immun.* 1: 88-97). The peptidoglycan structure of both Gram-positive and Gram-negative bacteria comprises repeating disaccharide backbones of N-acetylglucosamine (NAG) and β-(1-4)-N-acetylmuramic acid (NAM) that are cross-linked by peptide stem chains attached to the NAM residues (Bourhis et al., 2007, *Microbes Infect.* 9(5): 629-636). The peptide and glycopeptide fragments of PGN are commonly referred to as "muropeptides." PGN hydrolases are defined by their catalytic specificities. Two classes of these enzymes digest the PGN glycan backbone, N-acetylmuramidases which cleave PGN between the NAG-NAM bond upstream of NAM and N-acetylglucosaminidases which cleave the NAM-NAG bond. In contrast, N-acetylmuramyl-L-alanine amidases cleave between NAM and the first alanine of the peptide chain. Thus, catalysis by N-acetylmuramyl-L-alanine amidases separate the PGN sugar backbones from the stem peptide chain (Fournier et al., 2005, *Clin. Microbiol. Rev.* 18(3): 521-540). The enzymes of the invention comprise an N-acetylmuramyl-L-alanine amidase (EC 3.5.1.28) domain. In the context of the present invention, N-acetylmuramyl-L-alanine amidases may also be termed peptidoglycan amidohydrolases. The enzymes of the invention comprise in addition to the amidase domain also a peptidoglycan lyase domain (GH23-like). The GH 23 family comprises lysozyme type G (EC 3.2.1.17), peptidoglycan lyase (EC 4.2.2.n1, peptidoglycan lytic exotransglycosylase, and 4.2.2.n2, peptidoglycan lytic endotransglycosylase) and chitinases (EC 3.2.1.14). The domain comprised by the enzymes of the invention is a peptidoglycan lyase domain (EC 4.2.2.n1 or 4.2.2.n2). Peptidoglycan lyases are also termed lytic transglycosylases. Peptidoglycan lyases of GH23 constitute Family 1 of the organizational scheme of Blackburn and Clarke (Blackburn et al., 2001, *J. Mol. Evol.* 52(1):78-84). The enzymes of this family cleave the β-1,4-linkage between N-acetylmuramyl and N-acetylglucosaminyl residues in peptidoglycan. However, unlike lysozyme, peptidoglycan lyases are not hydrolases but rather catalyze an intramolecular transglycosylation to the C-6 hydroxyl group of the muramyl residue, leading to the generation of a terminal 1,6-anhydromuramic acid product that is an acetal, and not a hemiacetal (Höltje, 1975, *J. Bacteriol.* 124(3):1067-1076. The enzymes of the invention are thus distinct from lysozymes.

The enzymes of the invention preferably comprise an N-acetylmuramyl-L-alanine amidase (EC 3.5.1.28) domain as well as a peptidoglycan lyase domain (EC 4.2.2.n1 or 4.2.2.n2). Thus, in the present invention peptidoglycan degrading enzymes are preferably N-acetylmuramyl-L-alanine amidases (EC 3.5.1.28) and peptidoglycan lyases (EC 4.2.2.n1 or 4.2.2.n2) having amidase and lyase activity towards peptidoglycan.

For purposes of the present invention, peptidoglycan lyase activity and N-acetylmuramyl-L-alanine amidase activity may be determined according to the procedures described below in the example section.

The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

A biofilm is organic matter produced by any group of microorganisms in which cells stick to each other or stick to a surface, such as a textile, dishware or hard surface or another kind of surface. These adherent cells are frequently embedded within a self-produced matrix of extracellular polymeric substance (EPS). Biofilm EPS is a polymeric conglomeration generally composed of extracellular DNA, proteins, and polysaccharides. Biofilms may form on living or non-living surfaces. The microbial cells growing in a biofilm are physiologically distinct from planktonic cells of the same organism, which, by contrast, are single cells that may float or swim in a liquid medium. Bacteria living in a biofilm usually have significantly different properties from planktonic bacteria of the same species, as the dense and protected environment of the film allows them to cooperate and interact in various ways. One benefit of this environment for the microorganisms is increased resistance to detergents and antibiotics, as the dense extracellular matrix and the outer layer of cells protect the interior of the community. The biofilm living bacteria do not lose their ability to live as planktonic cells if the biofilm matrix is compromised. On laundry, biofilm- or EPS-producing bacteria can be found among the following species: *Acinetobacter* sp., *Aeromicrobium* sp., *Brevundimonas* sp., *Microbacterium* sp., *Micrococcus luteus*, *Pseudomonas* sp., *Staphylococcus epidermidis*, and *Stenotrophomonas* sp. In one aspect, the biofilm- or EPS-producing strain is *Pseudomonas*, for example *Pseudomonas aeruginosa*, *Pseudomonas alcaliphila* or *Pseudomonas fluorescens*.

The term "catalytic domain" means the region of an enzyme containing the catalytic machinery of the enzyme.

The term "cDNA" means a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

The term "clade" means a group of polypeptides clustered together on the basis of homologous features traced to a common ancestor. Polypeptide clades can be visualized as phylogenetic trees and a clade is a group of polypeptides that consists of a common ancestor and all its lineal descendants. Example 6 describes the generation of phylogenetic trees.

The term "coding sequence" means a polynucleotide which directly specifies the amino acid sequence of a polypeptide. The boundaries of the coding sequence are generally determined by an open reading frame, which begins with a start codon such as ATG, GTG, or TTG and ends with a stop codon such as TAA, TAG, or TGA. The coding sequence may be a genomic DNA, cDNA, synthetic DNA, or a combination thereof.

The term "control sequences" means nucleic acid sequences necessary for expression of a polynucleotide encoding a mature polypeptide of the present invention. Each control sequence may be native (i.e., from the same gene) or foreign (i.e., from a different gene) to the polynucleotide encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a polypeptide.

The term "cleaning component" means, e.g., a detergent adjunct ingredient that is different from the polypeptides of this invention. The precise nature of these additional cleaning or adjunct components, and levels of incorporation thereof, will depend on the physical form of the composition and the nature of the operation for which it is to be used. Suitable cleaning components include, but are not limited to the components described below, such as surfactants, builders and co-builders, flocculating aid, chelating agents, dye transfer inhibitors, enzymes (other than the enzymes of the invention), enzyme stabilizers, enzyme inhibitors, catalytic materials, bleach activators, hydrogen peroxide, sources of hydrogen peroxide, preformed peracids, polymeric agents, clay soil removal/anti-redeposition agents, brighteners, suds suppressors, dyes, perfumes, structure elasticizing agents, fabric softeners, carriers, hydrotropes, fabric hueing agents, anti-foaming agents, dispersants, processing aids, and/or pigments.

The term "cleaning composition" includes "detergent composition" and refers to compositions that find use in the removal of undesired compounds from items to be cleaned, such as textiles. The detergent composition may be used to, e.g., clean textiles for both household cleaning and industrial cleaning. The term encompasses any materials/compounds selected for the particular type of cleaning composition desired and the form of the product (e.g., liquid, gel, powder, granulate, paste, or spray compositions) and includes, but is not limited to, detergent compositions such as liquid and/or solid laundry detergents and fine fabric detergents; fabric fresheners; fabric softeners; and textile and laundry prespotters/pretreatment. In addition to containing the enzyme of the invention, the detergent formulation may contain one or more additional enzymes (such as proteases, amylases, lipases, cutinases, cellulases, endoglucanases, xyloglucanases, pectinases, pectin lyases, xanthanases, peroxidases, haloperoxygenases, catalases, mannanases, nucleases or any mixture thereof), and/or detergent adjunct ingredients such as surfactants, builders, chelators or chelating agents, bleach system or bleach components, polymers, fabric conditioners, foam boosters, suds suppressors, dyes, perfume, tannish inhibitors, optical brighteners, bactericides, fungicides, soil suspending agents, anti-corrosion agents, enzyme inhibitors or stabilizers, enzyme activators, transferase(s), hydrolytic enzymes, oxidoreductases, bluing agents and fluorescent dyes, antioxidants, and solubilizers.

The term "expression" includes any step involved in the production of a polypeptide including, but not limited to, transcription, post-transcriptional modification, translation, post-translational modification, and secretion.

The term "expression vector" means a linear or circular DNA molecule that comprises a polynucleotide encoding a polypeptide and is operably linked to control sequences that provide for its expression.

The term "fragment" means a polypeptide having one or more amino acids absent from the amino and/or carboxyl terminus of a mature polypeptide or domain; wherein the fragment has peptidoglycan degradation activity.

The term "host cell" means any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication.

The term "isolated" means a substance in a form or environment that does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., recombinant production in a host cell; multiple copies of a gene encoding the substance; and use of a stronger promoter than the promoter naturally associated with the gene encoding the substance). An isolated substance may be present in a fermentation broth sample; e.g., a host cell may be genetically modified to express the polypeptide of the invention. The fermentation broth from that host cell will comprise the isolated polypeptide. It will be apparent to persons skilled in the art that the polypeptides disclosed herein are preferably in isolated form.

The term "laundering" relates to both household laundering and industrial laundering and means the process of treating textiles with a solution containing a cleaning or detergent composition of the present invention. The laundering process can for example be carried out using, e.g., a household or an industrial washing machine or can be carried out by hand.

The term "malodor" means an odor which is not desired on clean items. The cleaned item should smell fresh and clean without malodors adhered to the item. One example of malodor is compounds with an unpleasant smell, which may be produced by microorganisms. Another example is unpleasant smells which can be sweat or body odor adhered to an item which has been in contact with human or animal.

Another example of malodor can be the odor from spices, which sticks to items for example curry or other spices which smell strongly.

The term "mature polypeptide" means a polypeptide in its mature form following N terminal processing (e.g., removal of signal peptide).

In one aspect, the mature polypeptide is amino acids 1 to 431 of SEQ ID NO: 2. Amino acids −29 to −1 of SEQ ID NO: 2 are a signal peptide. In one aspect, the mature polypeptide is amino acids 1 to 485 of SEQ ID NO: 5. Amino acids −30 to −1 of SEQ ID NO: 5 are a signal peptide. In one aspect, the mature polypeptide is amino acids 1 to 483 of SEQ ID NO: 8. Amino acids −26 to −1 of SEQ ID NO: 8 are a signal peptide. In one aspect, the mature polypeptide is amino acids 1 to 471 of SEQ ID NO: 11. Amino acids −22 to −1 of SEQ ID NO: 11 are a signal peptide. In one aspect, the mature polypeptide is amino acids 1 to 639 of SEQ ID NO: 14. In one aspect, the mature polypeptide is amino acids 1 to 484 of SEQ ID NO: 17. Amino acids −31 to −1 of SEQ ID NO: 17 are a signal peptide. In one aspect, the mature polypeptide is amino acids 1 to 480 of SEQ ID NO: 20. Amino acids −30 to −1 of SEQ ID NO: 20 are a signal peptide. In one aspect, the mature polypeptide is amino acids 1 to 485 of SEQ ID NO: 23. Amino acids −31 to −1 of SEQ ID NO: 23 are a signal peptide. In one aspect, the mature polypeptide is amino acids 1 to 491 of SEQ ID NO: 26. Amino acids −28 to −1 of SEQ ID NO: 26 are a signal peptide. In one aspect, the mature polypeptide is amino acids 1 to 289 of SEQ ID NO: 29. Amino acids −19 to −1 of SEQ ID NO: 29 are a signal peptide. In one aspect, the mature polypeptide is amino acids 1 to 245 of SEQ ID NO: 32. Amino acids −15 to −1 of SEQ ID NO: 32 are a signal peptide. In one aspect, the mature polypeptide is amino acids 1 to 280 of SEQ ID NO: 35. Amino acids −19 to −1 of SEQ ID NO: 35 are a signal peptide. In one aspect, the mature polypeptide is amino acids 1 to 238 of SEQ ID NO: 38. Amino acids −22 to −1 of SEQ ID NO: 38 are a signal peptide. In one aspect, the mature polypeptide is amino acids 1 to 498 of SEQ ID NO: 41. Amino acids −23 to −1 of SEQ ID NO: 41 are a signal peptide. In one aspect, the mature polypeptide is amino acids 1 to 476 of SEQ ID NO: 44. Amino acids −25 to −1 of SEQ ID NO: 44 are a signal peptide. In one aspect, the mature polypeptide is amino acids 1 to 474 of SEQ ID NO: 47. Amino acids −28 to −1 of SEQ ID NO: 47 are a signal peptide. In one aspect, the mature polypeptide is amino acids 1 to 473 of SEQ ID NO: 50. Amino acids −29 to −1 of SEQ ID NO: 50 are a signal peptide. In one aspect, the mature polypeptide is amino acids 1 to 414 of SEQ ID NO: 53. Amino acids −25 to −1 of SEQ ID NO: 53 are a signal peptide. In one aspect, the mature polypeptide is amino acids 1 to 412 of SEQ ID NO: 56. Amino acids −31 to −1 of SEQ ID NO: 56 are a signal peptide. In one aspect, the mature polypeptide is amino acids 1 to 637 of SEQ ID NO: 59. Amino acids −35 to −1 of SEQ ID NO: 59 are a signal peptide. In one aspect, the mature polypeptide is amino acids 1 to 599 of SEQ ID NO: 62. Amino acids −33 to −1 of SEQ ID NO: 62 are a signal peptide. In one aspect, the mature polypeptide is amino acids 1 to 605 of SEQ ID NO: 65. Amino acids −31 to −1 of SEQ ID NO: 65 are a signal peptide. In one aspect, the mature polypeptide is amino acids 1 to 610 of SEQ ID NO: 68. Amino acids −36 to −1 of SEQ ID NO: 68 are a signal peptide. In one aspect, the mature polypeptide is amino acids 1 to 216 of SEQ ID NO: 71. Amino acids −20 to −1 of SEQ ID NO: 71 are a signal peptide. In one aspect, the mature polypeptide is amino acids 1 to 425 of SEQ ID NO: 74. Amino acids −26 to −1 of SEQ ID NO: 74 are a signal peptide. In one aspect, the mature polypeptide is amino acids 1 to 304 of SEQ ID NO: 77. Amino acids −25 to −1 of SEQ ID NO: 77 are a signal peptide. In one aspect, the mature polypeptide is amino acids 1 to 306 of SEQ ID NO: 80. Amino acids −29 to −1 of SEQ ID NO: 80 are a signal peptide. In one aspect, the mature polypeptide is amino acids 1 to 306 of SEQ ID NO: 83. Amino acids −23 to −1 of SEQ ID NO: 83 are a signal peptide. In one aspect, the mature polypeptide is amino acids 1 to 632 of SEQ ID NO: 86. Amino acids −35 to −1 of SEQ ID NO: 86 are a signal peptide. In one aspect, the mature polypeptide is amino acids 1 to 216 of SEQ ID NO: 89. Amino acids −24 to −1 of SEQ ID NO: 89 are a signal peptide. In one aspect, the mature polypeptide is amino acids 1 to 306 of SEQ ID NO: 92. Amino acids −27 to −1 of SEQ ID NO: 92 are a signal peptide. In one aspect, the mature polypeptide is amino acids 1 to 453 of SEQ ID NO: 95. Amino acids −29 to −1 of SEQ ID NO: 95 are a signal peptide. In one aspect, the mature polypeptide is amino acids 1 to 473 of SEQ ID NO: 98. Amino acids −29 to −1 of SEQ ID NO: 98 are a signal peptide. In one aspect, the mature polypeptide is amino acids 1 to 209 of SEQ ID NO: 101. Amino acids −27 to −1 of SEQ ID NO: 101 are a signal peptide. In one aspect, the mature polypeptide is amino acids 1 to 281 of SEQ ID NO: 104. Amino acids −24 to −1 of SEQ ID NO: 104 are a signal peptide. In one aspect, the mature polypeptide is amino acids 1 to 582 of SEQ ID NO: 107. Amino acids −57 to −1 of SEQ ID NO: 107 are a signal peptide.

It is known in the art that a host cell may produce a mixture of two of more different mature polypeptides (i.e., with a different C-terminal and/or N-terminal amino acid) expressed by the same polynucleotide. It is also known in the art that different host cells process polypeptides differently, and thus, one host cell expressing a polynucleotide may produce a different mature polypeptide (e.g., having a different C-terminal and/or N-terminal amino acid) as compared to another host cell expressing the same polynucleotide.

The term "mature polypeptide coding sequence" means a polynucleotide that encodes a mature polypeptide having peptidoglycan degrading activity.

In one aspect, the mature polypeptide coding sequence is nucleotides 88 to 1380 of SEQ ID NO: 1 and nucleotides 1 to 87 of SEQ ID NO: 1 encode a signal peptide. In one aspect, the mature polypeptide coding sequence is nucleotides 91 to 1545 of SEQ ID NO: 4 and nucleotides 1 to 90 of SEQ ID NO: 4 encode a signal peptide. In one aspect, the mature polypeptide coding sequence is nucleotides 79 to 1527 of SEQ ID NO: 7 and nucleotides 1 to 78 of SEQ ID NO: 7 encode a signal peptide. In one aspect, the mature polypeptide coding sequence is nucleotides 67 to 1479 of SEQ ID NO: 10 and nucleotides 1 to 66 of SEQ ID NO: 10 encode a signal peptide. In one aspect, the mature polypeptide coding sequence is nucleotides 1 to 1917 of SEQ ID NO: 13. In one aspect, the mature polypeptide coding sequence is nucleotides 94 to 1545 of SEQ ID NO: 16 and nucleotides 1 to 93 of SEQ ID NO: 16 encode a signal peptide. In one aspect, the mature polypeptide coding sequence is nucleotides 91 to 1530 of SEQ ID NO: 19 and nucleotides 1 to 90 of SEQ ID NO: 19 encode a signal peptide. In one aspect, the mature polypeptide coding sequence is nucleotides 94 to 1548 of SEQ ID NO: 22 and nucleotides 1 to 93 of SEQ ID NO: 22 encode a signal peptide. In one aspect, the mature polypeptide coding sequence is nucleotides 85 to 1557 of SEQ ID NO: 25 and nucleotides 1 to 84 of SEQ ID NO: 25 encode a signal peptide. In one aspect, the mature polypeptide coding sequence is nucleotides 58 to 924 of SEQ ID NO: 28 and nucleotides 1 to 57 of SEQ ID NO: 28 encode a signal peptide. In one aspect, the mature polypeptide coding sequence is nucleotides 46 to 780 of SEQ ID NO: 31 and nucleotides 1 to 45 of SEQ ID NO: 31 encode a signal peptide. In one aspect, the mature polypeptide coding sequence is nucleotides 58 to 897 of SEQ ID NO: 34 and nucleotides 1 to 57 of SEQ ID NO: 34 encode a signal peptide. In one aspect, the mature polypeptide coding sequence is nucleotides 67 to 780 of SEQ ID NO: 37 and nucleotides 1 to 66 of SEQ ID NO: 37 encode a signal peptide. In one aspect, the mature polypeptide coding sequence is nucleotides 70 to 1563 of SEQ ID NO: 40 and nucleotides 1 to 69 of SEQ ID NO: 40 encode a signal peptide. In one aspect, the mature polypeptide coding sequence is nucleotides 76 to 1503 of SEQ ID NO: 43 and nucleotides 1 to 75 of SEQ ID NO: 43 encode a signal peptide. In one aspect, the mature polypeptide coding sequence is nucleotides 85 to 1506 of SEQ ID NO: 46 and nucleotides 1 to 84 of SEQ ID NO: 46 encode a signal peptide. In one aspect, the mature polypeptide coding sequence is nucleotides 88 to 1506 of SEQ ID NO: 49 and nucleotides 1 to 87 of SEQ ID NO: 49 encode a signal peptide. In one aspect, the mature polypeptide coding sequence is nucleotides 76 to 1317 of SEQ ID NO: 52 and nucleotides 1 to 75 of SEQ ID NO: 52 encode a signal peptide. In one aspect, the mature polypeptide coding sequence is nucleotides 94 to 1329 of SEQ ID NO: 55 and nucleotides 1 to 93 of SEQ ID NO: 55 encode a signal peptide. In one aspect, the mature polypeptide coding sequence is nucleotides 106 to 2016 of SEQ ID NO: 58 and nucleotides 1 to 105 of SEQ ID NO: 58 encode a signal peptide. In one aspect, the mature polypeptide coding sequence is nucleotides 100 to 1896 of SEQ ID NO: 61 and nucleotides 1 to 99 of SEQ ID NO: 61 encode a signal peptide. In one aspect, the mature polypeptide coding sequence is nucleotides 94 to 1908 of SEQ ID NO: 64 and nucleotides 1 to 93 of SEQ ID NO: 64 encode a signal peptide. In one aspect, the mature polypeptide coding sequence is nucleotides 109 to 1938 of SEQ ID NO: 67 and nucleotides 1 to 108 of SEQ ID NO: 67 encode a signal peptide. In one aspect, the mature polypeptide coding sequence is nucleotides 61 to 708 of SEQ ID NO: 70 and nucleotides 1 to 60 of SEQ ID NO: 70 encode a signal peptide. In one aspect, the mature polypeptide coding sequence is nucleotides 79 to 1353 of SEQ ID NO: 73 and nucleotides 1 to 78 of SEQ ID NO: 73 encode a signal peptide. In one aspect, the mature polypeptide coding sequence is nucleotides 76 to 987 of SEQ ID NO: 76 and nucleotides 1 to 75 of SEQ ID NO: 76 encode a signal peptide. In one aspect, the mature polypeptide coding sequence is nucleotides 73 to 990 of SEQ ID NO: 79 and nucleotides 1 to 72 of SEQ ID NO: 79 encode a signal peptide. In one aspect, the mature polypeptide coding sequence is nucleotides 70 to 987 of SEQ ID NO: 82 and nucleotides 1 to 69 of SEQ ID NO: 82 encode a signal peptide. In one aspect, the mature polypeptide coding sequence is nucleotides 106 to 2001 of SEQ ID NO: 85 and nucleotides 1 to 105 of SEQ ID NO: 85 encode a signal peptide. In one aspect, the mature polypeptide coding sequence is nucleotides 73 to 720 of SEQ ID NO: 88 and nucleotides 1 to 72 of SEQ ID NO: 88 encode a signal peptide. In one aspect, the mature polypeptide coding sequence is nucleotides 82 to 999 of SEQ ID NO: 91 and nucleotides 1 to 81 of SEQ ID NO: 91 encode a signal peptide. In one aspect, the mature polypeptide coding sequence is nucleotides 88 to 1446 of SEQ ID NO: 94 and nucleotides 1 to 87 of SEQ ID NO: 94 encode a signal peptide. In one aspect, the mature polypeptide coding sequence is nucleotides 88 to 1506 of SEQ ID NO: 97 and nucleotides 1 to 87 of SEQ ID NO: 97 encode a signal peptide. In one aspect, the mature polypeptide coding sequence is nucleotides 82 to 708 of SEQ ID NO: 100 and nucleotides 1 to 81 of SEQ ID NO: 100 encode a signal peptide. In one aspect, the mature polypeptide coding sequence is nucleotides 73 to 915 of SEQ ID NO: 103 and nucleotides 1 to 72 of SEQ ID NO: 103 encode a signal peptide. In one aspect, the mature polypeptide coding sequence is nucleotides 172 to 1917 of SEQ ID NO: 106 and nucleotides 1 to 171 of SEQ ID NO: 106 encode a signal peptide.

The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more control sequences.

The term "operably linked" means a configuration in which a control sequence is placed at an appropriate position relative to the coding sequence of a polynucleotide such that the control sequence directs expression of the coding sequence.

The relatedness between two amino acid sequences or between two nucleotide sequences is described by the parameter "sequence identity". For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the -nobrief option) is used as the percent identity and is calculated as follows:

(Identical Residues×100)/(Length of Alignment−
Total Number of Gaps in Alignment)

For purposes of the present invention, the sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 5.0.0 or later. The parameters used are gap open penalty of 10, gap extension penalty of 0.5, and the EDNAFULL (EMBOSS version of NCBI NUC4.4) substitution matrix. The output of Needle labeled "longest identity" (obtained using the -nobrief option) is used as the percent identity and is calculated as follows:

(Identical Deoxyribonucleotides×100)/(Length of
Alignment−Total Number of Gaps in Alignment)

The term "very low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 45° C.

The term "low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 50° C.

The term "medium stringency conditions" means for probes of at least 100 nucleotides in length, prehybridization and hybridization at 42° ° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 2×SSC, 0.2% SDS at 55° C.

The term "medium-high stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 2×SSC, 0.2% SDS at 60° C.

The term "high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 65° C.

The term "very high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 70° C.

The term "variant" means a polypeptide having peptidoglycan degrading activity comprising an alteration, i.e., a substitution, insertion, and/or deletion, at one or more positions. A substitution means replacement of the amino acid occupying a position with a different amino acid; a deletion means removal of the amino acid occupying a position; and an insertion means adding an amino acid adjacent to and immediately following the amino acid occupying a position.

Nomenclature: For purposes of the present invention, the nomenclature [E/Q] or [EQ] means that the amino acid at this position may be a glutamic acid (Glu, E) or a glutamine (Gln, Q). Likewise, the nomenclature [V/G/A/I] or [VGAI] means that the amino acid at this position may be a valine (Val, V), glycine (Gly, G), alanine (Ala, A) or isoleucine (Ile, I), and so forth for other combinations as described herein. Unless otherwise limited further, the amino acid X is defined such that it may be any of the 20 natural amino acids.

DETAILED DESCRIPTION OF THE INVENTION

As mentioned in the background section above, textiles and surfaces such as laundry and dishes may become soiled with many different types of soiling. A single complex stain such as a food stain, sebum, dead cells debris, EPS or biofilm related stains is often composed of different organic material such as proteins, polysaccharides, grease etc., which are often difficult to remove completely with traditional detergent compositions. Further, such stains may give rise to disadvantages such as redeposition or malodor. The polypeptides of the invention address this problem, providing good cleaning effects on complex stains such as biofilm and EPS as well as reduced redeposition and malodor from, e.g., textiles and tableware. The polypeptides of the invention are peptidoglycan degrading enzymes having hydrolase activity and preferably N-acetylmuramyl-L-alanine amidase activity. The polypeptides of the invention comprise an amidase domain, preferably an Amidase_2 domain as defined in PFAM (PF01510, Pfam version 31.0 Finn (2016). Nucleic Acids Research, Database Issue 44: D279-D285). Also, clusters or clades are described herein, defined by specific motifs shared by the polypeptides of the specific clades. A phylogenetic tree was constructed of polypeptide sequences containing an Amidase_2 domain. The phylogenetic tree was constructed from a multiple alignment of mature polypeptide sequences containing at least one Amidase_2 domain as described in Example 6.

One embodiment of the invention relates to a peptidoglycan degrading enzyme having hydrolase activity and preferably N-acetylmuramyl-L-alanine amidase activity. One embodiment of the invention relates to a peptidoglycan degrading enzyme having hydrolase activity and preferably N-acetylmuramyl-L-alanine amidase activity, wherein the polypeptide comprises the motif N[IV]X[AG][GAS]A[AY][LV]L (SEQ ID NO: 111), where X can be any naturally occurring amino acid, situated in positions corresponding to positions 85 to 93 in *Micromonospora maritima* (SEQ ID NO: 6).

The polypeptides containing an Amidase_2 domain can be separated into distinct sub-clusters. The sub-clusters are defined by one or more short sequence motifs, as well as containing an Amidase_2 domain as defined in PFAM (PF01510, Pfam version 31.0). We denoted one sub-cluster comprising the motif N[IV]X[AG][GAS]A[AY][LV]L (SEQ ID NO: 111) as the PGL clade. All polypeptide sequences containing an Amidase_2 domain as well as the motif will be denoted as belonging to the PGL clade.

In an embodiment, the present invention relates to polypeptides having a sequence identity to the mature polypeptide of SEQ ID NO: 2 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which have peptidoglycan degrading activity. In one aspect, the polypeptides differ by up to 10 amino acids, e.g., 1, 2, 3, 4, 5, 6, 7, 8, 9, or 10, from the mature polypeptide of SEQ ID NO: 2.

In a particular embodiment, the invention relates to polypeptides having a sequence identity to the mature polypeptide of SEQ ID NO: 2 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least 70% of the peptide degrading activity of the mature polypeptide of SEQ ID NO: 2.

In an embodiment, the present invention relates to polypeptides having a sequence identity to the mature polypeptide of SEQ ID NO: 5 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which have peptidoglycan degrading activity. In one aspect, the polypeptides differ by up to 10 amino acids, e.g., 1, 2, 3, 4, 5, 6, 7, 8, 9, or 10, from the mature polypeptide of SEQ ID NO: 5.

In a particular embodiment, the invention relates to polypeptides having a sequence identity to the mature polypeptide of SEQ ID NO: 5 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least 70% of the peptidoglycan degrading activity of the mature polypeptide of SEQ ID NO: 5.

In an embodiment, the present invention relates to polypeptides having a sequence identity to the mature polypeptide of SEQ ID NO: 8 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which have peptidoglycan degrading activity. In one aspect, the polypeptides differ by up to 10 amino acids, e.g., 1, 2, 3, 4, 5, 6, 7, 8, 9, or 10, from the mature polypeptide of SEQ ID NO: 8.

In a particular embodiment, the invention relates to polypeptides having a sequence identity to the mature polypeptide of SEQ ID NO: 8 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least 70% of the peptidoglycan degrading activity of the mature polypeptide of SEQ ID NO: 8.

In an embodiment, the present invention relates to polypeptides having a sequence identity to the mature polypeptide of SEQ ID NO: 11 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which have peptidoglycan degrading activity. In one aspect, the polypeptides differ by up to 10 amino acids, e.g., 1, 2, 3, 4, 5, 6, 7, 8, 9, or 10, from the mature polypeptide of SEQ ID NO: 11.

In a particular embodiment, the invention relates to polypeptides having a sequence identity to the mature polypeptide of SEQ ID NO: 11 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least 70% of the peptidoglycan degrading activity of the mature polypeptide of SEQ ID NO: 11.

In an embodiment, the present invention relates to polypeptides having a sequence identity to the mature polypeptide of SEQ ID NO: 14 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which have peptidoglycan degrading activity. In one aspect, the polypeptides differ by up to 10 amino acids, e.g., 1, 2, 3, 4, 5, 6, 7, 8, 9, or 10, from the mature polypeptide of SEQ ID NO: 14.

In a particular embodiment, the invention relates to polypeptides having a sequence identity to the mature polypeptide of SEQ ID NO: 14 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least 70% of the peptidoglycan degrading activity of the mature polypeptide of SEQ ID NO: 14.

In an embodiment, the present invention relates to polypeptides having a sequence identity to the mature polypeptide of SEQ ID NO: 17 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which have peptidoglycan degrading activity. In one aspect, the polypeptides differ by up to 10 amino acids, e.g., 1, 2, 3, 4, 5, 6, 7, 8, 9, or 10, from the mature polypeptide of SEQ ID NO: 17.

In a particular embodiment, the invention relates to polypeptides having a sequence identity to the mature polypeptide of SEQ ID NO: 17 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least 70% of the peptidoglycan degrading activity of the mature polypeptide of SEQ ID NO: 17.

In an embodiment, the present invention relates to polypeptides having a sequence identity to the mature polypeptide of SEQ ID NO: 20 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which have peptidoglycan degrading activity. In one aspect, the polypeptides differ by up to 10 amino acids, e.g., 1, 2, 3, 4, 5, 6, 7, 8, 9, or 10, from the mature polypeptide of SEQ ID NO: 20.

In a particular embodiment, the invention relates to polypeptides having a sequence identity to the mature polypeptide of SEQ ID NO: 20 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least 70% of the peptidoglycan degrading activity of the mature polypeptide of SEQ ID NO: 20.

In an embodiment, the present invention relates to polypeptides having a sequence identity to the mature polypeptide of SEQ ID NO: 23 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which have peptidoglycan degrading activity. In one aspect, the polypeptides differ by up to 10 amino acids, e.g., 1, 2, 3, 4, 5, 6, 7, 8, 9, or 10, from the mature polypeptide of SEQ ID NO: 23. In a particular embodiment, the invention relates to polypeptides having a sequence identity to the mature polypeptide of SEQ ID NO: 23 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least 70% of the peptidoglycan degrading activity of the mature polypeptide of SEQ ID NO: 23.

In an embodiment, the present invention relates to polypeptides having a sequence identity to the mature polypeptide of SEQ ID NO: 26 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which have peptidoglycan degrading activity. In one aspect, the polypeptides differ by up to 10 amino acids, e.g., 1, 2, 3, 4, 5, 6, 7, 8, 9, or 10, from the mature polypeptide of SEQ ID NO: 26.

In a particular embodiment, the invention relates to polypeptides having a sequence identity to the mature polypeptide of SEQ ID NO: 26 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least 70% of the peptidoglycan degrading activity of the mature polypeptide of SEQ ID NO: 26.

In an embodiment, the present invention relates to polypeptides having a sequence identity to the mature polypeptide of SEQ ID NO: 29 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which have peptidoglycan degrading activity. In one aspect, the polypeptides differ by up to 10 amino acids, e.g., 1, 2, 3, 4, 5, 6, 7, 8, 9, or 10, from the mature polypeptide of SEQ ID NO: 29.

In a particular embodiment, the invention relates to polypeptides having a sequence identity to the mature polypeptide of SEQ ID NO: 29 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least 70% of the peptidoglycan degrading activity of the mature polypeptide of SEQ ID NO: 29.

In an embodiment, the present invention relates to polypeptides having a sequence identity to the mature polypeptide of SEQ ID NO: 32 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which have peptidoglycan degrading activity. In one aspect, the polypeptides differ by up to 10 amino acids, e.g., 1, 2, 3, 4, 5, 6, 7, 8, 9, or 10, from the mature polypeptide of SEQ ID NO: 32.

In a particular embodiment, the invention relates to polypeptides having a sequence identity to the mature polypeptide of SEQ ID NO: 32 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least 70% of the peptidoglycan degrading activity of the mature polypeptide of SEQ ID NO: 32.

In an embodiment, the present invention relates to polypeptides having a sequence identity to the mature polypeptide of SEQ ID NO: 35 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which have peptidoglycan degrading activity. In one aspect, the polypeptides differ by up to 10 amino acids, e.g., 1, 2, 3, 4, 5, 6, 7, 8, 9, or 10, from the mature polypeptide of SEQ ID NO: 35.

In a particular embodiment, the invention relates to polypeptides having a sequence identity to the mature polypeptide of SEQ ID NO: 35 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least 70% of the peptidoglycan degrading activity of the mature polypeptide of SEQ ID NO: 35.

In an embodiment, the present invention relates to polypeptides having a sequence identity to the mature polypeptide of SEQ ID NO: 38 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which have peptidoglycan degrading activity. In one aspect, the polypeptides differ by up to 10 amino acids, e.g., 1, 2, 3, 4, 5, 6, 7, 8, 9, or 10, from the mature polypeptide of SEQ ID NO: 38.

In a particular embodiment, the invention relates to polypeptides having a sequence identity to the mature polypeptide of SEQ ID NO: 38 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least 70% of the peptidoglycan degrading activity of the mature polypeptide of SEQ ID NO: 38.

In an embodiment, the present invention relates to polypeptides having a sequence identity to the mature polypeptide of SEQ ID NO: 41 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which have peptidoglycan degrading activity. In one aspect, the polypeptides differ by up to 10 amino acids, e.g., 1, 2, 3, 4, 5, 6, 7, 8, 9, or 10, from the mature polypeptide of SEQ ID NO: 41.

In a particular embodiment, the invention relates to polypeptides having a sequence identity to the mature polypeptide of SEQ ID NO: 41 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least 70% of the peptidoglycan degrading activity of the mature polypeptide of SEQ ID NO: 41.

In an embodiment, the present invention relates to polypeptides having a sequence identity to the mature polypeptide of SEQ ID NO: 44 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which have peptidoglycan degrading activity. In one aspect, the polypeptides differ by up to 10 amino acids, e.g., 1, 2, 3, 4, 5, 6, 7, 8, 9, or 10, from the mature polypeptide of SEQ ID NO: 44.

In a particular embodiment, the invention relates to polypeptides having a sequence identity to the mature polypeptide of SEQ ID NO: 44 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least 70% of the peptidoglycan degrading activity of the mature polypeptide of SEQ ID NO: 44.

In an embodiment, the present invention relates to polypeptides having a sequence identity to the mature polypeptide of SEQ ID NO: 47 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which have peptidoglycan degrading activity. In one aspect, the polypeptides differ by up to 10 amino acids, e.g., 1, 2, 3, 4, 5, 6, 7, 8, 9, or 10, from the mature polypeptide of SEQ ID NO: 47.

In a particular embodiment, the invention relates to polypeptides having a sequence identity to the mature polypeptide of SEQ ID NO: 47 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least 70% of the peptidoglycan degrading activity of the mature polypeptide of SEQ ID NO: 47.

In an embodiment, the present invention relates to polypeptides having a sequence identity to the mature polypeptide of SEQ ID NO: 50 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which have peptidoglycan degrading activity. In one aspect, the polypeptides differ by up to 10 amino acids, e.g., 1, 2, 3, 4, 5, 6, 7, 8, 9, or 10, from the mature polypeptide of SEQ ID NO: 50.

In a particular embodiment, the invention relates to polypeptides having a sequence identity to the mature polypeptide of SEQ ID NO: 50 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least 70% of the peptidoglycan degrading activity of the mature polypeptide of SEQ ID NO: 50.

In an embodiment, the present invention relates to polypeptides having a sequence identity to the mature polypeptide of SEQ ID NO: 53 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which have peptidoglycan degrading activity. In one aspect, the polypeptides differ by up to 10 amino acids, e.g., 1, 2, 3, 4, 5, 6, 7, 8, 9, or 10, from the mature polypeptide of SEQ ID NO: 53.

In a particular embodiment, the invention relates to polypeptides having a sequence identity to the mature polypeptide of SEQ ID NO: 53 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least 70% of the peptidoglycan degrading activity of the mature polypeptide of SEQ ID NO: 53.

In an embodiment, the present invention relates to polypeptides having a sequence identity to the mature polypeptide of SEQ ID NO: 56 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which have peptidoglycan degrading activity. In one aspect, the polypeptides differ by up to 10 amino acids, e.g., 1, 2, 3, 4, 5, 6, 7, 8, 9, or 10, from the mature polypeptide of SEQ ID NO: 56.

In a particular embodiment, the invention relates to polypeptides having a sequence identity to the mature polypeptide of SEQ ID NO: 56 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least 70% of the peptidoglycan degrading activity of the mature polypeptide of SEQ ID NO: 56.

In an embodiment, the present invention relates to polypeptides having a sequence identity to the mature polypeptide of SEQ ID NO: 59 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which have peptidoglycan degrading activity. In one aspect, the polypeptides differ by up to 10 amino acids, e.g., 1, 2, 3, 4, 5, 6, 7, 8, 9, or 10, from the mature polypeptide of SEQ ID NO: 59.

In a particular embodiment, the invention relates to polypeptides having a sequence identity to the mature polypeptide of SEQ ID NO: 59 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least 70% of the peptidoglycan degrading activity of the mature polypeptide of SEQ ID NO: 59.

In an embodiment, the present invention relates to polypeptides having a sequence identity to the mature polypeptide of SEQ ID NO: 62 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which have peptidoglycan degrading activity. In one aspect, the polypeptides differ by up to 10 amino acids, e.g., 1, 2, 3, 4, 5, 6, 7, 8, 9, or 10, from the mature polypeptide of SEQ ID NO: 62.

In a particular embodiment, the invention relates to polypeptides having a sequence identity to the mature polypeptide of SEQ ID NO: 62 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least 70% of the peptidoglycan degrading activity of the mature polypeptide of SEQ ID NO: 62.

In an embodiment, the present invention relates to polypeptides having a sequence identity to the mature polypeptide of SEQ ID NO: 65 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which have peptidoglycan degrading activity. In one aspect, the polypeptides differ by up to 10 amino acids, e.g., 1, 2, 3, 4, 5, 6, 7, 8, 9, or 10, from the mature polypeptide of SEQ ID NO: 65.

In a particular embodiment, the invention relates to polypeptides having a sequence identity to the mature polypeptide of SEQ ID NO: 65 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least 70% of the peptidoglycan degrading activity of the mature polypeptide of SEQ ID NO: 65.

In an embodiment, the present invention relates to polypeptides having a sequence identity to the mature polypeptide of SEQ ID NO: 68 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which have peptidoglycan degrading activity. In one aspect, the polypeptides differ by up to 10 amino acids, e.g., 1, 2, 3, 4, 5, 6, 7, 8, 9, or 10, from the mature polypeptide of SEQ ID NO: 68.

In a particular embodiment, the invention relates to polypeptides having a sequence identity to the mature polypeptide of SEQ ID NO: 68 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least 70% of the peptidoglycan degrading activity of the mature polypeptide of SEQ ID NO: 68.

In an embodiment, the present invention relates to polypeptides having a sequence identity to the mature polypeptide of SEQ ID NO: 71 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which have peptidoglycan degrading activity. In one aspect, the polypeptides differ by up to 10 amino acids, e.g., 1, 2, 3, 4, 5, 6, 7, 8, 9, or 10, from the mature polypeptide of SEQ ID NO: 71.

In a particular embodiment, the invention relates to polypeptides having a sequence identity to the mature polypeptide of SEQ ID NO: 71 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least 70% of the peptidoglycan degrading activity of the mature polypeptide of SEQ ID NO: 71.

In an embodiment, the present invention relates to polypeptides having a sequence identity to the mature polypeptide of SEQ ID NO: 74 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which have peptidoglycan degrading activity. In one aspect, the polypeptides differ by up to 10 amino acids, e.g., 1, 2, 3, 4, 5, 6, 7, 8, 9, or 10, from the mature polypeptide of SEQ ID NO: 74.

In a particular embodiment, the invention relates to polypeptides having a sequence identity to the mature polypeptide of SEQ ID NO: 74 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least 70% of the peptidoglycan degrading activity of the mature polypeptide of SEQ ID NO: 74.

In an embodiment, the present invention relates to polypeptides having a sequence identity to the mature polypeptide of SEQ ID NO: 77 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which have peptidoglycan degrading activity. In one aspect, the polypeptides differ by up to 10 amino acids, e.g., 1, 2, 3, 4, 5, 6, 7, 8, 9, or 10, from the mature polypeptide of SEQ ID NO: 77.

In a particular embodiment, the invention relates to polypeptides having a sequence identity to the mature polypeptide of SEQ ID NO: 77 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least 70% of the peptidoglycan degrading activity of the mature polypeptide of SEQ ID NO: 77.

In an embodiment, the present invention relates to polypeptides having a sequence identity to the mature polypeptide of SEQ ID NO: 80 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which have peptidoglycan degrading activity. In one aspect, the polypeptides differ by up to 10 amino acids, e.g., 1, 2, 3, 4, 5, 6, 7, 8, 9, or 10, from the mature polypeptide of SEQ ID NO: 80.

In a particular embodiment, the invention relates to polypeptides having a sequence identity to the mature polypeptide of SEQ ID NO: 80 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least 70% of the peptidoglycan degrading activity of the mature polypeptide of SEQ ID NO: 80.

In an embodiment, the present invention relates to polypeptides having a sequence identity to the mature polypeptide of SEQ ID NO: 83 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which have peptidoglycan degrading activity. In one aspect, the polypeptides differ by up to 10 amino acids, e.g., 1, 2, 3, 4, 5, 6, 7, 8, 9, or 10, from the mature polypeptide of SEQ ID NO: 83.

In a particular embodiment, the invention relates to polypeptides having a sequence identity to the mature polypeptide of SEQ ID NO: 83 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least 70% of the peptidoglycan degrading activity of the mature polypeptide of SEQ ID NO: 83.

In an embodiment, the present invention relates to polypeptides having a sequence identity to the mature polypeptide of SEQ ID NO: 86 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which have peptidoglycan degrading activity. In one aspect, the polypeptides differ by up to 10 amino acids, e.g., 1, 2, 3, 4, 5, 6, 7, 8, 9, or 10, from the mature polypeptide of SEQ ID NO: 86.

In a particular embodiment, the invention relates to polypeptides having a sequence identity to the mature polypeptide of SEQ ID NO: 86 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least 70% of the peptidoglycan degrading activity of the mature polypeptide of SEQ ID NO: 86.

In an embodiment, the present invention relates to polypeptides having a sequence identity to the mature polypeptide of SEQ ID NO: 89 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which have peptidoglycan degrading activity. In one aspect, the polypeptides differ by up to 10 amino acids, e.g., 1, 2, 3, 4, 5, 6, 7, 8, 9, or 10, from the mature polypeptide of SEQ ID NO: 89.

In a particular embodiment, the invention relates to polypeptides having a sequence identity to the mature polypeptide of SEQ ID NO: 89 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least 70% of the peptidoglycan degrading activity of the mature polypeptide of SEQ ID NO: 89.

In an embodiment, the present invention relates to polypeptides having a sequence identity to the mature polypeptide of SEQ ID NO: 92 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which have peptidoglycan degrading activity. In one aspect, the polypeptides differ by up to 10 amino acids, e.g., 1, 2, 3, 4, 5, 6, 7, 8, 9, or 10, from the mature polypeptide of SEQ ID NO: 92.

In a particular embodiment, the invention relates to polypeptides having a sequence identity to the mature polypeptide of SEQ ID NO: 92 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least 70% of the peptidoglycan degrading activity of the mature polypeptide of SEQ ID NO: 92.

In an embodiment, the present invention relates to polypeptides having a sequence identity to the mature polypeptide of SEQ ID NO: 95 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which have peptidoglycan degrading activity. In one aspect, the polypeptides differ by up to 10 amino acids, e.g., 1, 2, 3, 4, 5, 6, 7, 8, 9, or 10, from the mature polypeptide of SEQ ID NO: 95.

In a particular embodiment, the invention relates to polypeptides having a sequence identity to the mature polypeptide of SEQ ID NO: 95 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least 70% of the peptidoglycan degrading activity of the mature polypeptide of SEQ ID NO: 95.

In an embodiment, the present invention relates to polypeptides having a sequence identity to the mature polypeptide of SEQ ID NO: 98 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which have peptidoglycan degrading activity. In one aspect, the polypeptides differ by up to 10 amino acids, e.g., 1, 2, 3, 4, 5, 6, 7, 8, 9, or 10, from the mature polypeptide of SEQ ID NO: 98.

In a particular embodiment, the invention relates to polypeptides having a sequence identity to the mature polypeptide of SEQ ID NO: 98 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least 70% of the peptidoglycan degrading activity of the mature polypeptide of SEQ ID NO: 98.

In an embodiment, the present invention relates to polypeptides having a sequence identity to the mature polypeptide of SEQ ID NO: 101 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which have peptidoglycan degrading activity. In one aspect, the polypeptides differ by up to 10 amino acids, e.g., 1, 2, 3, 4, 5, 6, 7, 8, 9, or 10, from the mature polypeptide of SEQ ID NO: 101.

In a particular embodiment, the invention relates to polypeptides having a sequence identity to the mature polypeptide of SEQ ID NO: 101 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least 70% of the peptidoglycan degrading activity of the mature polypeptide of SEQ ID NO: 101.

In an embodiment, the present invention relates to polypeptides having a sequence identity to the mature polypeptide of SEQ ID NO: 104 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which have peptidoglycan degrading activity. In one aspect, the polypeptides differ by up to 10 amino acids, e.g., 1, 2, 3, 4, 5, 6, 7, 8, 9, or 10, from the mature polypeptide of SEQ ID NO: 104.

In a particular embodiment, the invention relates to polypeptides having a sequence identity to the mature polypeptide of SEQ ID NO: 104 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least 70% of the peptidoglycan degrading activity of the mature polypeptide of SEQ ID NO: 104.

In an embodiment, the present invention relates to polypeptides having a sequence identity to the mature polypeptide of SEQ ID NO: 107 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which have peptidoglycan degrading activity. In one aspect, the polypeptides differ by up to 10 amino acids, e.g., 1, 2, 3, 4, 5, 6, 7, 8, 9, or 10, from the mature polypeptide of SEQ ID NO: 107.

In a particular embodiment, the invention relates to polypeptides having a sequence identity to the mature polypeptide of SEQ ID NO: 107 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least 70% of the peptidoglycan degrading activity of the mature polypeptide of SEQ ID NO: 107.

In a particular embodiment, the invention relates to polypeptides having a sequence identity to the polypeptide of SEQ ID NO: 3 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, and wherein the polypeptide has peptidoglycan degradation activity.

In a particular embodiment, the invention relates to polypeptides having a sequence identity to the polypeptide of SEQ ID NO: 6 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, and wherein the polypeptide has peptidoglycan degradation activity.

In a particular embodiment, the invention relates to polypeptides having a sequence identity to the polypeptide of SEQ ID NO: 9 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, and wherein the polypeptide has peptidoglycan degradation activity.

In a particular embodiment, the invention relates to polypeptides having a sequence identity to the polypeptide of SEQ ID NO: 12 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, and wherein the polypeptide has peptidoglycan degradation activity.

In a particular embodiment, the invention relates to polypeptides having a sequence identity to the polypeptide of SEQ ID NO: 15 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, and wherein the polypeptide has peptidoglycan degradation activity.

In a particular embodiment, the invention relates to polypeptides having a sequence identity to the polypeptide of SEQ ID NO: 18 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, and wherein the polypeptide has peptidoglycan degradation activity.

In a particular embodiment, the invention relates to polypeptides having a sequence identity to the polypeptide of SEQ ID NO: 21 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, and wherein the polypeptide has peptidoglycan degradation activity.

In a particular embodiment, the invention relates to polypeptides having a sequence identity to the polypeptide of SEQ ID NO: 24 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, and wherein the polypeptide has peptidoglycan degradation activity.

In a particular embodiment, the invention relates to polypeptides having a sequence identity to the polypeptide of SEQ ID NO: 27 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, and wherein the polypeptide has peptidoglycan degradation activity.

In a particular embodiment, the invention relates to polypeptides having a sequence identity to the polypeptide of SEQ ID NO: 30 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, and wherein the polypeptide has peptidoglycan degradation activity.

In a particular embodiment, the invention relates to polypeptides having a sequence identity to the polypeptide of SEQ ID NO: 33 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, and wherein the polypeptide has peptidoglycan degradation activity.

In a particular embodiment, the invention relates to polypeptides having a sequence identity to the polypeptide of SEQ ID NO: 36 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, and wherein the polypeptide has peptidoglycan degradation activity.

In a particular embodiment, the invention relates to polypeptides having a sequence identity to the polypeptide of SEQ ID NO: 39 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, and wherein the polypeptide has peptidoglycan degradation activity.

In a particular embodiment, the invention relates to polypeptides having a sequence identity to the polypeptide of SEQ ID NO: 42 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, and wherein the polypeptide has peptidoglycan degradation activity.

In a particular embodiment, the invention relates to polypeptides having a sequence identity to the polypeptide of SEQ ID NO: 45 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, and wherein the polypeptide has peptidoglycan degradation activity.

In a particular embodiment, the invention relates to polypeptides having a sequence identity to the polypeptide of SEQ ID NO: 48 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, and wherein the polypeptide has peptidoglycan degradation activity.

In a particular embodiment, the invention relates to polypeptides having a sequence identity to the polypeptide of SEQ ID NO: 51 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, and wherein the polypeptide has peptidoglycan degradation activity.

In a particular embodiment, the invention relates to polypeptides having a sequence identity to the polypeptide of SEQ ID NO: 54 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, and wherein the polypeptide has peptidoglycan degradation activity.

In a particular embodiment, the invention relates to polypeptides having a sequence identity to the polypeptide of SEQ ID NO: 57 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, and wherein the polypeptide has peptidoglycan degradation activity.

In a particular embodiment, the invention relates to polypeptides having a sequence identity to the polypeptide of SEQ ID NO: 60 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, and wherein the polypeptide has peptidoglycan degradation activity.

In a particular embodiment, the invention relates to polypeptides having a sequence identity to the polypeptide of SEQ ID NO: 63 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, and wherein the polypeptide has peptidoglycan degradation activity.

In a particular embodiment, the invention relates to polypeptides having a sequence identity to the polypeptide of SEQ ID NO: 66 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, and wherein the polypeptide has peptidoglycan degradation activity.

In a particular embodiment, the invention relates to polypeptides having a sequence identity to the polypeptide of SEQ ID NO: 69 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, and wherein the polypeptide has peptidoglycan degradation activity.

In a particular embodiment, the invention relates to polypeptides having a sequence identity to the polypeptide of SEQ ID NO: 72 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, and wherein the polypeptide has peptidoglycan degradation activity.

In a particular embodiment, the invention relates to polypeptides having a sequence identity to the polypeptide of SEQ ID NO: 75 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, and wherein the polypeptide has peptidoglycan degradation activity.

In a particular embodiment, the invention relates to polypeptides having a sequence identity to the polypeptide of SEQ ID NO: 78 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, and wherein the polypeptide has peptidoglycan degradation activity.

In a particular embodiment, the invention relates to polypeptides having a sequence identity to the polypeptide of SEQ ID NO: 81 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, and wherein the polypeptide has peptidoglycan degradation activity.

In a particular embodiment, the invention relates to polypeptides having a sequence identity to the polypeptide of SEQ ID NO: 84 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, and wherein the polypeptide has peptidoglycan degradation activity.

In a particular embodiment, the invention relates to polypeptides having a sequence identity to the polypeptide of SEQ ID NO: 87 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, and wherein the polypeptide has peptidoglycan degradation activity.

In a particular embodiment, the invention relates to polypeptides having a sequence identity to the polypeptide of SEQ ID NO: 90 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, and wherein the polypeptide has peptidoglycan degradation activity.

In a particular embodiment, the invention relates to polypeptides having a sequence identity to the polypeptide of SEQ ID NO: 93 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, and wherein the polypeptide has peptidoglycan degradation activity.

In a particular embodiment, the invention relates to polypeptides having a sequence identity to the polypeptide of SEQ ID NO: 96 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, and wherein the polypeptide has peptidoglycan degradation activity.

In a particular embodiment, the invention relates to polypeptides having a sequence identity to the polypeptide of SEQ ID NO: 99 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, and wherein the polypeptide has peptidoglycan degradation activity.

In a particular embodiment, the invention relates to polypeptides having a sequence identity to the polypeptide of SEQ ID NO: 102 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, and wherein the polypeptide has peptidoglycan degradation activity.

In a particular embodiment, the invention relates to polypeptides having a sequence identity to the polypeptide of SEQ ID NO: 105 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, and wherein the polypeptide has peptidoglycan degradation activity.

In a particular embodiment, the invention relates to polypeptides having a sequence identity to the polypeptide of SEQ ID NO: 108 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, and wherein the polypeptide has peptidoglycan degradation activity.

One embodiment of the invention relates to a polypeptide wherein the polypeptide comprises the motif N[IV]X[AG][GAS]A[AY][LV]L (SEQ ID NO: 111), wherein the polypeptide is selected from the group consisting of: SEQ ID NO: 6, SEQ ID NO: 9, SEQ ID NO: 12, SEQ ID NO: 15, SEQ ID NO: 18, SEQ ID NO: 21, SEQ ID NO: 24, SEQ ID NO: 27, SEQ ID NO: 42, SEQ ID NO: 45, SEQ ID NO: 48, SEQ ID NO: 51, SEQ ID NO: 54, SEQ ID NO: 60, SEQ ID NO: 63, SEQ ID NO: 66, SEQ ID NO: 69, SEQ ID NO: 75, SEQ ID NO: 87, SEQ ID NO: 96, SEQ ID NO: 99 and SEQ ID NO: 108 and polypeptides having at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity thereto, and wherein the polypeptide has peptidoglycan degradation activity.

One embodiment of the invention relates to a polypeptide wherein the polypeptide comprises the motif N[IV]X[AG][GAS]A[AY][LV]L (SEQ ID NO: 111), wherein the polypeptide is selected from the group consisting of: SEQ ID NO: 6, SEQ ID NO: 9, SEQ ID NO: 12, SEQ ID NO: 15, SEQ ID NO: 18, SEQ ID NO: 21, SEQ ID NO: 24, SEQ ID NO: 27, SEQ ID NO: 42, SEQ ID NO: 45, SEQ ID NO: 48, SEQ ID NO: 51, SEQ ID NO: 54, SEQ ID NO: 60, SEQ ID NO: 63, SEQ ID NO: 66, SEQ ID NO: 69, SEQ ID NO: 75, SEQ ID NO: 87, SEQ ID NO: 96, SEQ ID NO: 99 and SEQ ID NO: 108 and polypeptides having at least 60% sequence identity thereto, and wherein the polypeptide has peptidoglycan degradation activity.

One embodiment of the invention relates to a polypeptide wherein the polypeptide comprises the motif N[IV]X[AG][GAS]A[AY][LV]L (SEQ ID NO: 111), wherein the polypeptide is selected from the group consisting of: SEQ ID NO: 6, SEQ ID NO: 9, SEQ ID NO: 12, SEQ ID NO: 15, SEQ ID NO: 18, SEQ ID NO: 21, SEQ ID NO: 24, SEQ ID NO: 27, SEQ ID NO: 42, SEQ ID NO: 45, SEQ ID NO: 48, SEQ ID NO: 51, SEQ ID NO: 54, SEQ ID NO: 60, SEQ ID NO: 63, SEQ ID NO: 66, SEQ ID NO: 69, SEQ ID NO: 75, SEQ ID NO: 87, SEQ ID NO: 96, SEQ ID NO: 99 and SEQ ID NO: 108 and polypeptides having at least 70% sequence identity thereto, and wherein the polypeptide has peptidoglycan degradation activity.

One embodiment of the invention relates to a polypeptide wherein the polypeptide comprises the motif N[IV]X[AG][GAS]A[AY][LV]L (SEQ ID NO: 111), wherein the polypeptide is selected from the group consisting of: SEQ ID NO: 6, SEQ ID NO: 9, SEQ ID NO: 12, SEQ ID NO: 15, SEQ ID NO: 18, SEQ ID NO: 21, SEQ ID NO: 24, SEQ ID NO: 27, SEQ ID NO: 42, SEQ ID NO: 45, SEQ ID NO: 48, SEQ ID NO: 51, SEQ ID NO: 54, SEQ ID NO: 60, SEQ ID NO: 63, SEQ ID NO: 66, SEQ ID NO: 69, SEQ ID NO: 75, SEQ ID NO: 87, SEQ ID NO: 96, SEQ ID NO:
  99 and SEQ ID NO: 108 and polypeptides having at least 80% sequence identity thereto, and wherein the polypeptide has peptidoglycan degradation activity.

One embodiment of the invention relates to a polypeptide wherein the polypeptide comprises the motif N[IV]X[AG][GAS]A[AY][LV]L (SEQ ID NO: 111), wherein the polypeptide is selected from the group consisting of: SEQ ID NO: 6, SEQ ID NO: 9, SEQ ID NO: 12, SEQ ID NO: 15, SEQ ID NO: 18, SEQ ID NO: 21, SEQ ID NO: 24, SEQ ID NO: 27, SEQ ID NO: 42, SEQ ID NO: 45, SEQ ID NO: 48, SEQ ID NO: 51, SEQ ID NO: 54, SEQ ID NO: 60, SEQ ID NO: 63, SEQ ID NO: 66, SEQ ID NO: 69, SEQ ID NO: 75, SEQ ID NO: 87, SEQ ID NO: 96, SEQ ID NO: 99 and SEQ ID NO: 108 and polypeptides having at least 90% sequence identity thereto, and wherein the polypeptide has peptidoglycan degradation activity.

One embodiment of the invention relates to a polypeptide wherein the polypeptide comprises the motif N[IV]X[AG][GAS]A[AY][LV]L (SEQ ID NO: 111), wherein the polypeptide is selected from the group consisting of: SEQ ID NO: 6, SEQ ID NO: 9, SEQ ID NO: 12, SEQ ID NO: 15, SEQ ID NO: 18, SEQ ID NO: 21, SEQ ID NO: 24, SEQ ID NO: 27, SEQ ID NO: 42, SEQ ID NO: 45, SEQ ID NO: 48, SEQ ID NO: 51, SEQ ID NO: 54, SEQ ID NO: 60, SEQ ID NO: 63, SEQ ID NO: 66, SEQ ID NO: 69, SEQ ID NO: 75, SEQ ID NO: 87, SEQ ID NO: 96, SEQ ID NO: 99 and SEQ ID NO: 108 and polypeptides having at least 95% sequence identity thereto, and wherein the polypeptide has peptidoglycan degradation activity.

One embodiment of the invention relates to a polypeptide wherein the polypeptide comprises the motif N[IV]X[AG][GAS]A[AY][LV]L (SEQ ID NO: 111), wherein the polypeptide is selected from the group consisting of: SEQ ID NO: 6, SEQ ID NO: 9, SEQ ID NO: 12, SEQ ID NO: 15, SEQ ID NO: 18, SEQ ID NO: 21, SEQ ID NO: 24, SEQ ID NO: 27, SEQ ID NO: 42, SEQ ID NO: 45, SEQ ID NO: 48, SEQ ID NO: 51, SEQ ID NO: 54, SEQ ID NO: 60, SEQ ID NO: 63, SEQ ID NO: 66, SEQ ID NO: 69, SEQ ID NO: 75, SEQ ID NO: 87, SEQ ID NO: 96, SEQ ID NO:
  99 and SEQ ID NO: 108 and polypeptides having at least 98% sequence identity thereto, and wherein the polypeptide has peptidoglycan degradation activity.

One embodiment of the invention relates to a polypeptide wherein the polypeptide comprises the motif N[IV]X[AG][GAS]A[AY][LV]L (SEQ ID NO: 111), wherein the polypeptide is selected from the group consisting of: SEQ ID NO: 6, SEQ ID NO: 9, SEQ ID NO: 12, SEQ ID NO: 15, SEQ ID NO: 18, SEQ ID NO: 21, SEQ ID NO: 24, SEQ ID NO: 27, SEQ ID NO: 42, SEQ ID NO: 45, SEQ ID NO: 48, SEQ ID NO: 51, SEQ ID NO: 54, SEQ ID NO: 60, SEQ ID NO: 63, SEQ ID NO: 66, SEQ ID NO: 69, SEQ ID NO: 75, SEQ ID NO: 87, SEQ ID NO: 96, SEQ ID NO: 99 and SEQ ID NO: 108 and polypeptides having at least 99% sequence identity thereto, and wherein the polypeptide has peptidoglycan degradation activity.

In any of the embodiments disclosed herein, the polypeptide has preferably been isolated, i.e., the polypeptide is in an "isolated" form or environment as defined above.

One polypeptide of the present invention preferably comprises or consists of the amino acid sequence of SEQ ID NO: 2 or an allelic variant thereof; or is a fragment thereof having peptidoglycan degradation activity. In another aspect, the polypeptide comprises or consists of the mature polypeptide shown in SEQ ID NO: 3. In another aspect, the polypeptide comprises or consists of amino acids 1 to 431 of SEQ ID NO: 2.

A polypeptide of the present invention preferably comprises or consists of the amino acid sequence of SEQ ID NO: 5 or an allelic variant thereof; or is a fragment thereof having peptidoglycan degradation activity. In another aspect, the polypeptide comprises or consists of the mature polypeptide shown in SEQ ID NO: 6. In another aspect, the polypeptide comprises or consists of amino acids 1 to 485 of SEQ ID NO: 5.

A polypeptide of the present invention preferably comprises or consists of the amino acid sequence of SEQ ID NO: 8 or an allelic variant thereof; or is a fragment thereof having peptidoglycan degradation activity. In another aspect, the polypeptide comprises or consists of the mature polypeptide shown in SEQ ID NO: 9. In another aspect, the polypeptide comprises or consists of amino acids 1 to 483 of SEQ ID NO: 8.

A polypeptide of the present invention preferably comprises or consists of the amino acid sequence of SEQ ID NO: 11 or an allelic variant thereof; or is a fragment thereof having peptidoglycan degradation activity. In another aspect, the polypeptide comprises or consists of the mature polypeptide shown in SEQ ID NO: 12. In another aspect, the polypeptide comprises or consists of amino acids 1 to 471 of SEQ ID NO: 11.

A polypeptide of the present invention preferably comprises or consists of the amino acid sequence of SEQ ID NO: 14 or an allelic variant thereof; or is a fragment thereof having peptidoglycan degradation activity. In another aspect, the polypeptide comprises or consists of the mature polypeptide shown in SEQ ID NO: 15. In another aspect, the polypeptide comprises or consists of amino acids 1 to 639 of SEQ ID NO: 14.

A polypeptide of the present invention preferably comprises or consists of the amino acid sequence of SEQ ID NO: 17 or an allelic variant thereof; or is a fragment thereof having peptidoglycan degradation activity. In another aspect, the polypeptide comprises or consists of the mature polypeptide shown in SEQ ID NO: 18. In another aspect, the polypeptide comprises or consists of amino acids 1 to 484 of SEQ ID NO: 17.

A polypeptide of the present invention preferably comprises or consists of the amino acid sequence of SEQ ID NO: 20 or an allelic variant thereof; or is a fragment thereof having peptidoglycan degradation activity. In another aspect, the polypeptide comprises or consists of the mature polypeptide shown in SEQ ID NO: 21. In another aspect, the polypeptide comprises or consists of amino acids 1 to 480 of SEQ ID NO: 20.

A polypeptide of the present invention preferably comprises or consists of the amino acid sequence of SEQ ID NO: 23 or an allelic variant thereof; or is a fragment thereof having peptidoglycan degradation activity. In another aspect, the polypeptide comprises or consists of the mature polypeptide shown in SEQ ID NO: 24. In another aspect, the polypeptide comprises or consists of amino acids 1 to 485 of SEQ ID NO: 23.

A polypeptide of the present invention preferably comprises or consists of the amino acid sequence of SEQ ID NO: 26 or an allelic variant thereof; or is a fragment thereof having peptidoglycan degradation activity. In another aspect, the polypeptide comprises or consists of the mature polypeptide shown in SEQ ID NO: 27. In another aspect, the polypeptide comprises or consists of amino acids 1 to 491 of SEQ ID NO: 26.

A polypeptide of the present invention preferably comprises or consists of the amino acid sequence of SEQ ID NO: 29 or an allelic variant thereof; or is a fragment thereof having peptidoglycan degradation activity. In another aspect, the polypeptide comprises or consists of the mature polypeptide shown in SEQ ID NO: 30. In another aspect, the polypeptide comprises or consists of amino acids 1 to 289 of SEQ ID NO: 29.

A polypeptide of the present invention preferably comprises or consists of the amino acid sequence of SEQ ID NO: 32 or an allelic variant thereof; or is a fragment thereof having peptidoglycan degradation activity. In another aspect, the polypeptide comprises or consists of the mature polypeptide shown in SEQ ID NO: 33. In another aspect, the polypeptide comprises or consists of amino acids 1 to 245 of SEQ ID NO: 32.

A polypeptide of the present invention preferably comprises or consists of the amino acid sequence of SEQ ID NO: 35 or an allelic variant thereof; or is a fragment thereof having peptidoglycan degradation activity. In another aspect, the polypeptide comprises or consists of the mature polypeptide shown in SEQ ID NO: 36. In another aspect, the polypeptide comprises or consists of amino acids 1 to 280 of SEQ ID NO: 35.

A polypeptide of the present invention preferably comprises or consists of the amino acid sequence of SEQ ID NO: 38 or an allelic variant thereof; or is a fragment thereof having peptidoglycan degradation activity. In another aspect, the polypeptide comprises or consists of the mature polypeptide shown in SEQ ID NO: 39. In another aspect, the polypeptide comprises or consists of amino acids 1 to 238 of SEQ ID NO: 38.

A polypeptide of the present invention preferably comprises or consists of the amino acid sequence of SEQ ID NO: 41 or an allelic variant thereof; or is a fragment thereof having peptidoglycan degradation activity. In another aspect, the polypeptide comprises or consists of the mature polypeptide shown in SEQ ID NO: 42. In another aspect, the polypeptide comprises or consists of amino acids 1 to 498 of SEQ ID NO: 41.

A polypeptide of the present invention preferably comprises or consists of the amino acid sequence of SEQ ID NO: 44 or an allelic variant thereof; or is a fragment thereof having peptidoglycan degradation activity. In another aspect, the polypeptide comprises or consists of the mature polypeptide shown in SEQ ID NO: 45. In another aspect, the polypeptide comprises or consists of amino acids 1 to 476 of SEQ ID NO: 44.

A polypeptide of the present invention preferably comprises or consists of the amino acid sequence of SEQ ID NO: 47 or an allelic variant thereof; or is a fragment thereof having peptidoglycan degradation activity. In another aspect, the polypeptide comprises or consists of the mature polypeptide shown in SEQ ID NO: 48. In another aspect, the polypeptide comprises or consists of amino acids 1 to 474 of SEQ ID NO: 47.

A polypeptide of the present invention preferably comprises or consists of the amino acid sequence of SEQ ID NO: 50 or an allelic variant thereof; or is a fragment thereof having peptidoglycan degradation activity. In another aspect, the polypeptide comprises or consists of the mature polypeptide shown in SEQ ID NO: 51. In another aspect, the polypeptide comprises or consists of amino acids 1 to 473 of SEQ ID NO: 50.

A polypeptide of the present invention preferably comprises or consists of the amino acid sequence of SEQ ID NO: 53 or an allelic variant thereof; or is a fragment thereof having peptidoglycan degradation activity. In another aspect, the polypeptide comprises or consists of the mature polypeptide shown in SEQ ID NO: 54. In another aspect, the polypeptide comprises or consists of amino acids 1 to 414 of SEQ ID NO: 53.

A polypeptide of the present invention preferably comprises or consists of the amino acid sequence of SEQ ID NO: 56 or an allelic variant thereof; or is a fragment thereof having peptidoglycan degradation activity. In another aspect, the polypeptide comprises or consists of the mature polypeptide shown in SEQ ID NO: 57. In another aspect, the polypeptide comprises or consists of amino acids 1 to 412 of SEQ ID NO: 56.

A polypeptide of the present invention preferably comprises or consists of the amino acid sequence of SEQ ID NO: 59 or an allelic variant thereof; or is a fragment thereof having peptidoglycan degradation activity. In another aspect, the polypeptide comprises or consists of the mature polypeptide shown in SEQ ID NO: 60. In another aspect, the polypeptide comprises or consists of amino acids 1 to 637 of SEQ ID NO: 59.

A polypeptide of the present invention preferably comprises or consists of the amino acid sequence of SEQ ID NO: 62 or an allelic variant thereof; or is a fragment thereof having peptidoglycan degradation activity. In another aspect, the polypeptide comprises or consists of the mature polypeptide shown in SEQ ID NO: 63. In another aspect, the polypeptide comprises or consists of amino acids 1 to 599 of SEQ ID NO: 62.

A polypeptide of the present invention preferably comprises or consists of the amino acid sequence of SEQ ID NO: 65 or an allelic variant thereof; or is a fragment thereof having peptidoglycan degradation activity. In another aspect, the polypeptide comprises or consists of the mature polypeptide shown in SEQ ID NO: 66. In another aspect, the polypeptide comprises or consists of amino acids 1 to 605 of SEQ ID NO: 65.

A polypeptide of the present invention preferably comprises or consists of the amino acid sequence of SEQ ID NO: 68 or an allelic variant thereof; or is a fragment thereof having peptidoglycan degradation activity. In another aspect, the polypeptide comprises or consists of the mature polypeptide shown in SEQ ID NO: 69. In another aspect, the polypeptide comprises or consists of amino acids 1 to 610 of SEQ ID NO: 68.

A polypeptide of the present invention preferably comprises or consists of the amino acid sequence of SEQ ID NO: 71 or an allelic variant thereof; or is a fragment thereof having peptidoglycan degradation activity. In another aspect, the polypeptide comprises or consists of the mature polypeptide shown in SEQ ID NO: 72. In another aspect, the polypeptide comprises or consists of amino acids 1 to 216 of SEQ ID NO: 71.

A polypeptide of the present invention preferably comprises or consists of the amino acid sequence of SEQ ID NO: 74 or an allelic variant thereof; or is a fragment thereof having peptidoglycan degradation activity. In another aspect, the polypeptide comprises or consists of the mature polypeptide shown in SEQ ID NO: 75. In another aspect, the polypeptide comprises or consists of amino acids 1 to 425 of SEQ ID NO: 74.

A polypeptide of the present invention preferably comprises or consists of the amino acid sequence of SEQ ID NO: 77 or an allelic variant thereof; or is a fragment thereof having peptidoglycan degradation activity. In another aspect, the polypeptide comprises or consists of the mature polypeptide shown in SEQ ID NO: 78. In another aspect, the polypeptide comprises or consists of amino acids 1 to 304 of SEQ ID NO: 77.

A polypeptide of the present invention preferably comprises or consists of the amino acid sequence of SEQ ID NO: 80 or an allelic variant thereof; or is a fragment thereof having peptidoglycan degradation activity. In another aspect, the polypeptide comprises or consists of the mature polypeptide shown in SEQ ID NO: 81. In another aspect, the polypeptide comprises or consists of amino acids 1 to 306 of SEQ ID NO: 80.

A polypeptide of the present invention preferably comprises or consists of the amino acid sequence of SEQ ID NO: 83 or an allelic variant thereof; or is a fragment thereof having peptidoglycan degradation activity. In another aspect, the polypeptide comprises or consists of the mature polypeptide shown in SEQ ID NO: 84. In another aspect, the polypeptide comprises or consists of amino acids 1 to 306 of SEQ ID NO: 83.

A polypeptide of the present invention preferably comprises or consists of the amino acid sequence of SEQ ID NO: 86 or an allelic variant thereof; or is a fragment thereof having peptidoglycan degradation activity. In another aspect, the polypeptide comprises or consists of the mature polypeptide shown in SEQ ID NO: 87. In another aspect, the polypeptide comprises or consists of amino acids 1 to 632 of SEQ ID NO: 86.

A polypeptide of the present invention preferably comprises or consists of the amino acid sequence of SEQ ID NO: 89 or an allelic variant thereof; or is a fragment thereof having peptidoglycan degradation activity. In another aspect, the polypeptide comprises or consists of the mature polypeptide shown in SEQ ID NO: 90. In another aspect, the polypeptide comprises or consists of amino acids 1 to 216 of SEQ ID NO: 89.

A polypeptide of the present invention preferably comprises or consists of the amino acid sequence of SEQ ID NO: 92 or an allelic variant thereof; or is a fragment thereof having peptidoglycan degradation activity. In another aspect, the polypeptide comprises or consists of the mature polypeptide shown in SEQ ID NO: 93. In another aspect, the polypeptide comprises or consists of amino acids 1 to 306 of SEQ ID NO: 92.

A polypeptide of the present invention preferably comprises or consists of the amino acid sequence of SEQ ID NO: 95 or an allelic variant thereof; or is a fragment thereof having peptidoglycan degradation activity. In another aspect, the polypeptide comprises or consists of the mature polypeptide shown in SEQ ID NO: 96. In another aspect, the polypeptide comprises or consists of amino acids 1 to 453 of SEQ ID NO: 95.

A polypeptide of the present invention preferably comprises or consists of the amino acid sequence of SEQ ID NO: 98 or an allelic variant thereof; or is a fragment thereof having peptidoglycan degradation activity. In another aspect, the polypeptide comprises or consists of the mature polypeptide shown in SEQ ID NO: 99. In another aspect, the polypeptide comprises or consists of amino acids 1 to 473 of SEQ ID NO: 98.

A polypeptide of the present invention preferably comprises or consists of the amino acid sequence of SEQ ID NO: 101 or an allelic variant thereof; or is a fragment thereof having peptidoglycan degradation activity. In another aspect, the polypeptide comprises or consists of the mature polypeptide shown in SEQ ID NO: 102. In another aspect, the polypeptide comprises or consists of amino acids 1 to 209 of SEQ ID NO: 101.

A polypeptide of the present invention preferably comprises or consists of the amino acid sequence of SEQ ID NO: 104 or an allelic variant thereof; or is a fragment thereof having peptidoglycan degradation activity. In another aspect, the polypeptide comprises or consists of the mature polypeptide shown in SEQ ID NO: 105. In another aspect, the polypeptide comprises or consists of amino acids 1 to 281 of SEQ ID NO: 104.

A polypeptide of the present invention preferably comprises or consists of the amino acid sequence of SEQ ID NO: 107 or an allelic variant thereof; or is a fragment thereof having peptidoglycan degradation activity. In another aspect, the polypeptide comprises or consists of the mature polypeptide shown in SEQ ID NO: 108. In another aspect, the polypeptide comprises or consists of amino acids 1 to 582 of SEQ ID NO: 107.

In another embodiment, the present invention relates to a polypeptide having peptidoglycan degradation activity encoded by a polynucleotide that hybridizes under very low stringency conditions, low stringency conditions, medium stringency conditions, medium-high stringency conditions, high stringency conditions, or very high stringency conditions with (i) SEQ ID NO: 1, SEQ ID NO: 4, SEQ ID NO: 7, SEQ ID NO: 10, SEQ ID NO: 13, SEQ ID NO: 16, SEQ ID NO: 19, SEQ ID NO: 22, SEQ ID NO: 25, SEQ ID NO: 28, SEQ ID NO: 31, SEQ ID NO: 34, SEQ ID NO: 37, SEQ ID NO: 40, SEQ ID NO: 43, SEQ ID NO: 46, SEQ ID NO: 49, SEQ ID NO: 52, SEQ ID NO: 55, SEQ ID NO: 58, SEQ ID NO: 61, SEQ ID NO: 64, SEQ ID NO: 67, SEQ ID NO: 70, SEQ ID NO: 73, SEQ ID NO: 76, SEQ ID NO: 79, SEQ ID NO: 82, SEQ ID NO: 85, SEQ ID NO: 88, SEQ ID NO: 91, SEQ ID NO: 94, SEQ ID NO: 97, SEQ ID NO: 100, SEQ ID NO: 103 or SEQ ID NO: 106, (ii) the mature polypeptide coding sequence of SEQ ID NO: 1, SEQ ID NO: 4, SEQ ID NO: 7, SEQ ID NO: 10, SEQ ID NO: 13, SEQ ID NO: 16, SEQ ID NO: 19, SEQ ID NO: 22, SEQ ID NO: 25, SEQ ID NO: 28, SEQ ID NO: 31, SEQ ID NO: 34, SEQ ID NO: 37, SEQ ID NO: 40, SEQ ID NO: 43, SEQ ID NO: 46, SEQ ID NO: 49, SEQ ID NO: 52, SEQ ID NO: 55, SEQ ID NO: 58, SEQ ID NO: 61, SEQ ID NO: 64, SEQ ID NO: 67, SEQ ID NO: 70, SEQ ID NO: 73, SEQ ID NO: 76, SEQ ID NO: 79, SEQ ID NO: 82, SEQ ID NO: 85, SEQ ID NO: 88, SEQ ID NO: 91, SEQ ID NO: 94, SEQ ID NO: 97, SEQ ID NO: 100, SEQ ID NO: 103 or SEQ ID NO: 106; or (iii) the full-length complement of (i) or (ii) (Sambrook et al., 1989, *Molecular Cloning, A Laboratory Manual*, 2d edition, Cold Spring Harbor, New York). Such polypeptides have preferably been isolated.

The polynucleotide of SEQ ID NO: 1, SEQ ID NO: 4, SEQ ID NO: 7, SEQ ID NO: 10, SEQ ID NO: 13, SEQ ID NO: 16, SEQ ID NO: 19, SEQ ID NO: 22, SEQ ID NO: 25, SEQ ID NO: 28, SEQ ID NO: 31, SEQ ID NO: 34, SEQ ID NO: 37, SEQ ID NO: 40, SEQ ID NO: 43, SEQ ID NO: 46, SEQ ID NO: 49, SEQ ID NO: 52, SEQ ID NO: 55, SEQ ID NO: 58, SEQ ID NO: 61, SEQ ID NO: 64, SEQ ID NO: 67, SEQ ID NO: 70, SEQ ID NO: 73, SEQ ID NO: 76, SEQ ID NO: 79, SEQ ID NO: 82, SEQ ID NO: 85, SEQ ID NO: 88, SEQ ID NO: 91, SEQ ID NO: 94, SEQ ID NO: 97, SEQ ID NO: 100, SEQ ID NO: 103, SEQ ID NO: 106 or a subsequence thereof, as well as a fragment thereof may be used to design nucleic acid probes to identify and clone DNA encoding polypeptides having peptidoglycan degradation activity from strains of different genera or species according to methods well known in the art. In particular, such probes can be used for hybridization with the genomic DNA or cDNA of a cell of interest, following standard Southern blotting procedures, in order to identify and isolate the corresponding gene therein. Such probes can be considerably shorter than the entire sequence, but should be at least 15, e.g., at least 25, at least 35, or at least 70 nucleotides in length. Preferably, the nucleic acid probe is at least 100 nucleotides in length, e.g., at least 200 nucleotides, at least 300 nucleotides, at least 400 nucleotides, at least 500 nucleotides, at least 600 nucleotides, at least 700 nucleotides, at least 800 nucleotides, or at least 900 nucleotides in length. Both DNA and RNA probes can be used. The probes are typically labeled for detecting the corresponding gene (for example, with $^{32}$P, $^{3}$H, $^{35}$S, biotin, or avidin). Such probes are encompassed by the present invention.

A genomic DNA or cDNA library prepared from such other strains may be screened for DNA that hybridizes with the probes described above and encodes a polypeptide having peptidoglycan degradation activity. Genomic or other DNA from such other strains may be separated by agarose or polyacrylamide gel electrophoresis, or other separation techniques. DNA from the libraries or the separated DNA may be transferred to and immobilized on nitrocellulose or another suitable carrier material. In order to identify a clone or DNA that hybridizes with SEQ ID NO: 1, SEQ ID NO: 4, SEQ ID NO: 7, SEQ ID NO: 10, SEQ ID NO: 13, SEQ ID NO: 16, SEQ ID NO: 19, SEQ ID NO: 22, SEQ ID NO: 25, SEQ ID NO: 28, SEQ ID NO: 31, SEQ ID NO: 34, SEQ ID NO: 37, SEQ ID NO: 40, SEQ ID NO: 43, SEQ ID NO: 46, SEQ ID NO: 49, SEQ ID NO: 52, SEQ ID NO: 55, SEQ ID NO: 58, SEQ ID NO: 61, SEQ ID NO: 64, SEQ ID NO: 67, SEQ ID NO: 70, SEQ ID NO: 73, SEQ ID NO: 76, SEQ ID NO: 79, SEQ ID NO: 82, SEQ ID NO: 85, SEQ ID NO: 88, SEQ ID NO: 91, SEQ ID NO: 94, SEQ ID NO: 97, SEQ ID NO: 100, SEQ ID NO: 103, SEQ ID NO: 106 or a subsequence thereof, the carrier material is used in a Southern blot.

For purposes of the present invention, hybridization indicates that the polynucleotide hybridizes to a labeled nucleic acid probe corresponding to (i) SEQ ID NO: 1, SEQ ID NO: 4, SEQ ID NO: 7, SEQ ID NO: 10, SEQ ID NO: 13, SEQ ID NO: 16, SEQ ID NO: 19, SEQ ID NO: 22, SEQ ID NO: 25, SEQ ID NO: 28, SEQ ID NO: 31, SEQ ID NO: 34, SEQ ID NO: 37, SEQ ID NO: 40, SEQ ID NO: 43, SEQ ID NO: 46, SEQ ID NO: 49, SEQ ID NO: 52, SEQ ID NO: 55, SEQ ID NO: 58, SEQ ID NO: 61, SEQ ID NO: 64, SEQ ID NO: 67, SEQ ID NO: 70, SEQ ID NO: 73, SEQ ID NO: 76, SEQ ID NO: 79, SEQ ID NO: 82, SEQ ID NO: 85, SEQ ID NO: 88, SEQ ID NO: 91, SEQ ID NO: 94, SEQ ID NO: 97, SEQ ID NO: 100, SEQ ID NO: 103 or SEQ ID NO: 106; (ii) the mature polypeptide coding sequence of SEQ ID NO: 1, SEQ ID NO: 4, SEQ ID NO: 7, SEQ ID NO: 10, SEQ ID NO: 13, SEQ ID NO: 16, SEQ ID NO: 19, SEQ ID NO: 22, SEQ ID NO: 25, SEQ ID NO: 28, SEQ ID NO: 31, SEQ ID NO: 34, SEQ ID NO: 37, SEQ ID NO: 40, SEQ ID NO: 43, SEQ ID NO: 46, SEQ ID NO: 49, SEQ ID NO: 52, SEQ ID NO: 55, SEQ ID NO: 58, SEQ ID NO: 61, SEQ ID NO: 64, SEQ ID NO: 67, SEQ ID NO: 70, SEQ ID NO: 73, SEQ ID NO: 76, SEQ ID NO: 79, SEQ ID NO: 82, SEQ ID NO: 85, SEQ ID NO: 88, SEQ ID NO: 91, SEQ ID NO: 94, SEQ ID NO: 97, SEQ ID NO: 100, SEQ ID NO: 103 or SEQ ID NO: 106; (iii) the full-length complement thereof; or (iv) a subsequence thereof; under very low to very high stringency conditions. Molecules to which the nucleic acid probe hybridizes under these conditions can be detected using, for example, X-ray film or any other detection means known in the art.

In another embodiment, the present invention relates to a polypeptide having peptidoglycan degradation activity encoded by a polynucleotide having a sequence identity to the mature polypeptide coding sequence of SEQ ID NO: 1 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%.

In another embodiment, the present invention relates to a polypeptide having peptidoglycan degradation activity encoded by a polynucleotide having a sequence identity to the mature polypeptide coding sequence of SEQ ID NO: 4 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%.

In another embodiment, the present invention relates to a polypeptide having peptidoglycan degradation activity encoded by a polynucleotide having a sequence identity to the mature polypeptide coding sequence of SEQ ID NO: 7 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%.

In another embodiment, the present invention relates to a polypeptide having peptidoglycan degradation activity encoded by a polynucleotide having a sequence identity to the mature polypeptide coding sequence of SEQ ID NO: 10 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%.

In another embodiment, the present invention relates to a polypeptide having peptidoglycan degradation activity encoded by a polynucleotide having a sequence identity to the mature polypeptide coding sequence of SEQ ID NO: 13 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%.

In another embodiment, the present invention relates to a polypeptide having peptidoglycan degradation activity encoded by a polynucleotide having a sequence identity to the mature polypeptide coding sequence of SEQ ID NO: 16 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%.

In another embodiment, the present invention relates to a polypeptide having peptidoglycan degradation activity encoded by a polynucleotide having a sequence identity to the mature polypeptide coding sequence of SEQ ID NO: 19 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%.

In another embodiment, the present invention relates to a polypeptide having peptidoglycan degradation activity encoded by a polynucleotide having a sequence identity to the mature polypeptide coding sequence of SEQ ID NO: 22 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%.

In another embodiment, the present invention relates to a polypeptide having peptidoglycan degradation activity encoded by a polynucleotide having a sequence identity to the mature polypeptide coding sequence of SEQ ID NO: 25 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%.

In another embodiment, the present invention relates to a polypeptide having peptidoglycan degradation activity encoded by a polynucleotide having a sequence identity to the mature polypeptide coding sequence of SEQ ID NO: 28 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%.

In another embodiment, the present invention relates to a polypeptide having peptidoglycan degradation activity encoded by a polynucleotide having a sequence identity to the mature polypeptide coding sequence of SEQ ID NO: 31 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%.

In another embodiment, the present invention relates to a polypeptide having peptidoglycan degradation activity encoded by a polynucleotide having a sequence identity to the mature polypeptide coding sequence of SEQ ID NO: 34 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%.

In another embodiment, the present invention relates to a polypeptide having peptidoglycan degradation activity encoded by a polynucleotide having a sequence identity to the mature polypeptide coding sequence of SEQ ID NO: 37 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%.

In another embodiment, the present invention relates to a polypeptide having peptidoglycan degradation activity encoded by a polynucleotide having a sequence identity to the mature polypeptide coding sequence of SEQ ID NO: 40 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%.

In another embodiment, the present invention relates to a polypeptide having peptidoglycan degradation activity encoded by a polynucleotide having a sequence identity to the mature polypeptide coding sequence of SEQ ID NO: 43 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%.

In another embodiment, the present invention relates to a polypeptide having peptidoglycan degradation activity encoded by a polynucleotide having a sequence identity to the mature polypeptide coding sequence of SEQ ID NO: 46 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%.

In another embodiment, the present invention relates to a polypeptide having peptidoglycan degradation activity encoded by a polynucleotide having a sequence identity to the mature polypeptide coding sequence of SEQ ID NO: 49 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%.

In another embodiment, the present invention relates to a polypeptide having peptidoglycan degradation activity encoded by a polynucleotide having a sequence identity to the mature polypeptide coding sequence of SEQ ID NO: 52 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%.

In another embodiment, the present invention relates to a polypeptide having peptidoglycan degradation activity encoded by a polynucleotide having a sequence identity to the mature polypeptide coding sequence of SEQ ID NO: 55 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%.

In another embodiment, the present invention relates to a polypeptide having peptidoglycan degradation activity encoded by a polynucleotide having a sequence identity to the mature polypeptide coding sequence of SEQ ID NO: 58 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%.

In another embodiment, the present invention relates to a polypeptide having peptidoglycan degradation activity encoded by a polynucleotide having a sequence identity to the mature polypeptide coding sequence of SEQ ID NO: 61 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%.

In another embodiment, the present invention relates to a polypeptide having peptidoglycan degradation activity encoded by a polynucleotide having a sequence identity to the mature polypeptide coding sequence of SEQ ID NO: 64 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%.

In another embodiment, the present invention relates to a polypeptide having peptidoglycan degradation activity encoded by a polynucleotide having a sequence identity to the mature polypeptide coding sequence of SEQ ID NO: 67 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%.

In another embodiment, the present invention relates to a polypeptide having peptidoglycan degradation activity encoded by a polynucleotide having a sequence identity to the mature polypeptide coding sequence of SEQ ID NO: 70 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%.

In another embodiment, the present invention relates to a polypeptide having peptidoglycan degradation activity encoded by a polynucleotide having a sequence identity to the mature polypeptide coding sequence of SEQ ID NO: 73 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%.

In another embodiment, the present invention relates to a polypeptide having peptidoglycan degradation activity encoded by a polynucleotide having a sequence identity to the mature polypeptide coding sequence of SEQ ID NO: 76 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%.

In another embodiment, the present invention relates to a polypeptide having peptidoglycan degradation activity encoded by a polynucleotide having a sequence identity to the mature polypeptide coding sequence of SEQ ID NO: 79 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%.

In another embodiment, the present invention relates to a polypeptide having peptidoglycan degradation activity encoded by a polynucleotide having a sequence identity to the mature polypeptide coding sequence of SEQ ID NO: 82 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%.

In another embodiment, the present invention relates to a polypeptide having peptidoglycan degradation activity encoded by a polynucleotide having a sequence identity to the mature polypeptide coding sequence of SEQ ID NO: 85 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%.

In another embodiment, the present invention relates to a polypeptide having peptidoglycan degradation activity encoded by a polynucleotide having a sequence identity to the mature polypeptide coding sequence of SEQ ID NO: 88 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%.

In another embodiment, the present invention relates to a polypeptide having peptidoglycan degradation activity encoded by a polynucleotide having a sequence identity to the mature polypeptide coding sequence of SEQ ID NO: 91 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%.

In another embodiment, the present invention relates to a polypeptide having peptidoglycan degradation activity encoded by a polynucleotide having a sequence identity to the mature polypeptide coding sequence of SEQ ID NO: 94 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%.

In another embodiment, the present invention relates to a polypeptide having peptidoglycan degradation activity encoded by a polynucleotide having a sequence identity to the mature polypeptide coding sequence of SEQ ID NO: 97 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%.

In another embodiment, the present invention relates to a polypeptide having peptidoglycan degradation activity encoded by a polynucleotide having a sequence identity to the mature polypeptide coding sequence of SEQ ID NO: 100 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%.

In another embodiment, the present invention relates to a polypeptide having peptidoglycan degradation activity encoded by a polynucleotide having a sequence identity to the mature polypeptide coding sequence of SEQ ID NO: 103 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%.

In another embodiment, the present invention relates to a polypeptide having peptidoglycan degradation activity encoded by a polynucleotide having a sequence identity to the mature polypeptide coding sequence of SEQ ID NO: 106 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%.

In another embodiment, the present invention relates to variants of the polypeptide shown in SEQ ID NO: 3 comprising a substitution, deletion, and/or insertion at one or more positions. In an embodiment, the number of amino acid substitutions, deletions and/or insertions introduced into the polypeptide shown SEQ ID NO: 3 is up to 10, e.g., 1, 2, 3, 4, 5, 6, 7, 8, 9, or 10.

In another embodiment, the present invention relates to variants of the polypeptide shown in SEQ ID NO: 6 comprising a substitution, deletion, and/or insertion at one or more positions. In an embodiment, the number of amino acid substitutions, deletions and/or insertions introduced into the polypeptide shown SEQ ID NO: 6 is up to 10, e.g., 1, 2, 3, 4, 5, 6, 7, 8, 9, or 10.

In another embodiment, the present invention relates to variants of the polypeptide shown in SEQ ID NO: 9 comprising a substitution, deletion, and/or insertion at one or more positions. In an embodiment, the number of amino acid substitutions, deletions and/or insertions introduced into the polypeptide shown SEQ ID NO: 9 is up to 10, e.g., 1, 2, 3, 4, 5, 6, 7, 8, 9, or 10.

In another embodiment, the present invention relates to variants of the polypeptide shown in SEQ ID NO: 12 comprising a substitution, deletion, and/or insertion at one or more positions. In an embodiment, the number of amino acid substitutions, deletions and/or insertions introduced into the polypeptide shown SEQ ID NO: 12 is up to 10, e.g., 1, 2, 3, 4, 5, 6, 7, 8, 9, or 10.

In another embodiment, the present invention relates to variants of the polypeptide shown in SEQ ID NO: 15 comprising a substitution, deletion, and/or insertion at one or more positions. In an embodiment, the number of amino acid substitutions, deletions and/or insertions introduced into the polypeptide shown SEQ ID NO: 15 is up to 10, e.g., 1, 2, 3, 4, 5, 6, 7, 8, 9, or 10.

In another embodiment, the present invention relates to variants of the polypeptide shown in SEQ ID NO: 18 comprising a substitution, deletion, and/or insertion at one or more positions. In an embodiment, the number of amino acid substitutions, deletions and/or insertions introduced into the polypeptide shown SEQ ID NO: 18 is up to 10, e.g., 1, 2, 3, 4, 5, 6, 7, 8, 9, or 10.

In another embodiment, the present invention relates to variants of the polypeptide shown in SEQ ID NO: 21 comprising a substitution, deletion, and/or insertion at one or more positions. In an embodiment, the number of amino acid substitutions, deletions and/or insertions introduced into the polypeptide shown SEQ ID NO: 21 is up to 10, e.g., 1, 2, 3, 4, 5, 6, 7, 8, 9, or 10.

In another embodiment, the present invention relates to variants of the polypeptide shown in SEQ ID NO: 24 comprising a substitution, deletion, and/or insertion at one or more positions. In an embodiment, the number of amino acid substitutions, deletions and/or insertions introduced into the polypeptide shown SEQ ID NO: 24 is up to 10, e.g., 1, 2, 3, 4, 5, 6, 7, 8, 9, or 10.

In another embodiment, the present invention relates to variants of the polypeptide shown in SEQ ID NO: 27 comprising a substitution, deletion, and/or insertion at one or more positions. In an embodiment, the number of amino acid substitutions, deletions and/or insertions introduced into the polypeptide shown SEQ ID NO: 27 is up to 10, e.g., 1, 2, 3, 4, 5, 6, 7, 8, 9, or 10.

In another embodiment, the present invention relates to variants of the polypeptide shown in SEQ ID NO: 30 comprising a substitution, deletion, and/or insertion at one or more positions. In an embodiment, the number of amino acid substitutions, deletions and/or insertions introduced into the polypeptide shown SEQ ID NO: 30 is up to 10, e.g., 1, 2, 3, 4, 5, 6, 7, 8, 9, or 10.

In another embodiment, the present invention relates to variants of the polypeptide shown in SEQ ID NO: 33 comprising a substitution, deletion, and/or insertion at one or more positions. In an embodiment, the number of amino acid substitutions, deletions and/or insertions introduced into the polypeptide shown SEQ ID NO: 33 is up to 10, e.g., 1, 2, 3, 4, 5, 6, 7, 8, 9, or 10.

In another embodiment, the present invention relates to variants of the polypeptide shown in SEQ ID NO: 36 comprising a substitution, deletion, and/or insertion at one or more positions. In an embodiment, the number of amino acid substitutions, deletions and/or insertions introduced into the polypeptide shown SEQ ID NO: 36 is up to 10, e.g., 1, 2, 3, 4, 5, 6, 7, 8, 9, or 10.

In another embodiment, the present invention relates to variants of the polypeptide shown in SEQ ID NO: 39 comprising a substitution, deletion, and/or insertion at one or more positions. In an embodiment, the number of amino acid substitutions, deletions and/or insertions introduced into the polypeptide shown SEQ ID NO: 39 is up to 10, e.g., 1, 2, 3, 4, 5, 6, 7, 8, 9, or 10.

In another embodiment, the present invention relates to variants of the polypeptide shown in SEQ ID NO: 42 comprising a substitution, deletion, and/or insertion at one or more positions. In an embodiment, the number of amino acid substitutions, deletions and/or insertions introduced into the polypeptide shown SEQ ID NO: 42 is up to 10, e.g., 1, 2, 3, 4, 5, 6, 7, 8, 9, or 10.

In another embodiment, the present invention relates to variants of the polypeptide shown in SEQ ID NO: 45 comprising a substitution, deletion, and/or insertion at one or more positions. In an embodiment, the number of amino acid substitutions, deletions and/or insertions introduced into the polypeptide shown SEQ ID NO: 45 is up to 10, e.g., 1, 2, 3, 4, 5, 6, 7, 8, 9, or 10.

In another embodiment, the present invention relates to variants of the polypeptide shown in SEQ ID NO: 48 comprising a substitution, deletion, and/or insertion at one or more positions. In an embodiment, the number of amino acid substitutions, deletions and/or insertions introduced into the polypeptide shown SEQ ID NO: 48 is up to 10, e.g., 1, 2, 3, 4, 5, 6, 7, 8, 9, or 10.

In another embodiment, the present invention relates to variants of the polypeptide shown in SEQ ID NO: 51 comprising a substitution, deletion, and/or insertion at one or more positions. In an embodiment, the number of amino acid substitutions, deletions and/or insertions introduced into the polypeptide shown SEQ ID NO: 51 is up to 10, e.g., 1, 2, 3, 4, 5, 6, 7, 8, 9, or 10.

In another embodiment, the present invention relates to variants of the polypeptide shown in SEQ ID NO: 54 comprising a substitution, deletion, and/or insertion at one or more positions. In an embodiment, the number of amino acid substitutions, deletions and/or insertions introduced into the polypeptide shown SEQ ID NO: 54 is up to 10, e.g., 1, 2, 3, 4, 5, 6, 7, 8, 9, or 10.

In another embodiment, the present invention relates to variants of the polypeptide shown in SEQ ID NO: 57 comprising a substitution, deletion, and/or insertion at one or more positions. In an embodiment, the number of amino acid substitutions, deletions and/or insertions introduced into the polypeptide shown SEQ ID NO: 57 is up to 10, e.g., 1, 2, 3, 4, 5, 6, 7, 8, 9, or 10.

In another embodiment, the present invention relates to variants of the polypeptide shown in SEQ ID NO: 60 comprising a substitution, deletion, and/or insertion at one or more positions. In an embodiment, the number of amino acid substitutions, deletions and/or insertions introduced into the polypeptide shown SEQ ID NO: 60 is up to 10, e.g., 1, 2, 3, 4, 5, 6, 7, 8, 9, or 10.

In another embodiment, the present invention relates to variants of the polypeptide shown in SEQ ID NO: 63 comprising a substitution, deletion, and/or insertion at one or more positions. In an embodiment, the number of amino acid substitutions, deletions and/or insertions introduced into the polypeptide shown SEQ ID NO: 63 is up to 10, e.g., 1, 2, 3, 4, 5, 6, 7, 8, 9, or 10.

In another embodiment, the present invention relates to variants of the polypeptide shown in SEQ ID NO: 66 comprising a substitution, deletion, and/or insertion at one or more positions. In an embodiment, the number of amino acid substitutions, deletions and/or insertions introduced into the polypeptide shown SEQ ID NO: 66 is up to 10, e.g., 1, 2, 3, 4, 5, 6, 7, 8, 9, or 10.

In another embodiment, the present invention relates to variants of the polypeptide shown in SEQ ID NO: 69 comprising a substitution, deletion, and/or insertion at one or more positions. In an embodiment, the number of amino acid substitutions, deletions and/or insertions introduced into the polypeptide shown SEQ ID NO: 69 is up to 10, e.g., 1, 2, 3, 4, 5, 6, 7, 8, 9, or 10.

In another embodiment, the present invention relates to variants of the polypeptide shown in SEQ ID NO: 72 comprising a substitution, deletion, and/or insertion at one or more positions. In an embodiment, the number of amino acid substitutions, deletions and/or insertions introduced into the polypeptide shown SEQ ID NO: 72 is up to 10, e.g., 1, 2, 3, 4, 5, 6, 7, 8, 9, or 10.

In another embodiment, the present invention relates to variants of the polypeptide shown in SEQ ID NO: 75 comprising a substitution, deletion, and/or insertion at one or more positions. In an embodiment, the number of amino acid substitutions, deletions and/or insertions introduced into the polypeptide shown SEQ ID NO: 75 is up to 10, e.g., 1, 2, 3, 4, 5, 6, 7, 8, 9, or 10.

In another embodiment, the present invention relates to variants of the polypeptide shown in SEQ ID NO: 78 comprising a substitution, deletion, and/or insertion at one or more positions. In an embodiment, the number of amino acid substitutions, deletions and/or insertions introduced into the polypeptide shown SEQ ID NO: 78 is up to 10, e.g., 1, 2, 3, 4, 5, 6, 7, 8, 9, or 10.

In another embodiment, the present invention relates to variants of the polypeptide shown in SEQ ID NO: 81 comprising a substitution, deletion, and/or insertion at one or more positions. In an embodiment, the number of amino acid substitutions, deletions and/or insertions introduced into the polypeptide shown SEQ ID NO: 81 is up to 10, e.g., 1, 2, 3, 4, 5, 6, 7, 8, 9, or 10.

In another embodiment, the present invention relates to variants of the polypeptide shown in SEQ ID NO: 84 comprising a substitution, deletion, and/or insertion at one or more positions. In an embodiment, the number of amino acid substitutions, deletions and/or insertions introduced into the polypeptide shown SEQ ID NO: 84 is up to 10, e.g., 1, 2, 3, 4, 5, 6, 7, 8, 9, or 10.

In another embodiment, the present invention relates to variants of the polypeptide shown in SEQ ID NO: 87 comprising a substitution, deletion, and/or insertion at one or more positions. In an embodiment, the number of amino acid substitutions, deletions and/or insertions introduced into the polypeptide shown SEQ ID NO: 87 is up to 10, e.g., 1, 2, 3, 4, 5, 6, 7, 8, 9, or 10.

In another embodiment, the present invention relates to variants of the polypeptide shown in SEQ ID NO: 90 comprising a substitution, deletion, and/or insertion at one or more positions. In an embodiment, the number of amino acid substitutions, deletions and/or insertions introduced into the polypeptide shown SEQ ID NO: 90 is up to 10, e.g., 1, 2, 3, 4, 5, 6, 7, 8, 9, or 10.

In another embodiment, the present invention relates to variants of the polypeptide shown in SEQ ID NO: 93 comprising a substitution, deletion, and/or insertion at one or more positions. In an embodiment, the number of amino acid substitutions, deletions and/or insertions introduced into the polypeptide shown SEQ ID NO: 93 is up to 10, e.g., 1, 2, 3, 4, 5, 6, 7, 8, 9, or 10.

In another embodiment, the present invention relates to variants of the polypeptide shown in SEQ ID NO: 96 comprising a substitution, deletion, and/or insertion at one or more positions. In an embodiment, the number of amino acid substitutions, deletions and/or insertions introduced into the polypeptide shown SEQ ID NO: 96 is up to 10, e.g., 1, 2, 3, 4, 5, 6, 7, 8, 9, or 10.

In another embodiment, the present invention relates to variants of the polypeptide shown in SEQ ID NO: 99 comprising a substitution, deletion, and/or insertion at one or more positions. In an embodiment, the number of amino acid substitutions, deletions and/or insertions introduced into the polypeptide shown SEQ ID NO: 99 is up to 10, e.g., 1, 2, 3, 4, 5, 6, 7, 8, 9, or 10.

In another embodiment, the present invention relates to variants of the polypeptide shown in SEQ ID NO: 102 comprising a substitution, deletion, and/or insertion at one or more positions. In an embodiment, the number of amino acid substitutions, deletions and/or insertions introduced into the polypeptide shown SEQ ID NO: 102 is up to 10, e.g., 1, 2, 3, 4, 5, 6, 7, 8, 9, or 10.

In another embodiment, the present invention relates to variants of the polypeptide shown in SEQ ID NO: 105 comprising a substitution, deletion, and/or insertion at one or more positions. In an embodiment, the number of amino acid substitutions, deletions and/or insertions introduced into the polypeptide shown SEQ ID NO: 105 is up to 10, e.g., 1, 2, 3, 4, 5, 6, 7, 8, 9, or 10.

In another embodiment, the present invention relates to variants of the polypeptide shown in SEQ ID NO: 108 comprising a substitution, deletion, and/or insertion at one or more positions. In an embodiment, the number of amino acid substitutions, deletions and/or insertions introduced into the polypeptide shown SEQ ID NO: 108 is up to 10, e.g., 1, 2, 3, 4, 5, 6, 7, 8, 9, or 10.

The amino acid changes in any of the embodiments above or elsewhere herein may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a poly-histidine tag, an antigenic epitope or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, In, *The Proteins*, Academic Press, New York. Common substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

Essential amino acids in a polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant molecules are tested for peptidoglycan degradation activity to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identity of essential amino acids can also be inferred from an alignment with a related polypeptide.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochemistry* 30: 10832-10837; U.S. Pat. No. 5,223,409; WO 92/06204), and region-directed mutagenesis (Derbyshire et al., 1986, *Gene* 46: 145; Ner et al., 1988, *DNA* 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

The polypeptide may be a hybrid polypeptide in which a region of one polypeptide is fused at the N-terminus or the C-terminus of a region of another polypeptide.

The polypeptide may be a fusion polypeptide or cleavable fusion polypeptide in which another polypeptide is fused at the N-terminus or the C-terminus of the polypeptide of the present invention. A fusion polypeptide is produced by fusing a polynucleotide encoding another polypeptide to a polynucleotide of the present invention. Techniques for producing fusion polypeptides are known in the art, and include ligating the coding sequences encoding the polypeptides so that they are in frame and that expression of the fusion polypeptide is under control of the same promoter(s) and terminator. Fusion polypeptides may also be constructed using intein technology in which fusion polypeptides are created post-translationally (Cooper et al., 1993, *EMBO J.* 12: 2575-2583; Dawson et al., 1994, *Science* 266: 776-779).

A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, *J. Ind. Microbiol. Biotechnol.* 3: 568-576; Svetina et al., 2000, *J. Biotechnol.* 76: 245-251; Rasmussen-Wilson et al., 1997, *Appl. Environ. Microbiol.* 63: 3488-3493; Ward et al., 1995, *Biotechnology* 13: 498-503; and Contreras et al., 1991, *Biotechnology* 9: 378-381; Eaton et al., 1986, *Biochemistry* 25: 505-512; Collins-Racie et al., 1995, *Biotechnology* 13: 982-987; Carter et al., 1989, *Proteins: Structure, Function, and Genetics* 6: 240-248; and Stevens, 2003, *Drug Discovery World* 4: 35-48.

Sources of Polypeptides Having Peptidoglycan Degradation Activity

A polypeptide having peptidoglycan degradation activity of the present invention may be obtained from microorganisms of any genus. For purposes of the present invention, the term "obtained from" as used herein in connection with a given source shall mean that the polypeptide encoded by a polynucleotide is produced by the source or by a strain in which the polynucleotide from the source has been inserted. In one aspect, the polypeptide obtained from a given source is secreted extracellularly. In one aspect, the polypeptide is an *Alicyclobacillus* polypeptide. In one aspect, the polypeptide is a *Tumebacillus* polypeptide. In one aspect, the polypeptide is a *Halomonas* polypeptide. In one aspect, the polypeptide is a *Kribbella* polypeptide, e.g., a polypeptide obtained from *Kribbella aluminosa*. In one aspect, the polypeptide is a *Streptomyces* polypeptide, e.g., a polypeptide obtained from *Streptomyces griseus*. In one aspect, the polypeptide is a *Nonomuraea* polypeptide, e.g., a polypeptide obtained from *Nonomuraea coxensis, Nonomuraea dietziae* or *Nonomuraea guangzhouensis*. In one aspect, the polypeptide is a *Micromonospora* polypeptide, e.g., a polypeptide obtained from *Micromonospora peucetia, Micromonospora fulvopurpurea* or *Micromonospora maritima*. In one aspect, the polypeptide is a *Laceyella* polypeptide, e.g., a polypeptide obtained from *Laceyella sacchari*. In one aspect, the polypeptide is a *Bacillus* polypeptide, e.g., a polypeptide obtained from *Bacillus sporothermodurans* or *Bacillus cohnii*. In one aspect, the polypeptide is a *Lysobacter* polypeptide, e.g., a polypeptide obtained from *Lysobacter antibioticus* or *Lysobacter capsica*. In one aspect, the polypeptide is a *Hamadaea* polypeptide, e.g., a polypeptide obtained from *Hamadaea tsunoensis*. In one aspect, the polypeptide is a *Paenibacillus* polypeptide, e.g., a polypeptide obtained from *Paenibacillus pini*. In one aspect, the polypeptide is a *Thermostaphylospora* polypeptide, e.g., a polypeptide obtained from *Thermostaphylospora chromogena*. In one aspect, the polypeptide is a *Pseudomonas* polypeptide, e.g., a polypeptide obtained from *Pseudomonas peli* or *Pseudomonas pseudoalcaligenes*.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen und Zellkulturen GmbH (DSMZ), Centraalbureau Voor Schimmelcultures (CBS), and Agricultural Research Service Patent Culture Collection, Northern Regional Research Center (NRRL).

The polypeptide may be identified and obtained from other sources including microorganisms isolated from nature (e.g., soil, composts, water, etc.) or DNA samples obtained directly from natural materials (e.g., soil, composts, water, etc.) using the above-mentioned probes. Techniques for isolating microorganisms and DNA directly from natural habitats are well known in the art. A polynucleotide encoding the polypeptide may then be obtained by similarly screening a genomic DNA or cDNA library of another microorganism or mixed DNA sample. Once a polynucleotide encoding a polypeptide has been detected with the probe(s), the polynucleotide can be isolated or cloned by utilizing techniques that are known to those of ordinary skill in the art (see, e.g., Sambrook et al., 1989, supra).

Nucleic Acid Constructs

The present invention also relates to nucleic acid constructs comprising a polynucleotide of the present invention operably linked to one or more control sequences that direct the expression of the coding sequence in a suitable host cell under conditions compatible with the control sequences.

The polynucleotide may be manipulated in a variety of ways to provide for expression of the polypeptide. Manipulation of the polynucleotide prior to its insertion into a vector may be desirable or necessary depending on the expression vector. The techniques for modifying polynucleotides utilizing recombinant DNA methods are well known in the art.

The control sequence may be a promoter, a polynucleotide that is recognized by a host cell for expression of a polynucleotide encoding a polypeptide of the present invention. The promoter contains transcriptional control sequences that mediate the expression of the polypeptide. The promoter may be any polynucleotide that shows transcriptional activity in the host cell including variant, truncated, and hybrid promoters, and may be obtained from genes encoding extracellular or intracellular polypeptides either homologous or heterologous to the host cell.

Examples of suitable promoters for directing transcription of the nucleic acid constructs of the present invention in a bacterial host cell are the promoters obtained from the *Bacillus amyloliquefaciens* alpha-amylase gene (amyQ), *Bacillus licheniformis* alpha-amylase gene (amyL), *Bacillus licheniformis* penicillinase gene (penP), *Bacillus stearothermophilus* maltogenic amylase gene (amyM), *Bacillus subtilis* levansucrase gene (sacB), *Bacillus subtilis* xylA and xylB genes, *Bacillus thuringiensis* cryIIIA gene (Agaisse and Lereclus, 1994, *Molecular Microbiology* 13: 97-107), *E. coli* lac operon, *E. coli* trc promoter (Egon et al., 1988, *Gene* 69: 301-315), *Streptomyces coelicolor* agarase gene (dagA), and prokaryotic beta-lactamase gene (Villa-Kamaroff et al., 1978, *Proc. Natl. Acad. Sci. USA* 75: 3727-3731), as well as the tac promoter (DeBoer et al., 1983, *Proc. Natl. Acad. Sci. USA* 80: 21-25). Further promoters are described in "Useful proteins from recombinant bacteria" in Gilbert et al., 1980, *Scientific American* 242: 74-94; and in Sambrook et al., 1989, supra. Examples of tandem promoters are disclosed in WO 99/43835.

Examples of suitable promoters for directing transcription of the nucleic acid constructs of the present invention in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Daria (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor, as well as the NA2-tpi promoter (a modified promoter from an *Aspergillus* neutral alpha-amylase gene in which the untranslated leader has been replaced by an untranslated leader from an *Aspergillus* triose phosphate isomerase gene; non-limiting examples include modified promoters from an *Aspergillus niger* neutral alpha-amylase gene in which the untranslated leader has been replaced by an untranslated leader from an *Aspergillus nidulans* or *Aspergillus oryzae* triose phosphate isomerase gene); and variant, truncated, and hybrid promoters thereof. Other promoters are described in U.S. Pat. No. 6,011,147.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, *Yeast* 8: 423-488.

The control sequence may also be a transcription terminator, which is recognized by a host cell to terminate transcription. The terminator is operably linked to the 3'-terminus of the polynucleotide encoding the polypeptide. Any terminator that is functional in the host cell may be used in the present invention.

Preferred terminators for bacterial host cells are obtained from the genes for *Bacillus clausii* alkaline protease (aprH), *Bacillus licheniformis* alpha-amylase (amyL), and *Escherichia coli* ribosomal RNA (rrnB).

Preferred terminators for filamentous fungal host cells are obtained from the genes for *Aspergillus nidulans* acetamidase, *Aspergillus nidulans* anthranilate synthase, *Aspergillus niger* glucoamylase, *Aspergillus niger* alpha-glucosidase, *Aspergillus oryzae* TAKA amylase, *Fusarium oxysporum* trypsin-like protease, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be an mRNA stabilizer region downstream of a promoter and upstream of the coding sequence of a gene which increases expression of the gene.

Examples of suitable mRNA stabilizer regions are obtained from a *Bacillus thuringiensis* cryIIIA gene (WO 94/25612) and a *Bacillus subtilis* SP82 gene (Hue et al., 1995, *Journal of Bacteriology* 177: 3465-3471).

The control sequence may also be a leader, a nontranslated region of an mRNA that is important for translation by the host cell. The leader is operably linked to the 5'-terminus of the polynucleotide encoding the polypeptide. Any leader that is functional in the host cell may be used.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3'-terminus of the polynucleotide and, when transcribed, is recognized by the host cell as a signal to add polyadenosine residues to transcribed mRNA. Any polyadenylation sequence that is functional in the host cell may be used.

Preferred polyadenylation sequences for filamentous fungal host cells are obtained from the genes for *Aspergillus nidulans* anthranilate synthase, *Aspergillus niger* glucoamylase, *Aspergillus niger* alpha-glucosidase *Aspergillus oryzae* TAKA amylase, and *Fusarium oxysporum* trypsin-like protease.

Useful polyadenylation sequences for yeast host cells are described by Guo and Sherman, 1995, *Mol. Cellular Biol.* 15: 5983-5990.

The control sequence may also be a signal peptide coding region that encodes a signal peptide linked to the N-terminus of a polypeptide and directs the polypeptide into the cell's secretory pathway. The 5'-end of the coding sequence of the polynucleotide may inherently contain a signal peptide coding sequence naturally linked in translation reading frame with the segment of the coding sequence that encodes the polypeptide. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the polypeptide. However, any signal peptide coding sequence that directs the expressed polypeptide into the secretory pathway of a host cell may be used.

Effective signal peptide coding sequences for bacterial host cells are the signal peptide coding sequences obtained from the genes for *Bacillus* NCIB 11837 maltogenic amylase, *Bacillus licheniformis* subtilisin, *Bacillus licheniformis* beta-lactamase, *Bacillus stearothermophilus* alpha-amylase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

The control sequence may also be a propeptide coding sequence that encodes a propeptide positioned at the N-terminus of a polypeptide. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Myceliophthora thermophila* laccase (WO 95/33836), *Rhizomucor miehei* aspartic proteinase, and *Saccharomyces cerevisiae* alpha-factor.

Where both signal peptide and propeptide sequences are present, the propeptide sequence is positioned next to the N-terminus of a polypeptide and the signal peptide sequence is positioned next to the N-terminus of the propeptide sequence.

It may also be desirable to add regulatory sequences that regulate expression of the polypeptide relative to the growth of the host cell. Examples of regulatory sequences are those that cause expression of the gene to be turned on or off in response to a chemical or physical stimulus, including the presence of a regulatory compound. Regulatory sequences in prokaryotic systems include the lac, tac, and trp operator systems. In yeast, the ADH2 system or GAL1 system may be used. In filamentous fungi, the *Aspergillus niger* glucoamylase promoter, *Aspergillus oryzae* TAKA alpha-amylase promoter, and *Aspergillus oryzae* glucoamylase promoter, *Trichoderma reesei* cellobiohydrolase I promoter, and *Trichoderma reesei* cellobiohydrolase II promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the polypeptide would be operably linked to the regulatory sequence.

Expression Vectors

The present invention also relates to recombinant expression vectors comprising a polynucleotide of the present invention, a promoter, and transcriptional and translational stop signals. The various nucleotide and control sequences may be joined together to produce a recombinant expression vector that may include one or more convenient restriction sites to allow for insertion or substitution of the polynucleotide encoding the polypeptide at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are *Bacillus licheniformis* or *Bacillus subtilis* dal genes, or markers that confer antibiotic resistance such as ampicillin, chloramphenicol, kanamycin, neomycin, spectinomycin, or tetracycline resistance. Suitable markers for yeast host cells include, but are not limited to, ADE2, HIS3, LEU2, LYS2, MET3, TRP1, and URA3. Selectable markers for use in a filamentous fungal host cell include, but are not limited to, adeA (phosphoribosylaminoimidazole-succinocarboxamide synthase), adeB (phosphoribosylaminoimidazole synthase), amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are *Aspergillus nidulans* or *Aspergillus oryzae* amdS and pyrG genes and a *Streptomyces hygroscopicus* bar gene. Preferred for use in a *Trichoderma* cell are adeA, adeB, amdS, hph, and pyrG genes.

The selectable marker may be a dual selectable marker system as described in WO 2010/039889. In one aspect, the dual selectable marker is an hph-tk dual selectable marker system.

The vector preferably contains an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMß1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANS1 (Gems et al., 1991, *Gene* 98: 61-67; Cullen et al., 1987, *Nucleic Acids Res.* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of a polypeptide. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide of the present invention operably linked to one or more control sequences that direct the production of a polypeptide of the present invention. A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be any cell useful in the recombinant production of a polypeptide of the present invention, e.g., a prokaryote or a eukaryote.

The prokaryotic host cell may be any Gram-positive or Gram-negative bacterium. Gram-positive bacteria include, but are not limited to, *Bacillus, Clostridium, Enterococcus, Geobacillus, Lactobacillus, Lactococcus, Oceanobacillus, Staphylococcus, Streptococcus*, and *Streptomyces*. Gram-negative bacteria include, but are not limited to, *Campylobacter, E. coli, Flavobacterium, Fusobacterium, Helicobacter, Ilyobacter, Neisseria, Pseudomonas, Salmonella*, and *Ureaplasma*.

The bacterial host cell may be any *Bacillus* cell including, but not limited to, *Bacillus alkalophilus, Bacillus altitudinis, Bacillus amyloliquefaciens, B. amyloliquefaciens* subsp. *plantarum, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus methylotrophicus, Bacillus pumilus, Bacillus safensis, Bacillus stearothermophilus, Bacillus subtilis*, and *Bacillus thuringiensis* cells.

The bacterial host cell may also be any *Streptococcus* cell including, but not limited to, *Streptococcus equisimilis, Streptococcus pyogenes, Streptococcus uberis*, and *Streptococcus equi* subsp. *Zooepidemicus* cells.

The bacterial host cell may also be any *Streptomyces* cell including, but not limited to, *Streptomyces achromogenes, Streptomyces avermitilis, Streptomyces coelicolor, Streptomyces griseus*, and *Streptomyces lividans* cells.

The introduction of DNA into a *Bacillus* cell may be effected by protoplast transformation (see, e.g., Chang and Cohen, 1979, *Mol. Gen. Genet.* 168: 111-115), competent cell transformation (see, e.g., Young and Spizizen, 1961, *J. Bacteriol.* 81: 823-829, or Dubnau and Davidoff-Abelson, 1971, *J. Mol. Biol.* 56: 209-221), electroporation (see, e.g., Shigekawa and Dower, 1988, *Biotechniques* 6: 742-751), or conjugation (see, e.g., Koehler and Thorne, 1987, *J. Bacteriol.* 169: 5271-5278). The introduction of DNA into an *E. coli* cell may be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Streptomyces* cell may be effected by protoplast transformation, electroporation (see, e.g., Gong et al., 2004, *Folia Microbiol.* (Praha) 49: 399-405), conjugation (see, e.g., Mazodier et al., 1989, *J. Bacteriol.* 171: 3583-3585), or transduction (see, e.g., Burke et al., 2001, *Proc. Natl. Acad. Sci. USA* 98: 6289-6294). The introduction of DNA into a *Pseudomonas* cell may be effected by electroporation (see, e.g., Choi et al., 2006, *J. Microbiol. Methods* 64: 391-397) or conjugation (see, e.g., Pinedo and Smets, 2005, *Appl. Environ. Microbiol.* 71: 51-57). The introduction of DNA into a *Streptococcus* cell may be effected by natural competence (see, e.g., Perry and Kuramitsu, 1981, *Infect. Immun.* 32: 1295-1297), protoplast transformation (see, e.g., Catt and Jollick, 1991, *Microbios* 68: 189-207), electroporation (see, e.g., Buckley et al., 1999, *Appl. Environ. Microbiol.* 65: 3800-3804), or conjugation (see, e.g., Clewell, 1981, *Microbiol. Rev.* 45: 409-436). However, any method known in the art for introducing DNA into a host cell can be used.

The host cell may also be a eukaryote, such as a mammalian, insect, plant, or fungal cell.

The host cell may be a fungal cell. "Fungi" as used herein includes the phyla Ascomycota, Basidiomycota, Chytridiomycota, and Zygomycota as well as the Oomycota and all mitosporic fungi (as defined by Hawksworth et al., In, *Ainsworth and Bisby's Dictionary of The Fungi*, 8th edition, 1995, CAB International, University Press, Cambridge, UK).

The fungal host cell may be a yeast cell. "Yeast" as used herein includes ascosporogenous yeast (Endomycetales), basidiosporogenous yeast, and yeast belonging to the *Fungi imperfecti* (Blastomycetes). Since the classification of yeast may change in the future, for the purposes of this invention, yeast shall be defined as described in *Biology and Activities of Yeast* (Skinner, Passmore, and Davenport, editors, *Soc. App. Bacteriol. Symposium Series No. 9*, 1980).

The yeast host cell may be a *Candida, Hansenula, Kluyveromyces, Pichia, Saccharomyces, Schizosaccharomyces*, or *Yarrowia* cell, such as a *Kluyveromyces lactis, Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis*, or *Yarrowia lipolytica* cell.

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

The filamentous fungal host cell may be an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes*, or *Trichoderma* cell.

For example, the filamentous fungal host cell may be an *Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina Ceriporiopsis caregiea, Ceriporiopsis gilvescens, Ceriporiopsis pannocinta, Ceriporiopsis rivulose, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginose, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei*, or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023, Yelton et al., 1984, *Proc. Natl. Acad. Sci. USA* 81: 1470-1474, and Christensen et al., 1988, *Bio/Technology* 6: 1419-1422. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *J. Bacteriol.* 153: 163; and Hinnen et al., 1978, *Proc. Natl. Acad. Sci. USA* 75: 1920.

Methods of Production

The present invention also relates to methods of producing a polypeptide of the present invention, comprising (a) cultivating a cell, which in its wild-type form produces the polypeptide, under conditions conducive for production of the polypeptide; and optionally, (b) recovering the polypeptide.

The present invention also relates to recombinant methods of producing a polypeptide of the present invention, comprising (a) cultivating a recombinant host cell of the present invention capable of expressing the polypeptide under conditions conducive for production of the polypeptide; and optionally, (b) recovering the polypeptide.

One embodiment of the invention relates to a method of producing a polypeptide, wherein the polypeptide is selected from the group consisting of: SEQ ID NO: 3, SEQ ID NO: 6, SEQ ID NO: 9, SEQ ID NO: 12, SEQ ID NO: 15, SEQ ID NO: 18, SEQ ID NO: 21, SEQ ID NO: 24, SEQ ID NO: 27, SEQ ID NO: 30, SEQ ID NO: 33, SEQ ID NO: 36, SEQ ID NO: 39, SEQ ID NO: 42, SEQ ID NO: 45, SEQ ID NO: 48, SEQ ID NO: 51, SEQ ID NO: 54, SEQ ID NO: 57, SEQ ID NO: 60, SEQ ID NO: 63, SEQ ID NO: 66, SEQ ID NO:

69, SEQ ID NO: 72, SEQ ID NO: 75, SEQ ID NO: 78, SEQ ID NO: 81, SEQ ID NO: 84, SEQ ID NO: 87, SEQ ID NO: 90, SEQ ID NO: 93, SEQ ID NO: 96, SEQ ID NO: 99, SEQ ID NO: 102, SEQ ID NO: 105, SEQ ID NO: 108, and polypeptides having at least at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% hereto, comprising (a) cultivating a recombinant host cell of the present invention capable of expressing one of the polypeptides under conditions conducive for production of the polypeptide; and optionally, (b) recovering the polypeptide.

The host cells are cultivated in a nutrient medium suitable for production of the polypeptide using methods known in the art. For example, the cells may be cultivated by shake flask cultivation, or small-scale or large-scale fermentation (including continuous, batch, fed-batch, or solid-state fermentations) in laboratory or industrial fermentors in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptide may be detected using methods known in the art that are specific for the polypeptides. These detection methods include, but are not limited to, use of specific antibodies, formation of an enzyme product, or disappearance of an enzyme substrate. For example, an enzyme assay may be used to determine the activity of the polypeptide.

The polypeptide may be recovered using methods known in the art. For example, the polypeptide may be recovered from the nutrient medium by conventional procedures including, but not limited to, collection, centrifugation, filtration, extraction, spray-drying, evaporation, or precipitation. In one aspect, a fermentation broth comprising the polypeptide is recovered.

The polypeptide may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., Protein Purification, Janson and Ryden, editors, VCH Publishers, New York, 1989) to obtain substantially pure polypeptides.

In an alternative aspect, the polypeptide is not recovered, but rather a host cell of the present invention expressing the polypeptide is used as a source of the polypeptide. Another option is to use a supernatant in which the polypeptide has been expressed as a source of the polypeptide.

Formulation of Enzyme in Granules

Non-dusting granulates may be produced, e.g., as disclosed in U.S. Pat. Nos. 4,106,991 and 4,661,452 and may optionally be coated by methods known in the art. Examples of waxy coating materials are poly(ethylene oxide) products (polyethyleneglycol, PEG) with mean molar weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono-, di- and triglycerides of fatty acids. Examples of film-forming coating materials suitable for application by fluid bed techniques are given in GB 1483591. Liquid enzyme preparations may, for instance, be stabilized by adding a polyol such as propylene glycol, a sugar or sugar alcohol, lactic acid or boric acid according to established methods. Protected enzymes may be prepared according to the method disclosed in EP 238216.

The composition(s) of the invention may be formulated as a granule, for example as a co-granule that combines one or more enzymes. Each enzyme will then be present in more granules, securing a more uniform distribution of enzymes in the detergent. This also reduces the physical segregation of different enzymes due to different particle sizes. Methods for producing multi-enzyme co-granulates for the detergent industry are disclosed in the IP.com disclosure IPCOM000200739D.

Another example of formulation of enzymes by the use of co-granulates is disclosed in WO 2013/188331, which relates to a detergent composition comprising (a) a multi-enzyme co-granule; (b) less than 10 wt % zeolite (anhydrous basis); and (c) less than 10 wt % phosphate salt (anhydrous basis), wherein said enzyme co-granule comprises from 10 to 98 wt % moisture sink component and the composition additionally comprises from 20 to 80 wt % detergent moisture sink component. WO 2013/188331 also relates to a method of treating and/or cleaning a surface, preferably a fabric surface comprising the steps of (i) contacting said surface with the detergent composition in aqueous wash liquor, (ii) rinsing and/or drying the surface.

A multi-enzyme co-granule may comprise an enzyme of the invention and one or more enzymes selected from the group consisting of proteases, lipases, cellulases, xyloglucanases, perhydrolases, peroxidases, lipoxygenases, laccases, hemicellulases, proteases, cellulases, cellobiose dehydrogenases, xylanases, phospholipases, esterases, cutinases, pectinases, mannanases, pectate lyases, keratinases, reductases, oxidases, phenoloxidases, ligninases, pullulanases, tannases, pentosanases, lichenases, glucanases, arabinosidases, hyaluronidases, chondroitinase, amylases, nucleases, hexosaminidases and mixtures thereof.

An embodiment of the invention relates to an enzyme granule/particle comprising the enzyme of the invention. The granule is composed of a core, and optionally one or more coatings (outer layers) surrounding the core. Typically, the granule/particle size, measured as equivalent spherical diameter (volume based average particle size), of the granule is 20-2000 µm, particularly 50-1500 µm, 100-1500 µm or 250-1200 µm.

The core may include additional materials such as fillers, fibre materials (cellulose or synthetic fibers), stabilizing agents, solubilizing agents, suspension agents, viscosity regulating agents, light spheres, plasticizers, salts, lubricants and fragrances.

The core may include binders, such as synthetic polymer, wax, fat, or carbohydrate.

The core may comprise a salt of a multivalent cation, a reducing agent, an antioxidant, a peroxide decomposing catalyst and/or an acidic buffer component, typically as a homogenous blend.

The core may consist of an inert particle with the enzyme absorbed into it, or applied onto the surface, e.g., by fluid bed coating.

The core may have a diameter of 20-2000 µm, particularly 50-1500 µm, 100-1500 µm or 250-1200 µm.

The core can be prepared by granulating a blend of the ingredients, e.g., by a method comprising granulation techniques such as crystallization, precipitation, pan-coating, fluid bed coating, fluid bed agglomeration, rotary atomization, extrusion, prilling, spheronization, size reduction methods, drum granulation, and/or high shear granulation.

Methods for preparing the core can be found in Handbook of Powder Technology; Particle size enlargement by C. E. Capes; Volume 1; 1980; Elsevier.

The core of the enzyme granule/particle may be surrounded by at least one coating, e.g., to improve the storage stability, to reduce dust formation during handling, or for coloring the granule. The optional coating(s) may include a salt coating, or other suitable coating materials, such as polyethylene glycol (PEG), methyl hydroxy-propyl cellulose (MHPC) and polyvinyl alcohol (PVA). Examples of enzyme granules with multiple coatings are shown in WO 93/07263 and WO 97/23606.

The coating may be applied in an amount of at least 0.1% by weight of the core, e.g., at least 0.5%, 1% or 5%. The amount may be at most 100%, 70%, 50%, 40% or 30%.

The coating is preferably at least 0.1 μm thick, particularly at least 0.5 μm, at least 1 μm or at least 5 μm. In a particular embodiment, the thickness of the coating is below 100 μm. In a more particular embodiment the thickness of the coating is below 60 μm. In an even more particular embodiment the total thickness of the coating is below 40 μm.

The coating should encapsulate the core unit by forming a substantially continuous layer. A substantially continuous layer is to be understood as a coating having few or no holes, so that the core unit it is encapsulating/enclosing has few or none uncoated areas. The layer or coating should be homogeneous in thickness.

The coating can further contain other materials as known in the art, e.g., fillers, antisticking agents, pigments, dyes, plasticizers and/or binders, such as titanium dioxide, kaolin, calcium carbonate or talc.

A salt coating may comprise at least 60% by weight w/w of a salt, e.g., at least 65%, at least 70%, at least 75%, at least 80%, at least 85%, at least 90%, at least 95% or at least 99% by weight w/w.

The salt may be added from a salt solution where the salt is completely dissolved or from a salt suspension wherein the fine particles is less than 50 μm, such as less than 10 μm or less than 5 μm.

The salt coating may comprise a single salt or a mixture of two or more salts. The salt may be water soluble, in particular, having a solubility at least 0.1 grams in 100 g of water at 20° C., preferably at least 0.5 g per 100 g water, e.g., at least 1 g per 100 g water, e.g., at least 5 g per 100 g water.

The salt may be an inorganic salt, e.g., salts of sulfate, sulfite, phosphate, phosphonate, nitrate, chloride or carbonate or salts of simple organic acids (less than 10 carbon atoms, e.g., 6 or less carbon atoms) such as citrate, malonate or acetate. Examples of cations in these salts are alkali or earth alkali metal ions, the ammonium ion or metal ions of the first transition series, such as sodium, potassium, magnesium, calcium, zinc or aluminum. Examples of anions include chloride, bromide, iodide, sulfate, sulfite, bisulfite, thiosulfate, phosphate, monobasic phosphate, dibasic phosphate, hypophosphite, dihydrogen pyrophosphate, tetraborate, borate, carbonate, bicarbonate, metasilicate, citrate, malate, maleate, malonate, succinate, lactate, formate, acetate, butyrate, propionate, benzoate, tartrate, ascorbate or gluconate. In particular alkali- or earth alkali metal salts of sulfate, sulfite, phosphate, phosphonate, nitrate, chloride or carbonate or salts of simple organic acids such as citrate, malonate or acetate may be used.

The salt in the coating may have a constant humidity at 20° C. above 60%, particularly above 70%, above 80% or above 85%, or it may be another hydrate form of such a salt (e.g., anhydrate). The salt coating may be as described in WO 00/01793 or WO 2006/034710.

Specific examples of suitable salts are NaCl ($CH_{20°\ C.}$=76%), $Na_2CO_3$ ($CH_{20°\ C.}$=92%), $NaNO_3$ ($CH_{20°\ C.}$=73%), $Na_2HPO_4$ ($CH_{20°\ C.}$=95%), $Na_3PO_4$ ($CH_{25°\ C.}$=92%), $NH_4Cl$ ($CH_{20°\ C.}$=79.5%), $(NH_4)_2HPO_4$ ($CH_{20°\ C.}$=93.0%), $NH_4H_2PO_4$ ($CH_{20°\ C.}$=93.1%), $(NH_4)_2SO_4$ ($CH_{20°\ C.}$=81.1%), KCl ($CH_{20°\ C.}$=85%), $K_2HPO_4$ ($CH_{20°\ C.}$=92%), $KH_2PO_4$ ($CH_{20°\ C.}$=96.5%), $KNO_3$ ($CH_{20°\ C.}$=93.5%), $Na_2SO_4$ ($CH_{20°\ C.}$=93%), $K_2SO_4$ ($CH_{20°\ C.}$=98%), $KHSO_4$ ($CH_{20°\ C.}$=86%), $MgSO_4$ ($CH_{20°\ C.}$=90%), $ZnSO_4$ ($CH_{20°\ C.}$=90%) and sodium citrate ($CH_{25°\ C.}$=86%). Other examples include $NaH_2PO_4$, $(NH_4)H_2PO_4$, $CuSO_4$, $Mg(NO_3)_2$ and magnesium acetate.

The salt may be in anhydrous form, or it may be a hydrated salt, i.e., a crystalline salt hydrate with bound water(s) of crystallization, such as described in WO 99/32595. Specific examples include anhydrous sodium sulfate ($Na_2SO_4$), anhydrous magnesium sulfate ($MgSO_4$), magnesium sulfate heptahydrate ($MgSO_4 \cdot 7H_2O$), zinc sulfate heptahydrate ($ZnSO_4 \cdot 7H_2O$), sodium phosphate dibasic heptahydrate ($Na_2HPO_4 \cdot 7H_2O$), magnesium nitrate hexahydrate ($Mg(NO_3)_2(6H_2O)$), sodium citrate dihydrate and magnesium acetate tetrahydrate. Preferably the salt is applied as a solution of the salt, e.g., using a fluid bed.

Thus, in a further aspect, the present invention provides a granule, which comprises:
(a) a core comprising an enzyme according to the invention,
(b) optionally a coating consisting of one or more layer(s) surrounding the core; and
(c) preferably the granule is a co-granulate comprising one or more additional enzyme, preferably selected from proteases, amylases, cellulases.

In one embodiment, the present invention provides a granule, which comprises:
(a) a core comprising a polypeptide having peptidoglycan removal activity, wherein the polypeptide comprises the motif N[IV]X[AG][GAS]A[AY][LV]L (SEQ ID NO: 111),
(b) optionally a coating consisting of one or more layer(s) surrounding the core; and
(c) preferably the granule is a co-granulate comprising one or more additional enzyme, preferably selected from proteases, amylases, cellulases.

In one embodiment, the present invention provides a granule, which comprises:
(a) a core comprising a polypeptide having peptidoglycan removal activity, wherein the polypeptide is selected from the group consisting of: SEQ ID NO: 3, SEQ ID NO: 6, SEQ ID NO: 9, SEQ ID NO: 12, SEQ ID NO: 15, SEQ ID NO: 18, SEQ ID NO: 21, SEQ ID NO: 24, SEQ ID NO: 27, SEQ ID NO: 30, SEQ ID NO: 33, SEQ ID NO: 36, SEQ ID NO: 39, SEQ ID NO: 42, SEQ ID NO: 45, SEQ ID NO: 48, SEQ ID NO: 51, SEQ ID NO: 54, SEQ ID NO: 57, SEQ ID NO: 60, SEQ ID NO: 63, SEQ ID NO: 66, SEQ ID NO: 69, SEQ ID NO: 72, SEQ ID NO: 75, SEQ ID NO: 78, SEQ ID NO: 81, SEQ ID NO: 84, SEQ ID NO: 87, SEQ ID NO: 90, SEQ ID NO: 93, SEQ ID NO: 96, SEQ ID NO: 99, SEQ ID NO: 102, SEQ ID NO: 105, SEQ ID NO: 108 and polypeptides having at least at least 60%, e.g., at least 65% at least 70%, at least 75%, at least 80%, at least 85%, at least 90%, at least 91%, at least 92%, at least 93%, at least 94%, at least 95%, at least 96%, at least 97%, at least 98%, at least 99%, or 100% hereto,
(b) optionally a coating consisting of one or more layer(s) surrounding the core; and
(c) preferably the granule is a co-granulate comprising one or more additional enzyme, preferably selected from proteases, amylases, cellulases.

Fermentation Broth Formulations or Cell Compositions

The present invention also relates to a fermentation broth formulation or a cell composition comprising a polypeptide of the present invention. The fermentation broth product further comprises additional ingredients used in the fermentation process, such as, for example, cells (including the host cells containing the gene encoding the polypeptide of the present invention which are used to produce the polypeptide of interest), cell debris, biomass, fermentation media and/or fermentation products. In some embodiments, the composition is a cell-killed whole broth containing organic acid(s), killed cells and/or cell debris, and culture medium.

The term "fermentation broth" as used herein refers to a preparation produced by cellular fermentation that undergoes no or minimal recovery and/or purification. For example, fermentation broths are produced when microbial cultures are grown to saturation, incubated under carbon-limiting conditions to allow protein synthesis (e.g., expression of enzymes by host cells) and secretion into cell culture medium. The fermentation broth can contain unfractionated or fractionated contents of the fermentation materials derived at the end of the fermentation. Typically, the fermentation broth is unfractionated and comprises the spent culture medium and cell debris present after the microbial cells (e.g., filamentous fungal cells) are removed, e.g., by centrifugation. In some embodiments, the fermentation broth contains spent cell culture medium, extracellular enzymes, and viable and/or nonviable microbial cells.

In an embodiment, the fermentation broth formulation and cell compositions comprise a first organic acid component comprising at least one 1-5 carbon organic acid and/or a salt thereof and a second organic acid component comprising at least one 6 or more carbon organic acid and/or a salt thereof. In a specific embodiment, the first organic acid component is acetic acid, formic acid, propionic acid, a salt thereof, or a mixture of two or more of the foregoing and the second organic acid component is benzoic acid, cyclohexanecarboxylic acid, 4-methylvaleric acid, phenylacetic acid, a salt thereof, or a mixture of two or more of the foregoing.

In one aspect, the composition contains at least one organic acid, and optionally further contains killed cells and/or cell debris. In one embodiment, the killed cells and/or cell debris are removed from a cell-killed whole broth to provide a composition that is free of these components.

The fermentation broth formulations or cell compositions may further comprise a preservative and/or anti-microbial (e.g., bacteriostatic) agent, including, but not limited to, sorbitol, sodium chloride, potassium sorbate, and others known in the art.

The cell-killed whole broth or composition may contain the unfractionated contents of the fermentation materials derived at the end of the fermentation. Typically, the cell-killed whole broth or composition contains the spent culture medium and cell debris present after the microbial cells (e.g., filamentous fungal cells) are grown to saturation, incubated under carbon-limiting conditions to allow protein synthesis. In some embodiments, the cell-killed whole broth or composition contains the spent cell culture medium, extracellular enzymes, and killed filamentous fungal cells. In some embodiments, the microbial cells present in the cell-killed whole broth or composition can be permeabilized and/or lysed using methods known in the art.

A whole broth or cell composition as described herein is typically a liquid, but may contain insoluble components, such as killed cells, cell debris, culture media components, and/or insoluble enzyme(s). In some embodiments, insoluble components may be removed to provide a clarified liquid composition.

The whole broth formulations and cell compositions of the present invention may be produced by a method described in WO 90/15861 or WO 2010/096673.

Compositions

The present invention also relates to compositions comprising a polypeptide of the present invention. Preferably, the compositions are enriched in such a polypeptide. The term "enriched" indicates that the peptidoglycan degradation activity of the composition has been increased, e.g., with an enrichment factor of at least 1.1.

The compositions may comprise a polypeptide of the present invention as the major enzymatic component, e.g., a mono-component composition. Alternatively, the compositions may comprise multiple enzymatic activities, such as one or more enzymes selected from the group consisting of hydrolase, isomerase, ligase, lyase, oxidoreductase, or transferase, e.g., an alpha-galactosidase, alpha-glucosidase, aminopeptidase, amylase, beta-galactosidase, beta-glucosidase, beta-xylosidase, carbohydrase, carboxypeptidase, catalase, cellobiohydrolase, cyclodextrin cellulase, chitinase, cutinase, glycosyltransferase, deoxyribonuclease, endoglucanase, esterase, glucoamylase, invertase, laccase, lipase, mannosidase, mutanase, oxidase, pectinolytic enzyme, peroxidase, phytase, polyphenoloxidase, proteolytic enzyme, ribonuclease, transglutaminase, or xylanase.

The invention relates to cleaning compositions, e.g., detergent compositions comprising peptidoglycan degradation enzyme in combination with one or more additional cleaning composition components. The choice of additional components is within the skill of the artisan and includes conventional ingredients, including the exemplary non-limiting components set forth below.

One aspect of the invention relates to a cleaning composition comprising a polypeptide having peptidoglycan degradation activity, wherein the polypeptide comprises the motif N[IV]X[AG][GAS]A[AY][LV]L (SEQ ID NO: 111), and at least one cleaning component.

One aspect of the invention relates to a cleaning composition comprising:
a) a polypeptide having peptidoglycan degradation activity, wherein the polypeptide is selected from the group consisting of:
  i. a polypeptide having at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 3,
  ii. a polypeptide having at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 6,
  iii. a polypeptide having at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 9,
iv. a polypeptide having at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 12,
v. a polypeptide having at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 15,
vi. a polypeptide having at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 18,
vii. a polypeptide having at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 21,
viii. a polypeptide having at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 24,
ix. a polypeptide having at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 27,
x. a polypeptide having at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 30,
xi. a polypeptide having at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 33,
xii. a polypeptide having at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 36,
xiii. a polypeptide having at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 39,
xiv. a polypeptide having at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 42,
xv. a polypeptide having at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 45,
xvi. a polypeptide having at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 48,
xvii. a polypeptide having at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 51,
xviii. a polypeptide having at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 54,
xix. a polypeptide having at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 57,
xx. a polypeptide having at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 60,
xxi. a polypeptide having at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 63,
xxii. a polypeptide having at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 66,
xxiii. a polypeptide having at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 69,
xxiv. a polypeptide having at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 72,
xxv. a polypeptide having at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 75, xxvi. a polypeptide having at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 78, xxvii. a polypeptide having at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 81, xxviii. a polypeptide having at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 84, xxix. a polypeptide having at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 87, xxx. a polypeptide having at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 90, xxxi. a polypeptide having at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 93, xxxii. a polypeptide having at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 96, xxxiii. a polypeptide having at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 99, xxxiv. a polypeptide having at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 102, xxxv. a polypeptide having at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 105, and xxxvi. a polypeptide having at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 108, and b) at least one cleaning component, preferably selected from surfactants, builders, bleach components, polymers, dispersing agents and additional enzymes.

One embodiment relates to a cleaning composition comprising:

a) a polypeptide having peptidoglycan removal activity and which comprises the motif N[IV]X[AG][GAS]A[AY][LV]L (SEQ ID NO: 111), wherein the polypeptide is selected from the group consisting of: SEQ ID NO: 3, SEQ ID NO: 6, SEQ ID NO: 9, SEQ ID NO: 12, SEQ ID NO: 15, SEQ ID NO: 18, SEQ ID NO: 21, SEQ ID NO: 24, SEQ ID NO: 27, SEQ ID NO: 30, SEQ ID NO: 33, SEQ ID NO: 36, SEQ ID NO: 39, SEQ ID NO: 42, SEQ ID NO: 45, SEQ ID NO: 48, SEQ ID NO: 51, SEQ ID NO: 54, SEQ ID NO: 57, SEQ ID NO: 60, SEQ ID NO: 63, SEQ ID NO: 66, SEQ ID NO: 69, SEQ ID NO: 72, SEQ ID NO: 75, SEQ ID NO: 78, SEQ ID NO: 81, SEQ ID NO: 84, SEQ ID NO: 87, SEQ ID NO: 90, SEQ ID NO: 93, SEQ ID NO: 96, SEQ ID NO: 99, SEQ ID NO: 102, SEQ ID NO: 105, SEQ ID NO: 108 and polypeptides having at least at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% hereto; and b) at least one cleaning component, preferably selected from surfactants, builders, bleach components, polymers, dispersing agents and additional enzymes.

The peptidoglycan degradation enzyme may be included in the cleaning composition of the present invention at a level of at least 0.0001 to at least 100, at least 0.001 to at least 100, at least 0.01 to at least 100, at least 0.02 to at least 100, at least 0.01 to at least 100, at least 0.1 to at least 100, at least 0.2 to at least 100, at least 0.5 to at least 100 mg/mL, preferably, the concentration of peptidoglycan degradation enzyme in the cleaning composition, e.g., detergent is in the range 0.01 to 100, 0.1 to 50 or 1 to 10 mg/ml. Thus, the detergent composition may comprise at least 0.00008%, preferably at least 0.002%, 0.003%, 0.004%, 0.005%, 0.006%, 0.008%, 0.01%, 0.02%, 0.03%, 0.05%, 0.1%, 0.2%, 0.3%, 0.4%, 0.6%, 0.7%, 0.8%, 0.9% or 1.0% of peptidoglycan degradation enzyme protein.

The choice of cleaning components may include, for textile care, the consideration of the type of textile to be cleaned, the type and/or degree of soiling, the temperature at which cleaning is to take place, and the formulation of the detergent product. Although components mentioned below are categorized by general header according to a particular functionality, this is not to be construed as a limitation, as a component may comprise additional functionalities as will be appreciated by the skilled artisan.

Surfactants

The cleaning composition may comprise one or more surfactants, which may be anionic and/or cationic and/or non-ionic and/or semi-polar and/or zwitterionic, or a mixture thereof. In a particular embodiment, the detergent composition includes a mixture of one or more nonionic surfactants and one or more anionic surfactants. The surfactant(s) is typically present at a level of from about 1% to 70% by weight, such as about 1 wt % to about 40 wt %, or about 3 wt % to about 20 wt %, or about 3 wt % to about 10 wt %.

The surfactant(s) is chosen based on the desired cleaning application, and may include any conventional surfactant(s) known in the art.

When included therein the detergent will usually contain from about 1% to about 70% by weight of an anionic surfactant, such as from about 5 wt % to about 50 wt %, including from about 5 wt % to about 20 wt %, or from about 15 wt % to about 20 wt %, or from about 20 wt % to about 25 wt % or at least 30 wt %, at least 40 wt % or at least 50 wt % of an anionic surfactant. Non-limiting examples of anionic surfactants include sulfates and sulfonates, in particular, alkylbenzenesulfonates, such as linear alkylbenzenesulfonates (LAS), isomers of LAS, branched alkylbenzenesulfonates (BABS), phenylalkanesulfonates, alpha-olefinsulfonates (AOS), olefin sulfonates, alkene sulfonates, alkane-2,3-diylbis(sulfates), hydroxyalkanesulfonates and disulfonates, alkyl sulfates (AS) such as sodium dodecyl sulfate (SDS), fatty alcohol sulfates (FAS), primary alcohol sulfates (PAS), alcohol ethersulfates (AES or AEOS or FES, also known as alcohol ethoxysulfates or fatty alcohol ether sulfates), secondary alkanesulfonates (SAS), paraffin sulfonates (PS), ester sulfonates, sulfonated fatty acid glycerol esters, alpha-sulfo fatty acid methyl esters (alpha-SFMe or SES) including methyl ester sulfonate (MES), alkyl- or alkenylsuccinic acid, dodecenyl/tetradecenyl succinic acid (DTSA), fatty acid derivatives of amino acids, diesters and monoesters of sulfo-succinic acid or salt of fatty acids (soap), and combinations thereof.

When included therein the detergent will usually contain from about 1% to about 40% by weigh of a cationic surfactant, for example from about 0.5% to about 30%, in particular, from about 1% to about 20%, from about 3% to about 10%, such as from about 3% to about 5%, from about 8% to about 12% or from about 10% to about 12%. Non-limiting examples of cationic surfactants include alkyldimethylethanolamine quat (ADMEAQ), cetyltrimethylammonium bromide (CTAB), dimethyldistearylammonium chloride (DSDMAC), and alkylbenzyldimethylammonium, alkyl quaternary ammonium compounds, alkoxylated quaternary ammonium (AQA) compounds, ester quats, and combinations thereof.

When included therein, the detergent will usually contain from about 0.2% to about 40% by weight of a nonionic surfactant, for example from about 0.5 wt % to about 30 wt %, in particular from about 1 wt % to about 20 wt %, from about 3 wt % to about 10 wt %, such as from about 3% wt to about 5 wt %, from about 8 wt % to about 12 wt %, or from about 10 wt % to about 12 wt %. Non-limiting examples of nonionic surfactants include alcohol ethoxylates (AE or AEO), alcohol propoxylates, propoxylated fatty alcohols (PFA), alkoxylated fatty acid alkyl esters, such as ethoxylated and/or propoxylated fatty acid alkyl esters, alkylphenol ethoxylates (APE), nonylphenol ethoxylates (NPE), alkylpolyglycosides (APG), alkoxylated amines, fatty acid monoethanolamides (FAM), fatty acid diethanolamides (FADA), ethoxylated fatty acid monoethanolamides (EFAM), propoxylated fatty acid monoethanolamides (PFAM), polyhydroxyalkyl fatty acid amides, or N-acyl N-alkyl derivatives of glucosamine (glucamides, GA, or fatty acid glucamides, FAGA), as well as products available under the trade names SPAN and TWEEN, and combinations thereof.

When included therein the detergent will usually contain from about 0.01% to about 10% by weight of a semipolar surfactant. Non-limiting examples of semipolar surfactants include amine oxides (AO) such as alkyldimethylamineoxide, N-(coco alkyl)-N,N-dimethylamine oxide and N-(tallow-alkyl)-N,N-bis(2-hydroxyethyl)amine oxide, and combinations thereof.

When included therein the detergent will usually contain from about 0.01% to about 10% by weight of a zwitterionic surfactant. Non-limiting examples of zwitterionic surfactants include betaines such as alkyldimethylbetaines, sulfobetaines, and combinations thereof.

Typically, more than one surfactant is present in the cleaning composition, e.g., at least one anionic and at least one non-ionic surfactant. Preferably the amount of all surfactant present (total amount) i.e., the amount of anionic, non-ionic, zwitterionic and cationic surfactant present is preferably from about 1 wt % to 80 wt % by weight, such as about 1 wt % to 70 wt %, such as about 1 wt % to 50 wt % such as about 1 wt % to about 40 wt %, or about 5 wt % to about 40 wt %, or about 10 wt % to about 60 wt %. The ratio between the surfactants present depends on the specific composition but the weight ratios may be when an anionic and non-ionic surfactant is included in the composition a weight ratio of the anionic to nonionic surfactant from; 30:1 to 10:1, 20:1 to 1:10, 25:1 to 1:2, 20:1 to 1:5.

One embodiment relates to a cleaning composition comprising a peptidoglycan degrading enzyme, preferably having N-acetylmuramyl-L-alanine amidase and peptidoglycan lyase activity and wherein the cleaning component is at least one surfactant, preferably anionic and/or nonionic, preferably wherein the composition comprises from 1 to 70 wt %, preferably from 5 to 40 wt % surfactant, wherein the surfactant preferably is selected from alkylbenzenesulfonates, e.g., LAS, alkyl sulfates (AS) and mixtures thereof, preferably the cleaning composition comprises at least 20 wt % alkylbenzenesulfonate surfactant.

One embodiment relates to a cleaning composition comprising a peptidoglycan degrading enzyme, preferably having N-acetylmuramyl-L-alanine amidase and peptidoglycan lyase activity, wherein the cleaning composition comprises at least one anionic surfactant and wherein the cleaning composition additionally comprises a nonionic surfactant, and preferably wherein the weight ratio of the anionic to nonionic surfactant is from 25:1 to 1:2 or from 1.5:1 to 1:10.

Builders and Co-Builders

The cleaning composition may contain about 0-65% by weight, such as about 5% to about 50%, such as about 0.5% to about 20% of a detergent builder or co-builder, or a mixture thereof. In a dish wash detergent, the level of builder is typically 40-65%, particularly 50-65%. The builder and/or co-builder may particularly be a chelating agent that forms water-soluble complexes with Ca and Mg. Any builder and/or co-builder known in the art for use in cleaning detergents may be utilized. Non-limiting examples of builders include zeolites, diphosphates (pyrophosphates), triphosphates such as sodium triphosphate (STP or STPP), carbonates such as sodium carbonate, soluble silicates such as sodium metasilicate, layered silicates (e.g., SKS-6 from Hoechst), ethanolamines such as 2-aminoethan-1-ol (MEA), diethanolamine (DEA, also known as 2,2'-iminodiethan-1-ol), triethanolamine (TEA, also known as 2,2',2"-nitrilotriethan-1-ol), and (carboxymethyl)inulin (CMI), and combinations thereof.

The detergent composition may also contain 0-50% by weight, such as about 5% to about 30%, of a detergent co-builder. The detergent composition may include a co-builder alone, or in combination with a builder, for example a zeolite builder. Non-limiting examples of co-builders include homopolymers of polyacrylates or copolymers thereof, such as poly(acrylic acid) (PAA) or copoly(acrylic acid/maleic acid) (PAA/PMA). Further non-limiting examples include citrate, chelators such as aminocarboxylates, aminopolycarboxylates and phosphonates, and alkyl- or alkenylsuccinic acid. Additional specific examples include 2,2',2"-nitrilotriacetic acid (NTA), ethylenediaminetetraacetic acid (EDTA), diethylenetriaminepentaacetic acid (DTPA), iminodisuccinic acid (IDS), ethylenediamine-N,N'-disuccinic acid (EDDS), methylglycinediacetic acid (MGDA), glutamic acid-N,N-diacetic acid (GLDA), 1-hydroxyethane-1,1-diphosphonic acid (HEDP), ethylenediaminetetra(methylenephosphonic acid) (EDTMPA), diethylenetriaminepentakis-(methylenephosphonic acid) (DTMPA or DTPMPA), N-(2-hydroxyethyl)iminodiacetic acid (EDG), aspartic acid-N-monoacetic acid (ASMA), aspartic acid-N,N-diacetic acid (ASDA), aspartic acid-N-monopropionic acid (ASMP), iminodisuccinic acid (IDA), N-(2-sulfomethyl)-aspartic acid (SMAS), N-(2-sulfoethyl)-aspartic acid (SEAS), N-(2-sulfomethyl)-glutamic acid (SMGL), N-(2-sulfoethyl)-glutamic acid (SEGL), N-methyliminodiacetic acid (MIDA), α-alanine-N,N-diacetic acid (α-ALDA), serine-N,N-diacetic acid (SEDA), isoserine-N,N-diacetic acid (ISDA), phenylalanine-N,N-diacetic acid (PHDA), anthranilic acid-N,N-diacetic acid (ANDA), sulfanilic acid-N,N-diacetic acid (SLDA), taurine-N,N-diacetic acid (TUDA) and sulfomethyl-N,N-diacetic acid (SMDA), N-(2-hydroxyethyl)ethylenediamine-N,N',N"-triacetic acid (HEDTA), diethanolglycine (DEG), diethylenetriamine penta(methylenephosphonic acid) (DTPMP), aminotris(methylenephosphonic acid) (ATMP), and combinations and salts thereof. Further exemplary builders and/or co-builders are described in, e.g., WO 2009/102854, U.S. Pat. No. 5,977,053.

Bleaching Systems

The cleaning composition may contain 0-30% by weight, such as about 1% to about 20%, such as about 0.01% to about 10% of a bleaching system. Any bleaching system comprising components known in the art for use in cleaning detergents may be utilized. Suitable bleaching system components include sources of hydrogen peroxide; sources of peracids; and bleach catalysts or boosters.

Sources of Hydrogen Peroxide:

Suitable sources of hydrogen peroxide are inorganic persalts, including alkali metal salts such as sodium percarbonate and sodium perborates (usually mono- or tetrahydrate), and hydrogen peroxide-urea (1/1).

Sources of Peracids:

Peracids may be (a) incorporated directly as preformed peracids or (b) formed in situ in the wash liquor from hydrogen peroxide and a bleach activator (perhydrolysis) or (c) formed in situ in the wash liquor from hydrogen peroxide and a perhydrolase and a suitable substrate for the latter, e.g., an ester.

a) Suitable preformed peracids include, but are not limited to, peroxycarboxylic acids such as peroxybenzoic acid and its ring-substituted derivatives, peroxy-α-naphthoic acid, peroxyphthalic acid, peroxylauric acid, peroxystearic acid, ε-phthalimidoperoxycaproic acid [phthalimidoperoxyhexanoic acid (PAP)], and o-carboxybenzamidoperoxycaproic acid; aliphatic and aromatic diperoxydicarboxylic acids such as diperoxydodecanedioic acid, diperoxyazelaic acid, diperoxysebacic acid, diperoxybrassylic acid, 2-decyldiperoxybutanedioic acid, and diperoxyphthalic, -isophthalic and -terephthalic acids; perimidic acids; peroxymonosulfuric acid; peroxydisulfuric acid; peroxyphosphoric acid; peroxysilicic acid; and mixtures of said compounds. It is understood that the peracids mentioned may in some cases be best added as suitable salts, such as alkali metal salts (e.g., Oxone®) or alkaline earth-metal salts.

b) Suitable bleach activators include those belonging to the class of esters, amides, imides, nitriles or anhydrides and, where applicable, salts thereof. Suitable examples are tetraacetylethylenediamine (TAED), sodium 4-[(3,5,5-trimethylhexanoyl)oxy]benzene-1-sulfonate (ISONOBS), sodium 4-(dodecanoyloxy)benzene-1-sulfonate (LOBS), sodium 4-(decanoyloxy) benzene-1-sulfonate, 4-(decanoyloxy)benzoic 4-acid (DOBA), sodium (nonanoyloxy)benzene-1-sulfonate (NOBS), and/or those disclosed in WO 98/17767. A particular family of bleach activators of interest was disclosed in EP 624154 and particularly preferred in that family is acetyl triethyl citrate (ATC). ATC or a short chain triglyceride like triacetin has the advantage that they are environmentally friendly. Furthermore, acetyl triethyl citrate and triacetin have good hydrolytical stability in the product upon storage and are efficient bleach activators. Finally, ATC is multifunctional, as the citrate released in the perhydrolysis reaction may function as a builder.

Bleach Catalysts and Boosters

The bleaching system may also include a bleach catalyst or booster. Some non-limiting examples of bleach catalysts that may be used in the compositions of the present invention include manganese oxalate, manganese acetate, manganese-collagen, cobalt-amine catalysts and manganese triazacyclononane (MnTACN) catalysts; particularly preferred are complexes of manganese with 1,4,7-trimethyl-1,4,7-triazacyclononane (Me3-TACN) or 1,2,4,7-tetramethyl-1,4,7-triazacyclononane (Me4-TACN), in particular Me3-TACN, such as the dinuclear manganese complex [(Me3-TACN)Mn(O)3Mn(Me3-TACN)](PF6)2, and [2,2',2"-nitrilotris(ethane-1,2-diylazanylylidene-κN-methanylylidene)triphenolato-κ3O]manganese(III). The bleach catalysts may also be other metal compounds; such as iron or cobalt complexes.

In some embodiments, where a source of a peracid is included, an organic bleach catalyst or bleach booster may be used having one of the following formulae:

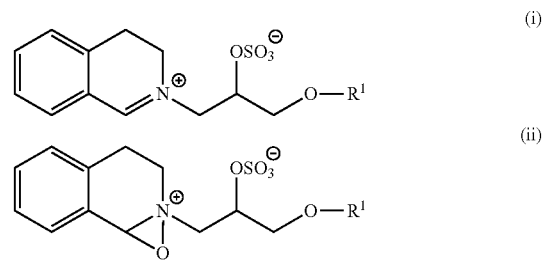

(iii) and mixtures thereof; wherein each R1 is independently a branched alkyl group containing from 9 to 24 carbons or linear alkyl group containing from 11 to 24 carbons, preferably each R1 is independently a branched alkyl group containing from 9 to 18 carbons or linear alkyl group containing from 11 to 18 carbons, more preferably each R1 is independently selected from the group consisting of 2-propylheptyl, 2-butyloctyl, 2-pentylnonyl, 2-hexyldecyl, dodecyl, tetradecyl, hexadecyl, octadecyl, isononyl, isodecyl, isotridecyl and isopentadecyl.

Other exemplary bleaching systems are described in, e.g., WO 2007/087258, WO 2007/087244, WO 2007/087259, EP 1867708 (Vitamin K) and WO 2007/087242. Suitable photobleaches may for example be sulfonated zinc or aluminum phthalocyanines.

Metal Care Agents

Metal care agents may prevent or reduce the tarnishing, corrosion or oxidation of metals, including aluminium, stainless steel and non-ferrous metals, such as silver and copper. Suitable examples include one or more of the following:
(a) benzatriazoles, including benzotriazole or bis-benzotriazole and substituted derivatives thereof. Benzotriazole derivatives are those compounds in which the available substitution sites on the aromatic ring are partially or completely substituted. Suitable substituents include linear or branch-chain C1-C20-alkyl groups (e.g., C1-C20-alkyl groups) and hydroxyl, thio, phenyl or halogen such as fluorine, chlorine, bromine and iodine.
(b) metal salts and complexes chosen from the group consisting of zinc, manganese, titanium, zirconium, hafnium, vanadium, cobalt, gallium and cerium salts and/or complexes, the metals being in one of the oxidation states II, III, IV, V or VI. In one aspect, suitable metal salts and/or metal complexes may be chosen from the group consisting of Mn(II) sulphate, Mn(II) citrate, Mn(II) stearate, Mn(II) acetylacetonate, K^TiF6 (e.g., K2TiF6), K^ZrF6 (e.g., K2ZrF6), CoSO4, Co(NOs)2 and Ce(NOs)3, zinc salts, for example zinc sulphate, hydrozincite or zinc acetate;
(c) silicates, including sodium or potassium silicate, sodium disilicate, sodium metasilicate, crystalline phyllosilicate and mixtures thereof.

Further suitable organic and inorganic redox-active substances that act as silver/copper corrosion inhibitors are disclosed in WO 94/26860 and WO 94/26859. Preferably, the composition of the invention comprises from 0.1 to 5% by weight of the composition of a metal care agent, preferably the metal care agent is a zinc salt.

Hydrotropes

The cleaning composition may contain 0-10% by weight, for example 0-5% by weight, such as about 0.5 to about 5%, or about 3% to about 5%, of a hydrotrope. Any hydrotrope known in the art for use in detergents may be utilized. Non-limiting examples of hydrotropes include sodium benzenesulfonate, sodium p-toluene sulfonate (STS), sodium xylene sulfonate (SXS), sodium cumene sulfonate (SCS), sodium cymene sulfonate, amine oxides, alcohols and polyglycolethers, sodium hydroxynaphthoate, sodium hydroxynaphthalene sulfonate, sodium ethylhexyl sulfate, and combinations thereof.

Polymers

The cleaning composition may contain 0-10% by weight, such as 0.5-5%, 2-5%, 0.5-2% or 0.2-1% of a polymer. Any polymer known in the art for use in detergents may be utilized. The polymer may function as a co-builder as mentioned above, or may provide antiredeposition, fiber protection, soil release, dye transfer inhibition, grease cleaning and/or anti-foaming properties. Some polymers may have more than one of the above-mentioned properties and/or more than one of the below-mentioned motifs. Exemplary polymers include (carboxymethyl)cellulose (CMC), poly(vinyl alcohol) (PVA), poly(vinylpyrrolidone) (PVP), poly(ethyleneglycol) or poly(ethylene oxide) (PEG), ethoxylated poly(ethyleneimine), carboxymethyl inulin (CMI), and polycarboxylates such as PAA, PAA/PMA, poly-aspartic acid, and lauryl methacrylate/acrylic acid copolymers, hydrophobically modified CMC (HM-CMC) and silicones, copolymers of terephthalic acid and oligomeric glycols, copolymers of poly(ethylene terephthalate) and poly(oxyethene terephthalate) (PET-POET), PVP, poly (vinylimidazole) (PVI), poly(vinylpyridine-N-oxide) (PVPO or PVPNO) and polyvinylpyrrolidone-vinylimidazole (PVPVI). Suitable examples include PVP-K15, PVP-K30, ChromaBond S-400, ChromaBond S-403E and Chromabond S-100 from Ashland Aqualon, and Sokalan® HP 165, Sokalan® HP 50 (Dispersing agent), Sokalan® HP 53 (Dispersing agent), Sokalan® HP 59 (Dispersing agent), Sokalan® HP 56 (dye transfer inhibitor), Sokalan® HP 66 K (dye transfer inhibitor) from BASF. Further exemplary polymers include sulfonated polycarboxylates, polyethylene oxide and polypropylene oxide (PEO-PPO) and diquaternium ethoxy sulfate. Other exemplary polymers are disclosed in, e.g., WO 2006/130575. Salts of the above-mentioned polymers are also contemplated. Particularly preferred polymer is ethoxylated homopolymer Sokalan® HP 20 from BASF, which helps to prevent redeposition of soil in the wash liquor.

Fabric Hueing Agents

The cleaning compositions of the present invention may also include fabric hueing agents such as dyes or pigments, which when formulated in detergent compositions can deposit onto a fabric when said fabric is contacted with a wash liquor comprising said detergent compositions and thus altering the tint of said fabric through absorption/reflection of visible light. Fluorescent whitening agents emit at least some visible light. In contrast, fabric hueing agents alter the tint of a surface as they absorb at least a portion of the visible light spectrum. Suitable fabric hueing agents include dyes and dye-clay conjugates, and may also include pigments. Suitable dyes include small molecule dyes and polymeric dyes. Suitable small molecule dyes include small molecule dyes selected from the group consisting of dyes falling into the Colour Index (C.I.) classifications of Direct Blue, Direct Red, Direct Violet, Acid Blue, Acid Red, Acid Violet, Basic Blue, Basic Violet and Basic Red, or mixtures thereof, for example as described in WO 2005/003274, WO 2005/003275, WO 2005/003276 and EP1876226 (hereby incorporated by reference). The detergent composition preferably comprises from about 0.00003 wt % to about 0.2 wt %, from about 0.00008 wt % to about 0.05 wt %, or even from about 0.0001 wt % to about 0.04 wt % fabric hueing agent. The composition may comprise from 0.0001 wt % to 0.2 wt % fabric hueing agent, this may be especially preferred when the composition is in the form of a unit dose pouch. Suitable hueing agents are also disclosed in, e.g., WO 2007/087257 and WO 2007/087243.

Dispersants

The cleaning compositions of the present invention can also contain dispersants. In particular, powdered detergents may comprise dispersants. Suitable water-soluble organic materials include the homo- or co-polymeric acids or their salts, in which the polycarboxylic acid comprises at least two carboxyl radicals separated from each other by not more than two carbon atoms. Suitable dispersants are for example described in Powdered Detergents, Surfactant science series volume 71, Marcel Dekker, Inc.

Dye Transfer Inhibiting Agents

The cleaning compositions of the present invention may also include one or more dye transfer inhibiting agents. Suitable polymeric dye transfer inhibiting agents include, but are not limited to, polyvinylpyrrolidone polymers, polyamine N-oxide polymers, copolymers of N-vinylpyrrolidone and N-vinylimidazole, polyvinyloxazolidones and polyvinylimidazoles or mixtures thereof. When present in a subject composition, the dye transfer inhibiting agents may be present at levels from about 0.0001% to about 10%, from about 0.01% to about 5% or even from about 0.1% to about 3% by weight of the composition.

Fluorescent Whitening Agent

The cleaning compositions of the present invention will preferably also contain additional components that may tint articles being cleaned, such as fluorescent whitening agents or optical brighteners. Where present the brightener is preferably at a level of about 0.01% to about 0.5%. Any fluorescent whitening agent suitable for use in a laundry detergent composition may be used in the composition of the present invention. The most commonly used fluorescent whitening agents are those belonging to the classes of diaminostilbene-sulfonic acid derivatives, diarylpyrazoline derivatives and bisphenyl-distyryl derivatives. Examples of the diaminostilbene-sulfonic acid derivative type of fluorescent whitening agents include the sodium salts of: 4,4'-bis-(2-diethanolamino-4-anilino-s-triazin-6-ylamino) stilbene-2,2'-disulfonate, 4,4'-bis-(2,4-dianilino-s-triazin-6-ylamino) stilbene-2.2'-disulfonate, 4,4'-bis-(2-anilino-4-(N-methyl-N-2-hydroxy-ethylamino)-s-triazin-6-ylamino) stilbene-2,2'-disulfonate, 4,4'-bis-(4-phenyl-1,2,3-triazol-2-yl)stilbene-2,2'-disulfonate and sodium 5-(2H-naphtho[1,2-d][1,2,3]triazol-2-yl)-2-[(E)-2-phenylvinyl]-benzenesulfonate.

Preferred fluorescent whitening agents are Tinopal DMS and Tinopal CBS available from Ciba-Geigy AG, Basel, Switzerland. Tinopal DMS is the disodium salt of 4,4'-bis-(2-morpholino-4-anilino-s-triazin-6-ylamino) stilbene-2,2'-disulfonate. Tinopal CBS is the disodium salt of 2,2'-bis-(phenyl-styryl)-disulfonate. Also preferred are fluorescent whitening agents is the commercially available Parawhite KX, supplied by Paramount Minerals and Chemicals, Mumbai, India. Other fluorescers suitable for use in the invention include the 1-3-diaryl pyrazolines and the 7-alkylaminocoumarins. Suitable fluorescent brightener levels include lower levels of from about 0.01, from 0.05, from about 0.1 or even from about 0.2 wt % to upper levels of 0.5 or even 0.75 wt %.

Soil Release Polymers

The cleaning compositions of the present invention may also include one or more soil release polymers which aid the removal of soils from fabrics such as cotton and polyester based fabrics, in particular the removal of hydrophobic soils from polyester based fabrics. The soil release polymers may for example be nonionic or anionic terephthalate based polymers, polyvinyl caprolactam and related copolymers, vinyl graft copolymers, polyester polyamides see for example Chapter 7 in Powdered Detergents, Surfactant science series volume 71, Marcel Dekker, Inc. Another type of soil release polymers is amphiphilic alkoxylated grease cleaning polymers comprising a core structure and a plurality of alkoxylate groups attached to that core structure. The core structure may comprise a polyalkylenimine structure or a polyalkanolamine structure as described in detail in WO 2009/087523 (hereby incorporated by reference). Furthermore, random graft co-polymers are suitable soil release polymers. Suitable graft co-polymers are described in more detail in WO 2007/138054, WO 2006/108856 and WO 2006/113314 (hereby incorporated by reference). Suitable polyethylene glycol polymers include random graft co-polymers comprising: (i) hydrophilic backbone comprising polyethylene glycol; and (ii) side chain(s) selected from the group consisting of: C4-C25 alkyl group, polypropylene, polybutylene, vinyl ester of a saturated C1-C6 mono-carboxylic acid, C1-C6 alkyl ester of acrylic or methacrylic acid, and mixtures thereof. Suitable polyethylene glycol polymers have a polyethylene glycol backbone with random grafted polyvinyl acetate side chains. The average molecular weight of the polyethylene glycol backbone can be in the range of from 2,000 Da to 20,000 Da, or from 4,000 Da to 8,000 Da. The molecular weight ratio of the polyethylene glycol backbone to the polyvinyl acetate side chains can be in the range of from 1:1 to 1:5, or from 1:1.2 to 1:2. The average number of graft sites per ethylene oxide units can be less than 1, or less than 0.8, the average number of graft sites per ethylene oxide units can be in the range of from 0.5 to 0.9, or the average number of graft sites per ethylene oxide units can be in the range of from 0.1 to 0.5, or from 0.2 to 0.4. A suitable polyethylene glycol polymer is Sokalan HP22. Other soil release polymers are substituted polysaccharide structures especially substituted cellulosic structures such as modified cellulose deriviatives such as those described in EP 1867808 or WO 2003/040279 (both are hereby incorporated by reference). Suitable cellulosic polymers include cellulose, cellulose ethers, cellulose esters, cellulose amides and mixtures thereof. Suitable cellulosic polymers include anionically modified cellulose, nonionically modified cellulose, cationically modified cellulose, zwitterionically modified cellulose, and mixtures thereof. Suitable cellulosic polymers include methyl cellulose, carboxy methyl cellulose, ethyl cellulose, hydroxyl ethyl cellulose, hydroxyl propyl methyl cellulose, ester carboxy methyl cellulose, and mixtures thereof.

Anti-Redeposition Agents

The cleaning compositions of the present invention may also include one or more anti-redeposition agents such as carboxymethylcellulose (CMC), polyvinyl alcohol (PVA), polyvinylpyrrolidone (PVP), polyoxyethylene and/or polyethyleneglycol (PEG), homopolymers of acrylic acid, copolymers of acrylic acid and maleic acid, and ethoxylated polyethyleneimines. The cellulose based polymers described under soil release polymers above may also function as anti-redeposition agents.

Rheology Modifiers

The cleaning compositions of the present invention may also include one or more rheology modifiers, structurants or thickeners, as distinct from viscosity reducing agents. The rheology modifiers are selected from the group consisting of non-polymeric crystalline, hydroxy-functional materials, polymeric rheology modifiers which impart shear thinning characteristics to the aqueous liquid matrix of a liquid detergent composition. The rheology and viscosity of the detergent can be modified and adjusted by methods known in the art, for example as shown in EP 2169040.

Other suitable cleaning composition components include, but are not limited to, anti-shrink agents, anti-wrinkling agents, bactericides, binders, carriers, dyes, enzyme stabilizers, fabric softeners, fillers, foam regulators, hydrotropes, perfumes, pigments, sod suppressors, solvents, and structurants for liquid detergents and/or structure elasticizing agents.

Polymers

The cleaning composition may contain 0-10% by weight, such as 0.5-5%, 2-5%, 0.5-2% or 0.2-1% of a polymer. Any polymer known in the art for use in detergents may be utilized. The polymer may function as a co-builder as mentioned above, or may provide antiredeposition, fiber protection, soil release, dye transfer inhibition, grease cleaning and/or anti-foaming properties. Some polymers may have more than one of the above-mentioned properties and/or more than one of the below-mentioned motifs. Exemplary polymers include (carboxymethyl)cellulose (CMC), poly(vinyl alcohol) (PVA), poly(vinylpyrrolidone) (PVP), poly(ethyleneglycol) or poly(ethylene oxide) (PEG), ethoxylated poly(ethyleneimine), carboxymethyl inulin (CMI), and polycarboxylates such as PAA, PAA/PMA, poly-aspartic acid, and lauryl methacrylate/acrylic acid copolymers, hydrophobically modified CMC (HM-CMC) and silicones, copolymers of terephthalic acid and oligomeric glycols, copolymers of poly(ethylene terephthalate) and poly(oxyethene terephthalate) (PET-POET), PVP, poly(vinylimidazole) (PVI), poly(vinylpyridine-N-oxide) (PVPO or PVPNO) and polyvinylpyrrolidone-vinylimidazole (PVPVI). Suitable examples include PVP-K15, PVP-K30, ChromaBond S-400, ChromaBond S-403E and Chromabond S-100 from Ashland Aqualon, and Sokalan® HP 165, Sokalan® HP 50 (Dispersing agent), Sokalan® HP 53 (Dispersing agent), Sokalan® HP 59 (Dispersing agent), Sokalan® HP 56 (dye transfer inhibitor), Sokalan® HP 66 K (dye transfer inhibitor) from BASF. Further exemplary polymers include sulfonated polycarboxylates, polyethylene oxide and polypropylene oxide (PEO-PPO) and diquaternium ethoxy sulfate. Other exemplary polymers are disclosed in, e.g., WO 2006/130575. Salts of the above-mentioned polymers are also contemplated. Particularly preferred polymer is ethoxylated homopolymer Sokalan® HP 20 from BASF, which helps to prevent redeposition of soil in the wash liquor.

Enzymes

The cleaning composition may comprise one or more additional enzymes such as one or more lipase, cutinase, an amylase, carbohydrase, cellulase, pectinase, mannanase, arabinase, galactanase, xylanase, oxidase, e.g., a laccase, and/or peroxidase. In general, the properties of the selected enzyme(s) should be compatible with the selected detergent, (i.e., pH-optimum, compatibility with other enzymatic and non-enzymatic ingredients, etc.), and the enzyme(s) should be present in effective amounts.

Mannanases

Suitable mannanases include those of bacterial or fungal origin. Chemically or genetically modified mutants are included. The mannanase may be an alkaline mannanase of Family 5 or 26. It may be a wild-type from *Bacillus* or *Humicola*, particularly *B. agaradhaerens, B. licheniformis, B. halodurans, B. clausii*, or *H. insolens*. Suitable mannanases are described in WO 1999/064619. A commercially available mannanase is Mannaway (Novozymes A/S).

Cellulases

Suitable cellulases include complete cellulases or mono-component endoglucanases of bacterial or fungal origin. Chemically or genetically modified mutants are included. The cellulase may for example be a mono-component or a mixture of mono-component endo-1,4-beta-glucanase often just termed endoglucanases. Suitable cellulases include a fungal cellulase from *Humicola insolens* (U.S. Pat. No. 4,435,307) or from *Trichoderma*, e.g., *T. reesei* or *T. viride*. Examples of cellulases are described in EP 0 495 257. Other suitable cellulases are from *Thielavia*, e.g., *Thielavia terrestris* as described in WO 96/29397 or *Fusarium oxysporum* as described in WO 91/17244 or from *Bacillus* as described in, WO 02/099091 and JP 2000210081. Other examples are cellulase variants such as those described in WO 94/07998, EP 0 531 315, U.S. Pat. Nos. 5,457,046, 5,686,593, 5,763,254, WO 95/24471, WO 98/12307 Commercially available cellulases include Carezyme®, Celluzyme®, Celluclean®, Celluclast® and Endolase®; Renozyme®; Whitezyme® (Novozymes A/S) Puradax®, Puradax HA, and Puradax EG (available from Genencor).

Proteases

Suitable proteases may be of any origin, but are preferably of bacterial or fungal origin, optionally in the form of protein engineered or chemically modified mutants. The protease may be an alkaline protease, such as a serine protease or a metalloprotease. A serine protease may for example be of the S1 family, such as trypsin, or the S8 family such as a subtilisin. A metalloprotease may for example be a thermolysin, e.g., from the M4 family, or another metalloprotease such as those from the M5, M7 or M35 families.

The term "subtilases" refers to a sub-group of serine proteases according to Siezen et al., 1991, *Protein Eng.* 4: 719-737 and Siezen et al., 1997, *Protein Sci.* 6: 501-523. Serine proteases are a subgroup of proteases characterized by having a serine in the active site, which forms a covalent adduct with the substrate. The subtilases may be divided into six subdivisions, the Subtilisin family, the Thermitase family, the Proteinase K family, the Lantibiotic peptidase family, the Kexin family and the Pyrolysin family.

Although proteases suitable for detergent use may be obtained from a variety of organisms, including fungi such as *Aspergillus*, detergent proteases have generally been obtained from bacteria and in particular from *Bacillus*. Examples of *Bacillus* species from which subtilases have been derived include *Bacillus lentus, Bacillus alkalophilus, Bacillus subtilis, Bacillus amyloliquefaciens, Bacillus licheniformis, Bacillus pumilus* and *Bacillus gibsonii*. Particular subtilisins include subtilisin *lentus*, subtilisin Novo, subtilisin Carlsberg, subtilisin BPN', subtilisin 309, subtilisin 147 and subtilisin 168 and, e.g., protease PD138 (described in WO 93/18140). Other useful proteases are, e.g., those described in WO 01/16285 and WO 02/16547.

Examples of trypsin-like proteases include the *Fusarium* protease described in WO 94/25583 and WO 2005/040372, and the chymotrypsin proteases derived from *Cellumonas* described in WO 2005/052161 and WO 2005/052146.

Examples of metalloproteases include the neutral metalloproteases described in WO 2007/044993 such as those derived from *Bacillus amyloliquefaciens*, as well as, e.g., the metalloproteases described in WO 2015/158723 and WO 2016/075078.

Examples of useful proteases are the protease variants described in WO 89/06279 WO 92/19729, WO 96/34946, WO 98/20115, WO 98/20116, WO 99/11768, WO 01/44452, WO 2003/006602, WO 2004/003186, WO 2004/041979, WO 2007/006305, WO 2011/036263, WO 2014/207227, WO 2016/087617 and WO 2016/174234. Preferred protease variants may, for example, comprise one or more of the mutations selected from the group consisting of: S3T, V41, S9R, S9E, A15T, S24G, S24R, K27R, N42R, S55P, G59E, G59D, N60D, N60E, V66A, N74D, S85R, A96S, S97G, S97D, S97A, S97SD, S99E, S99D, S99G, S99M, S99N, S99R, S99H, S101A, V102I, V102Y, V102N, S104A, G116V, G116R, H118D, H118N, A120S, S126L, P127Q, S128A, S154D, A156E, G157D, G157P, S158E, Y161A, R164S, Q176E, N179E, S182E, Q185N, A188P, G189E, V193M, N198D, V1991, Q200L, Y203W, S206G, L211Q, L211D, N212D, N212S, M216S, A226V, K229L, Q230H, Q239R, N246K, S253D, N255W, N255D, N255E, L256E, L256D T268A and R269H, wherein position numbers correspond to positions of the *Bacillus lentus* protease shown in SEQ ID NO: 1 of WO 2016/001449. Protease variants having one or more of these mutations are preferably variants of the *Bacillus lentus* protease (Savinase®, also known as subtilisin 309) shown in SEQ ID NO: 1 of WO 2016/001449 or of the *Bacillus amyloliquefaciens* protease (BPN') shown in SEQ ID NO: 2 of WO 2016/001449. Such protease variants preferably have at least 80% sequence identity to SEQ ID NO: 1 or to SEQ ID NO: 2 of WO 2016/001449.

Another protease of interest is the alkaline protease from *Bacillus lentus* DSM 5483, as described for example in WO 91/02792, and variants thereof which are described for example in WO 92/21760, WO 95/23221, EP 1921147, EP 1921148 and WO 2016/096711.

The protease may alternatively be a variant of the TY145 protease having SEQ ID NO: 1 of WO 2004/067737, for example a variant comprising a substitution at one or more positions corresponding to positions 27, 109, 111, 171, 173, 174, 175, 180, 182, 184, 198, 199 and 297 of SEQ ID NO: 1 of WO 2004/067737, wherein said protease variant has a sequence identity of at least 75% but less than 100% to SEQ ID NO: 1 of WO 2004/067737. TY145 variants of interest are described in, e.g., WO 2015/014790, WO 2015/014803, WO 2015/014804, WO 2016/097350, WO 2016/097352, WO 2016/097357 and WO 2016/097354.

Examples of preferred proteases include:
(a) variants of SEQ ID NO: 1 of WO 2016/001449 comprising two or more substitutions selected from the group consisting of S9E, N43R, N76D, Q206L, Y209W, S259D and L262E, for example a variant with the substitutions S9E, N43R, N76D, V205I, Q206L, Y209W, S259D, N261W and L262E, or with the substitutions S9E, N43R, N76D, N185E, S188E, Q191N, A194P, Q206L, Y209W, S259D and L262E, wherein position numbers are based on the numbering of SEQ ID NO: 2 of WO 2016/001449;
(b) a variant of the polypeptide of SEQ ID NO: 1 of WO 2016/001449 with the mutation S99SE, wherein position numbers are based on the numbering of SEQ ID NO: 2 of WO 2016/001449;
(c) a variant of the polypeptide of SEQ ID NO: 1 of WO 2016/001449 with the mutation S99AD, wherein position numbers are based on the numbering of SEQ ID NO: 2 of WO 2016/001449;
(d) a variant of the polypeptide of SEQ ID NO: 1 of WO 2016/001449 with the substitutions Y167A+R170S+A194P, wherein position numbers are based on the numbering of SEQ ID NO: 2 of WO 2016/001449;
(e) a variant of the polypeptide of SEQ ID NO: 1 of WO 2016/001449 with the substitutions S9R+A15T+V68A+N218D+Q245R, wherein position numbers are based on the numbering of SEQ ID NO: 2 of WO 2016/001449;
(f) a variant of the polypeptide of SEQ ID NO: 1 of WO 2016/001449 with the substitutions S9R+A15T+G61E+V68A+A194P+V205I+Q245R+N261D, wherein position numbers are based on the numbering of SEQ ID NO: 2 of WO 2016/001449;
(g) a variant of the polypeptide of SEQ ID NO: 1 of WO 2016/001449 with the substitutions S99D+S101R/E+S103A+V104I+G160S; for example a variant of SEQ ID NO: 1 of WO 2016/001449 with the substitutions S3T+V4I+S99D+S101E+S103A+V104I+G160S+V205I, wherein position numbers are based on the numbering of SEQ ID NO: 2 of WO 2016/001449;
(h) a variant of the polypeptide of SEQ ID NO: 2 of WO 2016/001449 with the substitutions S24G+S53G+S78N+S101N+G128A/S+Y217Q, wherein position numbers are based on the numbering of SEQ ID NO: 2 of WO 2016/001449;
(i) the polypeptide disclosed in GENESEQP under accession number BER84782, corresponding to SEQ ID NO: 302 in WO 2017/210295;
(j) a variant of the polypeptide of SEQ ID NO: 1 of WO 2016/001449 with the substitutions S99D+S101E+S103A+V104I+S156D+G160S+L262E, wherein position numbers are based on the numbering of SEQ ID NO: 2 of WO 2016/001449;
(k) a variant of the polypeptide of SEQ ID NO: 1 of WO 2016/001449 with the substitutions S9R+A15T+G61E+V68A+N76D+S99G+N218D+Q245R, wherein position numbers are based on the numbering of SEQ ID NO: 2 of WO 2016/001449;
(l) a variant of the polypeptide of SEQ ID NO: 1 of WO 2016/001449 with the substitutions V68A+S106A, wherein position numbers are based on the numbering of SEQ ID NO: 2 of WO 2016/001449; and
(m) a variant of the polypeptide of SEQ ID NO: 1 of WO 2004/067737 with the substitutions S27K+N109K+S111E+S171E+S173P+G174K+S175P+F180Y+G182A+L184F+Q198E+N199+T297P, wherein position numbers are based on the numbering of SEQ ID NO: 1 of WO 2004/067737.

Suitable commercially available protease enzymes include those sold under the trade names Alcalase®, Duralase™, Durazym™, Relase®, Relase® Ultra, Savinase®, Savinase® Ultra, Primase™, Polarzyme®, Kannase®, Liquanase®, Liquanase® Ultra, Ovozyme®, Coronase®, Coronase® Ultra, Blaze®, Blaze Evity® 100T, Blaze Evity® 125T, Blaze Evity® 150T, Blaze Evity® 200T, Neutrase®, Everlase®, Esperase®, Progress® Uno, Progress® In and Progress® Excel (Novozymes A/S), those sold under the tradename Maxatase™, Maxacal™, Maxapem®, Purafect® Ox, Purafect® OxP, Puramax®, FN2™, FN3™, FN4$^{e \times TM}$, Excellase®, Excellenz™ P1000, Excellenz™ P1250, Eraser™, Preferenz® P100, Purafect Prime, Preferenz P110™, Effectenz P1000™, Purafect®, Effectenz P1050™, Purafect® Ox, Effectenz™ P2000, Purafast™, Properase®, Opticlean™ and Optimase® (Danisco/DuPont), BLAP (sequence shown in FIG. 29 of U.S. Pat. No. 5,352,604) and variants hereof (Henkel AG), and KAP (*Bacillus alkalophilus* subtilisin) from Kao.

Lipases and Cutinases

Suitable lipases and cutinases include those of bacterial or fungal origin. Chemically modified or protein engineered mutant enzymes are included. Examples include lipase from *Thermomyces*, e.g., from *T. lanuginosus* (previously named *Humicola lanuginosa*) as described in EP 258068 and EP 305216, cutinase from *Humicola*, e.g., *H. insolens* (WO 96/13580), lipase from strains of *Pseudomonas* (some of these now renamed to *Burkholderia*), e.g., *P. alcaligenes* or *P. pseudoalcaligenes* (EP 218272), *P. cepacia* (EP 331376), *P.* sp. strain SD705 (WO 95/06720 & WO 96/27002), *P. wisconsinensis* (WO 96/12012), GDSL-type *Streptomyces* lipases (WO 2010/065455), cutinase from *Magnaporthe grisea* (WO 2010/107560), cutinase from *Pseudomonas mendocina* (U.S. Pat. No. 5,389,536), lipase from *Thermobifida fusca* (WO 2011/084412), *Geobacillus stearothermophilus* lipase (WO 2011/084417), lipase from *Bacillus subtilis* (WO 2011/084599), and lipase from *Streptomyces griseus* (WO 2011/150157) and *S. pristinaespiralis* (WO 2012/137147).

Other examples are lipase variants such as those described in EP 407225, WO 92/05249, WO 94/01541, WO 94/25578, WO 95/14783, WO 95/30744, WO 95/35381, WO 95/22615, WO 96/00292, WO 97/04079, WO 97/07202, WO 00/34450, WO 00/60063, WO 01/92502, WO 2007/087508 and WO 2009/109500.

Preferred commercial lipase products include Lipolase™, Lipex™; Lipolex™ and Lipoclean™ (Novozymes A/S), Lumafast (originally from Genencor) and Lipomax (originally from Gist-Brocades). Still other examples are lipases sometimes referred to as acyltransferases or perhydrolases, e.g., acyltransferases with homology to *Candida antarctica* lipase A (WO 2010/111143), acyltransferase from *Mycobacterium smegmatis* (WO 2005/056782), perhydrolases from the CE 7 family (WO 2009/067279), and variants of the *M. smegmatis* perhydrolase in particular the S54V variant used in the commercial product Gentle Power Bleach from Huntsman Textile Effects Pte Ltd (WO 2010/100028).

Amylases

Suitable amylases may be an alpha-amylase or a glucoamylase and may be of bacterial or fungal origin. Chemically modified or protein engineered mutants are included. Amylases include, for example, alpha-amylases obtained from *Bacillus*, e.g., a special strain of *Bacillus licheniformis*, described in more detail in GB 1,296,839.

Suitable amylases include amylases having SEQ ID NO: 2 in WO 95/10603 or variants having 90% sequence identity to SEQ ID NO: 3 thereof. Preferred variants are described in WO 94/02597, WO 94/18314, WO 97/43424 and SEQ ID NO: 4 of WO 99/19467, such as variants with substitutions in one or more of the following positions: 15, 23, 105, 106, 124, 128, 133, 154, 156, 178, 179, 181, 188, 190, 197, 201, 202, 207, 208, 209, 211, 243, 264, 304, 305, 391, 408, and 444.

Different suitable amylases include amylases having SEQ ID NO: 6 in WO 02/10355 or variants thereof having 90% sequence identity to SEQ ID NO: 6. Preferred variants of SEQ ID NO: 6 are those having a deletion in positions 181 and 182 and a substitution in position 193.

Other amylases which are suitable are hybrid alpha-amylase comprising residues 1-33 of the alpha-amylase derived from *B. amyloliquefaciens* shown in SEQ ID NO: 6 of WO 2006/066594 and residues 36-483 of the *B. licheniformis* alpha-amylase shown in SEQ ID NO: 4 of WO 2006/066594 or variants having 90% sequence identity thereof. Preferred variants of this hybrid alpha-amylase are those having a substitution, a deletion or an insertion in one of more of the following positions: G48, T49, G107, H156, A181, N190, M197, I201, A209 and Q264. Most preferred variants of the hybrid alpha-amylase comprising residues 1-33 of the alpha-amylase derived from *B. amyloliquefaciens* shown in SEQ ID NO: 6 of WO 2006/066594 and residues 36-483 of SEQ ID NO: 4 are those having the substitutions:
M197T;
H156Y+A181T+N190F+A209V+Q264S; or
G48A+T49I+G107A+H156Y+A181T+N190F+I201F+A209V+Q264S.

Further amylases which are suitable are amylases having SEQ ID NO: 6 in WO 99/19467 or variants thereof having 90% sequence identity to SEQ ID NO: 6. Preferred variants of SEQ ID NO: 6 are those having a substitution, a deletion or an insertion in one or more of the following positions: R181, G182, H183, G184, N195, I206, E212, E216 and K269. Particularly preferred amylases are those having deletion in positions R181 and G182, or positions H183 and G184.

Additional amylases which can be used are those having SEQ ID NO: 1, SEQ ID NO: 3, SEQ ID NO: 2 or SEQ ID NO: 7 of WO 96/23873 or variants thereof having 90% sequence identity to SEQ ID NO: 1, SEQ ID NO: 2, SEQ ID NO: 3 or SEQ ID NO: 7. Preferred variants of SEQ ID NO: 1, SEQ ID NO: 2, SEQ ID NO: 3 or SEQ ID NO: 7 are those having a substitution, a deletion or an insertion in one or more of the following positions: 140, 181, 182, 183, 184, 195, 206, 212, 243, 260, 269, 304 and 476, using SEQ ID NO: 2 of WO 96/23873 for numbering. More preferred variants are those having a deletion in two positions selected from 181, 182, 183 and 184, such as 181 and 182, 182 and 183, or positions 183 and 184. Most preferred amylase variants of SEQ ID NO: 1, SEQ ID NO: 2 or SEQ ID NO: 7 are those having a deletion in positions 183 and 184 and a substitution in one or more of positions 140, 195, 206, 243, 260, 304 and 476.

Other amylases which can be used are amylases having SEQ ID NO: 2 of WO 2008/153815, SEQ ID NO: 10 in WO 01/66712 or variants thereof having 90% sequence identity to SEQ ID NO: 2 of WO 2008/153815 or 90% sequence identity to SEQ ID NO: 10 in WO 01/66712. Preferred variants of SEQ ID NO: 10 in WO 01/66712 are those having a substitution, a deletion or an insertion in one of more of the following positions: 176, 177, 178, 179, 190, 201, 207, 211 and 264.

Further suitable amylases are amylases having SEQ ID NO: 2 of WO 2009/061380 or variants having 90% sequence identity to SEQ ID NO: 2 thereof. Preferred variants of SEQ ID NO: 2 are those having a truncation of the C-terminus and/or a substitution, a deletion or an insertion in one of more of the following positions: Q87, Q98, S125, N128, T131, T165, K178, R180, S181, T182, G183, M201, F202, N225, S243, N272, N282, Y305, R309, D319, Q320, Q359, K444 and G475. More preferred variants of SEQ ID NO: 2 are those having the substitution in one of more of the following positions: Q87E,R, Q98R, S125A, N128C, T131I, T165I, K178L, T182G, M201L, F202Y, N225E,R, N272E, R, S243Q,A,E,D, Y305R, R309A, Q320R, Q359E, K444E and G475K and/or deletion in position R180 and/or S181 or of T182 and/or G183. Most preferred amylase variants of SEQ ID NO: 2 are those having the substitutions:
N128C+K178L+T182G+Y305R+G475K;
N128C+K178L+T182G+F202Y+Y305R+D319T+G475K;
S125A+N128C+K178L+T182G+Y305R+G475K; or
S125A+N128C+T131I+T165I+K178L+T182G+Y305R+G475K wherein the variants are C-terminally truncated and optionally further comprises a substitution at position 243 and/or a deletion at position 180 and/or position 181.

Further suitable amylases are amylases having SEQ ID NO: 1 of WO 2013/184577 or variants having 90% sequence identity to SEQ ID NO: 1 thereof. Preferred variants of SEQ ID NO: 1 are those having a substitution, a deletion or an insertion in one of more of the following positions: K176, R178, G179, T180, G181, E187, N192, M199, I203, S241, R458, T459, D460, G476 and G477. More preferred variants of SEQ ID NO: 1 are those having the substitution in one of more of the following positions: K176L, E187P, N192FYH, M199L, I203YF, S241QADN, R458N, T459S, D460T, G476K and G477K and/or deletion in position R178 and/or S179 or of T180 and/or G181. Most preferred amylase variants of SEQ ID NO: 1 are those having the substitutions:
E187P+I203Y+G476K
E187P+I203Y+R458N+T459S+D460T+G476K wherein the variants optionally further comprise a substitution at position 241 and/or a deletion at position 178 and/or position 179.

Further suitable amylases are amylases having SEQ ID NO: 1 of WO 2010/104675 or variants having 90% sequence identity to SEQ ID NO: 1 thereof. Preferred variants of SEQ ID NO: 1 are those having a substitution, a deletion or an insertion in one of more of the following positions: N21, D97, V128 K177, R179, S180, I181, G182, M200, L204, E242, G477 and G478. More preferred variants of SEQ ID NO: 1 are those having the substitution in one or more of the following positions: N21D, D97N, V128I K177L, M200L, L204YF, E242QA, G477K and G478K and/or deletion in position R179 and/or S180 or of I181 and/or G182. Most preferred amylase variants of SEQ ID NO: 1 are those having the substitutions:

N21D+D97N+V128I, wherein the variants optionally further comprise a substitution at position 200 and/or a deletion at position 180 and/or position 181.

Other suitable amylases are the alpha-amylase having SEQ ID NO: 12 in WO 01/66712 or a variant having at least 90% sequence identity to SEQ ID NO: 12. Preferred amylase variants are those having a substitution, a deletion or an insertion in one of more of the following positions of SEQ ID NO: 12 in WO 01/66712: R28, R118, N174; R181, G182, D183, G184, G186, W189, N195, M202, Y298, N299, K302, S303, N306, R310, N314; R320, H324, E345, Y396, R400, W439, R444, N445, K446, Q449, R458, N471, N484. Particular preferred amylases include variants having a deletion of D183 and G184 and having the substitutions R118K, N195F, R320K and R458K, and a variant additionally having substitutions in one or more position selected from the group: M9, G149, G182, G186, M202, T257, Y295, N299, M323, E345 and A339, most preferred a variant that additionally has substitutions in all these positions.

Other examples are amylase variants such as those described in WO 2011/098531, WO 2013/001078 and WO 2013/001087.

Commercially available amylases are Duramyl™, Termamyl™, Fungamyl™, Stainzyme™ Stainzyme Plus™, Natalase™, Liquozyme X and BAN™ (from Novozymes A/S), and Rapidase™, Purastar™/Effectenz™, Powerase, Preferenz™ S1000, Preferenz™ S100, Preferenz™ S110 and Preferenz™ S210 (from Genencor International Inc./DuPont).

Peroxidases/Oxidases

A peroxidase may be an enzyme comprised by the enzyme classification EC 1.11.1.7, as set out by the Nomenclature Committee of the International Union of Biochemistry and Molecular Biology (IUBMB), or any fragment derived therefrom, exhibiting peroxidase activity. Suitable peroxidases include those of plant, bacterial or fungal origin. Chemically modified or protein engineered mutants are included. Examples of useful peroxidases include peroxidases from *Coprinopsis*, e.g., from *C. cinerea* (EP 179,486), and variants thereof as those described in WO 93/24618, WO 95/10602, and WO 98/15257. A peroxidase may also include a haloperoxidase enzyme, such as chloroperoxidase, bromoperoxidase and compounds exhibiting chloroperoxidase or bromoperoxidase activity. Haloperoxidases are classified according to their specificity for halide ions. Chloroperoxidases (E.C. 1.11.1.10) catalyze formation of hypochlorite from chloride ions. The haloperoxidase may be a chloroperoxidase. Preferably, the haloperoxidase is a vanadium haloperoxidase, i.e., a vanadate-containing haloperoxidase. In a preferred method the vanadate-containing haloperoxidase is combined with a source of chloride ion. Haloperoxidases have been isolated from many different fungi, in particular from the fungus group dematiaceous hyphomycetes, such as Caldariomyces, e.g., *C. fumago, Alternaria, Curvularia,* e.g., *C. verruculosa* and *C. inaequalis, Drechslera, Ulocladium* and *Botrytis*. Haloperoxidases have also been isolated from bacteria such as *Pseudomonas,* e.g., *P. pyrrocinia* and *Streptomyces,* e.g., *S. aureofaciens.*

The haloperoxidase may be derivable from *Curvularia* sp., in particular *Curvularia verruculosa* or *Curvularia inaequalis,* such as *C. inaequalis* CBS 102.42 as described in WO 95/27046; or *C. verruculosa* CBS 147.63 or *C. verruculosa* CBS 444.70 as described in WO 97/04102; or from *Drechslera hartlebii* as described in WO 01/79459, *Dendryphiella salina* as described in WO 01/79458, *Phaeotrichoconis crotalarie* as described in WO 01/79461, or *Geniculosporium* sp. as described in WO 01/79460.

Oxidases include any laccase enzyme comprised by the enzyme classification EC 1.10.3.2, or any fragment derived therefrom exhibiting laccase activity, or a compound exhibiting a similar activity, such as a catechol oxidase (EC 1.10.3.1), an o-aminophenol oxidase (EC 1.10.3.4), or a bilirubin oxidase (EC 1.3.3.5). Preferred laccase enzymes are enzymes of microbial origin. The enzymes may be derived from plants, bacteria or fungi (including filamentous fungi and yeasts). Suitable examples from fungi include a laccase derivable from a strain of *Aspergillus, Neurospora,* e.g., *N. crassa, Podospora, Botrytis, Collybia, Fomes, Lentinus, Pleurotus, Trametes,* e.g., *T. villosa* and *T. versicolor, Rhizoctonia,* e.g., *R. solani, Coprinopsis,* e.g., *C. cinerea, C. comatus, C. friesii,* and *C. plicatilis, Psathyrella,* e.g., *P. condelleana, Panaeolus,* e.g., *P. papilionaceus, Myceliophthora,* e.g., *M. thermophila, Schytalidium,* e.g., *S. thermophilum, Polyporus,* e.g., *P. pinsitus, Phlebia,* e.g., *P. radiata* (WO 92/01046), or *Coriolus,* e.g., *C. hirsutus* (JP 2238885). Suitable examples from bacteria include a laccase derivable from a strain of *Bacillus*. A laccase derived from *Coprinopsis* or *Myceliophthora* is preferred; in particular a laccase derived from *Coprinopsis cinerea,* as disclosed in WO 97/08325; or from *Myceliophthora thermophila,* as disclosed in WO 95/33836.

Microorganisms

The detergent additive as well as the detergent composition may also comprise one or more microorganisms, such as one or more fungi, yeast, or bacteria. In an embodiment, the one or more microorganisms are dehydrated (for example by lyophilization) bacteria or yeast, such as a strain of *Lactobacillus*. In another embodiment, the microorganisms are one or more microbial spores (as opposed to vegetative cells), such as bacterial spores; or fungal spores, conidia, hypha. Preferably, the one or more spores are *Bacillus* endospores; even more preferably the one or more spores are endospores of *Bacillus subtilis, Bacillus licheniformis, Bacillus amyloliquefaciens,* or *Bacillus megaterium.* The microorganisms may be included in the detergent composition or additive in the same way as enzymes (see above).

Formulation of Detergent Products

The cleaning composition of the present invention may be formulated, for example, as a hand or machine laundry detergent composition including a laundry additive composition suitable for pre-treatment of stained fabrics and a rinse added fabric softener composition, or be formulated as a detergent composition for use in general household hard surface cleaning operations, or be formulated for hand or machine dishwashing operations. In a specific aspect, the present invention provides a detergent additive comprising one or more enzymes as described herein. The cleaning composition of the invention may be in any convenient form, e.g., a bar, a homogenous tablet, a tablet having two or more layers, a pouch having one or more compartments, a regular or compact powder, a granule, a paste, a gel, or a regular, compact or concentrated liquid.

Pouches can be configured as single or multicompartments. It can be of any form, shape and material which is suitable for holding the composition, e.g., without allowing the release of the composition to release of the composition from the pouch prior to water contact. The pouch is made from water soluble film which encloses an inner volume. Said inner volume can be divided into compartments of the pouch. Preferred films are polymeric materials preferably polymers which are formed into a film or sheet. Preferred polymers, copolymers or derivates thereof are selected polyacrylates, and water-soluble acrylate copolymers, methyl cellulose, carboxy methyl cellulose, sodium dextrin, ethyl cellulose, hydroxyethyl cellulose, hydroxypropyl methyl cellulose, malto dextrin, poly methacrylates, most preferably polyvinyl alcohol copolymers and, hydroxypropyl methyl cellulose (HPMC). Preferably the level of polymer in the film for example PVA is at least about 60%. Preferred average molecular weight will typically be about 20,000 to about 150,000. Films can also be of blended compositions comprising hydrolytically degradable and water-soluble polymer blends such as polylactide and polyvinyl alcohol (known under the Trade reference M8630 as sold by MonoSol LLC, Indiana, USA) plus plasticisers like glycerol, ethylene glycerol, propylene glycol, sorbitol and mixtures thereof. The pouches can comprise a solid laundry cleaning composition or part components and/or a liquid cleaning composition or part components separated by the water-soluble film. The compartment for liquid components can be different in composition than compartments containing solids: US 2009/0011970.

Detergent ingredients can be separated physically from each other by compartments in water dissolvable pouches or in different layers of tablets. Thereby negative storage interaction between components can be avoided. Different dissolution profiles of each of the compartments can also give rise to delayed dissolution of selected components in the wash solution.

A liquid or gel detergent, which is not unit dosed, may be aqueous, typically containing at least 20% by weight and up to 95% water, such as up to about 70% water, up to about 65% water, up to about 55% water, up to about 45% water, up to about 35% water. Other types of liquids, including without limitation, alkanols, amines, diols, ethers and polyols may be included in an aqueous liquid or gel. An aqueous liquid or gel detergent may contain from 0-30% organic solvent. A liquid or gel detergent may be non-aqueous.

Uses

The present invention is also directed to methods for using the compositions thereof. Laundry/textile/fabric (Household laundry washing, Industrial laundry washing). Hard surface cleaning (ADW, car wash, Industrial surface).

Use of Cleaning Composition

The detergent composition of the present invention may be formulated, for example, as a hand or machine laundry detergent composition including a laundry additive composition suitable for pre-treatment of stained fabrics and a rinse added fabric softener composition, or be formulated as a detergent composition for use in general household hard surface cleaning operations, or be formulated for hand or machine dishwashing operations. In a specific aspect, the present invention provides a detergent additive comprising one or more enzymes as described herein.

Methods

The invention further relates to a method of treating a method of treating a fabric comprising:
 (a) contacting the fabric with an aqueous solution of peptidoglycan degradation enzyme, preferably having N-acetylmuramyl-L-alanine amidase and peptidoglycan lyase activity; and optionally
 (b) rinsing and drying the textile.

The invention further relates to a method for cleaning or laundering an item comprising the steps of:
 a. exposing an item to a wash liquor comprising at least one peptidoglycan degradation enzyme, preferably having N-acetylmuramyl-L-alanine amidase and/or peptidoglycan lyase activity or a detergent composition comprising such enzyme;
 b. completing at least one wash cycle; and optionally
 c. rinsing the item,
wherein the item is a fabric.

The invention further relates to a method for cleaning or laundering an item comprising the steps of:
 a. exposing an item to a wash liquor comprising a polypeptide or a detergent composition comprising a polypeptide, preferably wherein the polypeptide has N-acetylmuramyl-L-alanine amidase and/or peptidoglycan lyase activity;
 b. completing at least one wash cycle; and optionally
 c. rinsing the item,
wherein the item is a fabric.

The invention further relates to a method for cleaning or laundering an item comprising the steps of:
 a. exposing an item to a wash liquor comprising a polypeptide or a detergent composition comprising a polypeptide, preferably wherein the polypeptide has N-acetylmuramyl-L-alanine amidase and/or peptidoglycan lyase activity and wherein the polypeptide comprises the motif N[IV]X[AG][GAS]A[AY][LV]L (SEQ ID NO: 111);
 b. completing at least one wash cycle; and optionally
 c. rinsing the item,
wherein the item is a fabric.

The invention further relates to a method for cleaning or laundering an item comprising the steps of:
 a. exposing an item to a wash liquor comprising a polypeptide or a detergent composition comprising a polypeptide, preferably wherein the is selected from the group consisting of: SEQ ID NO: 3, SEQ ID NO: 6, SEQ ID NO: 9, SEQ ID NO: 12, SEQ ID NO: 15, SEQ ID NO: 18, SEQ ID NO: 21, SEQ ID NO: 24, SEQ ID NO: 27, SEQ ID NO: 30, SEQ ID NO: 33, SEQ ID NO: 36, SEQ ID NO: 39, SEQ ID NO: 42, SEQ ID NO: 45, SEQ ID NO: 48, SEQ ID NO: 51, SEQ ID NO: 54, SEQ ID NO: 57, SEQ ID NO: 60, SEQ ID NO: 63, SEQ ID NO: 66, SEQ ID NO: 69, SEQ ID NO: 72, SEQ ID NO: 75, SEQ ID NO: 78, SEQ ID NO: 81, SEQ ID NO: 84, SEQ ID NO: 87, SEQ ID NO: 90, SEQ ID NO: 93, SEQ ID NO: 96, SEQ ID NO: 99, SEQ ID NO: 102, SEQ ID NO: 105, SEQ ID NO: 108 and polypeptides having at least at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% hereto;
 b. completing at least one wash cycle; and optionally
 c. rinsing the item,
wherein the item is a fabric.

The pH of the liquid solution is in the range of 1 to 11, such as in the range 5.5 to 11, such as in the range of 7 to 9, in the range of 7 to 8 or in the range of 7 to 8.5.

The wash liquor may have a temperature in the range of 5° C. to 95° C., or in the range of 10° C. to 80° C., in the range of 10° C. to 70° C., in the range of 10° C. to 60° C., in the range of 10° C. to 50° C., in the range of 15° C. to 40° C. or in the range of 20° ° C. to 30° C. In one aspect, the temperature of the wash liquor is 30° C.

The concentration of the peptidoglycan degradation enzyme in the wash liquor is typically in the range of at least 0.00001 ppm to at least 10 ppm, at least 0.00002 ppm to at least 10 ppm, at least 0.0001 ppm to at least 10 ppm, at least 0.0002 ppm to at least 10 ppm, at least 0.001 ppm to at least 10 ppm, at least 0.002 ppm to at least 10 ppm, at least 0.01 ppm to at least 10 ppm, at least 0.02 ppm to at least 10 ppm, at least 0.1 ppm to at least 10 ppm, at least 0.2 ppm to at least 10 ppm, at least 0.5 ppm to at least 5 ppm.

The present invention is further described by the following examples that should not be construed as limiting the scope of the invention.

EXAMPLES

Media and Solutions

Model detergent A: 12 wt % LAS, 1.1 wt % AEO Biosoft N25-7 (NI), 7 wt % AEOS (SLES), 6 wt % MPG, 3 wt % ethanol, 3 wt % TEA (triethanolamine), 2.75 wt % cocoa soap, 2.75 wt % soya soap, 2 wt % glycerol, 2 wt % sodium hydroxide, 2 wt % sodium citrate, 1 wt % sodium formiate, 0.2 wt % DTMPA, 0.2 wt % PCA.

Model detergent O: 4 wt % sodium dodecylbenezenesulfonate (LAS), 8 wt % sodium lauryl ether sulfate (SLES/AEOS), 1 wt % soap (soy fatty acid), 4 wt % alcohol ethoxylate (AEO), 0.4 wt % triethanolamine (TEA), 2 wt % sodium citrate, 0.02 wt % calcium chloride dihydrate.

For Example 4, a wash liquor of model detergent A was prepared by dissolving 3.33 g/l of the detergent in water with a hardness of 15° dH.

For Example 5, 2.67 g/l model O and 0.44 g/l model A, respectively, were dissolved in tap water.

Assays

Peptidoglycan-Degrading Activity Measurement

The peptidoglycan-degrading activity was estimated using the Invitrogen™ EnzChek™ Lysozyme Assay Kit (ThermoFisher, E22013) as recommended by the manufacturer. The DQ™ substrate supplied with the kit was dissolved in miliQ-$H_2O$ to yield a 1.0 mg/ml substrate stock solution. This solution was further diluted to 50 µg/ml by mixing 50 µl stock substrate solution with 950 µl 1× Reaction buffer supplied with the kit. Concentrated enzyme solution was diluted to 2 µg/ml in the 1× Reaction buffer. 50 µl of the 50 µg/ml substrate solution was mixed with either 50 µl 1× Reaction buffer or 50 µl 2 µg/ml enzyme solution to yield a final enzyme concentration in the reaction of 1 µg/ml. The sample was incubated at 37° C. and fluorescence development was measured using a POLARstar Omega plate reader spectrophotometer (BMG LABTECH) with an excitation wavelength of 485 nm emission wavelength of 520 nm and a gain of 1500.

Fluorescence units were plotted against time and the initial slope was estimated. The results are given in the table below. Clear peptidoglycan-degrading enzyme activity is observed for the enzyme.

| Enzyme | Initial slope (fluorescence units/min) |
|---|---|
| No enzyme | −189.64 |
| SEQ ID NO: 6 | 13228 |

Example 1: Cloning and Expression of Polypeptides: Strains and DNA

DNA encoding the genes of SEQ ID NO: 1, SEQ ID NO: 4, SEQ ID NO: 7, SEQ ID NO: 10, SEQ ID NO: 13, SEQ ID NO: 16, SEQ ID NO: 19, SEQ ID NO: 22, SEQ ID NO: 25, SEQ ID NO: 28, SEQ ID NO: 31, SEQ ID NO: 34, SEQ ID NO: 37, SEQ ID NO: 40, SEQ ID NO: 43, SEQ ID NO: 46, SEQ ID NO: 49, SEQ ID NO: 52, SEQ ID NO: 55, SEQ ID NO: 58, SEQ ID NO: 61, SEQ ID NO: 64, SEQ ID NO: 67, SEQ ID NO: 70, SEQ ID NO: 73, SEQ ID NO: 76, SEQ ID NO: 79, SEQ ID NO: 82, SEQ ID NO: 85, SEQ ID NO: 88, SEQ ID NO: 91, SEQ ID NO: 94, SEQ ID NO: 97, SEQ ID NO: 100, SEQ ID NO: 103 and SEQ ID NO: 106 was isolated from bacterial strains and environmental bacterial communities isolated from soil samples collected in different countries (see Table 1). Chromosomal DNA from the different strains and bacterial communities was subjected to full genome sequencing using Illumina technology. The genome sequences were analyzed for protein sequences that contained an Amidase_2 domain, as defined in PFAM (PF01510, Pfam version 31.0 Finn (2016). Nucleic Acids Research, Database Issue 44: D279-D285).

TABLE 1

| Enzyme SEQ ID NO: | Donor | Country of origin |
|---|---|---|
| 3 | Alicyclobacillus sp. | Denmark |
| 6 | Hamadaea tsunoensis | Japan |
| 9 | Micromonospora maritima | United States |
| 12 | Paenibacillus sp. | United States |
| 15 | Nonomuraea sp. | United Kingdom |
| 18 | Lysobacter antibioticus | China |
| 21 | Micromonospora sp. | United Kingdom |
| 24 | Nonomuraea coxensis | Philippines 1990 |
| 27 | Micromonospora fulvopurpurea | unknown strain isolated 1970 |
| 30 | Alicyclobacillus sp. | Denmark |
| 33 | Halomonas sp. | United States |
| 36 | Pseudomonas peli | United States |
| 39 | Halomonas sp. | United States |
| 42 | Pseudomonas pseudoalcaligenes | United States |
| 45 | Tumebacillus sp. | United States |
| 48 | Nonomuraea dietziae | United Kingdom |
| 51 | Laceyella sacchari | Denmark |
| 54 | Thermostaphylospora chromogena | Unknown, date of sampling 22 Aug. 1990 |
| 57 | Kribbella aluminosa | China |
| 60 | Streptomyces griseus | United States |
| 63 | Micromonospora peucetia | United Kingdom |
| 66 | Bacillus sp. | Japan |
| 69 | Bacillus sporothermodurans | Denmark |
| 72 | Paenibacillus pini | Sweden |
| 75 | Bacillus cohnii | United States |
| 78 | Kribbella sp. | United Kingdom |
| 81 | Bacillus sp. | United States |
| 84 | Bacillus sp. | United States |
| 87 | Bacillus sp. | United States |
| 90 | Streptomyces sp. | China |
| 93 | Bacillus sp. | United States |
| 96 | Bacillus sp. | United States |
| 99 | Nonomuraea guangzhouensis | United Kingdom |
| 102 | Nonomuraea guangzhouensis | United Kingdom |
| 105 | Bacillus cohnii | Denmark |
| 108 | Halomonas sp. | United States |
| | Lysobacter capsica | United States |

Example 2: Cloning and Expression of Polypeptides of the Invention

DNA encoding the mature peptides of peptidoglycan degradation enzyme genes SEQ ID NO: 1, SEQ ID NO: 4, SEQ ID NO: 7, SEQ ID NO: 10, SEQ ID NO: 13, SEQ ID NO: 16, SEQ ID NO: 19, SEQ ID NO: 22, SEQ ID NO: 25, SEQ ID NO: 28, SEQ ID NO: 31, SEQ ID NO: 34, SEQ ID NO: 37, SEQ ID NO: 40, SEQ ID NO: 43, SEQ ID NO: 46, SEQ ID NO: 49, SEQ ID NO: 52, SEQ ID NO: 55, SEQ ID NO: 58, SEQ ID NO: 61, SEQ ID NO: 64, SEQ ID NO: 67, SEQ ID NO: 70, SEQ ID NO: 73, SEQ ID NO: 76, SEQ ID NO: 79, SEQ ID NO: 82, SEQ ID NO: 85, SEQ ID NO: 88, SEQ ID NO: 91, SEQ ID NO: 94, SEQ ID NO: 97, SEQ ID NO: 100, SEQ ID NO: 103 and SEQ ID NO: 106 was amplified from the genomic DNA of the corresponding bacterial strains by standard PCR techniques using specific primers containing an overhang to cloning vector. The amplified PCR fragments were inserted into a *Bacillus* expression vector as described in WO 2012/025577. Briefly, the DNA encoding the mature peptide of the gene was cloned in frame to a *Bacillus clausii* secretion signal (BcSP; with the following amino acid sequence: MKKPLGKIVAS-TALLISVAFSSSIASA (SEQ ID NO: 109). BcSP replaced the native secretion signal in the gene. Downstream of the BcSP sequence, an affinity tag sequence was introduced to ease the purification process (His-tag; with the following amino acid sequence: HHHHHHPR (SEQ ID NO: 110) The gene that was expressed therefore comprised the BcSP sequence followed by the His-tag sequence followed by the mature wild type gene sequence. The final expression plasmid (BcSP-His-tag-PGLGene) was transformed into a *Bacillus subtilis* expression host. The BcSP-fusion gene was integrated by homologous recombination into the *Bacillus subtilis* host cell genome upon transformation. The gene construct was expressed under the control of a triple promoter system (as described in WO 99/43835). The gene coding for chloramphenicol acetyltransferase was used as maker (as described in (Diderichsen et al., 1993, *Plasmid* 30: 312-315)). Transformants were selected on LB media agar supplemented with 6 microgram of chloramphenicol per ml. One recombinant *Bacillus subtilis* clone containing the PGL expression construct was selected and was cultivated on a rotary shaking table in 500 ml baffled Erlenmeyer flasks each containing 100 ml yeast extract-based media. After 3-5 days' cultivation time at 30° C. to 37° C., the enzyme-containing supernatant was harvested by centrifugation and the enzymes were purified by His-tag purification.

Example 3: His Tag Purification Method

The His-tagged enzymes were purified by immobilized metal chromatography (IMAC) using $Ni^{2+}$ as the metal ion on 5 mL HisTrap Excel columns (GE Healthcare Life Sciences). The purification took place at pH 7 and the bound protein was eluted with imidazole. The purity of the purified enzymes was checked by SDS-PAGE and the concentration of the enzyme determined by Absorbance 280 nm after a buffer exchange in 50 mM HEPES, 100 mM NaCl pH 7.0.

Example 4: Attachment of *Micrococcus luteus*

*M. luteus* is taken from −80° C. frozen stock and grown on TSA plates for 3 days. From here one colony is inoculated per 10 ml TSB glass tube, whirl mixed and incubated over night at 30° C. with 200 rpm shaking. Then the bacteria are transferred to 50 ml Falcon tubes at 3000 rpm 20° C. for 5 min in a Sorvall centrifuge. The supernatant is removed and re-suspended in 10 ml PBS per tube. Cells are washed twice, added to a 50 ml tube and mixed. A solution of the culture is made with an OD600 of 0.5 as measured in a CLARIOstar® reader. 100 mL is prepared and kept under constant stirring throughout the test.

A detergent solution containing 3.33 g/L model A detergent is prepared by mixing 0.167 g Model A detergent with 50 mL of tap water in a 100 mL BlueCap bottle, stirring for 2-5 min before use. This solution is used for the first and last rows in the setup where no bacteria is added (see below). A detergent solution with bacteria is made by preparing a tap water solution containing *M. luteus* with an OD600 of 0.5 and 0.33 g Model A detergent, stirring for 2-5 min. This is used as a mix for wells of 48-well plates (Thermo Scientific, Nunc A/S, non-treated, PS, sterile, cat. no. 150787). A setup of blanks and enzymes is created so as to randomize the positions for repetitions in the plates to account for the systematic molding variation. An example may look like the following:

| | 1 No bacteria added | 2 bacteria added | 3 bacteria added | 4 bacteria added | 5 bacteria added | 6 bacteria added | 7 bacteria added | 8 No bacteria added |
|---|---|---|---|---|---|---|---|---|
| A | Control, no enzyme | Blank, no enzyme | Enz1 | Enz3 | Enz2 | Enz4 | Ref enzyme | Control, no enzyme |
| B | Control, no enzyme | Blank, no enzyme | Enz1 | Enz3 | Enz2 | Enz4 | Ref enzyme | Control, no enzyme |
| C | Control, no enzyme | Blank, no enzyme | Enz1 | Enz3 | Enz2 | Enz4 | Ref enzyme | Control, no enzyme |
| D | Control, no enzyme | Ref enzyme | Enz2 | Enz4 | Enz1 | Enz3 | Blank, no enzyme | Control, no enzyme |
| E | Control, no enzyme | Ref enzyme | Enz2 | Enz4 | Enz1 | Enz3 | Blank, no enzyme | Control, no enzyme |
| F | Control, no enzyme | Ref enzyme | Enz2 | Enz4 | Enz1 | Enz3 | Blank, no enzyme | Control, no enzyme |

Detergent mix+/− bacteria is added to the wells by adding 0.5 mL *M. luteus* test solution to each well. 10 µl enzyme solution with the prepared concentration is added according to the setup. The plate is allowed to incubate at 30° C. for 1.5 h. After incubation, the solution is removed from the plates by turning the plate upside down on paper towel in a zip-lock bag. The plate is turned and punched two times, then rinsed with 0.75 mL 0.9% NaCl solution. Solution is removed from the plates by turning the plate upside down on paper towel in a zip-lock bag. The plate is turned and punched two times, and the rinsing and punching step is repeated. 0.5 mL crystal violet 0.095% is added to each well. It is allowed to incubate 15 min on the table, then the supernatant is removed from the plates by turning the plate upside down on paper towel in a zip-lock bag and punching the plate hard twice to secure best removal, repeating until drops of unbound dye solution are removed, followed by gentle rinsing with 1 mL 0.9% NaCl. The rinse solution is removed and punched as described earlier. The color in the wells is dissolved with 0.5 mL 96% ethanol, giving a quick shake by hand until the liquid is clear. Absorbance 595 is measured in the CLARIOstar® reader and if it is higher than 3 the samples are diluted in new wells.

The results, measured as follows, are provided in Table 2 below:

$Y$ % attachment inhibition from $A_{590}=(1-(A_{590control}/A_{590enzx}))*100\%$.

$A_{590}$control=$A_{590}$ attachment in detergent solution of *M. luteus;*

$A_{590}$enzx=$A_{590}$ attachment in detergent+enzyme.

TABLE 2

Inhibition of attachment of *M. luteus*

| Enzyme | Model A pH 7.0 Y % attachment inhibition | Model A pH 7.8 Y % attachment inhibition | 1 × PBS pH 6.0 Y % attachment inhibition |
|---|---|---|---|
| Day 1 | | | |
| SEQ ID NO: 6 (1 ppm) | 46.9 | 43 | 30.5 |
| SEQ ID NO: 30 (10 ppm) | — | −3.5 | 39.9 |
| Day 4 | | | |
| SEQ ID NO: 6 (1 ppm) | 41.8 | 45.6 | 22.4 |
| SEQ ID NO: 12 (1 ppm) | 40.9 | 17.5 | — |
| SEQ ID NO: 12 (10 ppm) | 40.8 | 33.9 | 72.9 |
| Day 14 | | | |
| SEQ ID NO: 6 (1 ppm) | — | 52.4 | 43.2 |
| SEQ ID NO: 15 (0.01 ppm) | — | 23.5 | — |
| SEQ ID NO: 15 (0.1 ppm) | — | 51.5 | — |
| SEQ ID NO: 15 (0.5 ppm) | — | 60.1 | — |
| SEQ ID NO: 15 (1 ppm) | — | 65.2 | — |
| SEQ ID NO: 15 (2 ppm) | — | 59.1 | — |
| SEQ ID NO: 15 (5 ppm) | — | 62.6 | 17.5 |
| Day 22 | | | |
| SEQ ID NO: 6 (1 ppm) | — | 50.7 | — |
| SEQ ID NO: 21 (1 ppm) | — | 5.4 | — |
| SEQ ID NO: 21 (10 ppm) | — | 34.8 | — |
| Day 23 | | | |
| SEQ ID NO: 6 (1 ppm) | — | 57.1 | — |
| SEQ ID NO: 99 (1 ppm) | — | 42.7 | — |
| SEQ ID NO: 99 (10 ppm) | — | 47.5 | — |
| Day 25 | | | |
| SEQ ID NO: 6 (1 ppm) | — | 73.9 | — |
| SEQ ID NO: 18 (1 ppm) | — | 67.1 | — |
| SEQ ID NO: 18 (10 ppm) | — | 88.2 | — |
| Day 28 | | | |
| SEQ ID NO: 6 (1 ppm) | — | 32.5 | — |
| SEQ ID NO: 108 (1 ppm) | — | 13.3 | — |
| SEQ ID NO: 108 (2.5 ppm) | — | 17.1 | — |
| SEQ ID NO: 108 (5 ppm) | — | 21.2 | — |
| SEQ ID NO: 108 (10 ppm) | — | 24.6 | — |
| Day 29 | | | |
| SEQ ID NO: 6 (1 ppm) | — | 31.8 | — |
| SEQ ID NO: 9 (1 ppm) | — | 17.8 | — |
| SEQ ID NO: 9 (10 ppm) | — | 52 | — |
| Day 30 | | | |
| SEQ ID NO: 6 (1 ppm) | — | 34.5 | — |
| SEQ ID NO: 27 (1 ppm) | — | 1.3 | — |
| SEQ ID NO: 27 (10 ppm) | — | 4.2 | — |
| SEQ ID NO: 45 (1 ppm) | — | 20.1 | — |
| SEQ ID NO: 45 (10 ppm) | — | 27.3 | — |
| Day 31 | | | |
| SEQ ID NO: 6 (1 ppm) | — | 30.7 | — |
| SEQ ID NO: 48 (10 ppm) | — | 12 | — |
| SEQ ID NO: 69 (10 ppm) | — | 3.2 | — |
| Day 32 | | | |
| SEQ ID NO: 6 (1 ppm) | — | 34.4 | — |
| SEQ ID NO: 87 (1 ppm) | — | 4.1 | — |
| SEQ ID NO: 87 (10 ppm) | — | 10 | — |

The test results have a certain day to day variation, due to, e.g., fluctuations in lab temperature and humidity as well as slight variations in day-to-day cell viability, and the attachment inhibition results should therefore be compared for the same day. Our experience with the assay and the enzymes has shown that the day-to-day fluctuations in attachment and inhibition patterns in general give the same pattern in performance between the enzymes when they are repeated another day. Some enzymes work better at pH 6.0 and 7.0 and others perform optimally at pH 7.8, which has been tested for selected enzymes. SEQ ID NO: 6 is used as a reference enzyme to control the assay and measure the day to day variation.

Conclusion: In this experiment, SEQ ID NO: 6 shows robust inhibitory effects of *M. luteus* attachment at pH 6, pH 7 and pH 7.8. 10 ppm of SEQ ID NO: 30 shows an inhibitory effect on *M. luteus* on par with the effect of SEQ ID NO: 6 at a concentration of 1 ppm at pH 6, but no performance at pH 7.8. SEQ ID NO: 12 shows good performance at pH 7 compared to the control enzyme SEQ ID NO: 6. The performance of SEQ ID NO: 12 is less prominent at pH 7.8, but there is still a significant effect. SEQ ID NO: 15 can be dosed very low (0.01 ppm) and still give robust anti-attachment benefits at pH 7.8. At 0.5 ppm and 1.0 ppm there is a tendency for the inhibitory effect of SEQ ID NO: 15 to be higher than that of SEQ ID NO: 6 at a pH of 7.8. At pH 6 performance seems to be lower for SEQ ID NO: 15 at 5 ppm compared to SEQ ID NO: 6 at 1 ppm. SEQ ID Nos: 21, 99, 108, 9, 27, 45, 48, 69 and 87 also show inhibitory attachment benefits. SEQ ID NO: 18 gives very high anti-attachment performance on *M. luteus* at pH 7.8 using 1 ppm and it increases using 10 ppm.

Example 5: Preparation of Crude Cell Wall Extracts from *Micrococcus luteus* and OD Drop Activity Assay Preparation of Cell Wall Extracts Cell wall extracts from *Micrococcus luteus* were prepared following the protocol described by Mukamolova et al., 2006, *Molecular Microbiology* 59(1): 84-98. Briefly, *M. luteus* cells grown overnight in 1 L LB medium were centrifuged at 10,000 g for 30 minutes, washed with deionized water, resuspended in 200 ml 5% (w/v) SDS and boiled for 20 minutes. Following centrifugation, the pellet was resuspended in 100 ml 4% (w/v) SDS and boiled again for 20 min. The pellet was then thoroughly washed six times with 100 ml hot (65° C.) water to remove the SDS. Finally, it was washed with 10 ml acetone, air dried overnight, weighed and stored at −20° C.

OD Drop Assay Using Crude Cell Wall Extracts from *M. luteus*

0.6 g of *M. luteus* cell wall extracts prepared as described above were resuspended in 15 ml of deionized water (stock solution 40 mg/ml) and passed through a syringe needle to disrupt the large flakes. This stock solution was stored at 4° C.

A cell wall extract working solution was prepared from the stock solution at 0.75 mg/ml in 50 mM MES (2-(N-morpholino) ethanesulfonic acid) pH 6 buffer and two model detergents, model O and A (2.67 g/L model O and 0.44 g/L model A, respectively, in tap water). These working solutions were prepared fresh each time when running an OD drop assay.

Next, 150 µL aliquots of the crude cell wall extract working solution were dispensed in the wells of a 96-well microtiter plate (Thermo Scientific, Nunclon Delta Surface, cat #167008) and mixed with 50 µL of a solution containing 80 ppm of a purified enzyme (3, 6, 9, 12, 15, 18, 21, 24, 27, 30, 33, 36, 39, 42, 45, 48, 51, 54, 57, 60, 63, 66, 69, 72, 75, 78, 81, 84, 87, 90, 93, 96, 99, 102, 105 or 108) in 50 mM HEPES 100 mM NaCl pH7 buffer, or the HEPES buffer as a control, and incubated at 30° C. with shaking at 600 rpm in an Eppendorf ThermoMixer C. The absorbance of the samples was measured at 600 nm in a SpectraMax M3 instrument at time=0 and after overnight incubation with the enzyme. Enzymes were tested in duplicate. The average of the OD drop measurements (calculated by the OD obtained after overnight incubation minus OD at time 0) are listed in Table 3 below.

TABLE 3

OD drop values (OD after overnight incubation minus OD time 0)

| SEQ ID NO: | MES + HEPES | Model A | Model O |
|---|---|---|---|
| 3 | 0.27 | 0.03 | 0.00 |
| 6 | 0.42 | 0.13 | 0.21 |
| 9 | 0.20 | 0.03 | 0.00 |
| 12 | 0.35 | 0.20 | 0.46 |
| 15 | 0.65 | 0.79 | 0.54 |
| 18 | 0.71 | 0.90 | 0.82 |
| 21 | 0.10 | 0.02 | 0.00 |
| 24 | 0.12 | 0.00 | 0.00 |
| 27 | 0.08 | 0.03 | 0.00 |
| 30 | 0.15 | 0.49 | 0.50 |
| 33 | 0.36 | 0.15 | 0.32 |
| 36 | 0.12 | 0.00 | 0.00 |
| 39 | 0.36 | 0.25 | 0.36 |
| 42 | 0.21 | 0.02 | 0.00 |
| 45 | 0.30 | 0.03 | 0.00 |
| 48 | 0.10 | 0.03 | 0.00 |
| 51 | 0.23 | 0.00 | 0.00 |
| 54 | 0.03 | 0.17 | 0.23 |
| 57 | 0.23 | 0.33 | 0.58 |
| 60 | 0.11 | 0.23 | 0.30 |
| 63 | 0.18 | 0.15 | 0.30 |
| 66 | 0.47 | 0.16 | 0.40 |
| 69 | 0.46 | 0.16 | 0.23 |
| 72 | 0.45 | 0.17 | 0.29 |
| 75 | 0.53 | 0.20 | 0.55 |
| 78 | 0.29 | 0.19 | 0.32 |
| 81 | 0.64 | 0.16 | 0.27 |
| 84 | 0.60 | 0.15 | 0.35 |
| 87 | 0.35 | 0.17 | 0.30 |
| 90 | 0.18 | 0.16 | 0.23 |
| 93 | 0.78 | 0.19 | 0.10 |
| 96 | 0.36 | 0.15 | 0.14 |

TABLE 3-continued

OD drop values (OD after overnight incubation minus OD time 0)

| SEQ ID NO: | MES + HEPES | Model A | Model O |
|---|---|---|---|
| 99 | 0.27 | 0.72 | 0.66 |
| 102 | 0.25 | 0.16 | 0.21 |
| 105 | 0.10 | 0.15 | 0.25 |
| 108 | 0.60 | 0.03 | 0.16 |

The results in Table 3 show that enzymes giving an OD drop can hydrolyze cell wall extracts present in the solution.

Example 6: Construction of the PGL Domain, Clades and Phylogenetic Trees

The polypeptides of the invention have hydrolase activity and comprise the Amidase_2 domain as well as clusters such as clades. A phylogenetic tree was constructed from polypeptide sequences containing an Amidase_2 domain, as defined in PFAM (PF01510, Pfam version 31.0 Finn (2016). Nucleic Acids Research, Database Issue 44: D279-D285). The phylogenetic tree was constructed from a multiple alignment of mature polypeptide sequences containing at least one Amidase_2 domain. The sequences were aligned using the MUSCLE algorithm version 3.8.31 (Edgar, 2004, *Nucleic Acids Research* 32(5): 1792-1797), and a tree was constructed using FastTree version 2.1.8 (Price et al., 2010, *PloS one* 5(3)) and visualized using iTOL (Letunic & Bork, 2007. *Bioinformatics* 23(1): 127-128).

Analysis of the phylogenetic tree showed that the polypeptides containing an Amidase_2 domain may be separated into distinct sub-clusters. The sub-clusters are defined by one or more short sequence motifs, as well as by containing an Amidase_2 domain as defined in PFAM (PF01510, Pfam version 31.0). We denoted one sub-cluster comprising the motif N[IV]X[AG][GAS]A[AY][LV]L (SEQ ID NO: 111), situated in positions corresponding to positions 324 to 328 in *Micromonospora maritima* (SEQ ID NO: 6), as the PGL clade. All polypeptide sequences containing an Amidase_2 domain as well as the motif will be denoted as belonging to the PGL clade. Polypeptides included in the clade are SEQ ID NO: 3, SEQ ID NO: 6, SEQ ID NO: 9, SEQ ID NO: 12, SEQ ID NO: 15, SEQ ID NO: 18, SEQ ID NO: 21, SEQ ID NO: 24, SEQ ID NO: 27, SEQ ID NO: 42, SEQ ID NO: 45, SEQ ID NO: 48, SEQ ID NO: 51, SEQ ID NO: 54, SEQ ID NO: 60, SEQ ID NO: 63, SEQ ID NO: 66, SEQ ID NO: 69, SEQ ID NO: 75, SEQ ID NO: 87, SEQ ID NO: 96, SEQ ID NO: 99 and SEQ ID NO: 108.

Example 7: N-Acetylmuramyl-L-Alanine Amidase Assay

Substrate Synthesis

The organic syntheses of peptidoglycan fragments (1) and (2) was performed in three steps from commercially available methyl 2-acetamido-4,6-O-benzylidene-2-deoxy-α-D-glucopyranoside and the appropriate peptide sequences. Both peptides used (here named *S. aureus* peptide and *M. luteus* peptide; see below) were synthesized and provided by TAG Copenhagen A/S. In the structural formulas below, an asterisk (*) denotes D-stereochemistry.

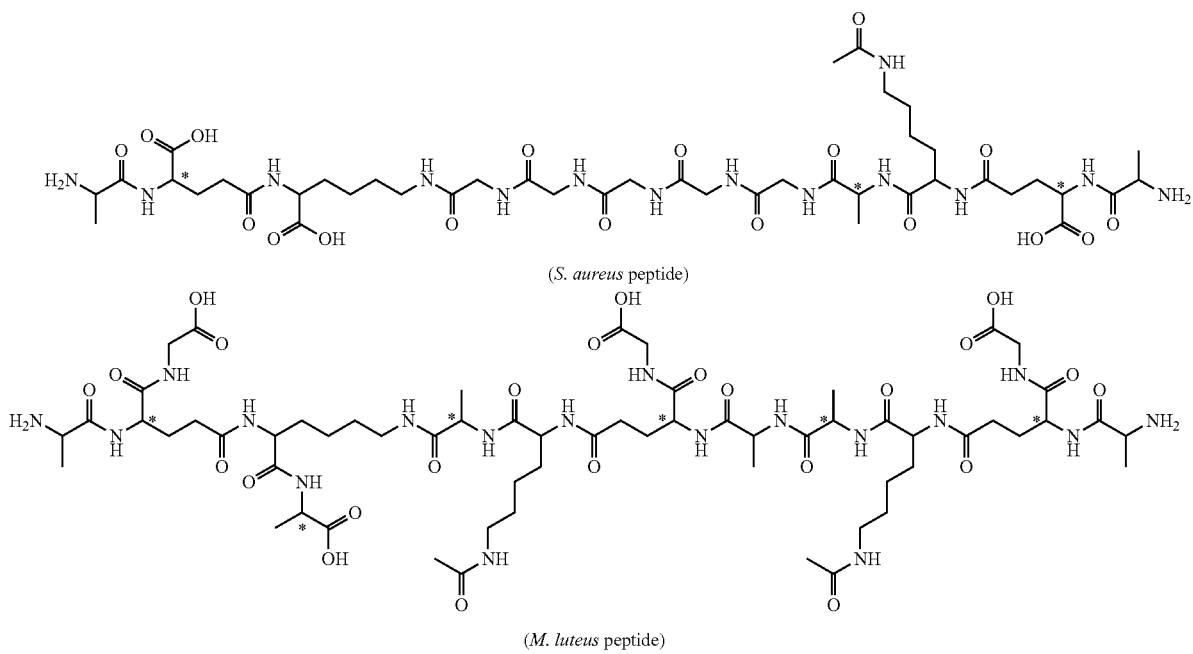

(*S. aureus* peptide)

(*M. luteus* peptide)

Synthesis of the peptides modified with muramic acid derivatives was performed, cf. the schematic overview below, by initially coupling methyl 2-acetamido-4,6-O-benzylidene-2-deoxy-α-D-glucopyranoside to (S)-2-chloropropionic acid using the protocol from D. Hesek et al., *J. Org. Chem.* 2004, 69, 778-784 to result in compound (3). Then the corresponding muramic acid NHS-ester derivative (4) was synthesized by treating 200 mg of (3) with N-(3-Dimethylaminopropyl)-N-ethylcarbodiimide hydrochloride (EDC-HCl, 1.5 eq.) and N-hydroxysuccinimide (1.15 eq.) in anhydrous dichloromethane (DCM, 2 mL) at room temperature (rt) for 4 hours before the solution was diluted with DCM (10 mL), washed with 2.5% NaHSO$_4$ and brine, dried over anhydrous NaSO$_4$, filtered and concentrated in vacuo. The desired product (4) was used without further purification in 2.1 eq. to couple to a peptide (20 mg) in anhydrous dimethylformamide (DMF, 300 μL) at room temperature in the presence of triethylamine (TEA, 3.5 eq.) by overnight reaction. The desired products (*S. aureus* substrate 1, or *M. luteus* substrate 2) were used without further purification for amidase assessment.

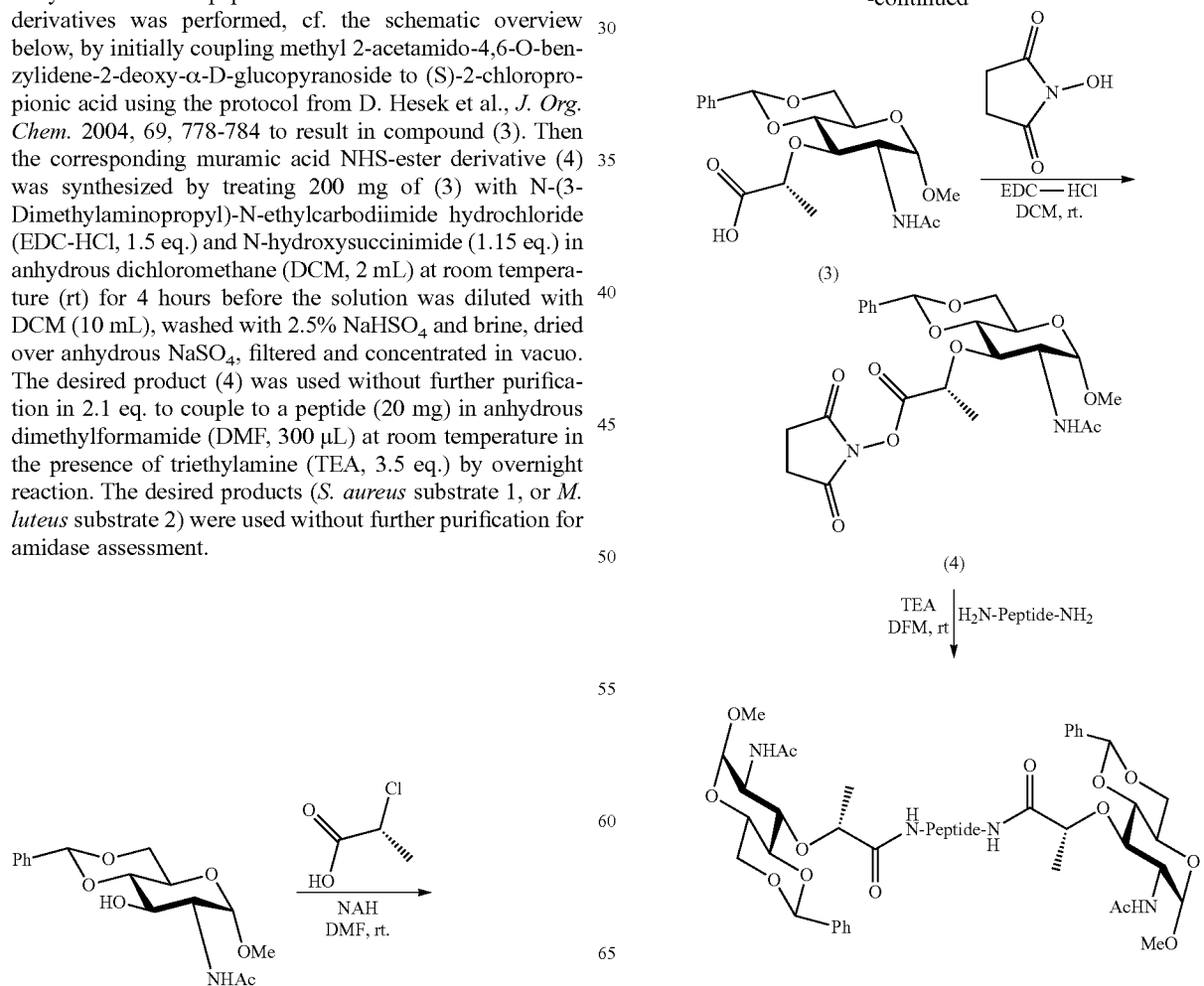

The result is the following modified peptides, *S. aureus* substrate 1 and *M. luteus* substrate 2:
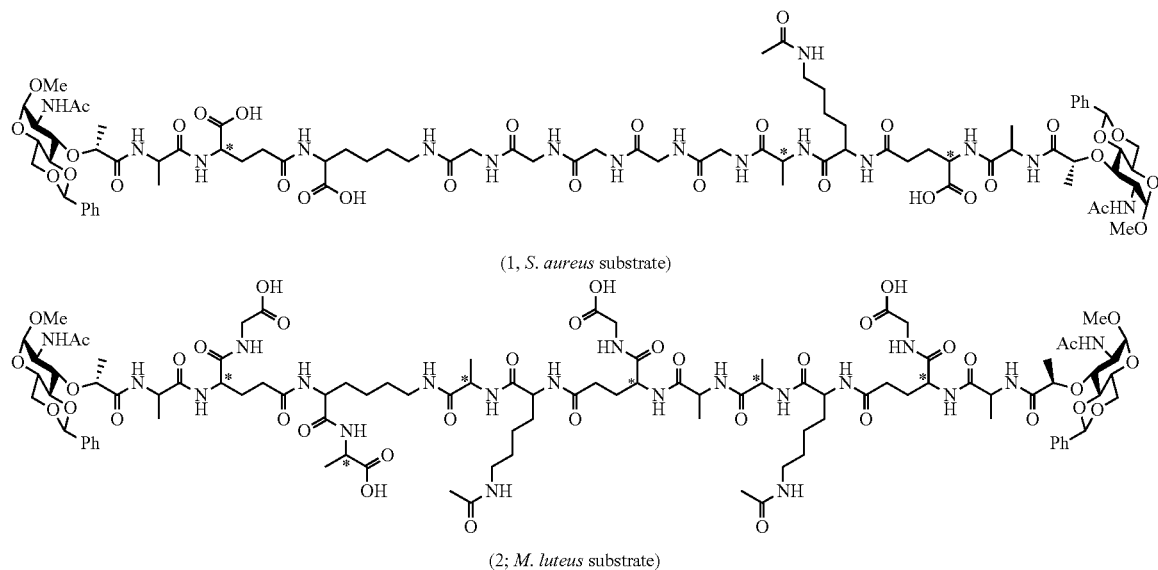
(1, *S. aureus* substrate)
(2; *M. luteus* substrate)
Amidase Assay
The amidases cleave between the peptide and the muramic acid (MurNAc) motifs to liberate one or two new N-termini, as illustrated in the following:
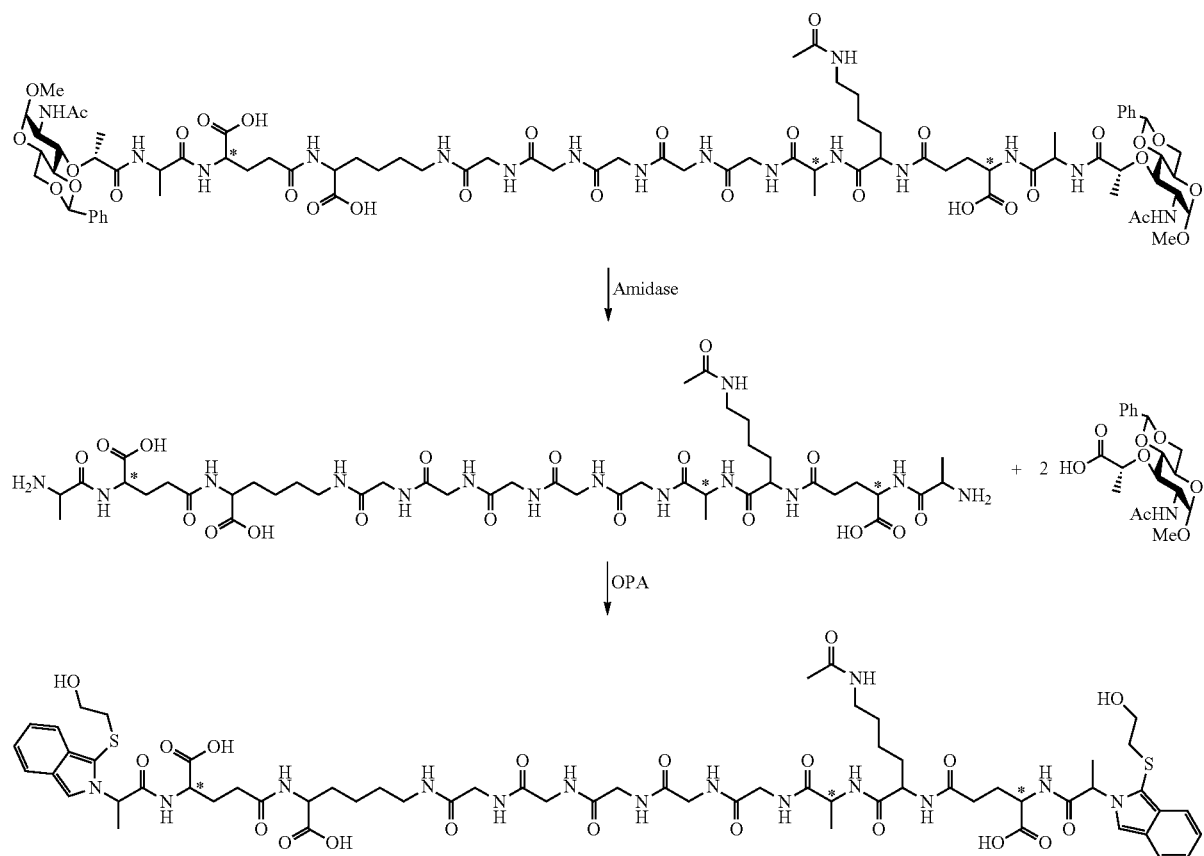

When exposed to standard o-phthaldehyde (OPA) assay conditions, the newly formed peptide amines (N-termini) react to yield a fluorescent readout (excitation=340 nm, emission=455 nm). OPA solution is prepared by dissolving 800 mg o-phthaldehyde in 10 mL 95% EtOH followed by addition of 1 L 0.5 M borate buffer (pH 9.0) containing 2 mL 2-mercaptoethanol.

Amidase reactions were performed by incubating and shaking the amidase (20 µg/mL final conc.) with the MurNAc-peptide-MurNAc substrate (substrate 1 or 2, 5 mM final conc.) in 50 mM MES buffer (pH 6.0, 100 mM NaCl) at 37° C. overnight, before the reaction products were analyzed by OPA assay and MALDI-TOF.

Amidase assessment (OPA assay) was performed by adding 100 µL OPA solution to 10 µL reaction sample. The mixture was transferred to a 96-well plate and monitored in a spectrophotometer (excitation=340 nm, emission=455 nm) after 5 min of incubation. The non-modified *S. aureus* and *M. luteus* peptides (i.e., with amino termini as shown above) were included as controls.

Results

Table 4 below shows the measured fluorescence for the *S. aureus* and *M. luteus* peptides (with amino termini) and substrates (with MurNAc termini) alone and after treatment with the amidases of SEQ ID NO: 6 or SEQ ID NO: 33, as well as for the amidases alone (negative control).

It can be seen that the MurNAc-peptide-MurNAc substrates (*S. aureus* substrate and *M. luteus* substrate) yield minimal OPA response until treated with the amidase of SEQ ID NO: 6 or SEQ ID NO: 33, where the fluorescent response increases significantly. The amidases appear to have no activity on the non-modified peptides (*S. aureus* peptide and *M. luteus* peptide), which was as expected.

MALDI-TOF MS analyses (data not shown) before and after treatment of the *S. aureus* and *M. luteus* substrates with the amidase of SEQ ID NO: 6 or SEQ ID NO: 33 confirmed that the OPA response is a result of enzymatic cleavage between the peptide and the MurNAc motifs to liberate the MurNAc motifs, yielding the free peptide N-termini.

TABLE 4

| Peptide/substrate + enzyme | Fluorescence (RFU; 340, 455 nm) |
|---|---|
| SEQ ID NO: 6 | 29 |
| SEQ ID NO: 33 | 27 |
| *S. aureus* peptide | 8420 |
| *S. aureus* peptide + SEQ ID NO: 6 | 8240 |
| *S. aureus* peptide + SEQ ID NO: 33 | 8547 |
| *S. aureus* substrate | 515 |
| *S. aureus* substrate + SEQ ID NO: 6 | 7077 |

TABLE 4-continued

| Peptide/substrate + enzyme | Fluorescence (RFU; 340, 455 nm) |
|---|---|
| *S. aureus* substrate + SEQ ID NO: 33 | 5704 |
| *M. luteus* peptide | 3447 |
| *M. luteus* peptide + SEQ ID NO: 6 | 3340 |
| *M. luteus* peptide + SEQ ID NO: 33 | 3298 |
| *M. luteus* substrate | 381 |
| *M. luteus* substrate + SEQ ID NO: 6 | 3166 |
| *M. luteus* substrate + SEQ ID NO: 33 | 1853 |

Example 8: N-Acetylmuramyl-L-Alanine Amidase Assay, Test of Additional Amidases

Several other enzymes within the same family as the amidase of SEQ ID NO: 6 were tested against the *S. aureus* substrate (substrate 1) as described in Example 7. This revealed that the amidases of SEQ ID NOs: 3, 45, 24 and 12 had comparable activity towards the *S. aureus* substrate; see the results in Table 5 below, where the individual enzymes (without peptide or substrate) are included as negative controls.

TABLE 5

| Peptide/substrate + enzyme | Fluorescence (RFU; 340, 455 nm) |
|---|---|
| *S. aureus* peptide | 8458 |
| *S. aureus* substrate | 735 |
| SEQ ID NO: 3 | 33 |
| SEQ ID NO: 6 | 21 |
| SEQ ID NO: 12 | 54 |
| SEQ ID NO: 24 | 108 |
| SEQ ID NO: 45 | 44 |
| *S. aureus* substrate + SEQ ID NO: 3 | 6810 |
| *S. aureus* substrate + SEQ ID NO: 6 | 7584 |
| *S. aureus* substrate + SEQ ID NO: 24 | 6903 |
| *S. aureus* substrate + SEQ ID NO: 12 | 6602 |
| *S. aureus* substrate + SEQ ID NO: 45 | 6851 |

The enzyme of SEQ ID NO: 105 was tested in a similar experiment and had comparable activity towards the *S. aureus* substrate; see Table 6.

TABLE 6

| Peptide/substrate + enzyme | Fluorescence (RFU; 340, 455 nm) |
|---|---|
| SEQ ID NO: 105 | 37 |
| *S. aureus* substrate | 756 |
| *S. aureus* substrate + SEQ ID NO: 105 | 6328 |

The invention claimed is:

1. A method of cleaning a textile, comprising washing the textile in a solution comprising a peptidoglycan degradation enzyme belonging to EC 3.5.1.28, EC 4.2.2.n1 or EC 4.2.2.n2 having peptidoglycan lyase activity or N-acetylmuramyl-L-alanine amidase activity, and 5 to 60 wt. % of at least one surfactant.

2. The method of claim 1, further comprising rinsing the textile.

3. The method of claim 1, wherein the solution further comprises 5 to 50 wt. % of at least one builder.

4. The method of claim 3, wherein the at least one builder comprises GLDA, MGDA, HEDP or DTMPA.

5. The method of claim 1, wherein the solution further comprises 1 to 20 wt. % of at least one bleach component.

6. The method of claim 5, wherein the at least one bleach component comprises MnTACN.

7. The method of claim 1, wherein the at least one surfactant comprises an anionic surfactant.

8. The method of claim 1, wherein the peptidoglycan degrading enzyme has N-acetylmuramyl-L-alanine amidase activity.

9. The method of claim 1, wherein the peptidoglycan degrading enzyme has peptidoglycan lyase activity.

10. The method of claim 1, wherein the peptidoglycan degrading enzyme has N-acetylmuramyl-L-alanine amidase activity and peptidoglycan lyase activity.

11. The method of claim 1, wherein the peptidoglycan degradation enzyme belongs to EC 3.5.1.28.

12. The method of claim 1, wherein the peptidoglycan degradation enzyme belongs to EC 4.2.2.n1.

13. The method of claim 1, wherein the peptidoglycan degradation enzyme belongs to EC 4.2.2.n2.

* * * * *